United States Patent
Sharma

(10) Patent No.: US 10,154,844 B2
(45) Date of Patent: Dec. 18, 2018

(54) MAGNETIC ANASTOMOSIS DEVICE AND DELIVERY SYSTEM

(71) Applicant: Virender K. Sharma, Paradise Valley, AZ (US)

(72) Inventor: Virender K. Sharma, Paradise Valley, AZ (US)

(*) Notice: Subject to any disclaimer, the term of this patent is extended or adjusted under 35 U.S.C. 154(b) by 0 days.

(21) Appl. No.: 15/605,286

(22) Filed: May 25, 2017

(65) Prior Publication Data
US 2018/0021043 A1 Jan. 25, 2018

Related U.S. Application Data

(60) Provisional application No. 62/425,951, filed on Nov. 23, 2016, provisional application No. 62/408,795, filed on Oct. 16, 2016, provisional application No. 62/366,185, filed on Jul. 25, 2016.

(51) Int. Cl.
| | |
|---|---|
| *A61B 17/11* | (2006.01) |
| *A61M 27/00* | (2006.01) |
| *A61B 17/00* | (2006.01) |

(52) U.S. Cl.
CPC ........ *A61B 17/1114* (2013.01); *A61M 27/002* (2013.01); *A61B 2017/00867* (2013.01); *A61B 2017/00876* (2013.01); *A61B 2017/1135* (2013.01)

(58) Field of Classification Search
CPC . A61B 17/11; A61B 17/1114; A61B 17/1128; A61B 17/1146; A61B 2017/1103–2017/1107; A61B 2017/1117–2017/1125; A61B 2017/1132–2017/1146
See application file for complete search history.

(56) References Cited

U.S. PATENT DOCUMENTS

| | | |
|---|---|---|
| 4,401,045 A | 8/1983 | Russell |
| 4,551,660 A | 11/1985 | Suzuki |
| 4,698,609 A | 10/1987 | Goehle |

(Continued)

FOREIGN PATENT DOCUMENTS

| | | |
|---|---|---|
| EP | 0123359 B1 | 3/1989 |
| EP | 0326757 B1 | 7/1993 |

(Continued)

OTHER PUBLICATIONS

"Choledochojejunostomy with an innovative magnetic compressive anastomosis: How to determine optimal pressure?" Fei Xue et al. World J Gastroenterol Feb. 21, 2016; 22(7): 2326-2335.

(Continued)

*Primary Examiner* — Robert Lynch
*Assistant Examiner* — Lindsey Bachman
(74) *Attorney, Agent, or Firm* — Novel IP

(57) ABSTRACT

An anastomosis device includes magnets coupled to a wire capable of changing shape from a straight wire into a coil when deployed within a body. The coil exerts compressive force upon layers of tissue caught between loops of the coil. The compressive force is enhanced by attractive forces between magnets coupled with adjacent loops of the coil and causes the coil to cut through the tissue layers, creating an anastomosis. One end of the wire is preferably provided with a connecting member, such as a screw or a nut, for connecting with a delivery device.

28 Claims, 76 Drawing Sheets

(56) References Cited

U.S. PATENT DOCUMENTS

| | | | |
|---|---|---|---|
| 4,899,744 A | 2/1990 | Fujitsuka | |
| 5,595,562 A | 1/1997 | Grier | |
| 5,631,613 A | 5/1997 | Niimi | |
| 5,660,487 A | 8/1997 | Cayzer | |
| 5,690,656 A | 11/1997 | Cope | |
| 6,171,320 B1 | 1/2001 | Monassevitch | |
| 6,217,339 B1 | 4/2001 | Tsubata | |
| 6,352,543 B1 | 3/2002 | Cole | |
| 6,361,545 B1* | 3/2002 | Macoviak et al. | A61B 17/12136 606/151 |
| 6,402,765 B1 | 6/2002 | Monassevitch | |
| 6,517,556 B1 | 2/2003 | Monassevitch | |
| 6,565,581 B1 | 5/2003 | Spence | |
| 6,607,542 B1* | 8/2003 | Wild | A61B 17/122 606/139 |
| 6,652,540 B1 | 11/2003 | Cole | |
| 6,719,768 B1 | 4/2004 | Cole | |
| 6,802,847 B1 | 10/2004 | Carson | |
| 6,884,250 B2 | 4/2005 | Monassevitch | |
| 6,896,684 B2 | 5/2005 | Monassevitch | |
| 6,932,827 B2 | 8/2005 | Cole | |
| 7,094,247 B2 | 8/2006 | Monassevitch | |
| 7,222,428 B2 | 5/2007 | Koike | |
| 7,232,449 B2 | 6/2007 | Sharkawy | |
| 7,241,300 B2 | 7/2007 | Sharkawy | |
| 7,282,057 B2 | 10/2007 | Surti | |
| 7,374,153 B2 | 5/2008 | Huang | |
| 7,393,027 B1 | 7/2008 | Chen | |
| 7,431,727 B2 | 10/2008 | Cole | |
| 7,527,185 B2 | 5/2009 | Harari | |
| 7,618,427 B2 | 11/2009 | Ortiz | |
| 7,635,374 B2 | 12/2009 | Monassevitch | |
| 7,728,707 B2 | 6/2010 | Gilardi | |
| 7,892,244 B2 | 2/2011 | Monassevitch | |
| 7,909,837 B2 | 3/2011 | Crews | |
| 7,938,841 B2 | 5/2011 | Sharkawy | |
| 8,118,821 B2* | 2/2012 | Mouw | A61B 17/1114 606/153 |
| 8,142,454 B2 | 3/2012 | Harrison | |
| 8,205,782 B2 | 6/2012 | Harari | |
| 8,262,680 B2 | 9/2012 | Swain | |
| 8,518,062 B2 | 8/2013 | Cole | |
| 8,556,919 B2 | 10/2013 | Aguirre | |
| 8,623,036 B2 | 1/2014 | Harrison | |
| 8,628,548 B2 | 1/2014 | Aguirre | |
| 8,629,572 B1 | 1/2014 | Phillips | |
| 8,679,139 B2 | 3/2014 | Aguirre | |
| 8,685,046 B2 | 4/2014 | Viola | |
| 8,728,105 B2 | 5/2014 | Aguirre | |
| 8,764,773 B2 | 7/2014 | Harari | |
| 8,828,031 B2 | 9/2014 | Fox | |
| 8,828,032 B2 | 9/2014 | McWeeney | |
| 8,845,663 B2 | 9/2014 | Chmura | |
| 8,864,781 B2 | 10/2014 | Surti | |
| 8,870,898 B2 | 10/2014 | Beisel | |
| 8,870,899 B2 | 10/2014 | Beisel | |
| 8,876,699 B2 | 11/2014 | Sato | |
| 8,910,366 B2 | 12/2014 | Fuse | |
| 8,920,446 B2 | 12/2014 | Viola | |
| 8,946,919 B2 | 2/2015 | Phillips | |
| 8,946,920 B2 | 2/2015 | Phillips | |
| 9,168,041 B2 | 10/2015 | Zaritsky | |
| 9,205,236 B2 | 12/2015 | McNamara | |
| 9,226,753 B2 | 1/2016 | Surti | |
| 9,232,997 B2 | 1/2016 | Sugimoto | |
| 9,240,710 B2 | 1/2016 | Kawarai | |
| 9,277,995 B2 | 3/2016 | Celermajer | |
| 9,332,990 B2 | 5/2016 | Requarth | |
| 9,358,371 B2 | 6/2016 | McNamara | |
| 9,364,238 B2 | 6/2016 | Bakos | |
| 9,456,812 B2 | 10/2016 | Finch | |
| 9,492,173 B2 | 11/2016 | McWeeney | |
| 2002/0183768 A1 | 12/2002 | Deem | |
| 2003/0014061 A1 | 1/2003 | Houser | |
| 2003/0153932 A1 | 8/2003 | Spence | |
| 2003/0229363 A1 | 12/2003 | Sharkawy | |
| 2004/0034377 A1 | 2/2004 | Sharkawy | |
| 2004/0059280 A1 | 3/2004 | Makower | |
| 2004/0102794 A1 | 5/2004 | Roy | |
| 2004/0116945 A1 | 6/2004 | Sharkawy | |
| 2004/0215214 A1 | 10/2004 | Crews | |
| 2005/0080439 A1 | 4/2005 | Carson | |
| 2005/0143763 A1* | 6/2005 | Ortiz | A61B 17/1114 606/153 |
| 2006/0111733 A1 | 5/2006 | Shriver | |
| 2006/0271107 A1 | 11/2006 | Harrison | |
| 2006/0282106 A1 | 12/2006 | Cole | |
| 2007/0118158 A1 | 5/2007 | Deem | |
| 2007/0213748 A1 | 9/2007 | Deem | |
| 2007/0250084 A1 | 10/2007 | Sharkawy | |
| 2008/0114384 A1 | 5/2008 | Chang | |
| 2008/0200934 A1 | 8/2008 | Fox | |
| 2008/0208214 A1* | 8/2008 | Sato | A61B 17/1114 606/139 |
| 2008/0208224 A1 | 8/2008 | Surti | |
| 2008/0300609 A1 | 12/2008 | Tabet | |
| 2009/0048618 A1 | 2/2009 | Harrison | |
| 2009/0125042 A1 | 5/2009 | Mouw | |
| 2009/0227828 A1 | 9/2009 | Swain | |
| 2010/0010508 A1* | 1/2010 | Takahashi | A61B 17/064 606/139 |
| 2010/0025605 A1 | 2/2010 | Galtz | |
| 2010/0036399 A1 | 2/2010 | Viola | |
| 2010/0049223 A1 | 2/2010 | Granja Filho | |
| 2010/0179510 A1 | 7/2010 | Fox | |
| 2010/0256659 A1 | 10/2010 | Aguirre | |
| 2010/0292729 A1 | 11/2010 | Aguirre | |
| 2010/0318015 A1 | 12/2010 | Kassab | |
| 2010/0331862 A1 | 12/2010 | Monassevitch | |
| 2011/0054498 A1 | 3/2011 | Monassevitch | |
| 2011/0087252 A1 | 4/2011 | Chmura | |
| 2011/0112559 A1 | 5/2011 | Monassevitch | |
| 2011/0118765 A1 | 5/2011 | Aguirre | |
| 2011/0144560 A1 | 6/2011 | Gagner | |
| 2011/0160752 A1 | 6/2011 | Aguirre | |
| 2011/0184505 A1 | 7/2011 | Sharkawy | |
| 2011/0295285 A1 | 12/2011 | McWeeney | |
| 2012/0035628 A1 | 2/2012 | Aguirre | |
| 2012/0150092 A1 | 6/2012 | McAllister | |
| 2012/0172782 A1 | 7/2012 | Thompson | |
| 2012/0197061 A1 | 8/2012 | Requarth | |
| 2012/0197062 A1 | 8/2012 | Requarth | |
| 2012/0259350 A1 | 10/2012 | Gagner | |
| 2012/0324975 A1 | 12/2012 | Anderson | |
| 2012/0330330 A1 | 12/2012 | Gagner | |
| 2013/0110141 A1 | 5/2013 | Chmura | |
| 2013/0226205 A1 | 8/2013 | Zaritsky | |
| 2013/0253548 A1 | 9/2013 | Harrison | |
| 2013/0253550 A1 | 9/2013 | Beisel | |
| 2013/0325042 A1 | 12/2013 | Fabian | |
| 2014/0100423 A1 | 4/2014 | Monassevitch | |
| 2014/0236064 A1 | 8/2014 | Binmoeller | |
| 2014/0236200 A1 | 8/2014 | Beisel | |
| 2014/0309669 A1 | 10/2014 | Fabian | |
| 2014/0309670 A1 | 10/2014 | Bakos | |
| 2014/0343583 A1 | 11/2014 | McWeeney | |
| 2014/0364881 A1 | 12/2014 | Meron | |
| 2014/0379011 A1 | 12/2014 | Viola | |
| 2015/0057687 A1 | 2/2015 | Gittard | |
| 2015/0057688 A1 | 2/2015 | Beisel | |
| 2015/0164508 A1 | 6/2015 | Hernandez | |
| 2015/0182224 A1 | 7/2015 | Altman | |
| 2015/0201943 A1* | 7/2015 | Brooks | A61B 17/11 606/153 |
| 2015/0222165 A1 | 8/2015 | Filippa | |
| 2015/0313595 A1* | 11/2015 | Houghton | A61B 17/1114 606/153 |
| 2016/0022266 A1 | 1/2016 | Lukin | |
| 2016/0120550 A1 | 5/2016 | McNamara | |

(56) References Cited

U.S. PATENT DOCUMENTS

| | | |
|---|---|---|
| 2016/0262761 A1 | 9/2016 | Beisel |
| 2016/0324523 A1 | 11/2016 | Lukin |
| 2017/0119394 A1 | 5/2017 | McWeeney |

FOREIGN PATENT DOCUMENTS

| | | |
|---|---|---|
| EP | 0754434 B1 | 9/1999 |
| EP | 1284660 A1 | 2/2003 |
| EP | 1307144 A1 | 5/2003 |
| EP | 1017047 B1 | 7/2003 |
| EP | 0910298 B1 | 8/2003 |
| EP | 1389984 A1 | 2/2004 |
| EP | 1435824 A2 | 7/2004 |
| EP | 1435856 A1 | 7/2004 |
| EP | 1435872 A2 | 7/2004 |
| EP | 0954248 B1 | 9/2004 |
| EP | 1550415 A2 | 7/2005 |
| EP | 1334696 B1 | 3/2007 |
| EP | 1938009 A1 | 7/2008 |
| EP | 1551313 B1 | 10/2008 |
| EP | 1301129 B1 | 9/2009 |
| EP | 2131752 A1 | 12/2009 |
| EP | 2151199 A1 | 2/2010 |
| EP | 1289428 B1 | 3/2010 |
| EP | 2236242 A1 | 10/2010 |
| EP | 1732473 B1 | 12/2010 |
| EP | 2258317 A2 | 12/2010 |
| EP | 2124759 B1 | 6/2011 |
| EP | 2332473 A1 | 6/2011 |
| EP | 2207488 B1 | 9/2012 |
| EP | 2519164 A1 | 11/2012 |
| EP | 2429625 B1 | 5/2013 |
| EP | 2086426 B1 | 7/2013 |
| EP | 2413813 B1 | 8/2013 |
| EP | 2632346 A2 | 9/2013 |
| EP | 2690767 A1 | 1/2014 |
| EP | 2485657 B1 | 8/2014 |
| EP | 2839796 A1 | 2/2015 |
| EP | 2424472 B1 | 12/2015 |
| EP | 2958527 A1 | 12/2015 |
| EP | 2967867 A1 | 1/2016 |
| EP | 2537490 B1 | 8/2016 |
| WO | 1997013463 A1 | 4/1997 |
| WO | 1998016161 A1 | 4/1998 |
| WO | 2001082803 A1 | 11/2001 |
| WO | 2002013704 A1 | 2/2002 |
| WO | 2002096327 A2 | 12/2002 |
| WO | 2003024307 A2 | 3/2003 |
| WO | 2003101311 A1 | 12/2003 |
| WO | 2003103510 A1 | 12/2003 |
| WO | 2004008937 A2 | 1/2004 |
| WO | 2004045383 A2 | 6/2004 |
| WO | 2004105693 A2 | 12/2004 |
| WO | 2005027736 A2 | 3/2005 |
| WO | 2005094334 A2 | 10/2005 |
| WO | 2006127236 A2 | 11/2006 |
| WO | 2007042016 A1 | 4/2007 |
| WO | 2007140557 A2 | 12/2007 |
| WO | 2007140562 A2 | 12/2007 |
| WO | 2008061024 A2 | 5/2008 |
| WO | 2008101077 A1 | 8/2008 |
| WO | 2008106279 A1 | 9/2008 |
| WO | 2009048954 A1 | 4/2009 |
| WO | 2009081948 A1 | 7/2009 |
| WO | 2010115116 A1 | 10/2010 |
| WO | 2010132356 A1 | 11/2010 |
| WO | 2011008988 A1 | 1/2011 |
| WO | 2011062831 A1 | 5/2011 |
| WO | 2011081988 A1 | 7/2011 |
| WO | 2011085006 A2 | 7/2011 |
| WO | 2012007042 A1 | 1/2012 |
| WO | 2012007052 A1 | 1/2012 |
| WO | 2012009431 A2 | 1/2012 |
| WO | 2012170502 A1 | 12/2012 |
| WO | 2013009886 A1 | 1/2013 |
| WO | 2013143495 A1 | 10/2013 |
| WO | 2013170474 A1 | 11/2013 |
| WO | 2013176993 A1 | 11/2013 |
| WO | 2014055193 A1 | 4/2014 |
| WO | 2014070720 A1 | 5/2014 |
| WO | 2014130850 A1 | 8/2014 |
| WO | 2014172194 A1 | 10/2014 |
| WO | 2015103346 A1 | 7/2015 |
| WO | 2015191859 A2 | 12/2015 |
| WO | 2015192022 A1 | 12/2015 |
| WO | 2016007917 A2 | 1/2016 |
| WO | 2016014644 A1 | 1/2016 |
| WO | 2016014821 | 1/2016 |

OTHER PUBLICATIONS

"Understanding gastric forces calculated from high-resolution pill tracking" Laulicht et al. Proceedings of the National Academy of Scienes of the United States of America, May 4, 2010; vol. 107, No. 18: 8201-8206.

Cronin et al., "Normal small bowel wall characteristics on MR enterography"; European Journal of Radiology 75 (2010) 207-211.

Mesenas et al., "Duodenal EUS to identify thickening of the extrahepatic biliary tree wall in primary sclerosing cholangitis"; Gastrointestinal Endoscopy vol. 63, No. 3: 2006, pp. 403-408.

Rapaccini, et al., "Gastric Wall Thickness in Normal and Neoplastic Subjects: A Prospective Study Performed by Abdominal Ultrasound"; Gastrointestinal Radiology 13: 197-199 (1998).

Shikata, et al., "Experimental Studies on the Hemodynamics of the Small Intestine Following Increased Intraluminal Pressure"; Surgery, Gynecology & Obstetrics: Feb. 1983, vol. 156, pp. 155-160.

Matcuk et al.; "Ultrasound Measurements of the Bile Ducts and Gallbladder"; Ultrasound Quarterly, vol. 30, No. 1, Mar. 2014, pp. 41-48.

International Search Report for PCT/US2017/034475, dated Sep. 1, 2017.

* cited by examiner

Coil Wires Cutting Through the Organ Wall

Coil Falls off and an Anastomosis is Formed

500

| Diameter | 1 Loop | 2 Loops | 4 Loops | 8 Loops | 16 Loops |
|---|---|---|---|---|---|
| 0.5 | 1.57 | 3.142857 | 6.285714 | 12.57143 | 25.14286 |
| 1 | 3.14 | 6.285714 | 12.57143 | 25.14286 | 50.28571 |
| 2 | 6.29 | 12.57143 | 25.14286 | 50.28571 | 100.5714 |
| 3 | 9.43 | 18.85714 | 37.71429 | 75.42857 | 150.8571 |
| 4 | 12.57 | 25.14286 | 50.28571 | 100.5714 | 201.1429 |
| 5 | 15.71 | 31.42857 | 62.85714 | 125.7143 | 251.4286 |

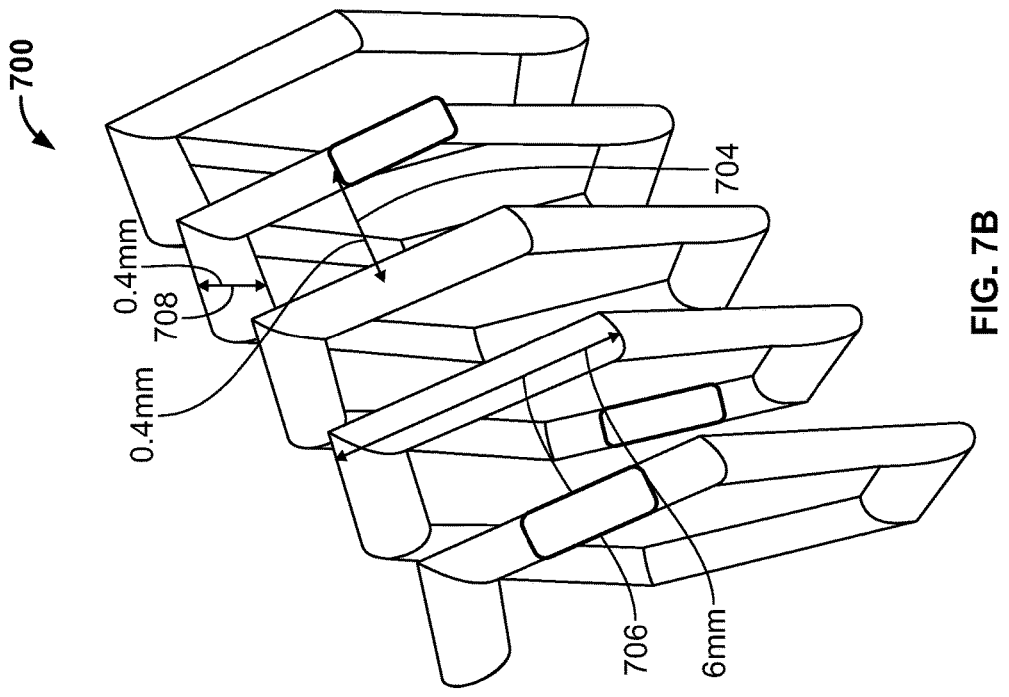
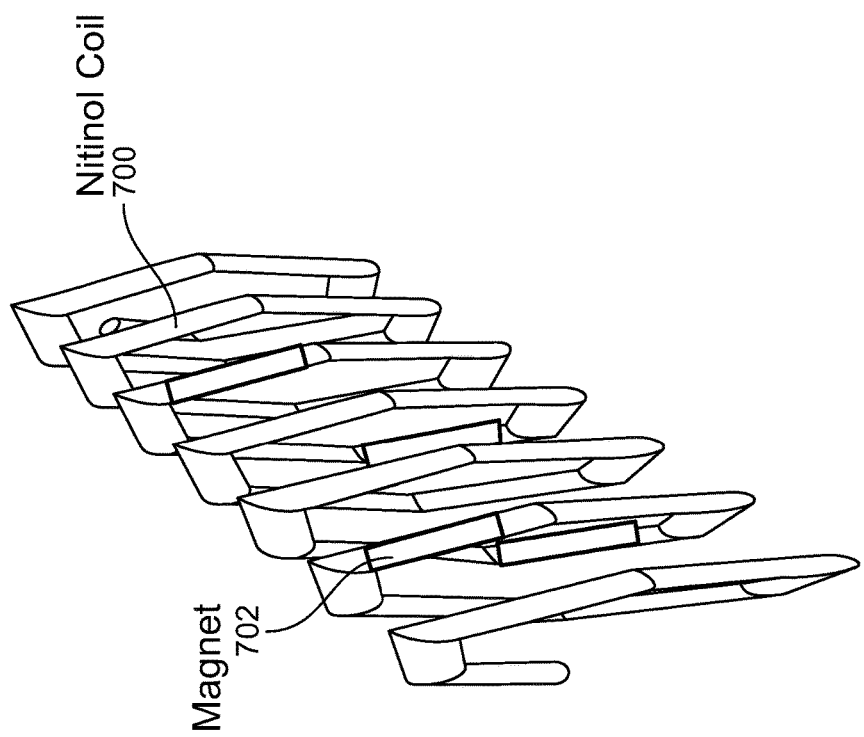
FIG. 7B
FIG. 7A

Area = $\dfrac{10 \cdot a \cdot r}{2}$

Perimeter = $10a$

Hexagon Coil r = inradius (apothem)
R = circumradius
a = side length
n = number of sides
x = interior angle
y = exterior angle
A = area
P = perimeter a = 5 mm
r = 4.33013 mm
R = 5 mm
A = 64.9519 mm$^2$
P = 30 mm
x = 120°
y = 60°

Octagon Coil r = inradius (apothem)
R = circumradius
a = side length
n = number of sides
x = interior angle
y = exterior angle
A = area
P = perimeter a = 5 mm
r = 6.03553 mm
R = 6.53281 mm
A = 120.711 mm$^2$
P = 40 mm
x = 135°
y = 45°

Decagonal Coil r = inradius (apothem)
R = circumradius
a = side length
n = number of sides
x = interior angle
y = exterior angle
A = area
P = perimeter a = 5 mm
r = 7.69421 mm
R = 8.09017 mm
A = 192.355 mm$^2$
P = 50 mm
x = 144°
y = 36°

Coil Design - Dodecagon
$a = 5$ mm
$r = 9.33013$ mm
$R = 9.65926$ mm
$A = 279.904$ mm$^2$
$P = 60$ mm
$x = 150°$
$y = 30°$
$r$ = inradius (apothem)
$R$ = circumradius
$a$ = side length
$n$ = number of sides
$x$ = interior angle
$y$ = exterior angle
$A$ = area
$P$ = perimeter
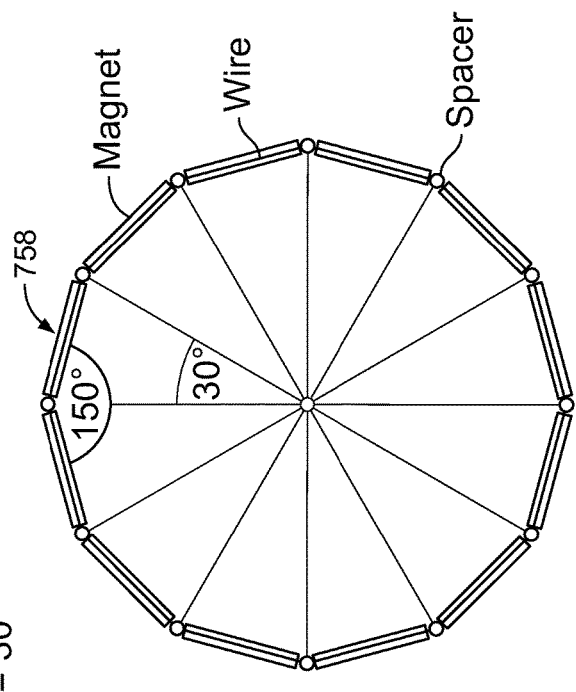
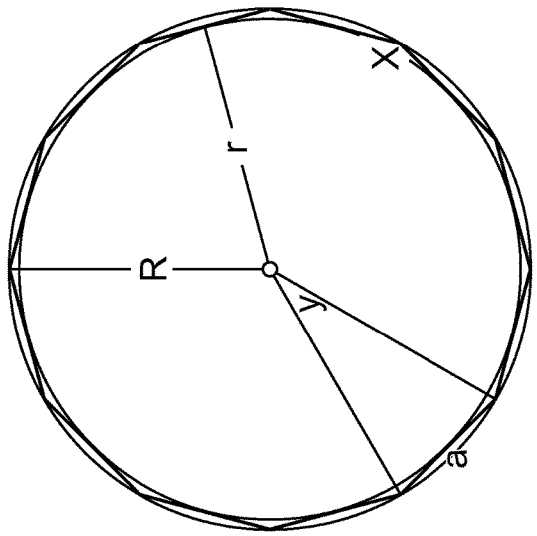
FIG. 7J Magnets between the Adjacent Coil Attracting Each Other

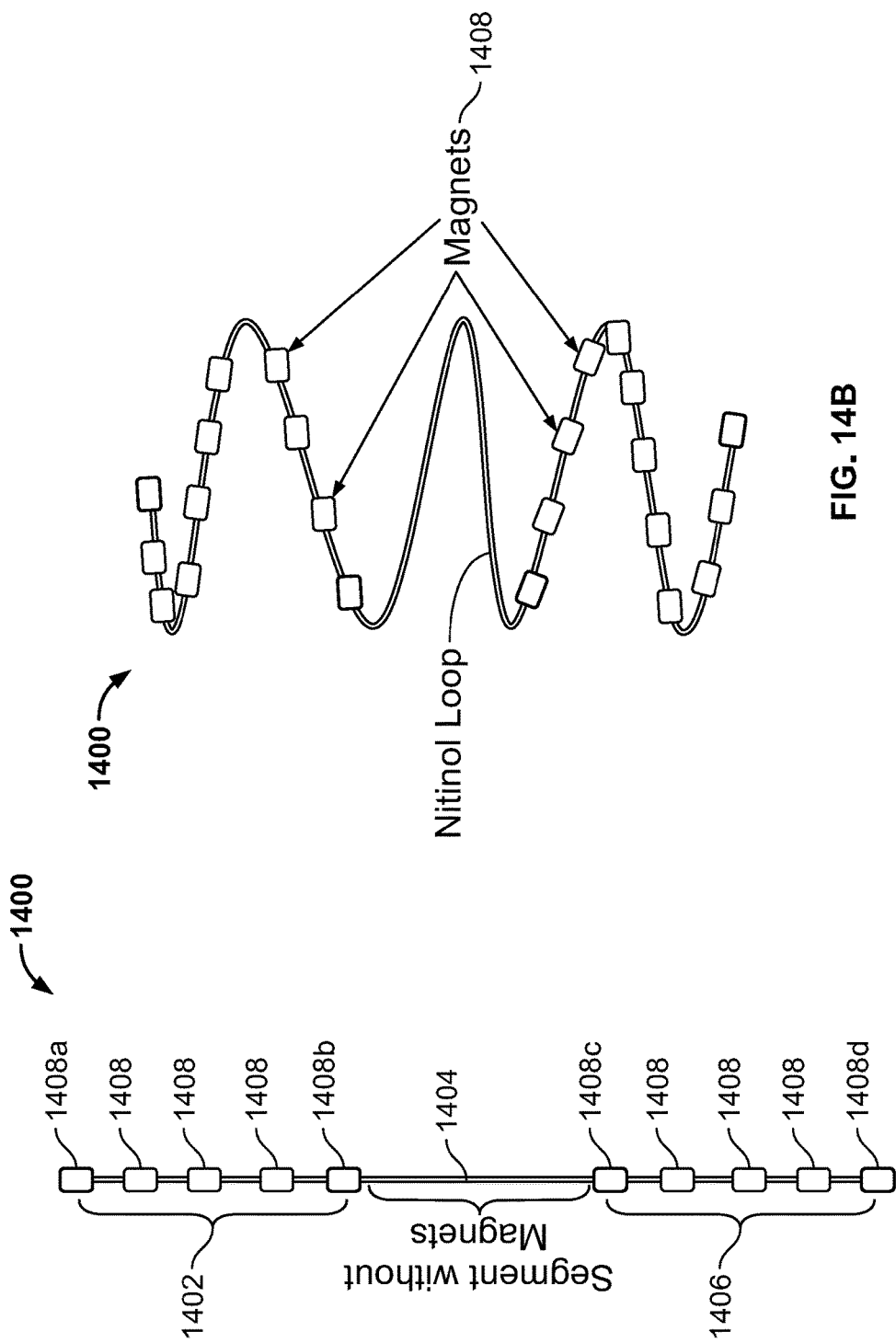

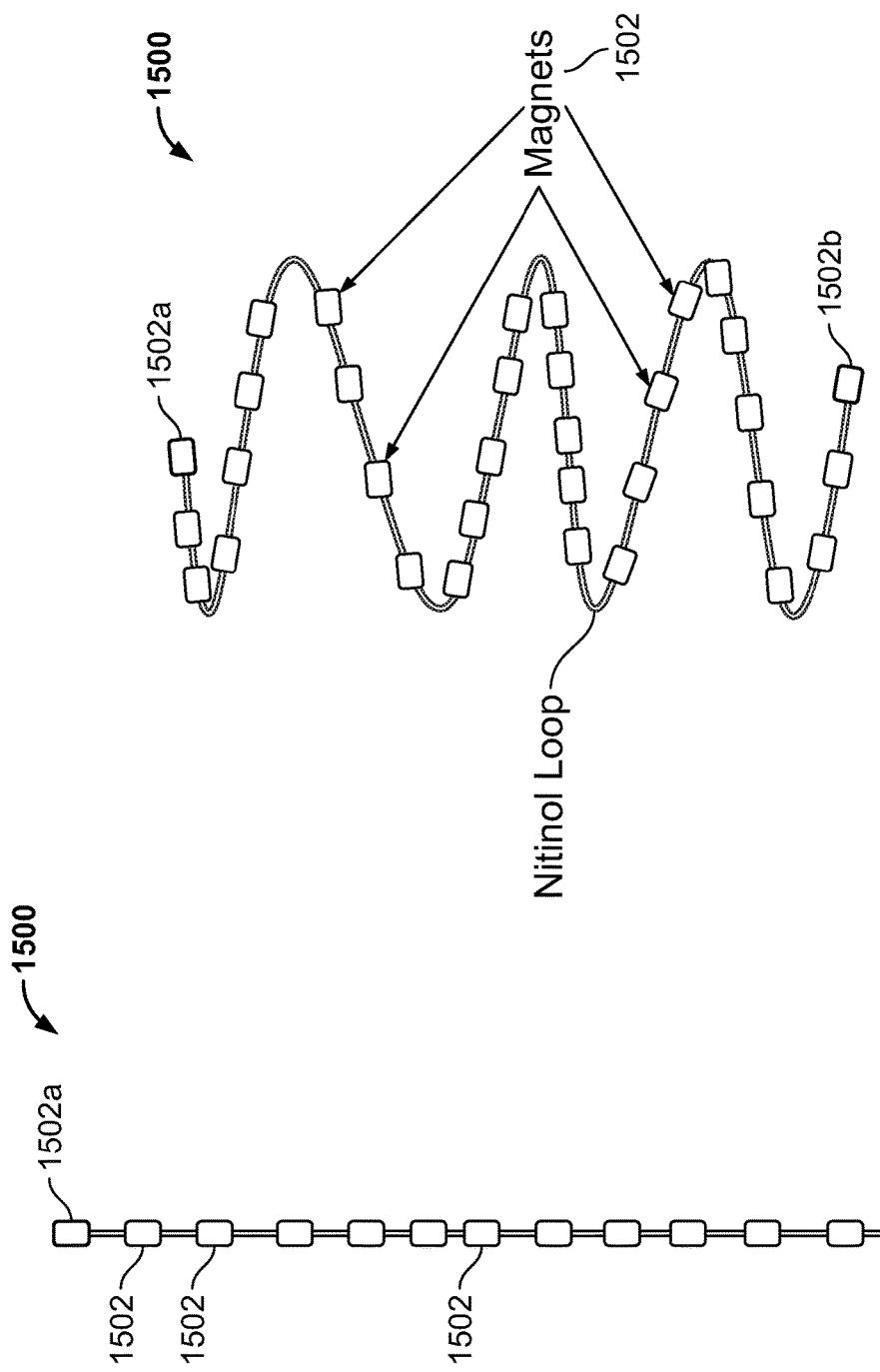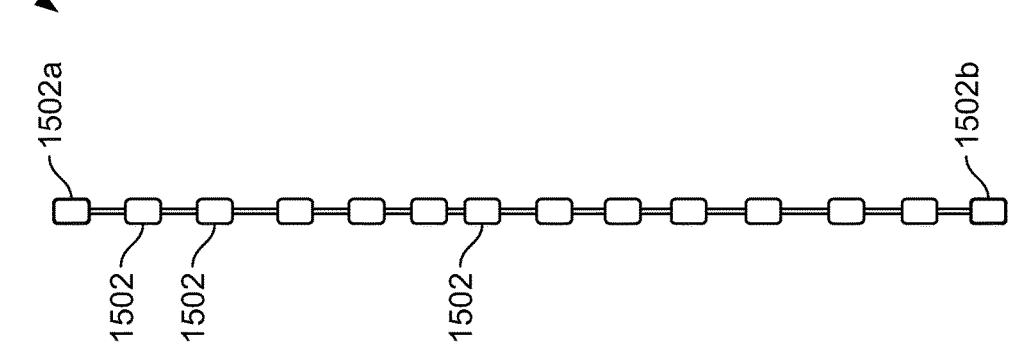

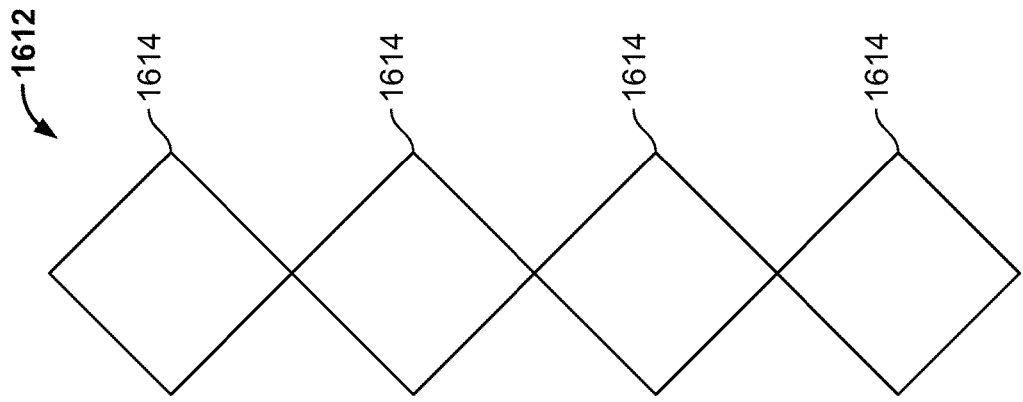
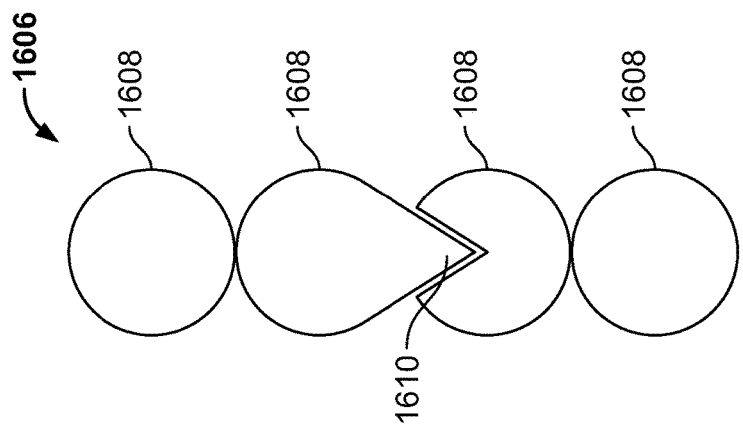
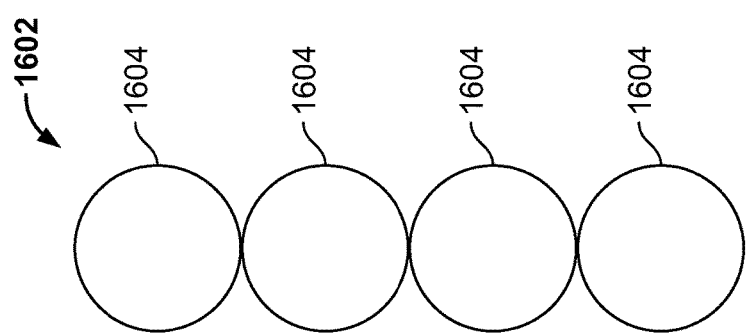
FIG. 16C
FIG. 16B
FIG. 16A

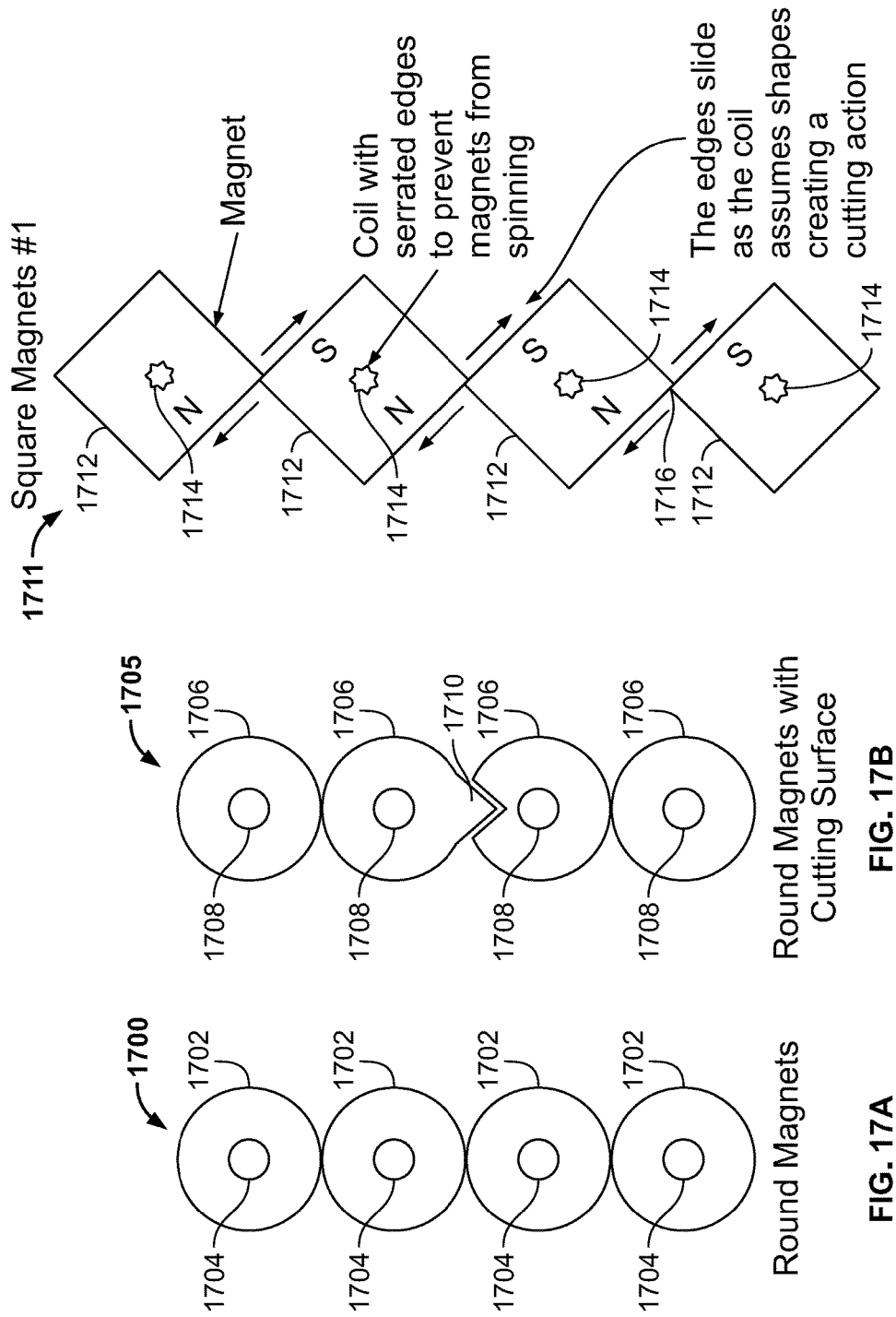

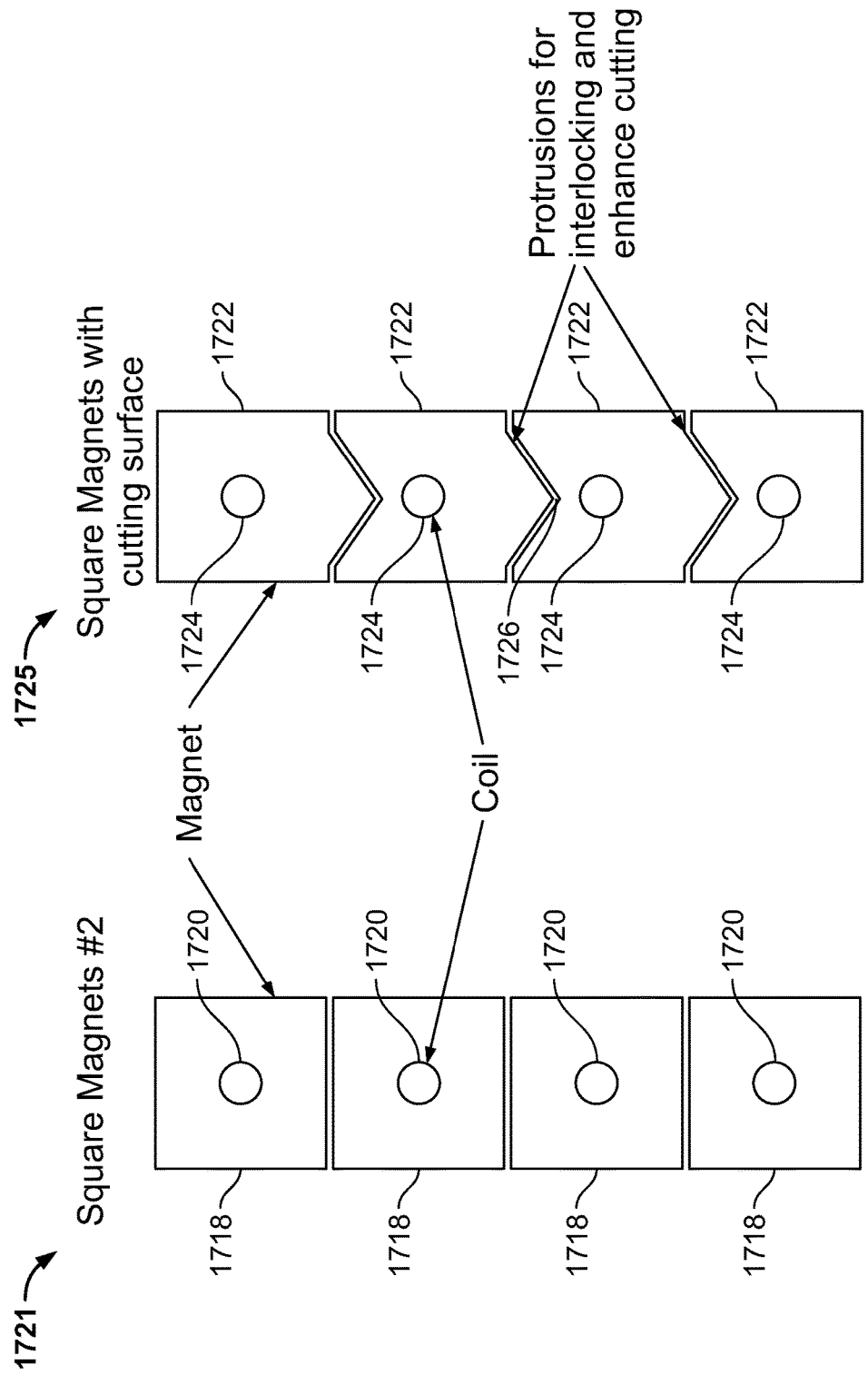

Round Magnets with Cutting Surface

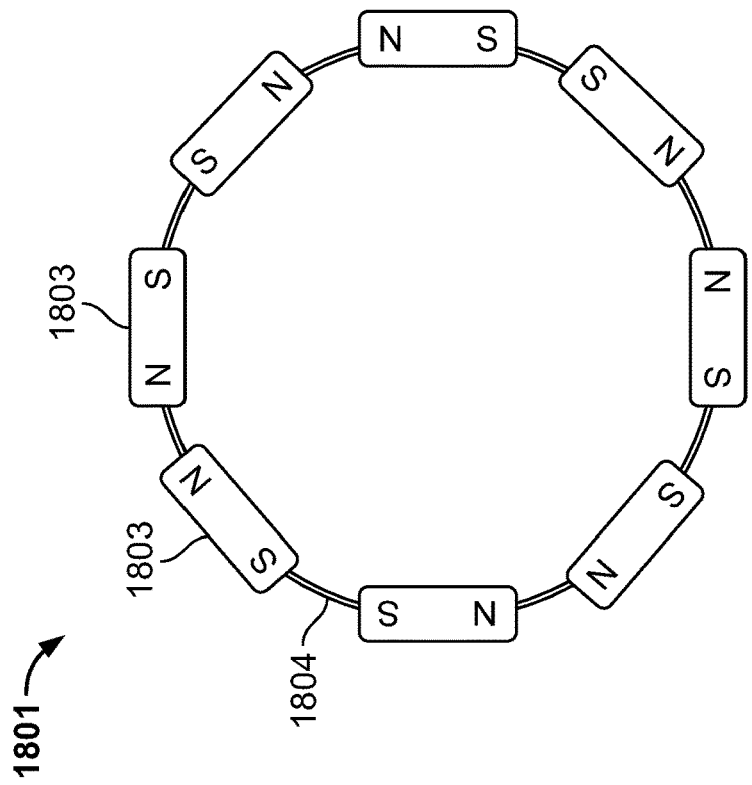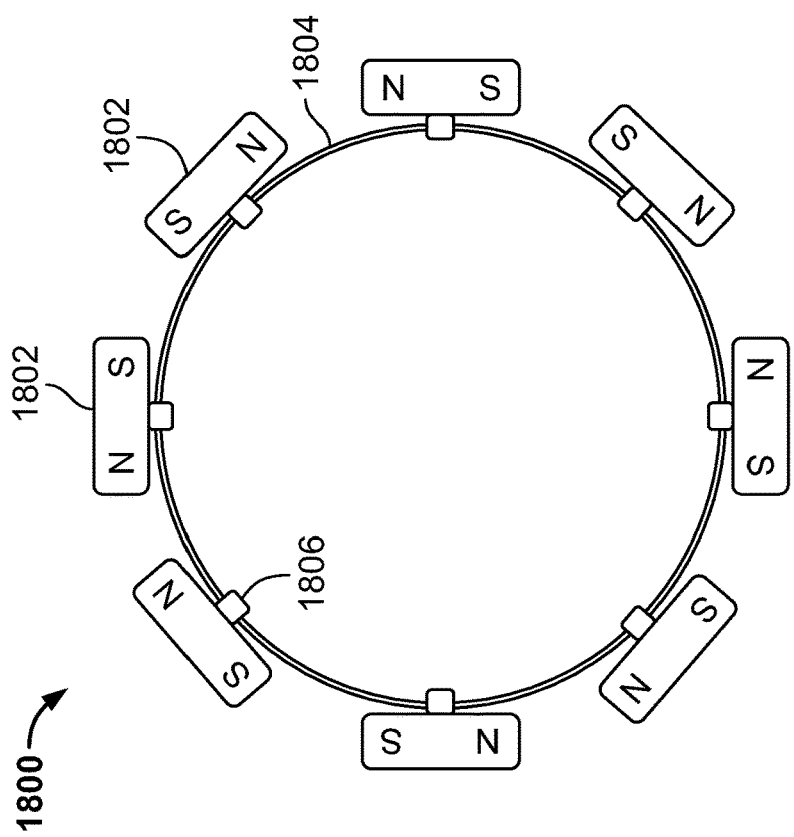

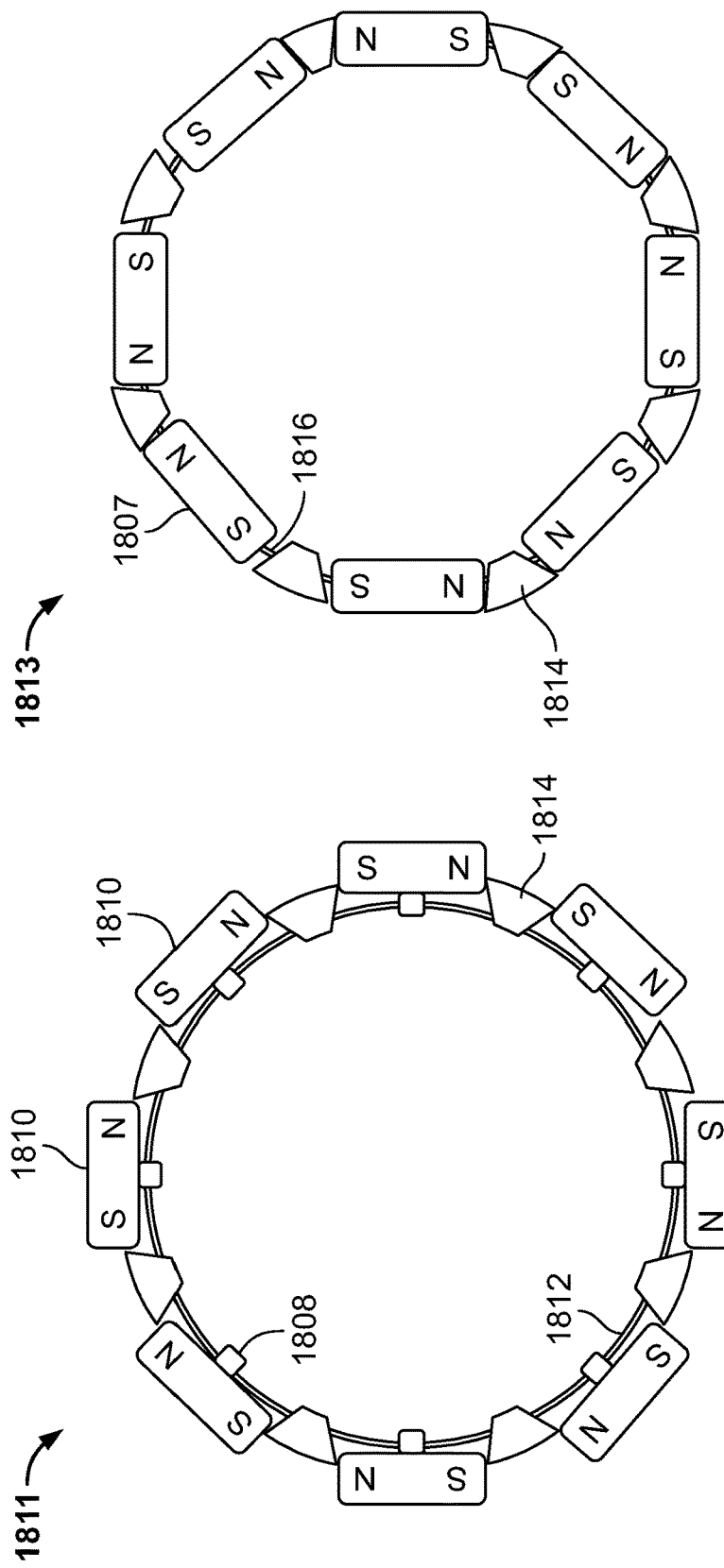

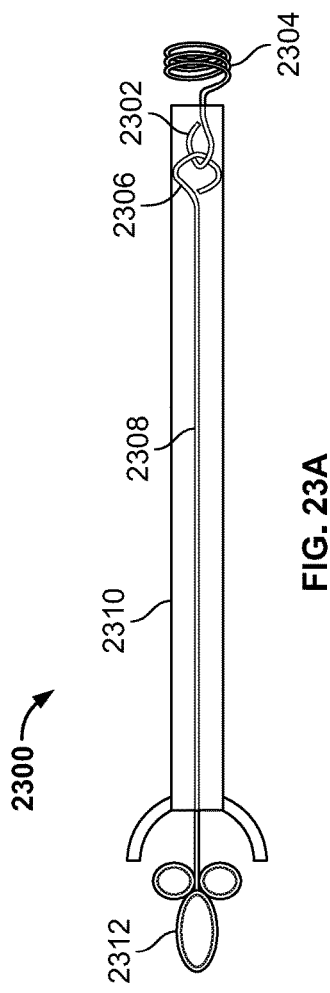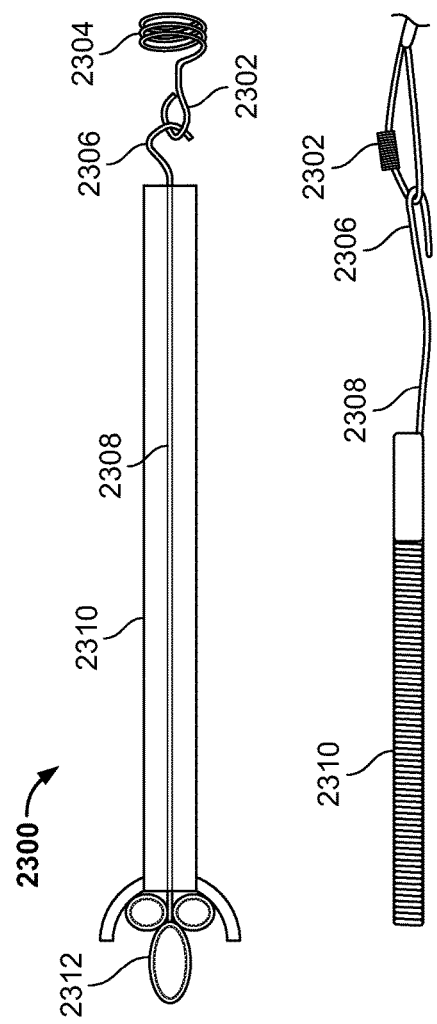
FIG. 23A
FIG. 23B

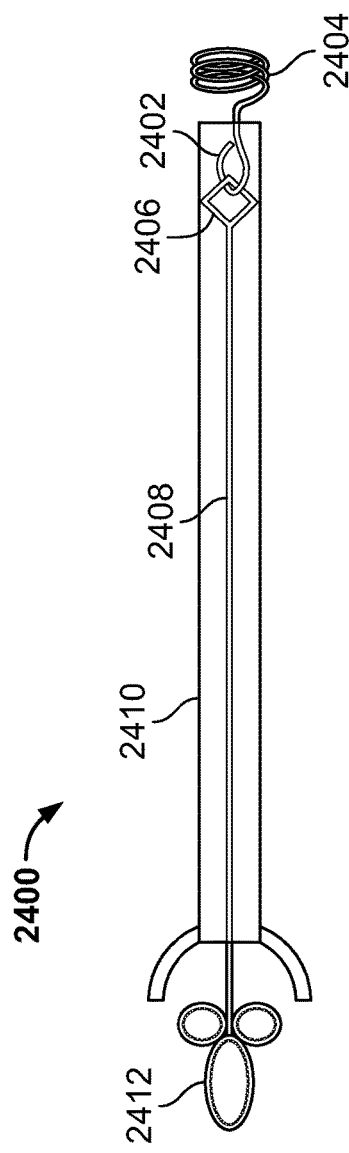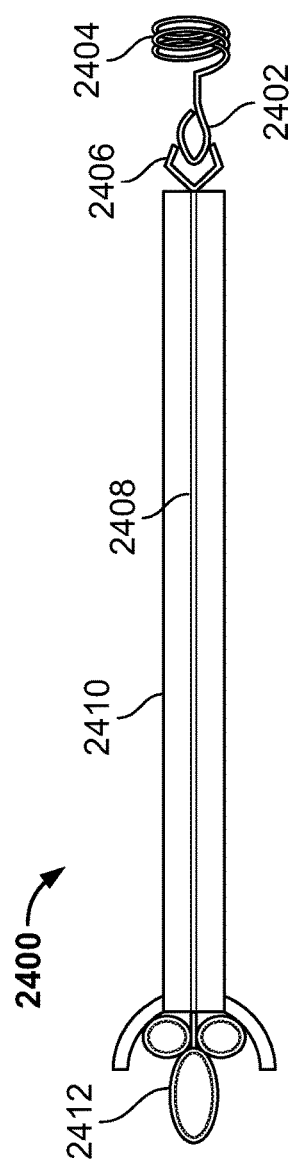
FIG. 24A
FIG. 24B

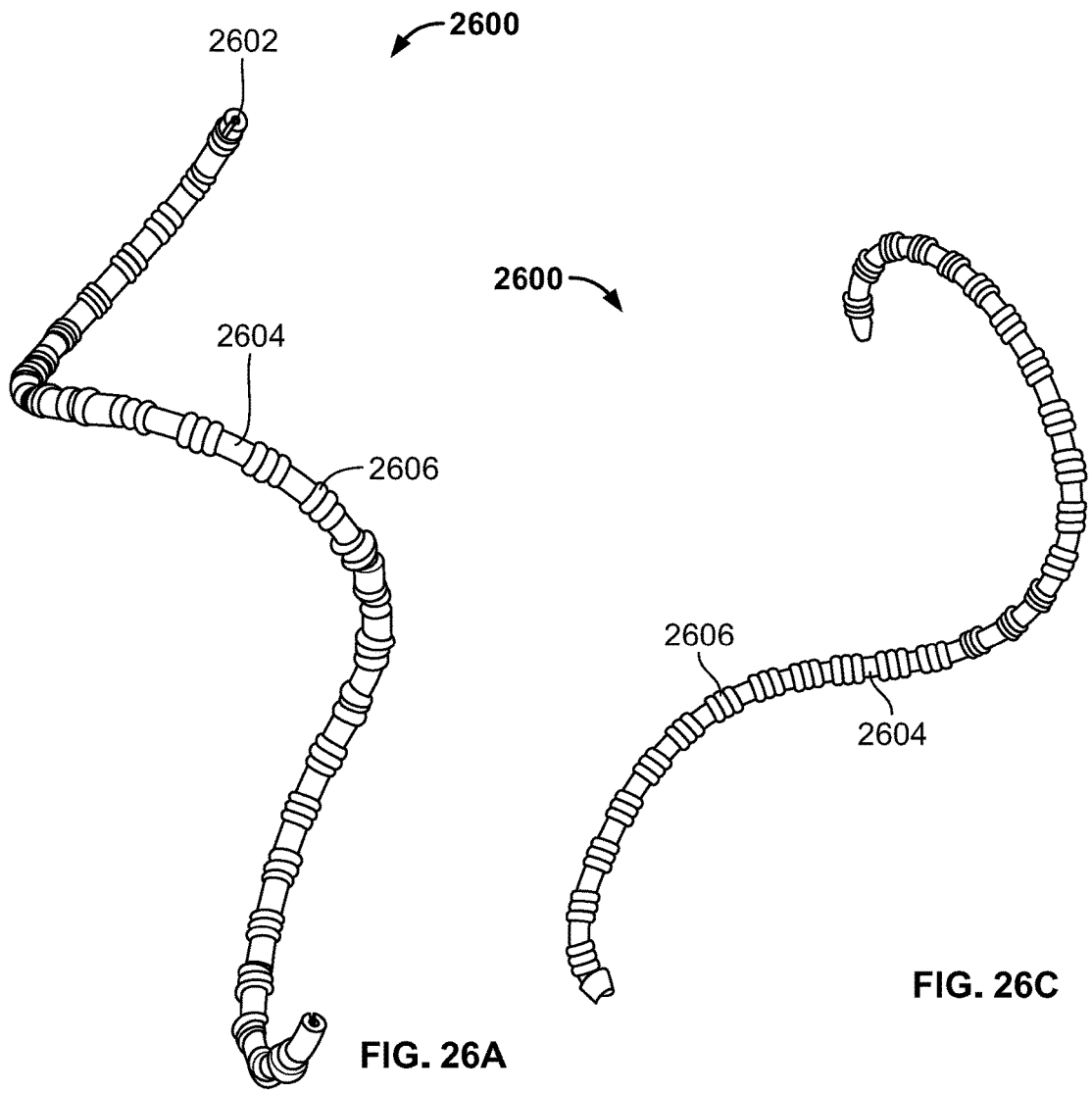
FIG. 26A
FIG. 26C
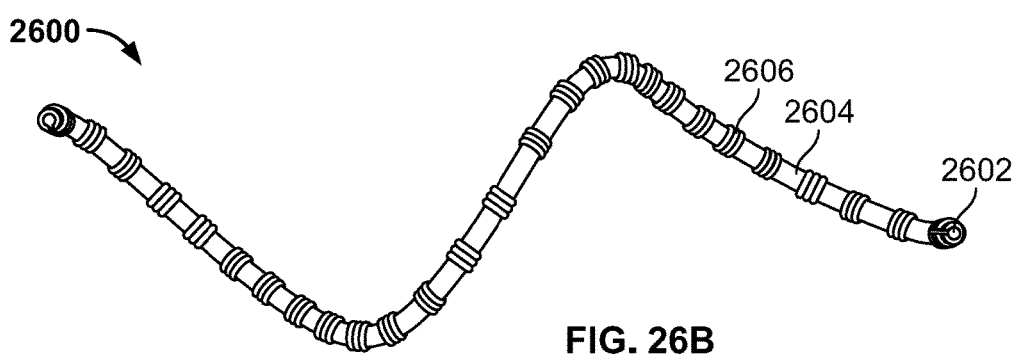
FIG. 26B

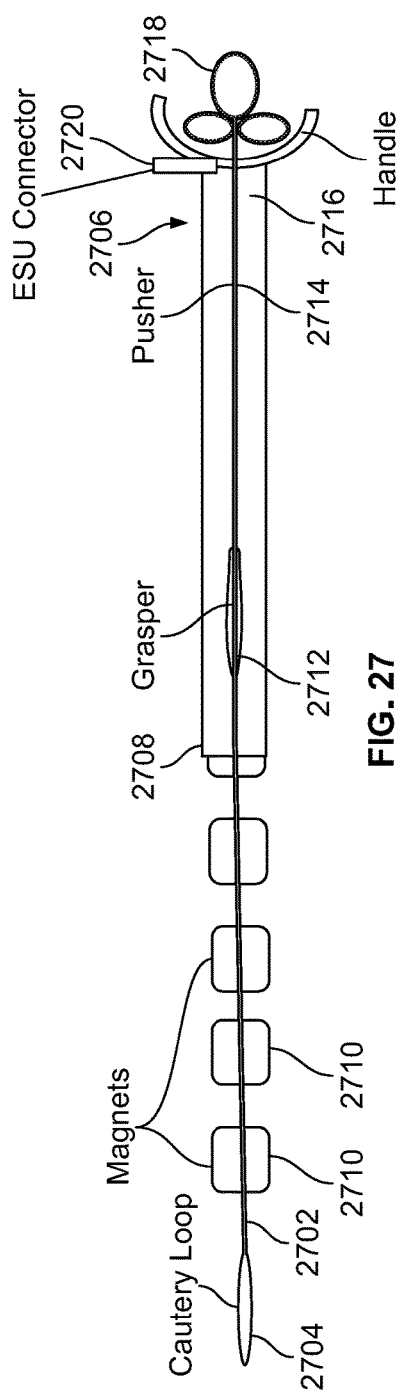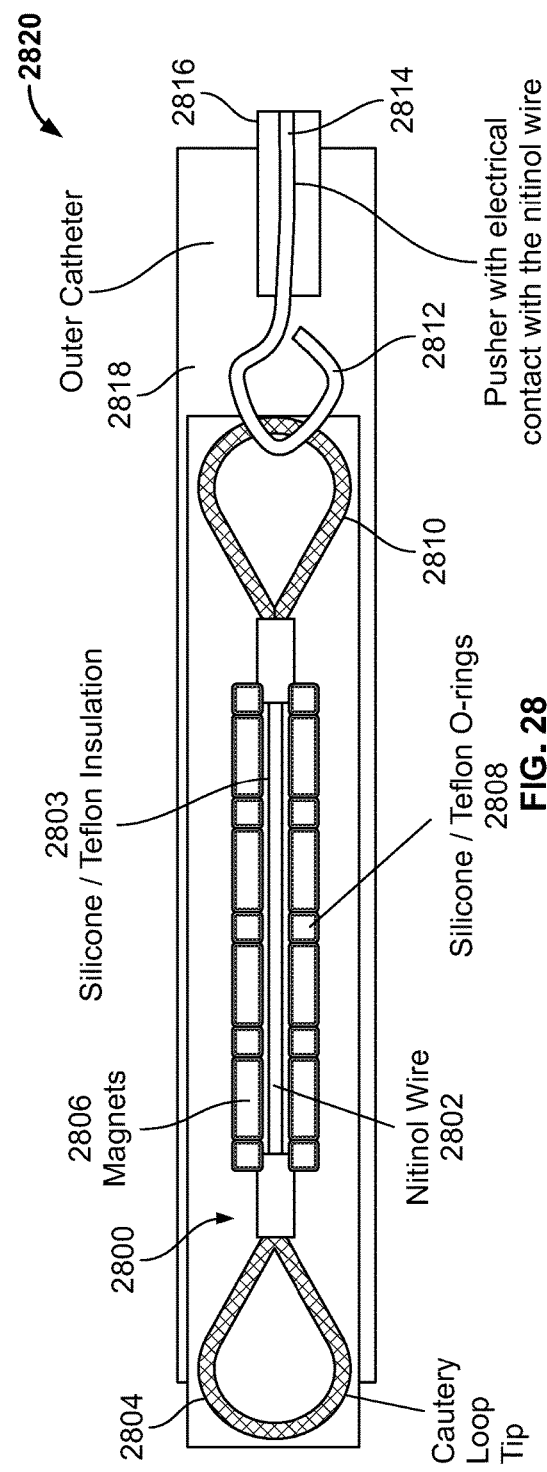

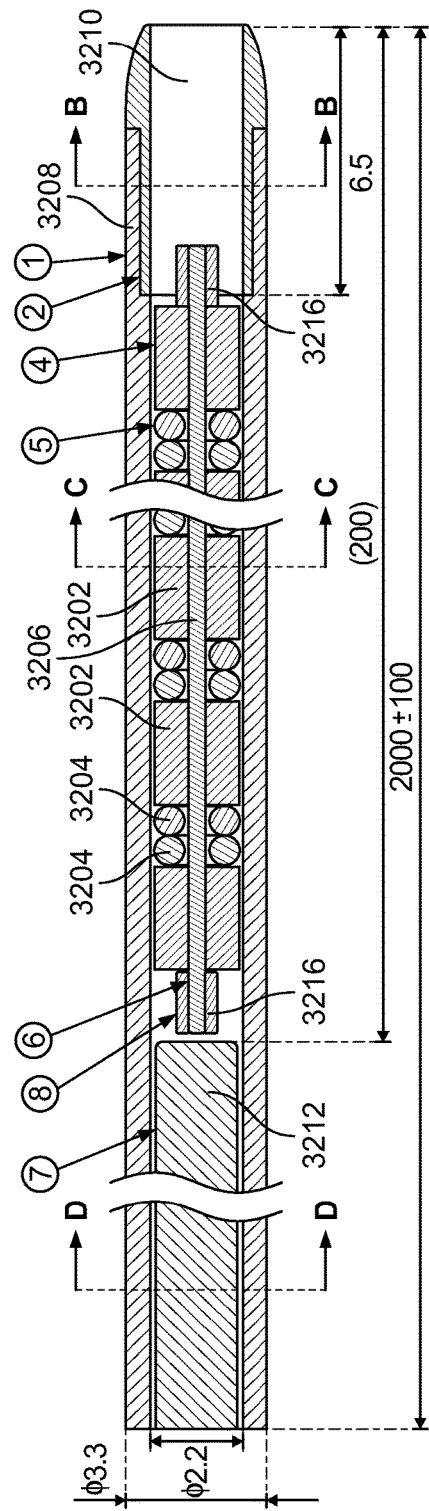
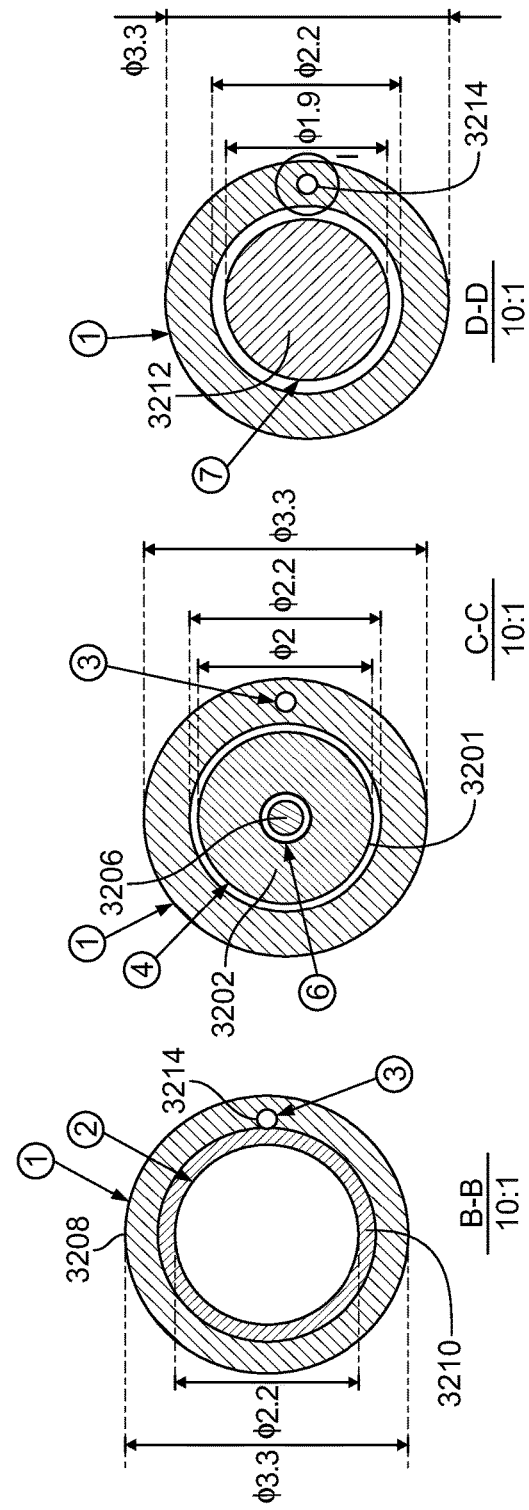
FIG. 32A
FIG. 32B
FIG. 32C
FIG. 32D

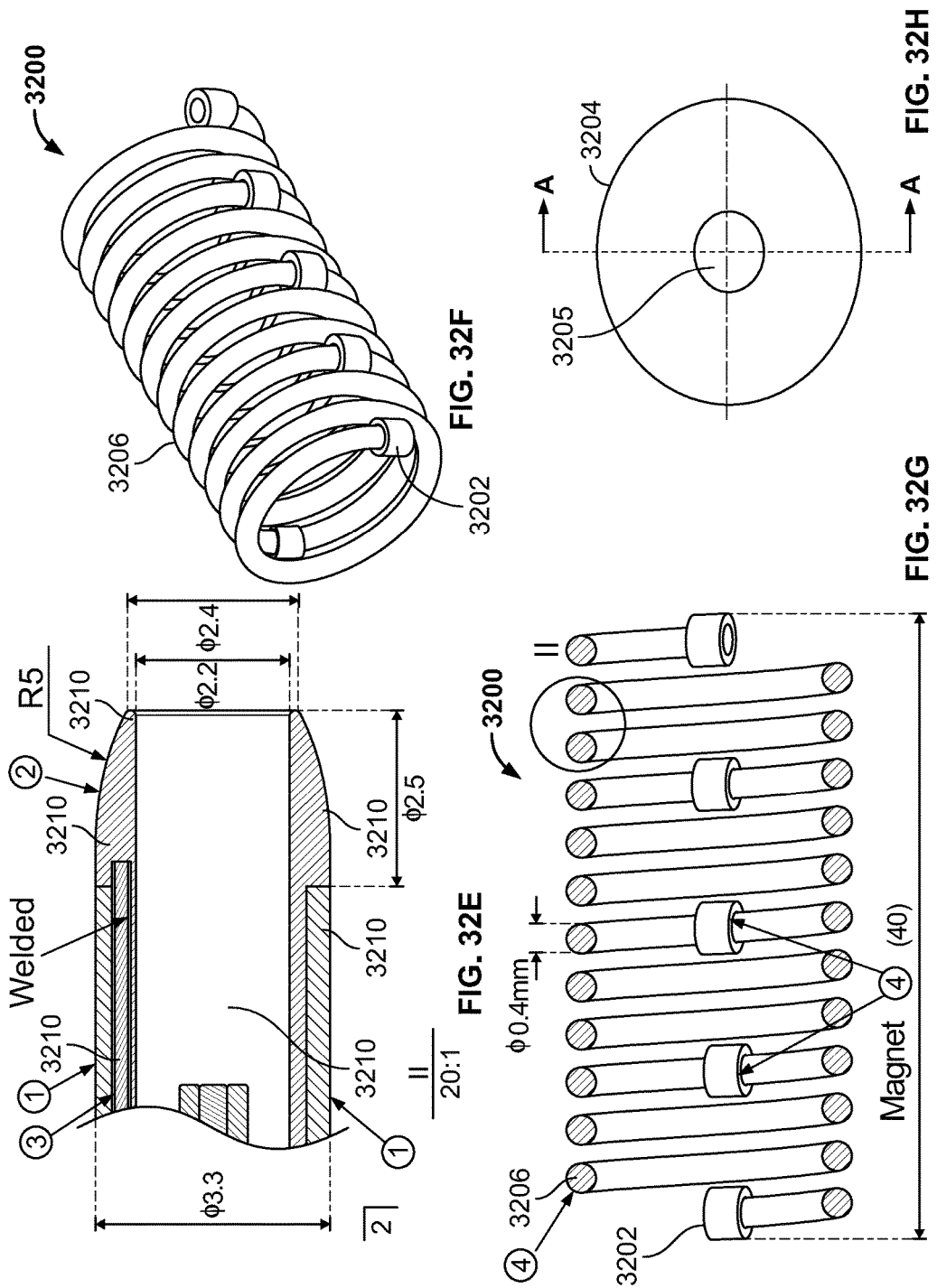

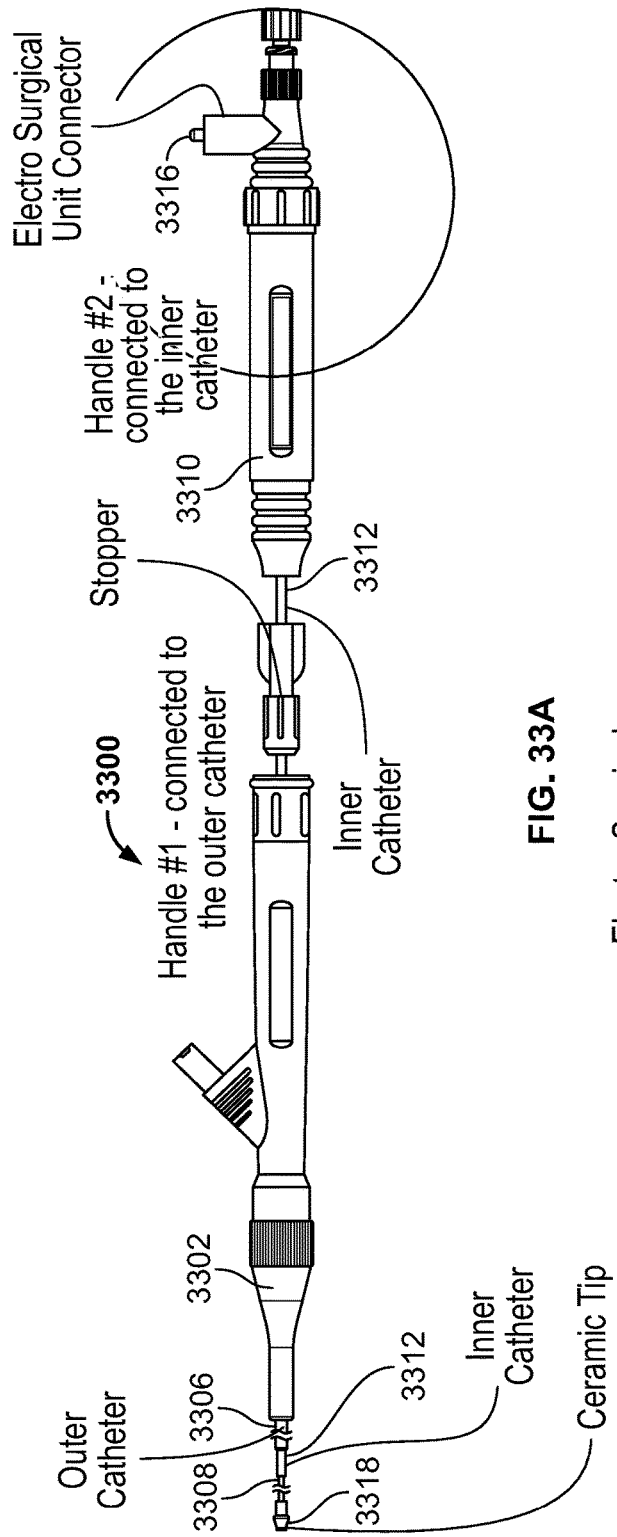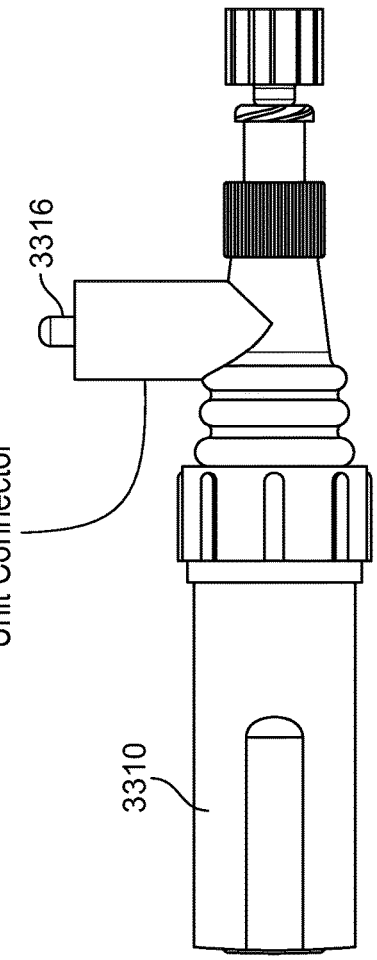
FIG. 33A
FIG. 33B

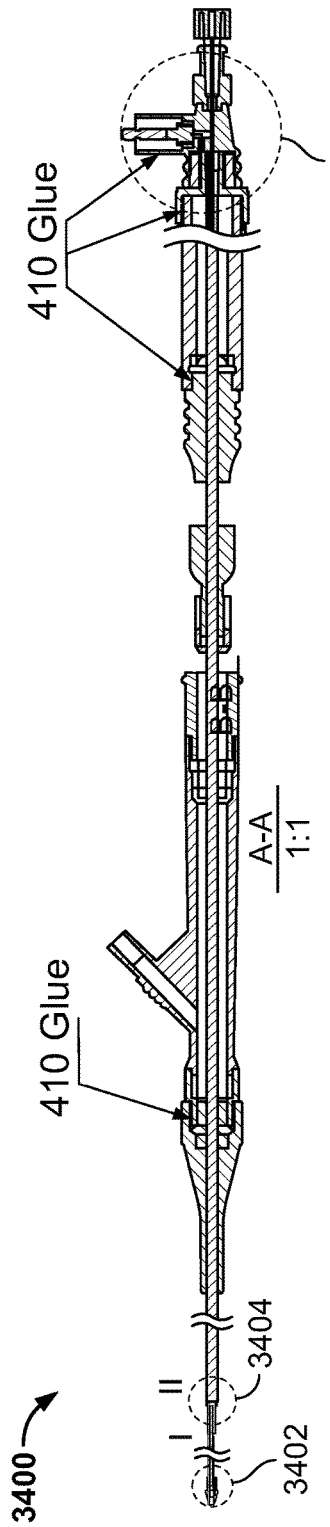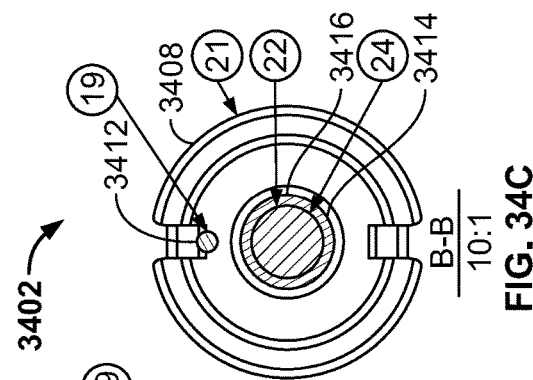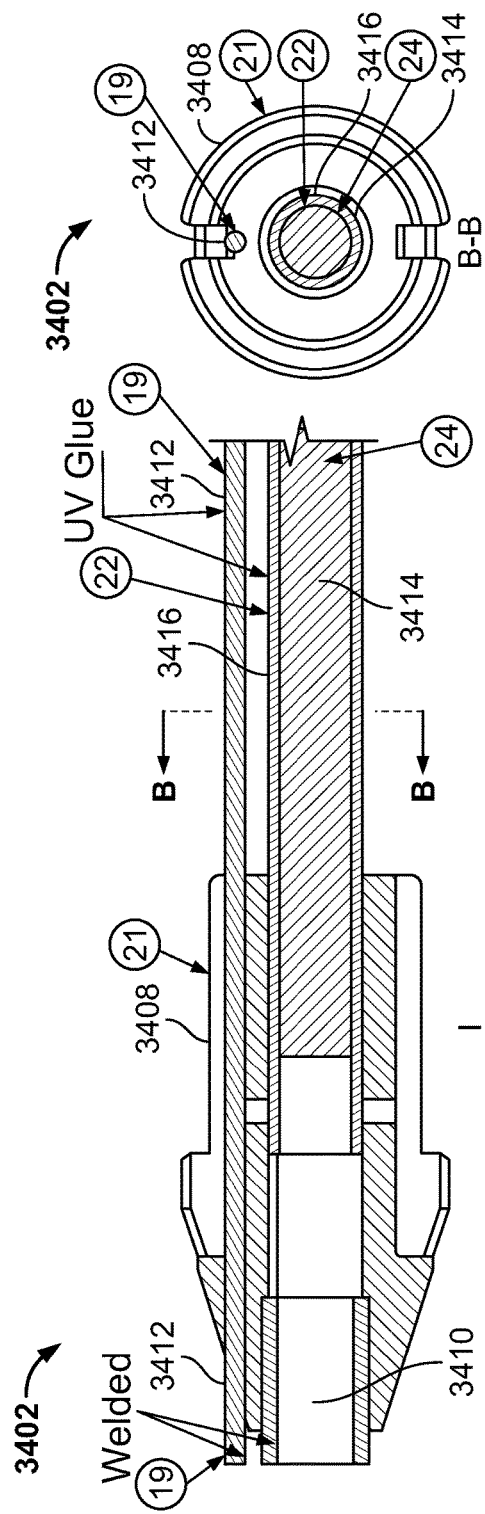
FIG. 34A
FIG. 34B
FIG. 34C

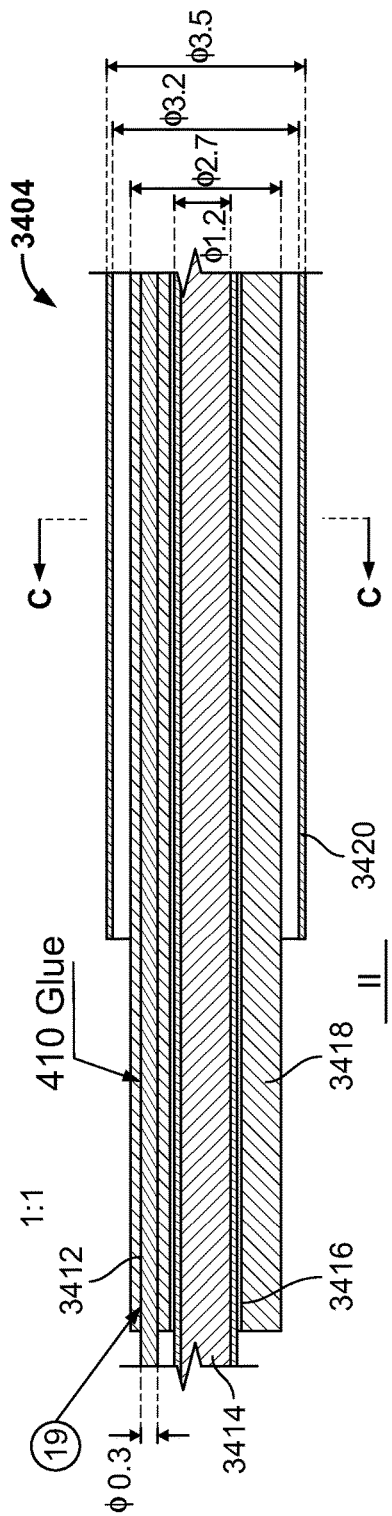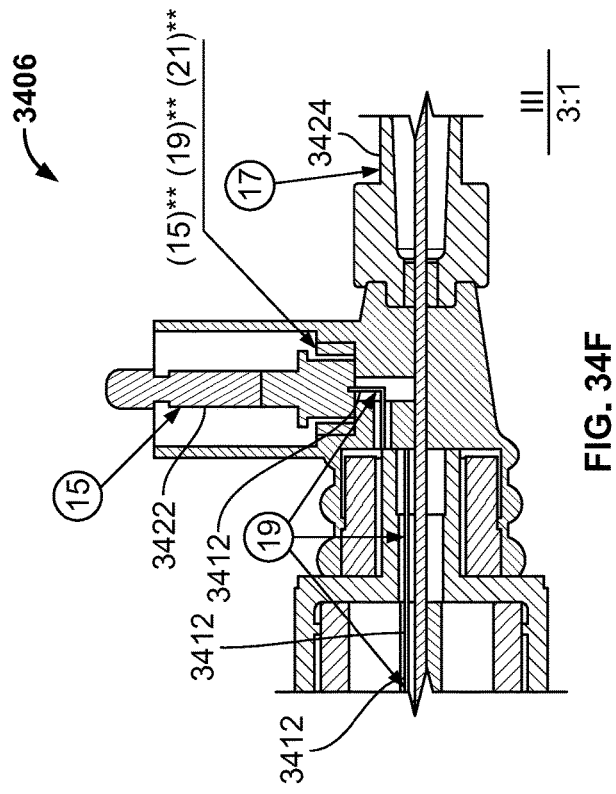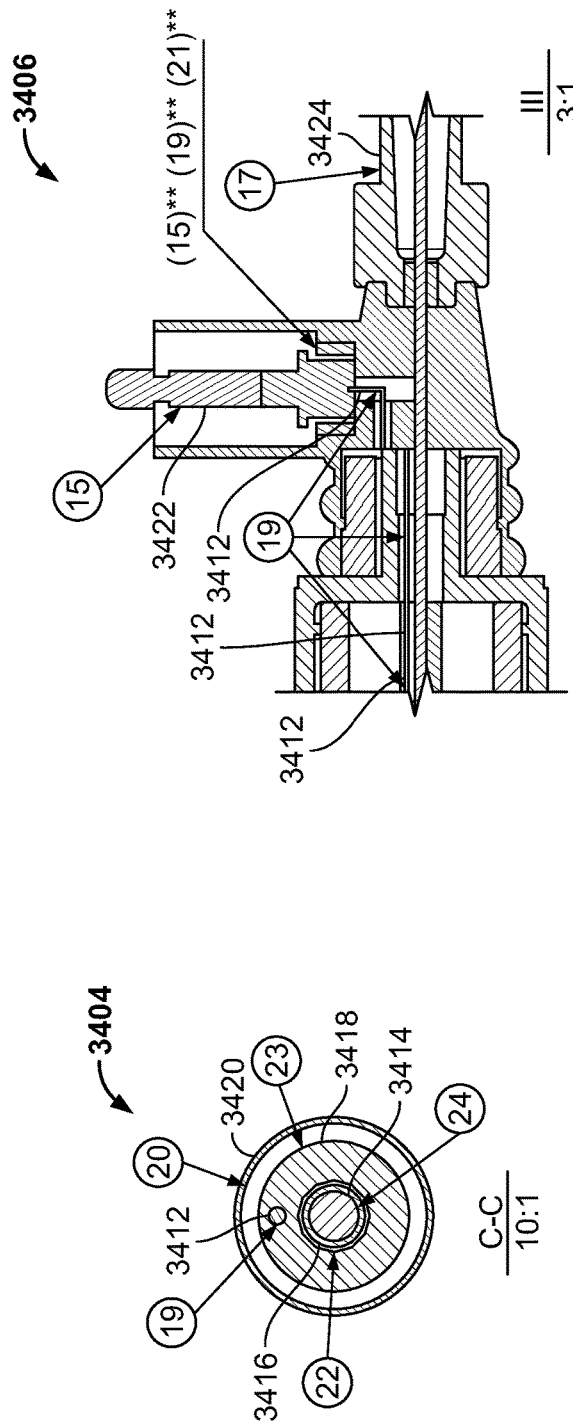
FIG. 34D
FIG. 34E
FIG. 34F

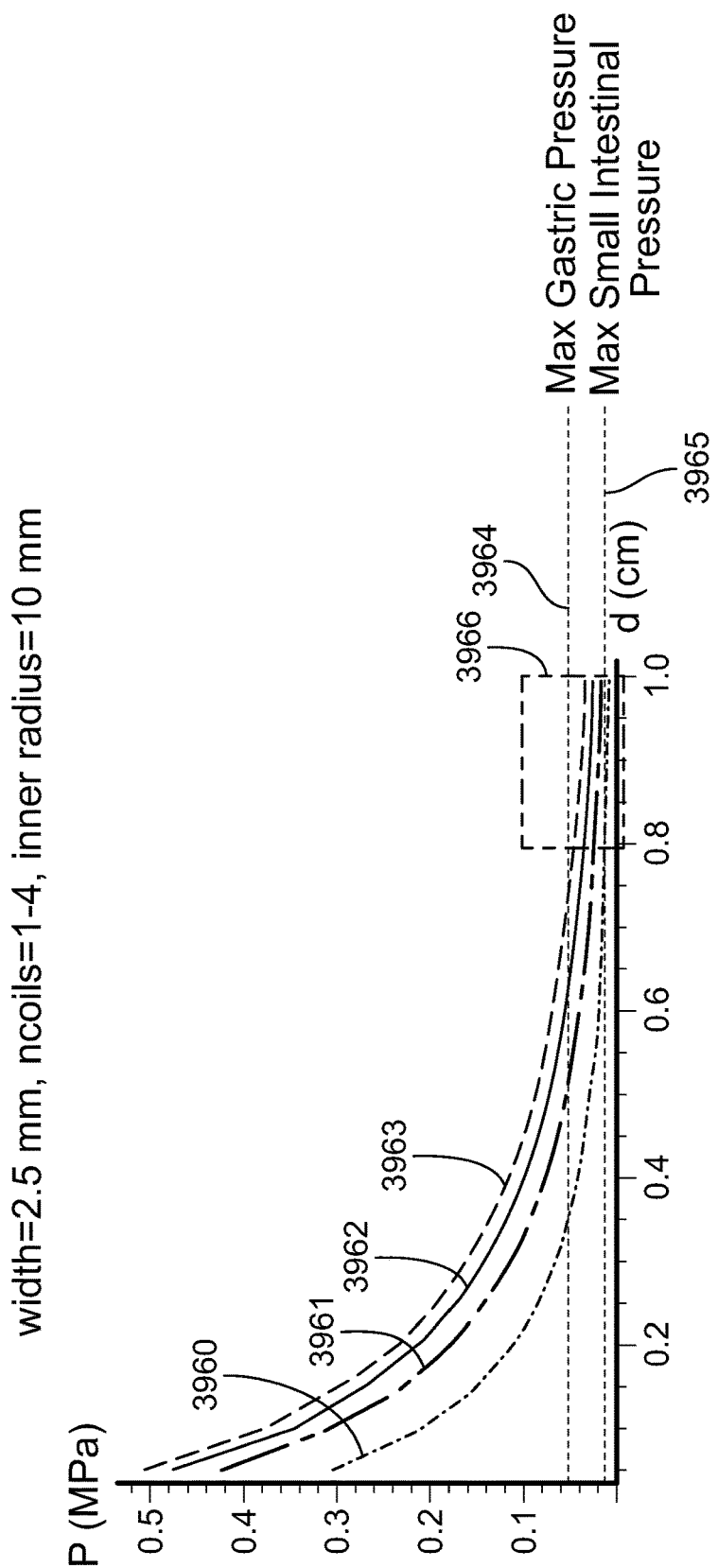

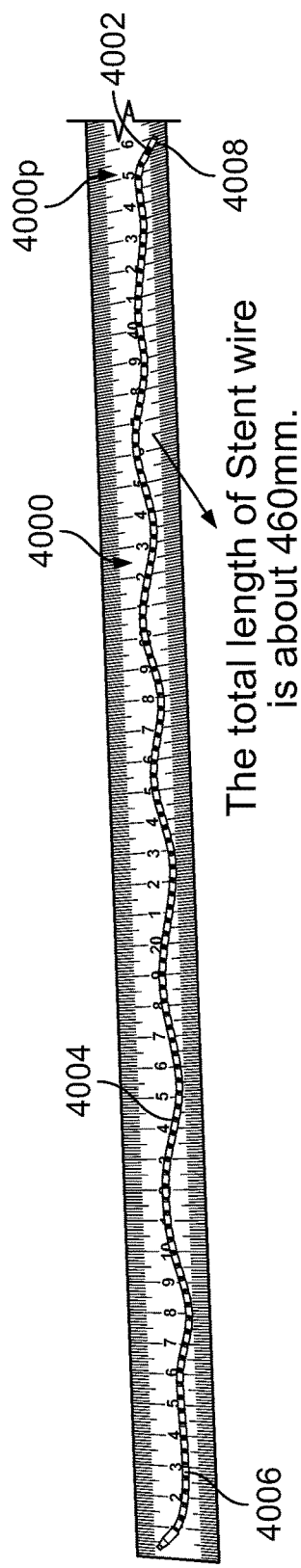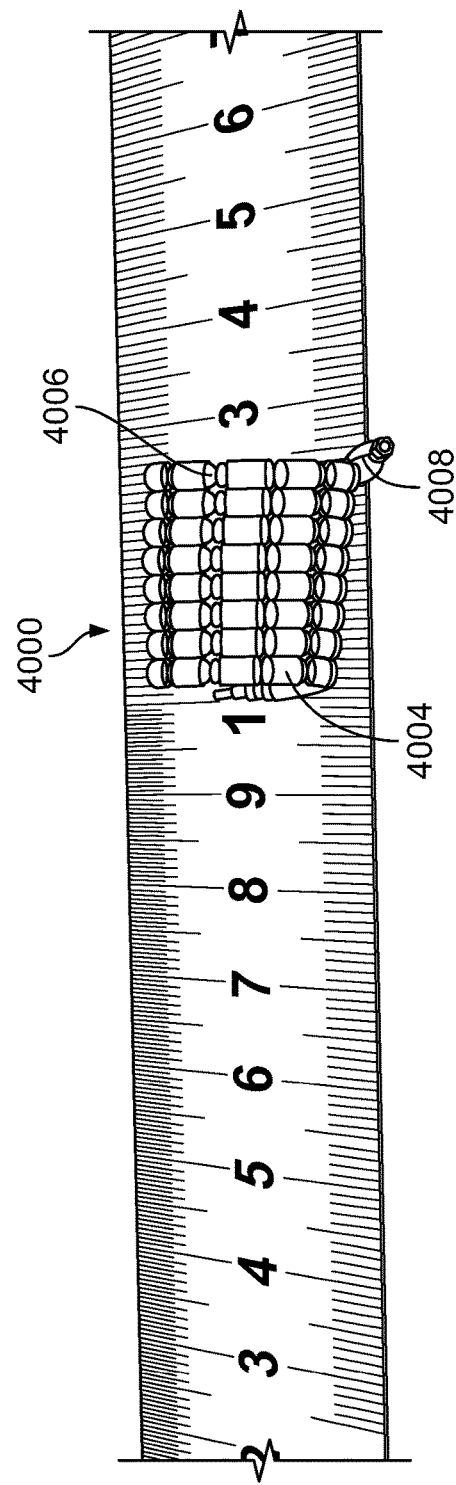
FIG. 40A
FIG. 40B

MAGNETIC ANASTOMOSIS DEVICE AND DELIVERY SYSTEM

CROSS REFERENCE

The present specification relies on U.S. Patent Provisional Application No. 62/425,951, entitled "Anastomosis Device and Delivery System", filed on Nov. 23, 2016, U.S. Patent Provisional Application No. 62/408,795, entitled "Anastomosis Device and Delivery System", filed on Oct. 16, 2016, and U.S. Patent Provisional Application No. 62/366,185, entitled "Anastomosis Device and Delivery System", filed on Jul. 25, 2016, all of which are incorporated herein by reference in their entirety.

FIELD

The present specification is directed toward formation of anastomoses in human bodies and, more specifically, to a device for the efficient creation of anastomoses and a delivery system for deploying the device at a desired location within the body.

BACKGROUND

The number of people diagnosed with gall stones is increasing all around the world. Every year, one million more Americans are diagnosed with gallstones, joining the 20 million others who already have the condition. This condition is treated by performing a cholecystectomy which involves the surgical removal of the patient's gallbladder. Commonly, the procedure is performed laparoscopically. Approximately 1.2 million laparoscopic procedures are carried out in the U.S. per year with mortality rate ranging from 0.22% to 0.4%. Sometimes the procedure leads to morbidity such as trocar/Veress needle injury, hemorrhage, post-cholecystectomy syndrome, common bile duct (CBD) injury or stricture, wound infection or abscess, ileus, gallstone spillage, and deep vein thrombosis. Such morbidity could be reduced by performing an endoscopic cholecystogastrostomy, cholecystoduodenostomy or a cholecystojejunostomy procedure allowing for drainage of the gallbladder and also for removal of the gallstones.

A pancreatic pseudocyst is a serious complication of pancreatitis and results in collection of fluid around the pancreas. The fluid in the cyst is usually pancreatic juice that has leaked out of a damaged pancreatic duct. Pancreatic pseudocysts arise after acute pancreatitis or chronic pancreatitis. In some patients, the pseudocyst may develop soon after an attack of acute pancreatitis. Often the patient can present many weeks or months after recovery from an attack of acute or chronic pancreatitis. The common symptoms that patients present are pain in the abdomen, a feeling of bloating, poor digestion of food, or complications related to the pseudocyst such as infection of the pseudocyst with a pancreatic abscess, bleeding into the pseudocyst, or blockage of parts of the intestine by the pseudocyst.

Usually, such morbidity is treatable by the laparoscopic or endoscopic formation of an anastomosis bypass which facilitates trans-gastric or trans-duodenal endoscopic drainage of symptomatic pancreatic pseudocysts greater than 6 cm in size, with greater than 70% fluid content that are adherent to the gastric or bowel wall. There are other multiple benign and malignant indications, such as cancer obstruction as well as the treatment of gastroparesis, diabetes and obesity, where gastro-enteric or entero-enteric anastomosis are desired. Most of these anastomoses are performed surgically.

Prior art devices for creating anastomoses often comprise a piercing tip which can be hazardous and cause injury to adjacent organs. The instruments often use a grasping mechanism which may be difficult to maneuver. Further, two punctures are required for the operation of some prior art instruments, which may increase the chance of leak from the puncture site from the grasper. Also, certain prior art devices are only able to appose the adjacent walls without enough pressure to damage and necrose the intervening tissue to thereby create a large enough anastomosis that will remain open for long durations to provide adequate drainage. Additional interventions would be needed to create a large opening. While stents made of materials such as a shape memory alloy (SMA), which are endoscopically inserted into a human body for creating an anastomosis and draining a pancreatic pseudocyst, are known, using these devices requires multiple interventions for the placement and removal of the stent and dealing with frequent clogging from debris in the pancreatic fluid.

In addition, prior art magnetic anastomosis methods typically require the use of two separate mating devices deployed individually in two adjacent organs. A first device is delivered to the lumen of a first organ and a second device is delivered to a lumen of a second organ. Magnetic forces pull the two devices together, capturing and compressing portions of the walls of the two organs between the devices, eventually leading to tissue necrosis and anastomosis formation. The devices usually have a single loop polygon shape deployment configuration, with no out-of-plane bending. The devices often include additional features to assist in creating the desired deployment shape, such as an exoskeleton and guide and opening/closing elements.

Hence, what is needed is an efficient and small anastomosis device which may be easily delivered within a human body without the need for graspers. What is also needed is an anastomosis device which may be deployed by a single operator using single endoscopic procedure making a single puncture in an organ wall to deliver the entire device. It is also desirable to have a piercing mechanism separate from the anastomosis device and which is not left in the body with the anastomosis device, decreasing the possibility of injury to internal organs. Further, there is need for an anastomosis device which exerts a sufficiently high enough compressive force on organ walls to create an anastomosis between the organs, yet remains a small enough profile to be delivered through an endoscope or laparoscopic or other minimally invasive tools. There is also a need for an anastomotic device that does not rely solely on the magnetic forces for correct orientation and positioning inside the human body and does not require the accurate manual positioning of two separate compressive elements. There is also a need for an anastomosis device that can connect two hollow organs without the need to advance an endoscope or laparoscope into both the organs and the device can be placed by endoscopically or laparoscopically accessing a first of the two organs while the second organ is accessed by the device delivery catheter.

SUMMARY

The present specification discloses an anastomosis device comprising a plurality of magnets coupled to a wire, said wire being comprised of a shape memory alloy (SMA), wherein said wire is adapted to change shape into a coil when deployed within a body, wherein the coil is adapted to exert a compressive force upon layers of tissue caught between loops of the coil, and wherein the plurality of magnets are adapted to provide a compressive force to adjacent loops of the coil, thereby further causing the coil to cut through the layers of tissue and create an anastomosis; wherein at least one end of the wire comprises a connection means for connecting with a delivery device.

Optionally, a diameter of the wire ranges between 0.1 mm to 10 mm and a length of the wire ranges from 1 cm to 250 cm.

Optionally, the connection means is one of a nut and a screw.

Optionally, a length of the wire is in a range of 440 to 460 mm.

Optionally, the SMA wire is a Nitinol wire.

Optionally, the magnets are positioned such that repulsive forces between adjacent magnets on the same coil cause said adjacent magnets to maintain a predefined distance between said adjacent magnets.

Optionally, the magnets are rare earth magnets covered with at least one of gold, nickel and titanium.

Optionally, when in a coiled state, a maximum cross sectional diameter of the SMA wire ranges from 5 mm to 50 mm.

Optionally, each of the magnets have a maximum cross sectional length ranging from 0.2 mm to 7 mm and/or a pull force ranging from 0.1 lb. to 4 lb.

Optionally, the compressive force ranges from 0.1 to 100 N and an associated pressure applied to said layers of tissue ranges between 0.15 psi-145 psi (0.001 and 1 MPa);

Optionally, a pull force between any two of the consecutively placed magnets on the wire is approximately 2.318N.

Optionally, a length, inner diameter and outer diameter of each of the magnets is 3 mm, 0.66 mm and 3 mm respectively.

Optionally, a shape of the anastomosis formed by using the SMA wire and magnets is determined by the shape of the coiled SMA wire.

Optionally, at least 50% of the adjacent magnets on each loop of the coil are arranged with like poles facing each other, thereby creating a repulsive force between two adjacent magnets in a single loop of the coil.

Optionally, said two adjacent magnets on the single loop of the coil are separated by a distance greater than a length of each of the two adjacent magnets.

Optionally, said two adjacent magnets on the single loop of the coil are separated by a distance less than a length of each of the two adjacent magnets.

The present specification also discloses a delivery device for deploying an anastomosis device at a predefined site within a body, the anastomosis device comprising a plurality of magnets coupled to a shape memory alloy (SMA) wire capable of changing shape from a non-coiled wire into a coil when deployed within a body, the delivery device comprising: a delivery catheter for pushing the device in through a channel of an endoscope and out at the site through a tip of an endoscope, wherein the delivery catheter comprises a mechanism for coupling with the anastomosis device and wherein the mechanism is adapted to open up to release the anastomosis device at the deployment site.

Optionally, the delivery device further includes a non-cautery needle comprising a lumen for carrying the anastomosis device, the needle being delivered at the site via an endoscope, wherein the needle is adapted to pierce a tissue for deploying the anastomosis device therein.

Optionally, the delivery device further includes a cautery needle, wherein the cautery needle is adapted to be delivered to the site with the anastomosis device via the channel of an endoscope and wherein the needle is adapted to pierce a tissue for entering the lumen of such tissue and deploying the anastomosis device therein.

Optionally, the non-coiled wire is substantially planar.

Optionally, the non-coiled wire comprises waves.

The present specification also discloses a method of creating an anastomosis by using an anastomosis device comprising a plurality of magnets coupled with a shape memory alloy (SMA) wire adapted to change shape from a non-coiled wire into a coil when deployed within a body, wherein the coil is adapted to exert a compressive force upon layers of tissue caught between loops of the coil, wherein the plurality of magnets are adapted to enhance a compressive force applied by adjacent loops of the coil, and wherein the compressive force causes one or more of the coil and magnets to cut through the layers of tissue, thereby creating an anastomosis, the method comprising: identifying a deployment site having adjacent walls of two organs requiring an anastomosis; delivering said SMA wire coupled with magnets at the identified site; piercing the adjacent organ walls at the deployment site and deploying the SMA wire therein; compressing adjacent organ wall tissue caught between loops of the coiled up wire, wherein body heat causes a coiling of the SMA wire and wherein compressive forces between the plurality of magnets cause said coiling to apply greater pressure to the tissue caught between loops of the coiled up wire; cutting through the adjacent tissue caught between loops of the coiled up wire forming an anastomosis; and removing the SMA coil after formation of a stable anastomosis.

Optionally, the magnets causing said compressive force are positioned in adjacent loops of the SMA coil.

Optionally, the compressive force between the coils increase over time.

Optionally, at least two magnets of said plurality of magnets are positioned on at least one loop of the coil and wherein said at least two magnets are arranged with opposite poles facing each other, thereby creating an attractive force between the at least two magnets on the at least one loop of the coil, and wherein said anastomosis device comprises a non-ferromagnetic spacer positioned on the at least one loop between the at least two magnets, thereby preventing the at least two magnets from attaching to each other.

Optionally, said non-ferromagnetic space has a length and wherein said length is adapted to keep a force of attraction between the at least two magnets below a bending force of the coil, thus not preventing the coil to change from a pre-coil shape to a coil shape after deployment.

Optionally, the time period required to create the anastomosis ranges between one day and fourteen days.

The present specification also discloses a method of creating an anastomosis between two adjacent body tissues comprising: positioning an anastomosis device, via a catheter, within a body cavity proximate at least one of said adjacent body tissues, wherein the anastomosis device comprises: a wire, wherein said wire has a first state and a second state, wherein, in said first state, the wire has a substantially linear form, wherein, in said second state, the wire forms a coil having at least a first loop and a second loop, and wherein said wire is adapted to transform from the first state to the second state when exposed to a temperature greater than a threshold value; and a plurality of magnets positioned over said wire, wherein each of said plurality of magnets has a lumen through which said wire extends, wherein, in each of said first loop and second loop, a portion of adjacent magnets of said plurality of magnets are configured to not attach to each other, and wherein a portion of said plurality of magnets in the first loop are configured to attract a portion of said plurality of magnets in the second loop; piercing the adjacent body tissues and positioning the anastomosis device through a hole created by said piercing; and releasing the anastomosis device such that, when it transforms from the first state to the second state, tissue between the two adjacent body tissues is caught between the first loop and the second loop, thereby being compressed and resulting in an anastomosis.

Optionally, the anastomosis device further comprises non-ferromagnetic spacers positioned between adjacent magnets of said plurality of magnets. Optionally, each of said non-ferromagnetic spacers has a length sufficient to keep a force of attraction between opposite poles of the adjacent magnets below a bending force of the coil. Optionally, when in the second state, a maximum cross sectional diameter of the first loop and the second loop ranges from 5 mm to 50 mm. Optionally, each of the plurality of magnets has a maximum cross sectional length or diameter ranging from 0.2 mm to 7 mm and a pull force ranging from 0.01 lb. to 4 lb (0.04-17.8 N). Optionally, in the first loop and in the second loop, at least 50% of the adjacent magnets of said plurality of magnets are arranged with like poles facing each other, thereby creating a repulsive force between said adjacent magnets in the first loop and a repulsive force between said adjacent magnets in the second loop of the coil.

Optionally, at least one end of the wire is connected to a delivery device. Optionally, the wire comprises a shape memory alloy. Optionally, the threshold value is 20 degrees Celsius. Optionally, the coil has at least one loop proximate to the first loop and at least one loop distal to the second loop. Optionally, each of the plurality of magnets is cylindrically shaped and is a rare earth magnet covered with at least one of gold, nickel, Teflon, parylene, copper, zinc, silicone, epoxy and titanium. Optionally, the method further comprises, before releasing the anastomosis device, exposing the anastomosis device to heat by passing electrical current through the anastomosis device to assist said transformation from the first state to the second state. Optionally, a diameter of the wire ranges between 0.1 mm to 10 mm and a length of the wire ranges from 1 cm to 250 cm. Optionally, a diameter of the wire ranges between 0.1 mm and 6 mm and has a maximum strain of less than 10% in the first state and wherein a maximum cross sectional dimension of the first loop and second loop ranges from 5 mm to 60 mm in the second state.

Optionally, the adjacent body tissues comprise a gall bladder and a duodenum and a maximum diameter of the first loop and the second loop is less than or equal to 30 mm. Optionally, the adjacent body tissues comprise a pancreatic or a biliary tissue and a maximum diameter of the first loop and the second loop is greater than or equal to 5 mm. Optionally, a diameter of the wire is less than 0.5 mm and a maximum cross sectional dimension of the first loop and second loop is less than or equal to 15 mm. Optionally, a diameter of the wire ranges from 0.5 mm to 1.0 mm and a maximum cross sectional dimension of the first loop and second loop ranges from 10 mm to 25 mm. Optionally, a diameter of the wire is greater than 1 mm and a maximum cross sectional dimension of the first loop and second loop is greater than 20 mm. Optionally, the first loop and the second loop have at least one of a circular shape, polygonal shape, and a star shape with four or more points. Optionally, a portion of the adjacent magnets of said plurality of magnets on the same loop are configured to repel each other.

Optionally, the wire is heated by passage of electrical current to assist in formation of the coil, wherein an increase in the temperature of the wire causes the wire to assume a coil shape as a result of its shape memory properties.

Optionally, the transition temperature of the wire is greater than 37° C. Optionally, the applied pressure is greater than or equal to 0.3 psi at two or more points that are on opposite sides of at least one of the first loop and the second loop.

The present specification also discloses a method of creating an anastomosis between two adjacent body tissues comprising: positioning an anastomosis device within a body cavity proximate at least one of said adjacent body tissues, wherein the anastomosis device comprises: a wire, wherein said wire has a first state and a second state, wherein, in said first state, the wire has a substantially linear form, wherein, in said second state, the wire forms a coil having at least a first loop and a second loop, and wherein said wire is adapted to transform from the first state to the second state when exposed to a temperature greater than 20 degrees Celsius; and a plurality of magnets positioned over said wire, wherein each of said plurality of magnets has a lumen through which said wire extends, wherein, in each of said first loop and second loop, a portion of adjacent magnets of said plurality of magnets are configured to not attach to each other, and wherein a portion of said plurality of magnets in the first loop are configured to attract a portion of said plurality of magnets in the second loop; piercing the adjacent body tissues and positioning the anastomosis device through a hole created by said piercing; and releasing the anastomosis device such that, when it transforms from the first state to the second state, tissue between the two adjacent body tissues is caught between the first loop and the second loop, thereby being compressed with a pressure of at least 1 psi and resulting in an anastomosis. Optionally, the pressure is at least 100 mm Hg (1.93 psi). Optionally the pressure is greater than 10 mm Hg (0.19 psi) but less than or equal to 7,500 mm Hg (145 psi) and every whole number or fractional increment therein.

Optionally, the applied pressure is greater than or equal to 0.3 psi at two or more points that are on opposite sides of at least one of the first loop and the second loop. Optionally, the anastomosis device further comprises non-ferromagnetic spacers positioned between adjacent magnets of said plurality of magnets. Optionally, the first loop and the second loop have at least one of a circular shape, polygonal shape, and a star shape with four or more points. Optionally, each of the plurality of magnets has a maximum cross sectional length ranging from 0.2 mm to 7 mm and a pull force ranging from 0.01 lb. to 4 lb (0.04-17.8 N). Optionally, in the first loop and in the second loop, at least 50% of the adjacent magnets of said plurality of magnets are arranged with like poles facing each other, thereby creating a repulsive force between said adjacent magnets in the first loop and the second loop of the coil. Optionally, the coil has at least one loop proximate to the first loop and at least one loop distal to the second loop. Optionally, a diameter of the wire ranges between 0.1 mm to 10 mm and a length of the wire ranges from 1 cm to 250 cm and wherein a maximum cross sectional dimension of the first loop and second loop ranges from 5 mm to 60 mm in the second state.

The present specification also discloses a magnet assembly for a magnetic anastomosis device used for forming an anastomosis between two bodily walls, the magnet assembly comprising: an elongated member, such as a solid wire without an inner passageway or lumen, having a proximal end and a distal end and a plurality of magnetic members disposed over the elongated member. The magnet assembly is operable between a delivery (pre-deployment) configuration and a deployed configuration, the elongated member extends generally linearly in the delivery configuration, the elongated member forms a spiral or coil shape in the deployed configuration where the proximal end and the distal end of the elongated member are not adjacent to each other and are separated from each other by a distance that is equal to or greater than a dimension of one of the plurality of magnetic members.

The aforementioned and other embodiments of the present shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings:

FIG. 7A illustrates a hexagonal SMA coil coupled with magnets for creating an anastomosis, in accordance with an embodiment of the present specification;

FIG. 7B illustrates exemplary dimensions of the hexagonal SMA coil shown in FIG. 7A, in accordance with an embodiment of the present specification;

FIG. 7J illustrates exemplary dimensions of a dodecagonal SMA coil in accordance with an embodiment of the present specification;

FIG. 14A illustrates an exemplary SMA wire coupled with magnets prior to deployment in a body for creating an anastomosis, in accordance with an embodiment of the present specification;

FIG. 14B illustrates the exemplary SMA wire coupled with magnets shown in FIG. 14A in a mid-deployment stage, in accordance with an embodiment of the present specification;

FIG. 15A illustrates an exemplary SMA wire coupled with magnets prior to deployment in a body for creating an anastomosis, in accordance with another embodiment of the present specification;

FIG. 15B illustrates the exemplary SMA wire coupled with magnets shown in FIG. 15A in a mid-deployment stage, in accordance with an embodiment of the present specification;

FIG. 16A illustrates an exemplary round shaped SMA coil used for creating an anastomosis, in accordance with an embodiment of the present specification;

FIG. 16B illustrates an exemplary round shaped SMA coil having a cutting edge, used for creating an anastomosis, in accordance with an embodiment of the present specification;

FIG. 16C illustrates an exemplary square shaped SMA coil used for creating an anastomosis, in accordance with an embodiment of the present specification;

FIG. 17A illustrates an exemplary device comprising round shaped magnets coupled with a SMA coil used for creating an anastomosis, in accordance with an embodiment of the present specification;

FIG. 17B illustrates an exemplary device comprising round shaped magnets coupled with a SMA coil used for creating an anastomosis, wherein at least one magnet comprises a cutting edge, in accordance with an embodiment of the present specification;

FIG. 17C illustrates an exemplary device comprising square shaped magnets coupled with a SMA coil with serrated edges, used for creating an anastomosis, in accordance with an embodiment of the present specification;

FIG. 17D illustrates an exemplary device comprising square shaped magnets coupled with a SMA coil used for creating an anastomosis, in accordance with another embodiment of the present specification;

FIG. 17E illustrates an exemplary device comprising square shaped magnets coupled with a SMA coil used for creating an anastomosis, wherein at least one magnet comprises a cutting edge, in accordance with an embodiment of the present specification;

FIG. 18A illustrates a first configuration of a plurality of magnets arranged around a loop of a SMA wire coil for creating an anastomosis, in accordance with an embodiment of the present specification;

FIG. 18B illustrates a second configuration of a plurality of magnets arranged around a loop of a SMA wire coil for creating anastomosis, in accordance with another embodiment of the present specification;

FIG. 18C illustrates a third configuration of a plurality of magnets arranged around a loop of a SMA wire coil separated by non-ferromagnetic spacers, for creating an anastomosis, in accordance with an embodiment of the present specification;

FIG. 18D illustrates a fourth configuration of a plurality of magnets arranged around a loop of a SMA wire coil separated by non-ferromagnetic spacers, for creating an anastomosis, in accordance with another embodiment of the present specification;

FIG. 23A illustrates a release mechanism of a SMA coil from a delivery catheter, in accordance with an embodiment of the present specification;

FIG. 23B illustrates the SMA coil being released from the delivery catheter shown in FIG. 23A, in accordance with an embodiment of the present specification;

FIG. 24A illustrates a release mechanism of a SMA coil from a delivery catheter, in accordance with another embodiment of the present specification;

FIG. 24B illustrates the SMA coil being released from the delivery catheter shown in FIG. 24A, in accordance with an embodiment of the present specification;

FIG. 26A illustrates a first view of an exemplary device for creating an anastomosis in a pre-coiled configuration, in accordance with an embodiment of the present specification;

FIG. 26B illustrates a second view of the device for creating an anastomosis of FIG. 26A in a pre-coiled configuration;

FIG. 26C illustrates a third view of the device for creating an anastomosis of FIG. 26A in a pre-coiled configuration;

FIG. 27 illustrates a SMA coil device for creating an anastomosis in a pre-deployment configuration with delivery catheter, in accordance with an embodiment of the present specification;

FIG. 28 illustrates a SMA coil device for creating an anastomosis in a pre-deployment configuration with delivery catheter, in accordance with another embodiment of the present specification;

FIG. 32A illustrates a cross sectional view of an anastomosis coil device in a pre-deployment configuration disposed in a delivery catheter, in accordance with another embodiment of the present specification;

FIG. 32B illustrates a cross sectional view along the BB axis shown in FIG. 32A;

FIG. 32C illustrates a cross sectional view along the CC axis shown in FIG. 32A;

FIG. 32D illustrates a cross sectional view along the DD axis shown in FIG. 32A;

FIG. 32E illustrates a blown up view of the conductor head shown in FIG. 32A;

FIG. 32F illustrates the anastomosis coil device shown in FIG. 32A in a post-deployment configuration after being delivered within a body;

FIG. 32G illustrates a cross sectional view of the anastomosis coil device shown in FIG. 32F;

FIG. 32H illustrates an O-ring being used as a spacer as shown in FIG. 32B;

FIG. 33A illustrates a dual handle delivery device for delivering an anastomosis coil device provided with a cauterizing tip, in accordance with an embodiment of the present specification;

FIG. 33B illustrates a blown up view of the second handle shown in FIG. 33A;

FIG. 34A illustrates a sectional view of a dual handle delivery device for delivering an anastomosis coil device provided with a cauterizing tip, in accordance with an embodiment of the present specification;

FIG. 34B illustrates a blown up sectional view of the tip portion shown in FIG. 34A;

FIG. 34C illustrates a cross sectional view of the tip portion shown in FIG. 34B;

FIG. 34D illustrates a blown up sectional view of the guidewire portion shown in FIG. 34A;

FIG. 34E illustrates a cross sectional view of the guidewire portion shown in FIG. 34D;

FIG. 34F illustrates a blown up sectional view of the handle portion shown in FIG. 34A;

FIG. 35 is a flowchart illustrating the steps of creating an anastomosis by using a shape memory wire and magnetic compression forces between adjacent organs or structures, in accordance with an embodiment of the present specification;

Figure 36:
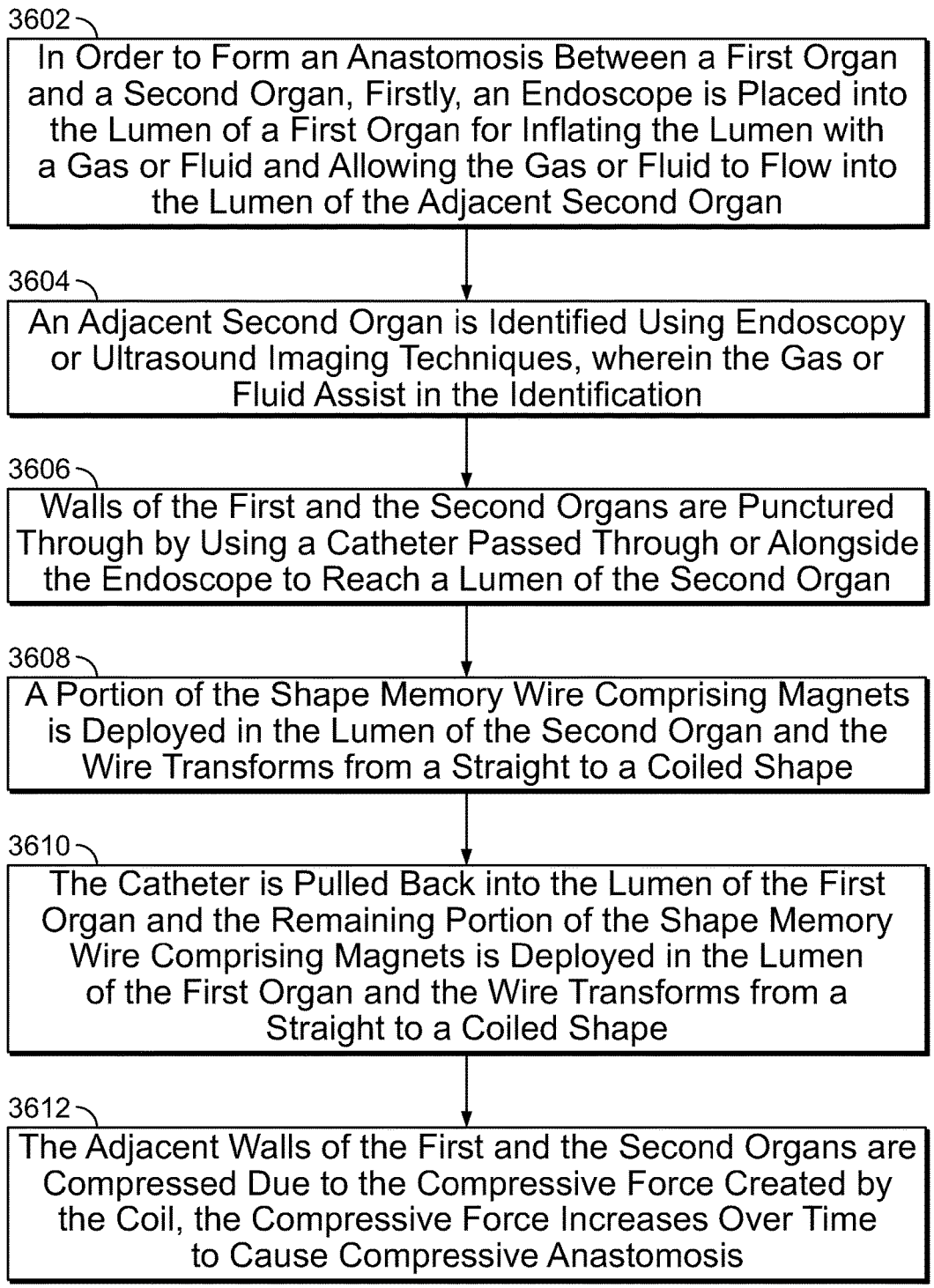
Figure 37:
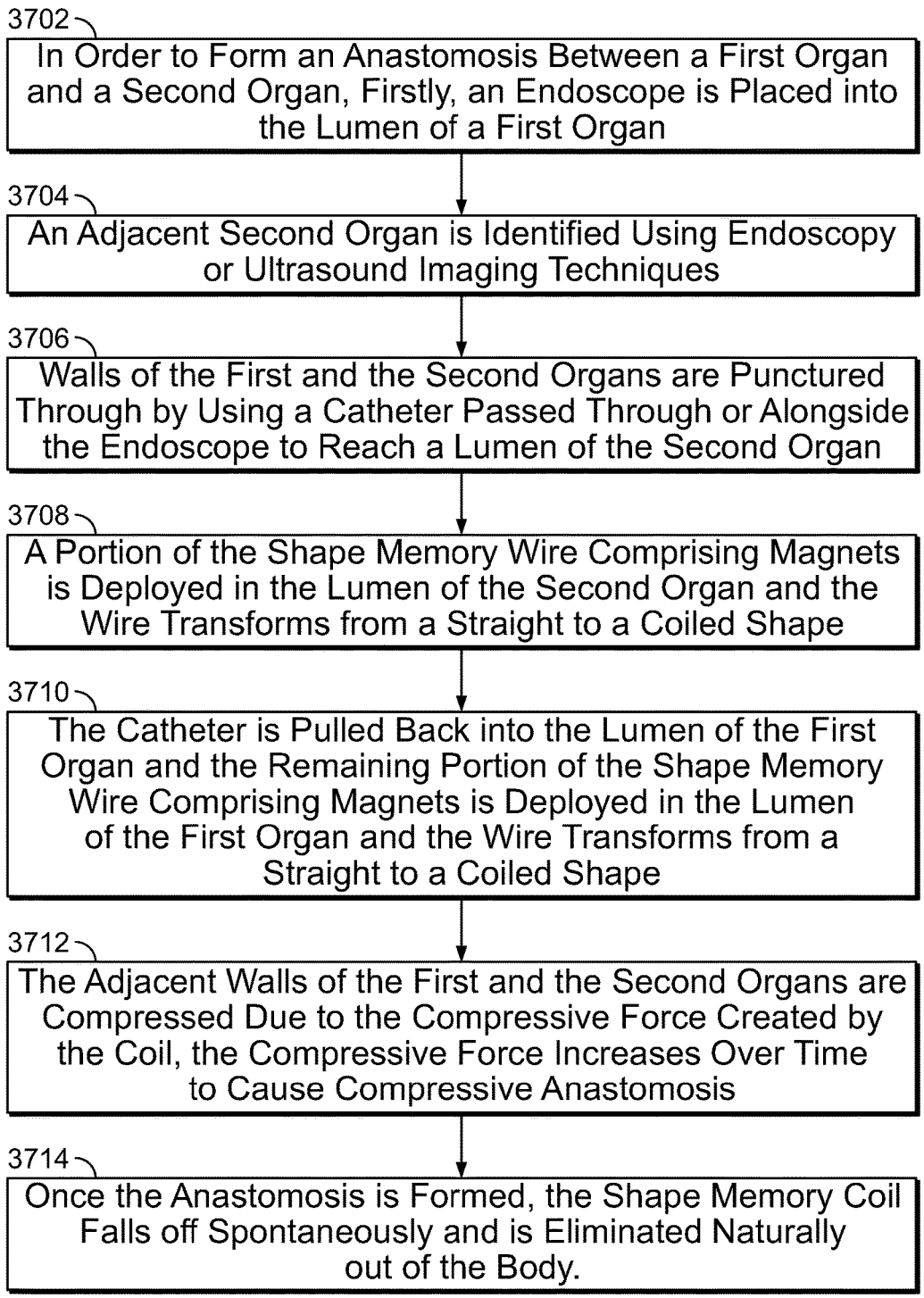
Figure 38:
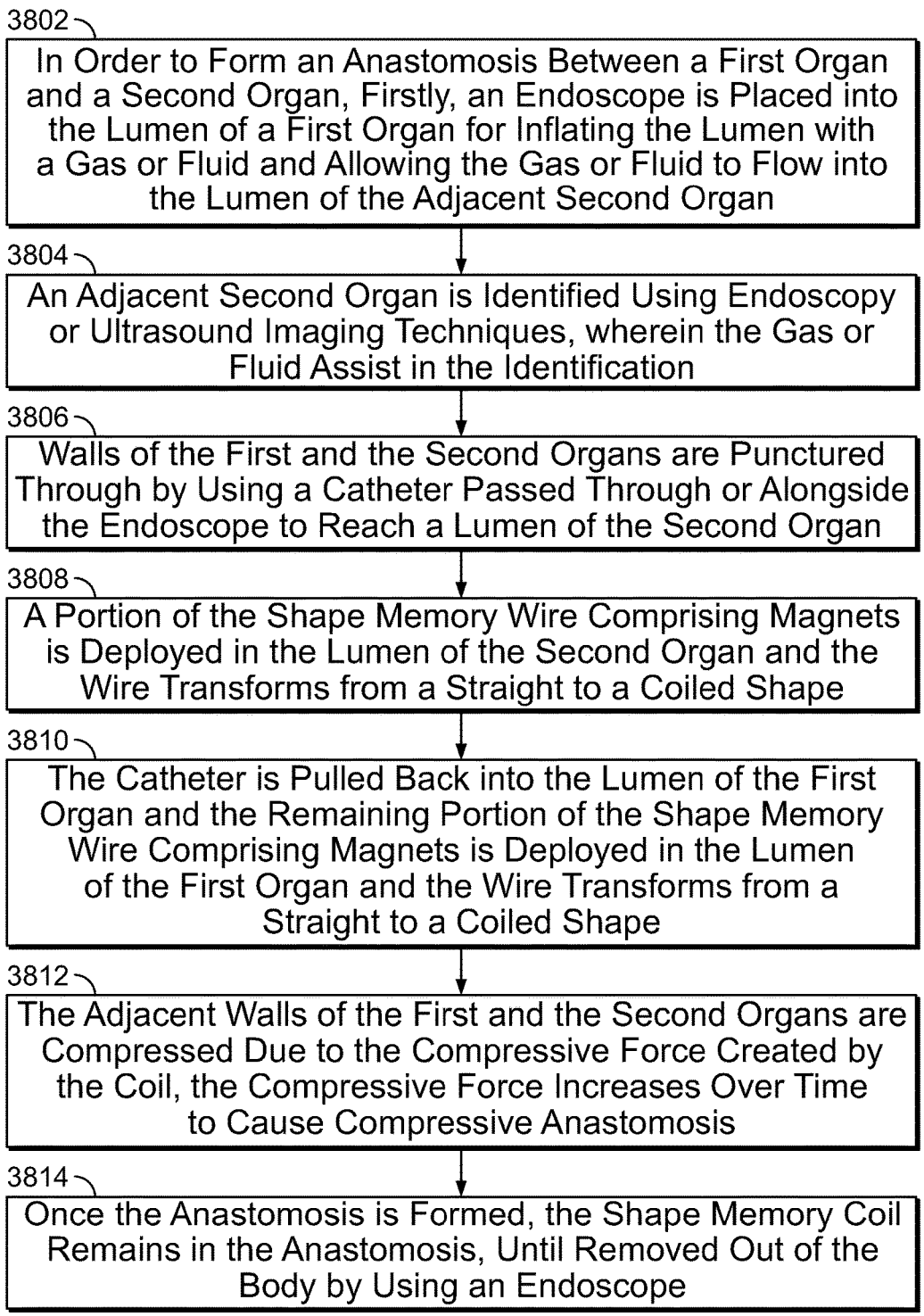
Figure 39A:
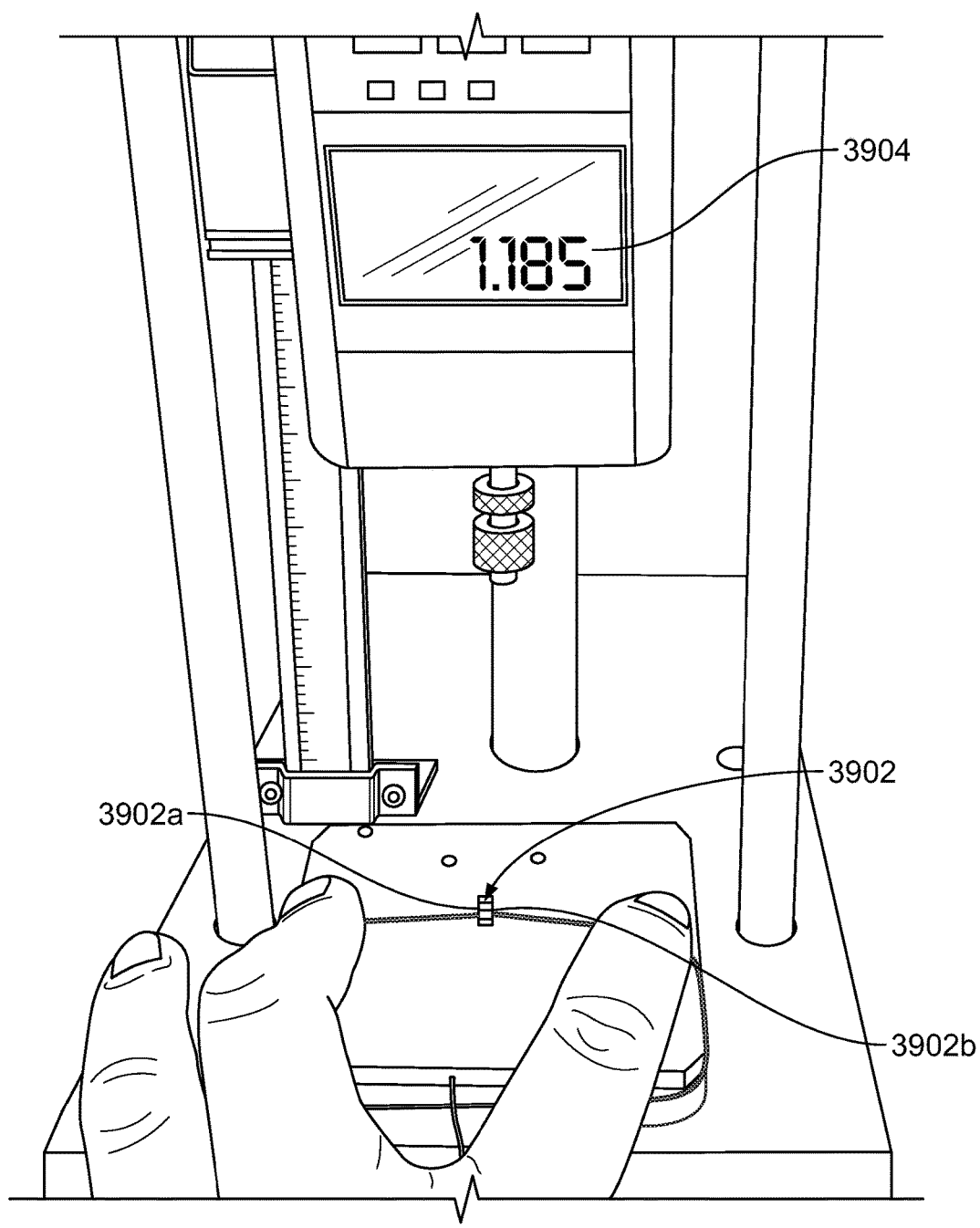
Figure 39B:
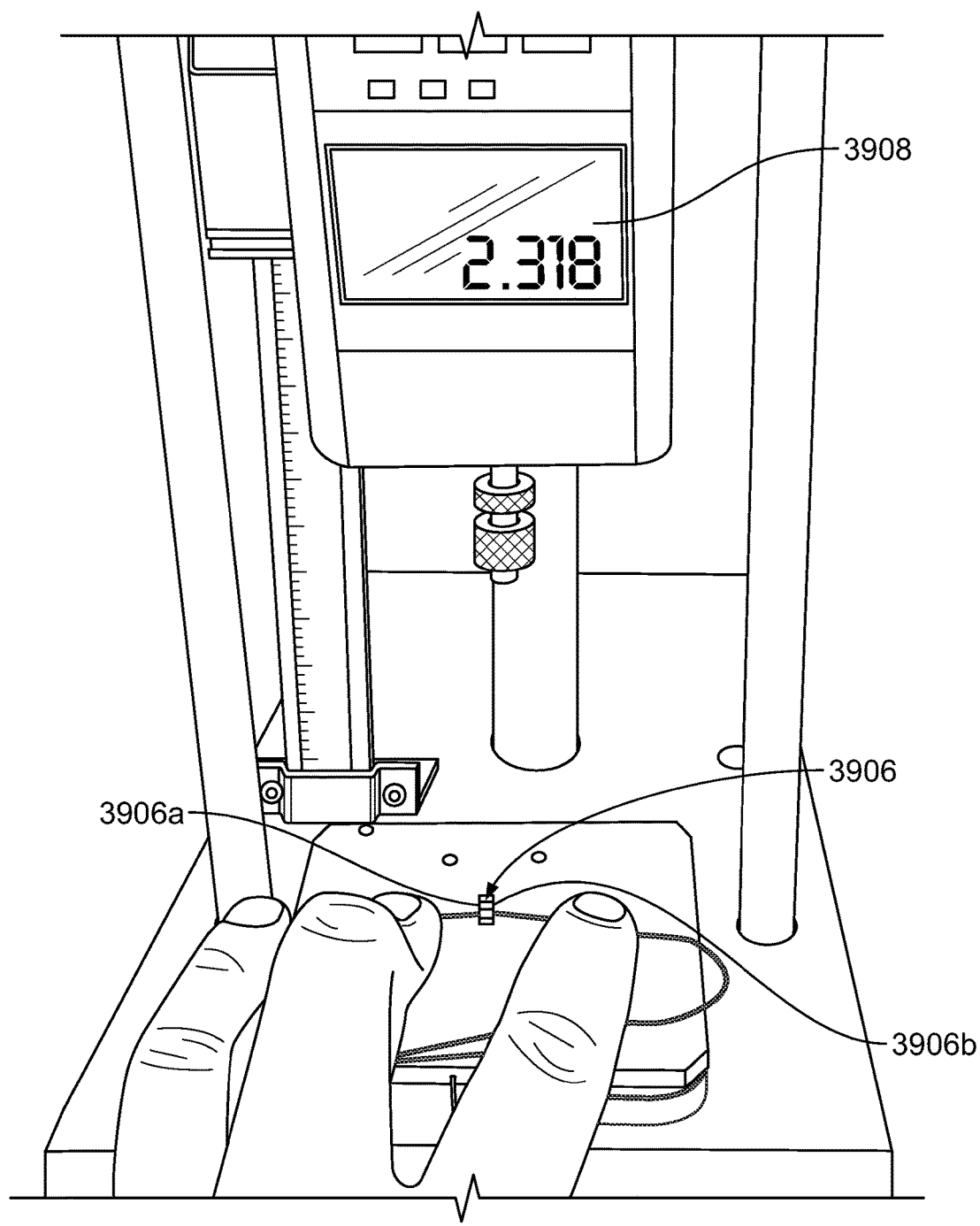
Figure 39C:
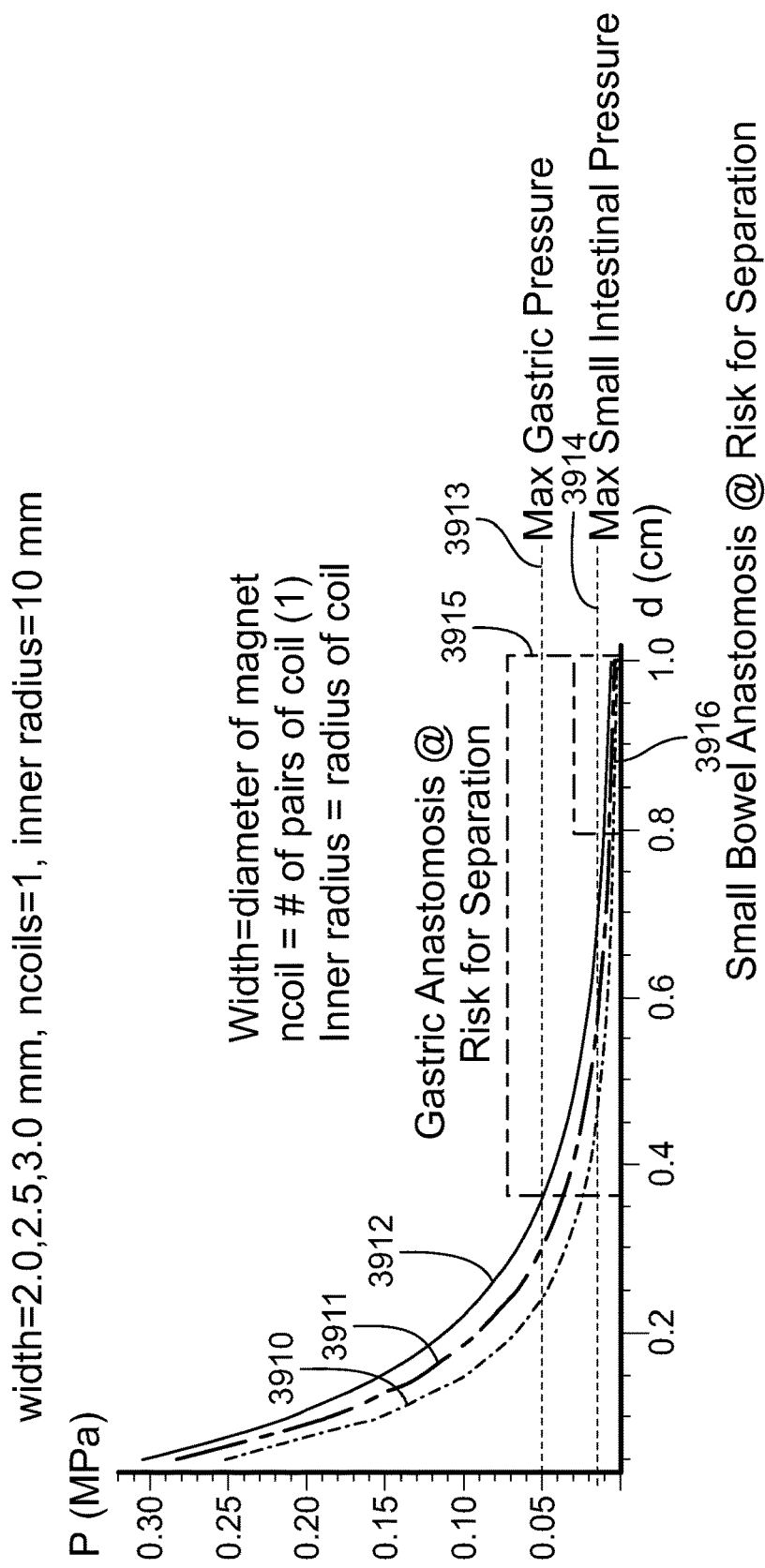
Figure 39D:
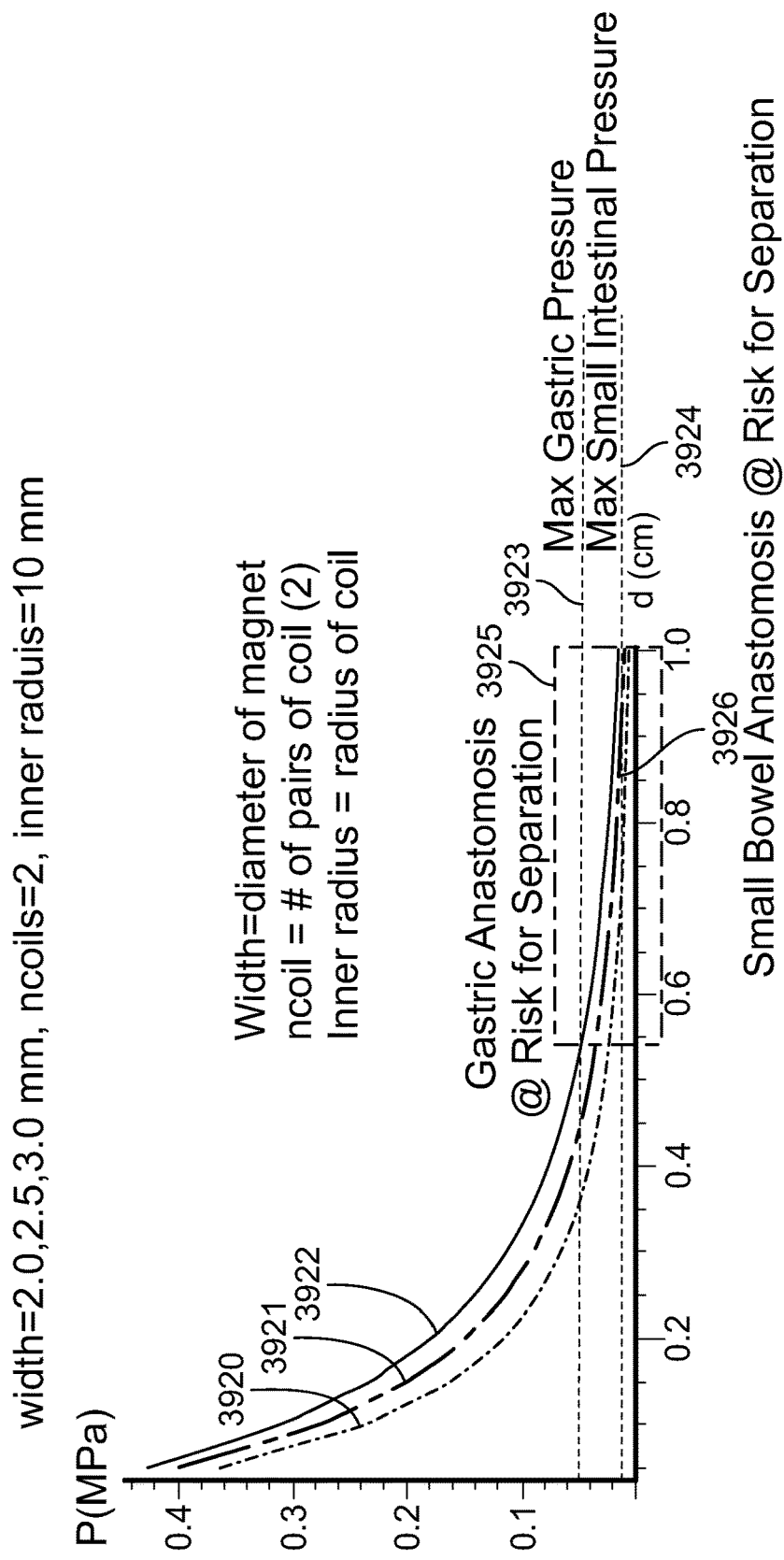
Figure 39E:
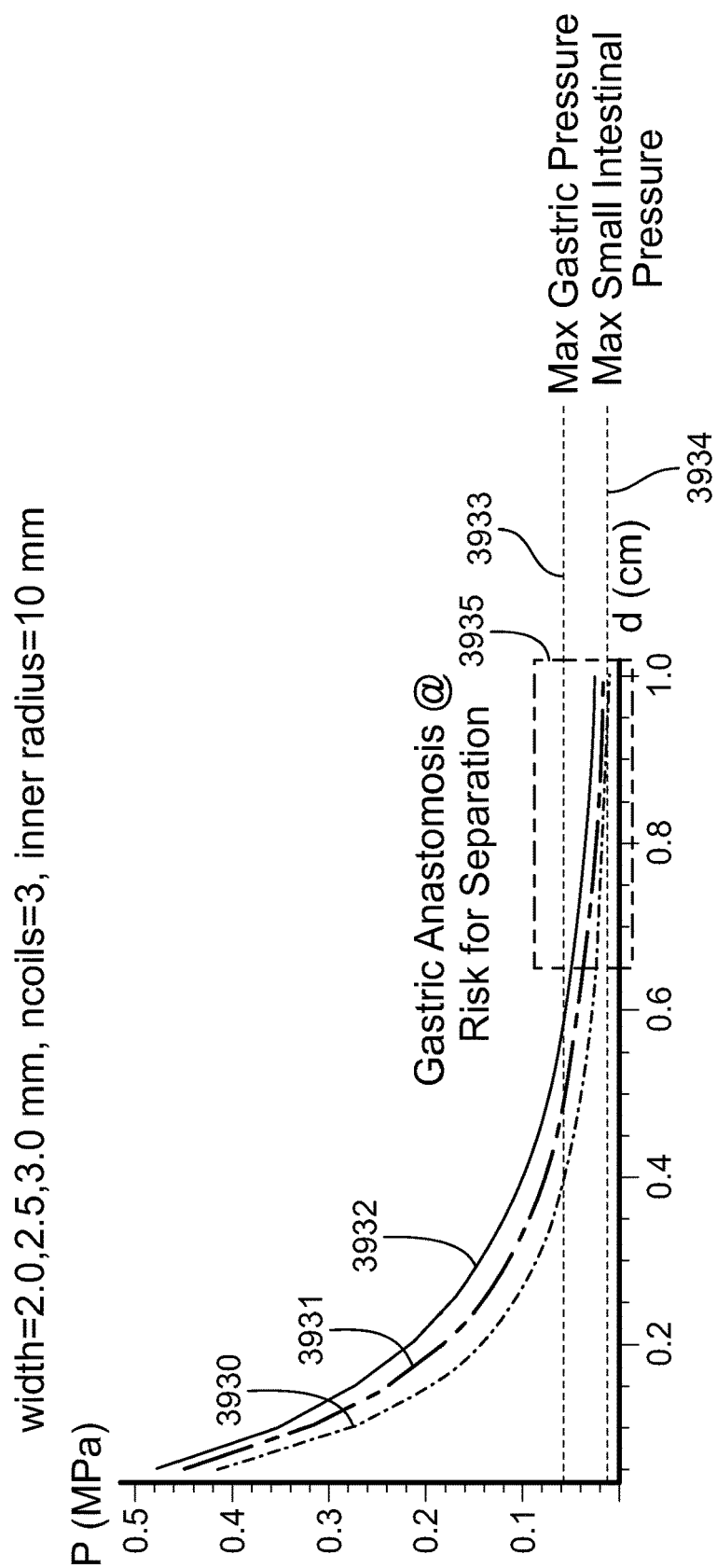
Figure 39F:
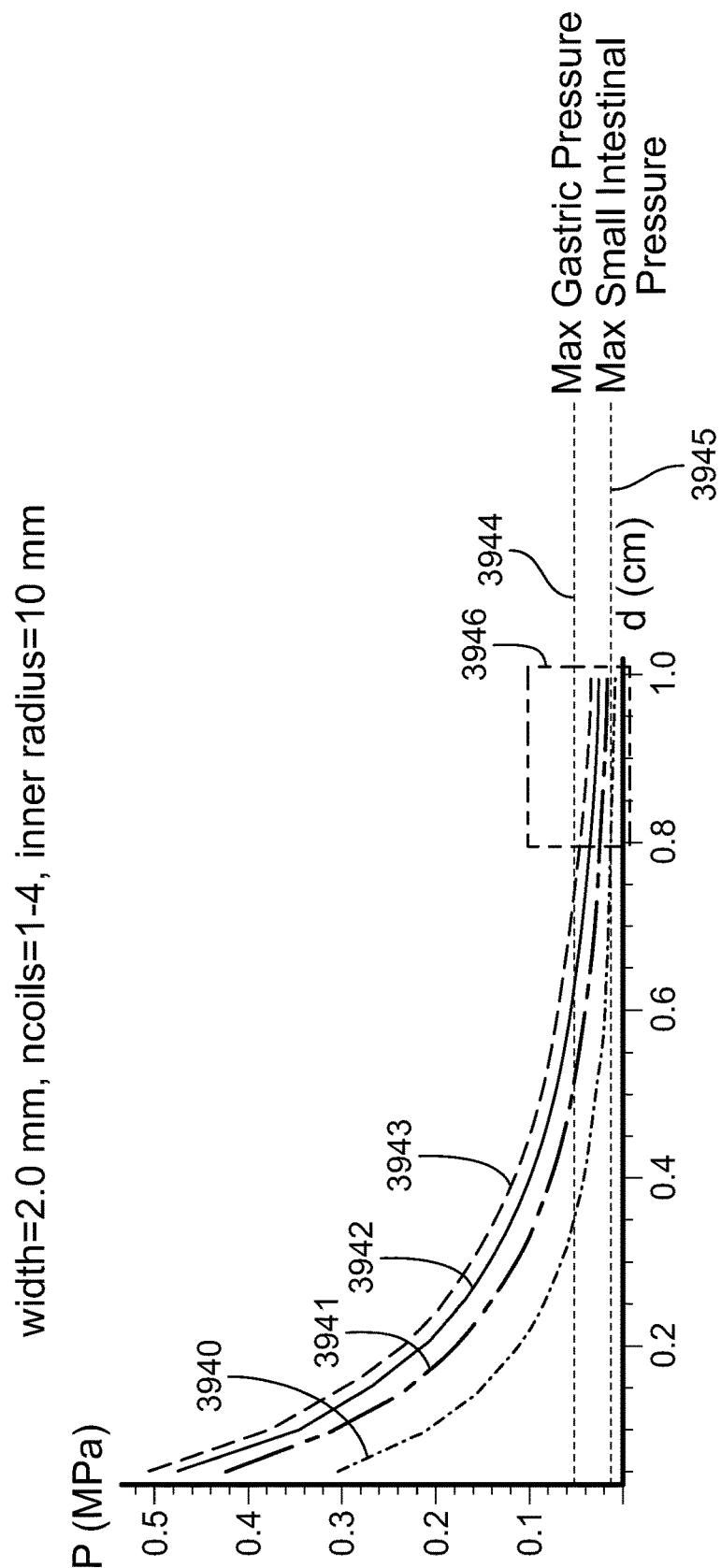
Figure 39G:
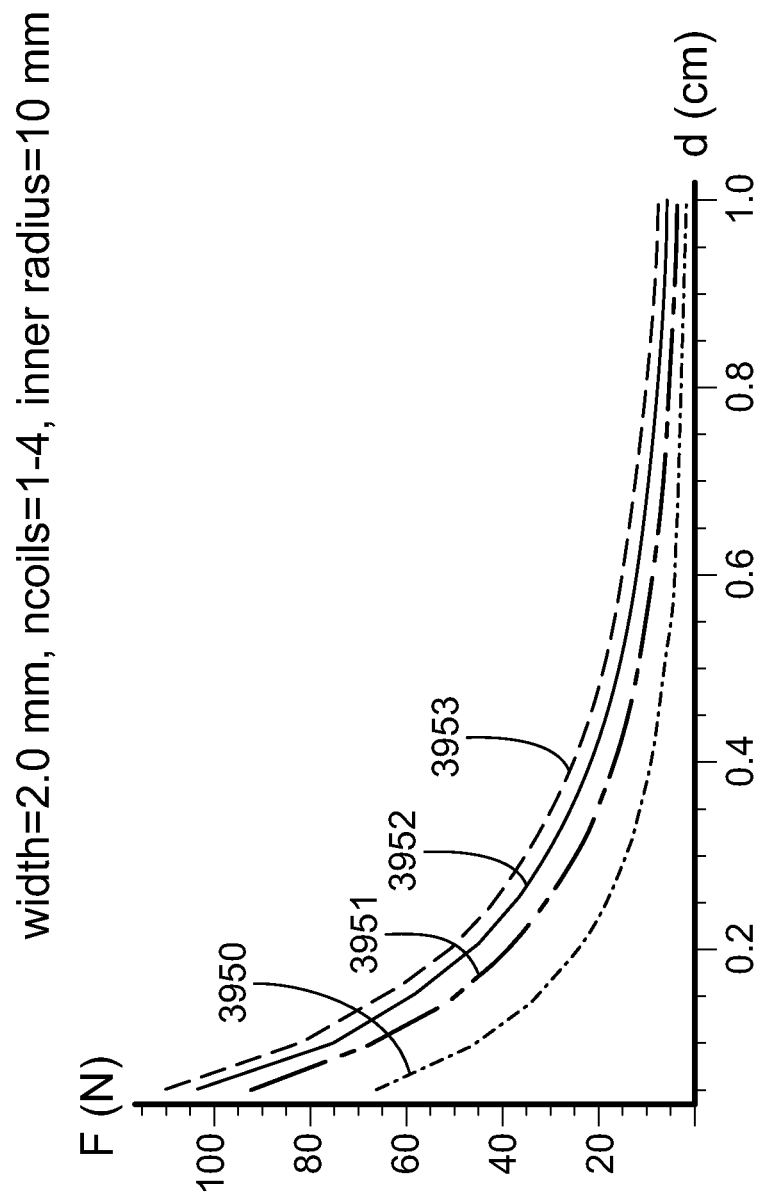
Figure 39I:
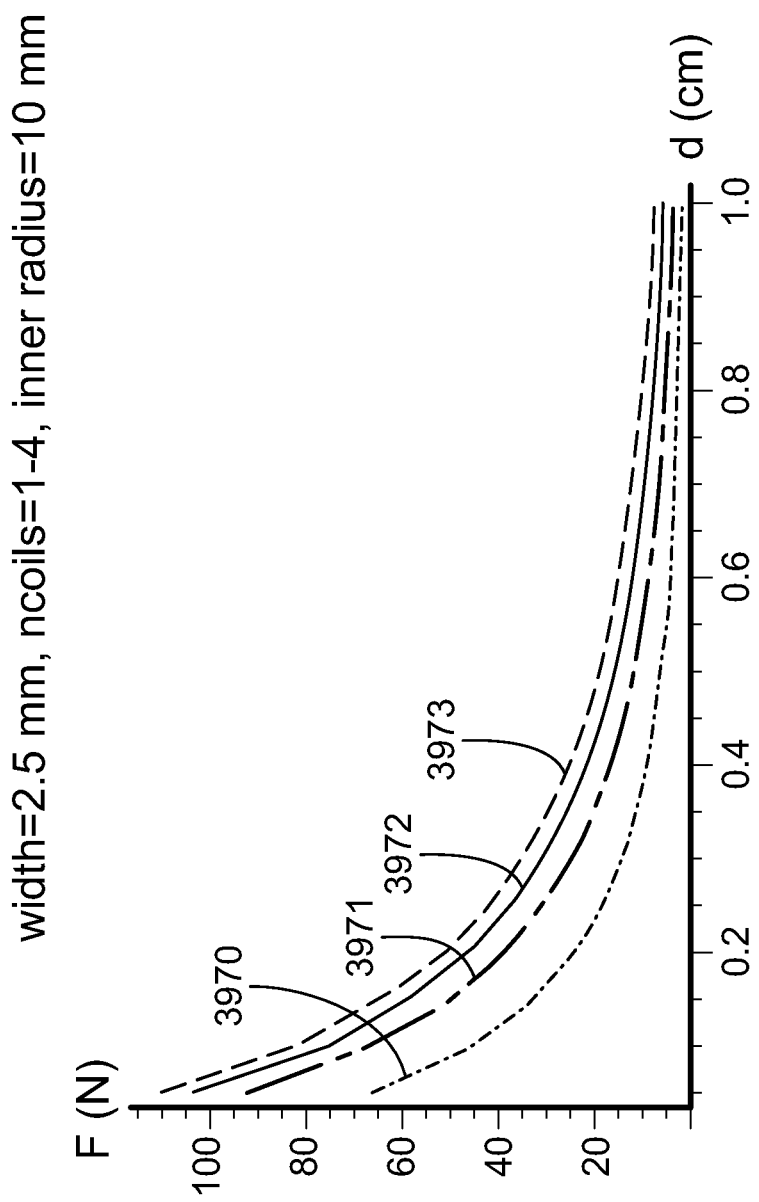
Figure 39J:
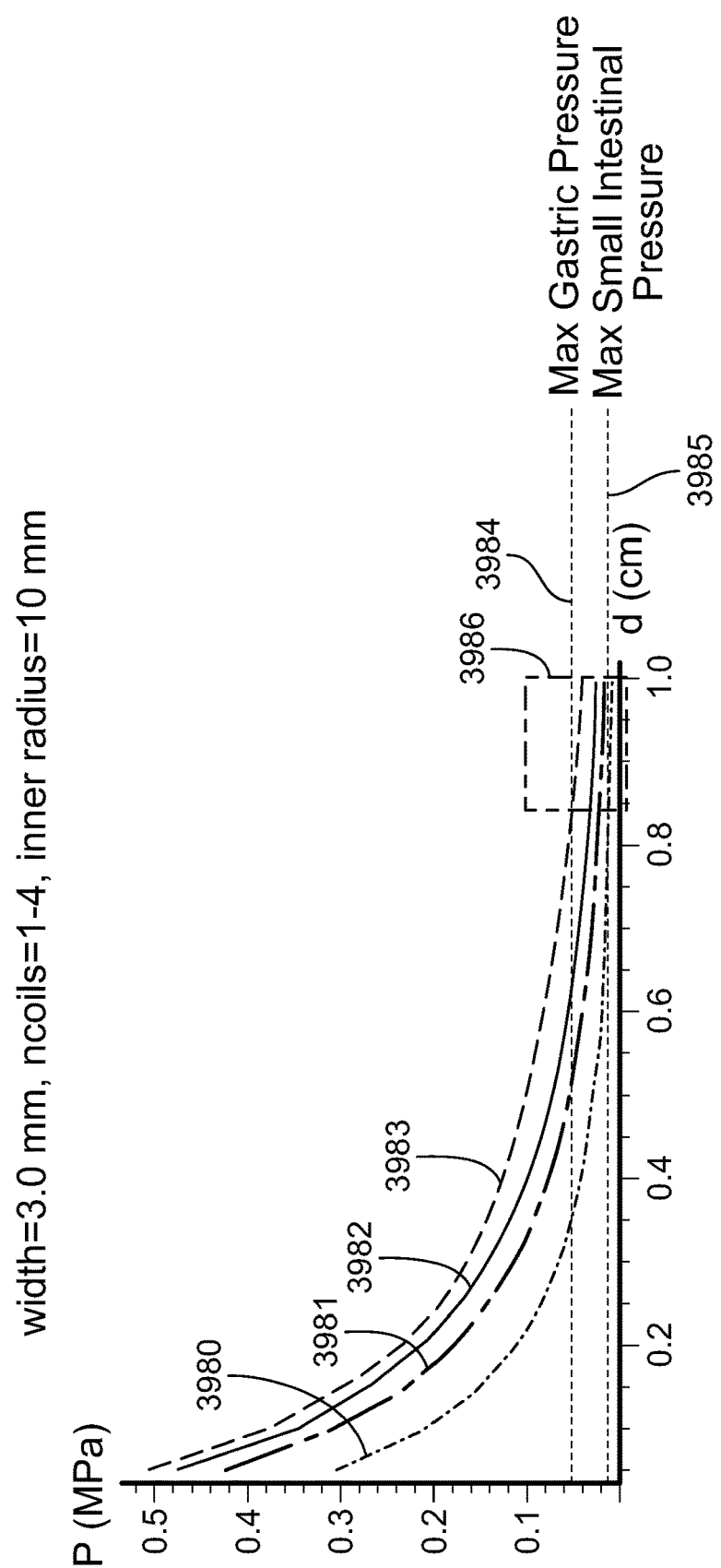
Figure 39K:
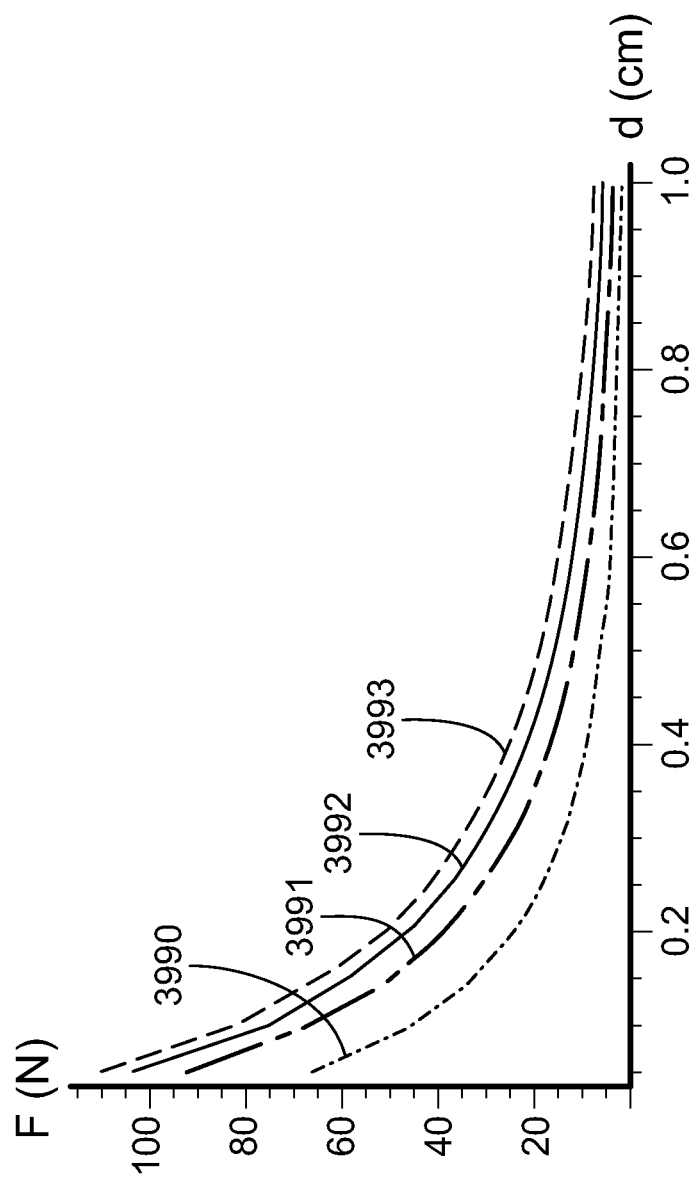
Figure 40C:
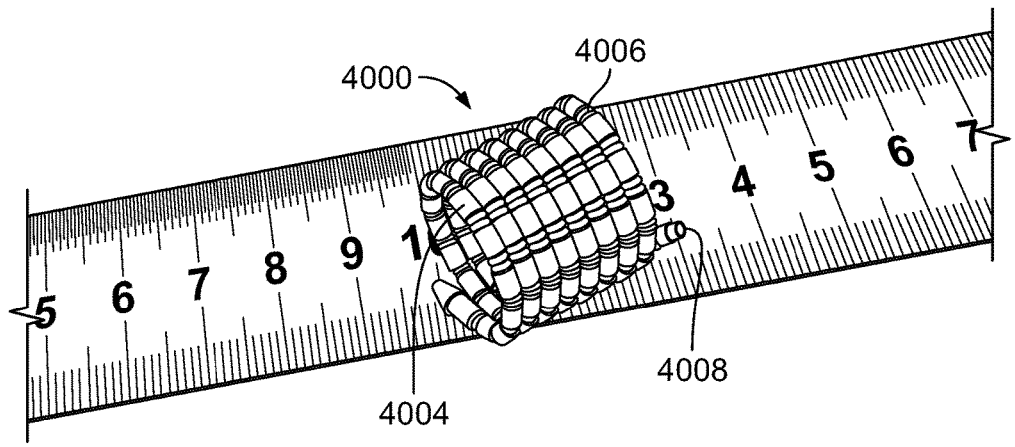
Figure 40D:
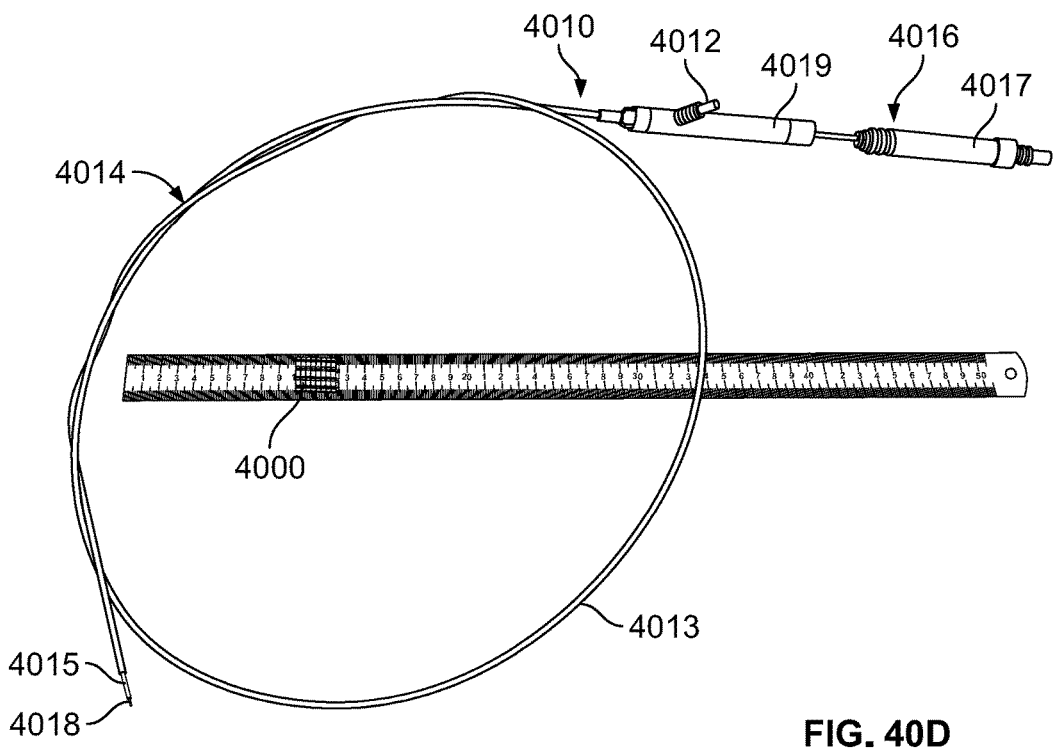
Figure 40E:
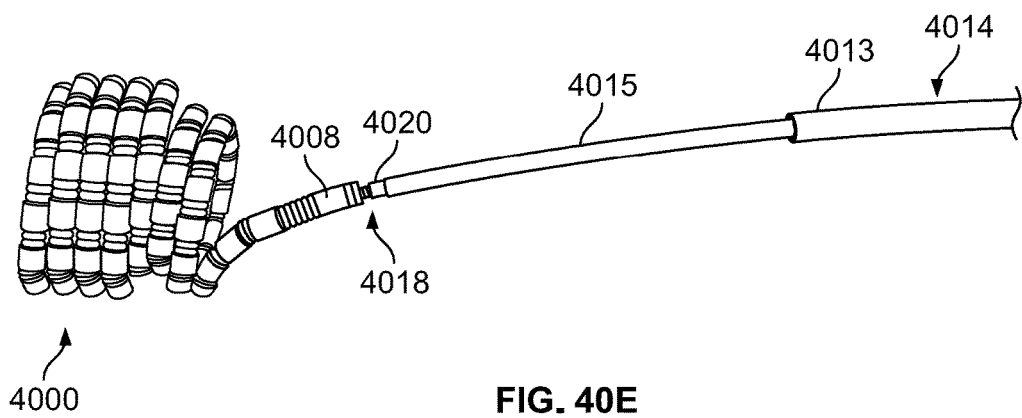
Figure 40F:
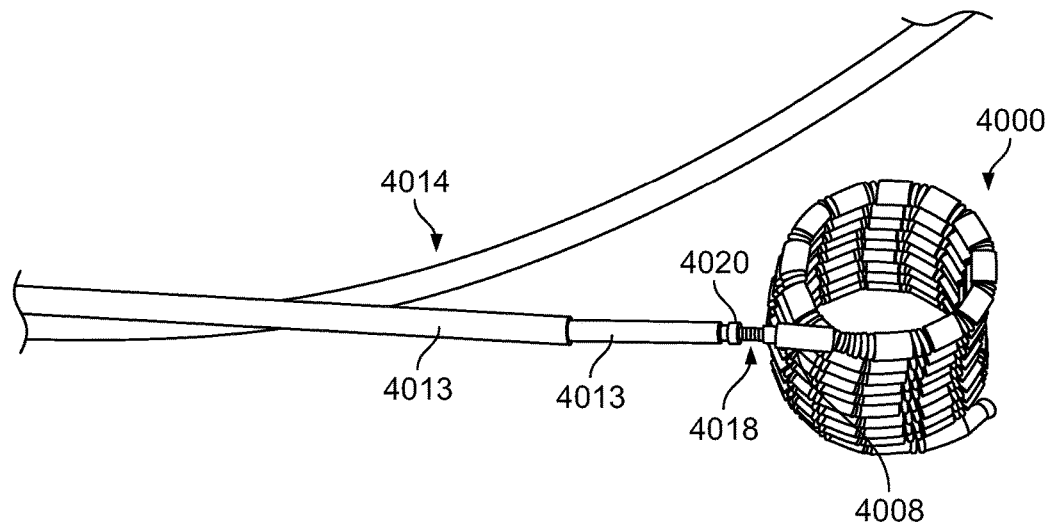
Figure 40G:
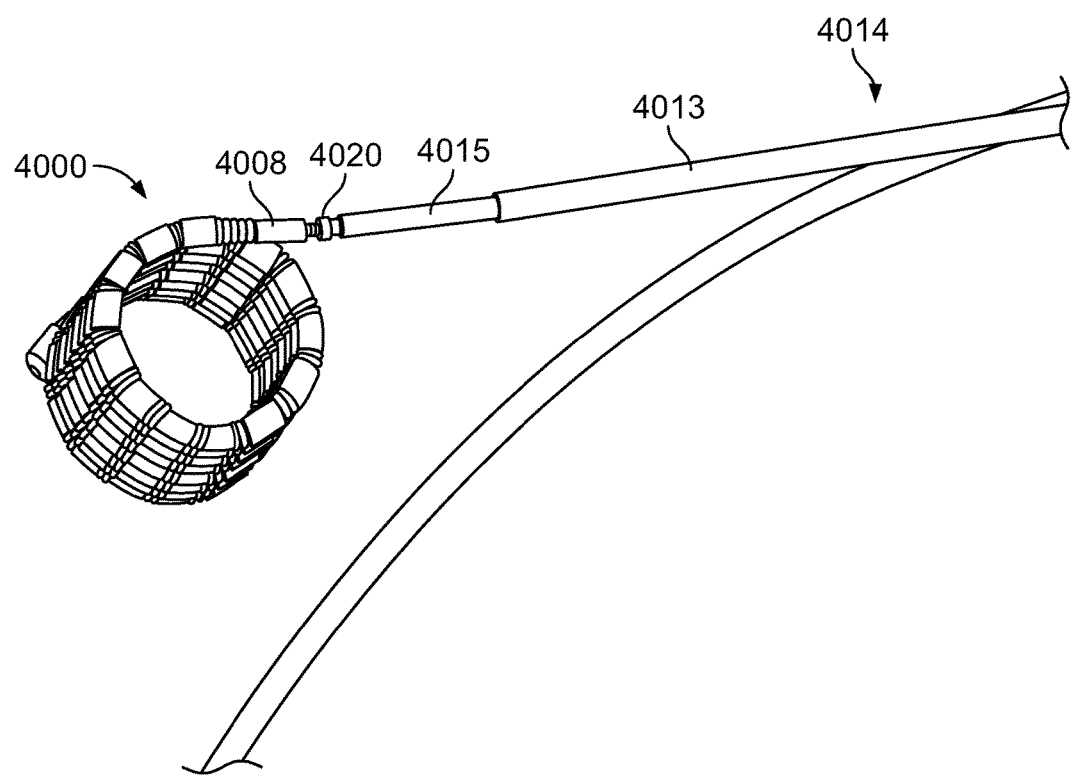
Figure 40H:
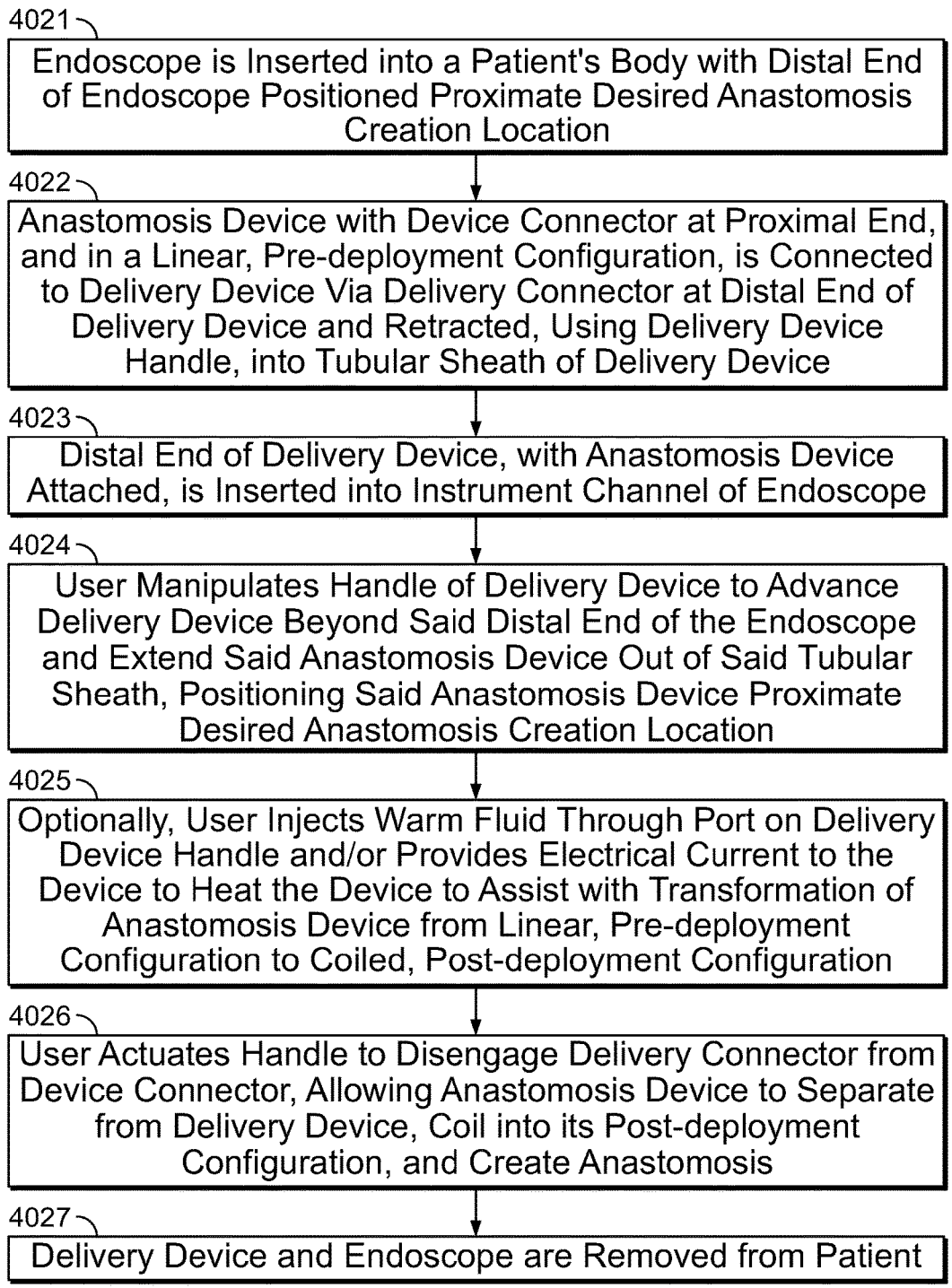

FIG. 36 is a flowchart illustrating the steps of creating an anastomosis by using a shape memory coil with magnets between adjacent organs, in accordance with an embodiment of the present specification; and FIG. 37 is a flowchart illustrating the steps of creating an anastomosis by using a shape memory wire and magnetic compression forces between adjacent organs or structures, in accordance with an embodiment of the present specification;

FIG. 38 is a flowchart illustrating the steps of creating an anastomosis by using a shape memory coil with magnets between adjacent organs, in accordance with an embodiment of the present specification;

FIG. 39A illustrates an exemplary magnet used with a device for creating an anastomosis, in accordance with an embodiment of the present specification;

FIG. 39B illustrates an exemplary magnet used with a device for creating an anastomosis, in accordance with another embodiment of the present specification;

FIG. 39C is a graph illustrating the relationship between compressive pressures and distances between coil loops provided by anastomosis devices having a single coil loop on each side of an anastomosis to be formed, in accordance with an embodiment of the present specification;

FIG. 39D is a graph illustrating the relationship between compressive pressures and distances between coil loops provided by anastomosis devices having two coil loops on each side of an anastomosis to be formed, in accordance with an embodiment of the present specification;

FIG. 39E is a graph illustrating the relationship between compressive pressures and distances between coil loops provided by anastomosis devices having three coil loops on each side of an anastomosis to be formed, in accordance with an embodiment of the present specification;

FIG. 39F is a graph illustrating the relationship between compressive pressures and distances between coil loops provided by anastomosis devices having 2.0 mm diameter magnets and varying numbers of coil loops on each side of an anastomosis to be formed, in accordance with an embodiment of the present specification;

FIG. 39G is a graph illustrating the relationship between force and distances between coil loops provided by anastomosis devices having 2.0 mm diameter magnets and varying numbers of coil loops on each side of an anastomosis to be formed, in accordance with an embodiment of the present specification;

FIG. 39H is a graph illustrating the relationship between compressive pressures and distances between coil loops provided by anastomosis devices having 2.5 mm diameter magnets and varying numbers of coil loops on each side of an anastomosis to be formed, in accordance with embodiments of the present specification;

FIG. 39I is a graph illustrating the relationship between force and distances between coil loops provided by anastomosis devices having 2.5 mm diameter magnets and varying numbers of coil loops on each side of an anastomosis to be formed, in accordance with embodiments of the present specification;

FIG. 39J is a graph illustrating the relationship between compressive pressures and distances between coil loops provided by anastomosis devices having 3.0 mm diameter magnets and varying numbers of coil loops on each side of an anastomosis to be formed, in accordance with embodiments of the present specification;

FIG. 39K is a graph illustrating the relationship between force and distances between coil loops provided by anastomosis devices having 3.0 mm diameter magnets and varying numbers of coil loops on each side of an anastomosis to be formed, in accordance with embodiments of the present specification;

FIG. 40A illustrates an exemplary device for creating an anastomosis in a pre-coiled configuration, in accordance with an embodiment of the present specification;

FIG. 40B illustrates the device for creating an anastomosis of FIG. 40A in a coiled configuration;

FIG. 40C illustrates another view of the device for creating an anastomosis of FIG. 40A in a coiled configuration;

FIG. 40D illustrates a delivery device for delivering the anastomosis device shown in FIGS. 40A, 40B, and 40C in a desired location within a body, in accordance with an embodiment of the present specification;

FIG. 40E illustrates the delivery device shown in FIG. 40D connected to the coiled anastomosis device shown in FIGS. 40B and 40C, in accordance with an embodiment of the present specification;

FIG. 40F illustrates another view of the delivery device shown in FIG. 40D connected to the coiled anastomosis device shown in FIGS. 40B and 40C, in accordance with an embodiment of the present specification;

FIG. 40G illustrates another view of the delivery device shown in FIG. 40D connected to the coiled anastomosis device shown in FIGS. 40B and 40C, in accordance with an embodiment of the present specification; and FIG. 40H is a flowchart listing the steps involved in a method of deploying an anastomosis device using a delivery device in accordance with one embodiment of the present specification.

DETAILED DESCRIPTION

In various embodiments, a shape memory alloy (SMA) or smart alloy wire is used to create an anastomosis by creating the desired shape and size of the anastomosis and cutting through tissue layers in a human body to create an opening or anastomosis. In an embodiment, a straight piece of a SMA wire or a longitudinally stretched coil, or any other substantially planar structure, is delivered at a location requiring an anastomosis within a body. In an embodiment, the SMA wire is either superelastic or heat sensitive and curls up into a spring like coil in response to body heat within the body. In various embodiments, the wire has a straight or a longitudinally stretched coil or an elongate shape at room temperature and a compressed coil shape at the human body temperature, which is in the preferred range of 97.7 degrees Fahrenheit (F.) to 99.5 degrees F. The coil may take a compressed shape at any temperature greater than 96 degrees F.

The compressed coil defines the desired shape and dimensions of the desired anastomosis. The compressing coil produces a compression force on tissue caught between loops of the coil. The coiling action also causes the wire to create ischemia, pressure necrosis and cut through the desired tissue layers, creating an anastomosis between two adjacent body tissues. In an embodiment, a plurality of magnets are provided on each concentric ring of the coiled wire. Magnets provided on adjacent rings attract each other, thereby enhancing the cutting action of the coil. In some embodiments, compression force is provided by the combination of the coiling wire and attraction force between the magnets. In some embodiments, the shape of the resultant anastomosis is predominantly determined by the shape of the coil and not by the forces between the magnets. In various embodiments, the number of magnets used and the length of the magnets are determined by the shape, dimensions or time needed to form an anastomosis. In various embodiments, the time period required to create the anastomosis ranges between one day and fourteen days. In various embodiments, the anastomosis is formed between two segments of the SMA wire, between two or more magnets, or between a segment of SMA wire and one or more magnets.

In various embodiments, an anastomosis device comprises a wire having a plurality of magnets provided on the wire. In various embodiments, only one anastomosis device is required to create the desired anastomosis. The device is delivered, using a delivery device, to a first lumen of a first organ, passed through a first wall of said first organ and through a second wall of a second organ and into a second lumen of said second organ, all while still at least partially maintained in a delivery configuration on said delivery device. The anastomosis device is then deployed such that a distal portion is disposed in said second lumen and a proximal portion of the device is disposed in said first lumen. Once deployed, the device curls into a coil shape having one or more coils such that a distal portion of the coil remains in said second lumen and a proximal portion of the coil remains in said first lumen. In other words, only a single anastomosis device as described in embodiments of the present specification is required to create the desired anastomosis, rather than two separate mating devices as encountered in the prior art, where a first device is deployed in a first lumen of a first organ and a second device is deployed in a second lumen of a second organ.

In various embodiments, the anastomosis devices of the present specification form a coil shape in a deployed configuration, having at least one coil with a proximal end and a distal end wherein said proximal end and said distal end are in different horizontal planes.

In various embodiments, the deployed coil shape of the anastomosis device is formed only through the actions of the shape memory wire and/or magnetic forces of the magnetic members and without the use of any additional guide element, manipulator, radial members, hinges, or opening members.

It should be appreciated that the presently disclosed embodiments have several advantages over the prior art. First, the wire, in a non-deployed state, transitioning to a coil structure, in a deployed state, enables an automatic compressive action without requiring the manual positioning of separate magnetic elements, which are not tethered to each other or positioned relative to each other in a fixed pre-deployment or post-deployment configuration. More specifically, the alignment of magnetic elements is achieved by their fixed position on a wire and it is the wire's natural transition from a straight, elongated member to a coil shape that achieves the requisite automatic alignment of the magnetic elements and compression of tissue. This is achieved because the embodiments disclosed herein provide magnetic elements which are tethered to each other or physically coupled such that the magnetic elements have a fixed, predefined position relative to each other in both the pre-deployment and post-deployment configurations. The coupling is preferably through a wire, although a suture, a tube, or other member, can be used to create the fixed relationship.

Therefore, the magnets used in the device have a fixed relation to each other both before and after deployment. The relative three dimensional position of a first magnet is known, and fixed, relative to the three dimensional position of a second magnet both in an undeployed configuration (along the length of a straight wire) and in a deployed configuration (in the shape of a coil). This fixed relation enables an automatic alignment because a user need not manually place the magnets into a particular position, relative to each other, before deployment, so that they will properly connect post deployment. Stated differently, when the device is in a deployed configuration, a first magnet in a first coil is in a predefined, fixed position relative to a second magnet in a second coil, where the coils are separated by the tissue subject to anastomosis. Note that the predefined fixed position may be one of several, but each of the positions are pre-defined and fixed. When the same device is in a non-deployed (straight wire, non-coil) configuration, the same first magnet (now along the length of the wire) is in a different (but still predefined and fixed) position relative to the second magnet (also along the length of the wire). These two relative positions, in the deployed and non-deployed configurations, are fixed and defined, regardless of human intervention. Therefore, the first magnet and second magnet transition from the first non-deployed relative fixed position to the second non-deployed relative fixed position automatically and, while a human deploying the device affects the transition from a non-deployed to deployed state, human intervention does not affect the predefined fixed position of the first magnet relative to the second magnet in the non-deployed state and the predefined fixed position of the first magnet relative to the second magnet in the deployed state.

In contrast, the prior art teaches separate magnetic assemblies (because they are not physically coupled to each other in a fixed configured in at least one of, or both, a pre-deployment or post-deployment shape) that must be manually aligned relative to each other in order to achieve the right compressive force. That means there is no predefined fixed position of the first magnet assembly relative to the second magnet assembly in the non-deployed state, since it is different every time and dependent on how the assembly is used. It also means that there is no predefined fixed position of the first magnet relative to the second magnet in the deployed state.

Operationally, this self-alignment feature improves the safety profile of the device. Various portions of the body are subject to tissue motion, such as peristalsis in the gastrointestinal (GI) tract, which can dislodge or separate the two opposing magnetic bodies that are compressing tissue. Because prior art devices comprise two independently moving magnetic structures, they always carry a high risk of detaching and re-attaching in a different configuration or location, thereby potentially creating an anastomosis in the wrong tissue, such as the wrong section of the patient's GI tract. In the presently disclosed embodiments, if, after the first magnetic element on a first coil attaches to a second magnetic element on a second coil, the two magnetic elements thereafter detach, the detachment will only be temporary and the two magnetic elements will automatically reattach over the target tissue region without requiring human intervention. First, the two magnetic elements are in a fixed relation, as described above. Second, they are in a fixed position relative to the target tissue because they have been inserted into place by puncturing through the target tissue. Accordingly, if they temporarily detach, the magnets will not travel (since the underlying wire has punctured through the target tissue) and they will coil back into their deployed configuration once the disruptive motion subsides. As a result, the two magnetic elements on opposing coils separated by target tissue automatically reattach to each other, after being momentarily separated by anatomical motion, at least 70% of the time, most likely at least 90%, 95%, and 99% of the time.

The aforementioned coupled structure also allows for an easier deployment procedure. Rather than having to individually deploy two separate assemblies on two opposing sides of the tissue subject to anastomosis, a physician deploys a single device, which is used to make an initial puncture through the tissue subject to anastomosis and then automatically coils, providing the requisite compressive force.

Second, the embodiments disclosed herein preferably use a solid wire, such as a Nitinol wire, to integrally couple the magnetic elements to each other. This has several benefits, including 1) being able to provide a conductive wire mechanism that integrates electrical cautery puncturing functionality into the anastomosis device itself, 2) avoiding the use of a tube, or a structure with any hollow lumen passing therethrough, which is more complicated to manufacture, is more challenging to deploy reliably, and results in a device that is either excessively thick or has magnets with too small a profile, thereby decreasing the amount of available compressive force, and 3) allowing physicians to place the device in locations that a thicker device or a catheter cannot reach, such as with pseudocysts. While a solid wire is a preferred embodiment, all of the presently disclosed embodiments can work with a hollow tube, such as a hollow Nitinol wire, through which a guide wire may be passed and used to position the device.

Third, the embodiments disclosed herein teach a wire with a plurality of magnetic elements that are preferably not fixedly attached to the wire but, rather, tightly positioned over the wire and separated from adjacent magnetic elements using a non-ferromagnetic spacer. This has several benefits. The disclosed devices are simpler to manufacture because each of the magnetic elements need not be individually fixed to the wire using solder, detents, tabs, glue, welding, or friction fits. Rather, magnetic elements may be individually manufactured with a lumen, allowing for greater tolerances, strung over the wire via their lumens, and separated from adjacent magnetic elements using non-ferromagnetic spacers, obviating any additional fixation step to attach the magnetic elements to the wire. This enables each magnetic element to have a fixed position relative to other magnetic elements on the same wire without actually having to attach each magnetic element to the wire. Furthermore, the fixed position of magnetic elements with non-ferromagnetic spacers in between each of the magnetic elements (thereby creating an alternating sequence of magnetic elements and non-ferromagnetic spacers) prevents the unwanted clumping or migration of magnets. While the prior art discloses the use of jackets or protrusions from the magnetic element, such structures fail to prevent clumping or the general migration of magnetics out of a preferred configuration or alignment. In fact, it is preferred for the magnetic elements to have smooth surfaces (no raised portions) to enable a more flexible degree of alignment and without having to align non-raised portions with raised portions. It should be appreciated, however, that in a less preferred embodiment, each magnetic element may be attached to the wire and separated from adjacent magnetic elements by a space (not a physical, non-ferromagnetic spacer made, for example, from plastic or other medically acceptable materials).

Fourth, the disclosed coil structure allows for the application of multiple magnetic layers, thereby increasing compressive force on a tissue surface, without increasing the complexity of a medical procedure. If prior art devices are used, one would have to manually mate multiple individual, physically separate magnetic assemblies, on both sides of the tissue surface, to achieve what the presently disclosed coil structures can achieve automatically: compression of tissue with multiple magnetic layers on both sides of the tissue that are automatically aligned with each other and in a fixed relative position in both the pre-deployment and post-deployment configurations.

The term "and/or" means one or all of the listed elements or a combination of any two or more of the listed elements.

In the description and claims of the application, each of the words "comprise" "include" and "have", and forms thereof, are not necessarily limited to members in a list with which the words may be associated.

Unless otherwise specified, "a," "an," "the," "one or more," and "at least one" are used interchangeably and mean one or more than one.

The term "pre-deployment" or "delivery" configuration refers to the configuration where the solid wire, over which the magnetic elements or members are placed, is substantially straight or linear.

The term "post-deployment" or "deployed" configuration refers to the configuration where the solid wire, over which the magnetic elements or members are placed, is substantially coiled or in a spiral shape.

For any method disclosed herein that includes discrete steps, the steps may be conducted in any feasible order. And, as appropriate, any combination of two or more steps may be conducted simultaneously.

Also herein, the recitations of numerical ranges by endpoints include all whole or fractional numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements. That said, it should be appreciated that the dimensions provided herein are of critical importance because they enable a device that is small enough to be delivered to the required physical spaces in the body while still having enough compressive force to create an anastomosis.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

Figure 1:
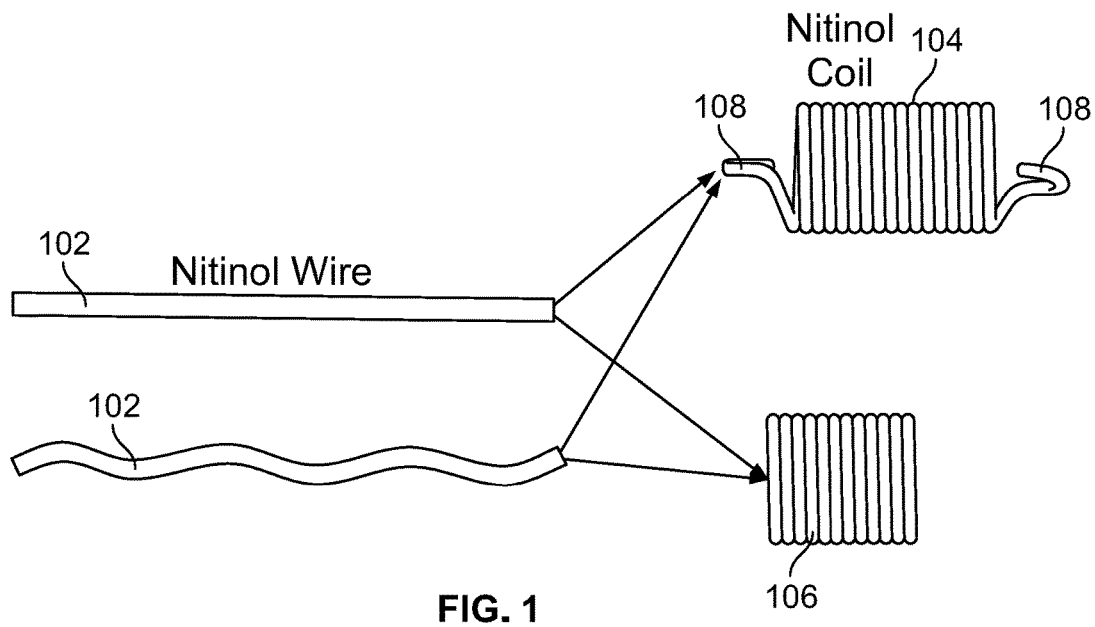
FIG. 1 illustrates a straight shape memory alloy (SMA) wire which coils within a human body, in accordance with an embodiment of the present specification.

FIG. 1 illustrates a straight SMA wire 102 which coils up within a human body, in accordance with an embodiment of the present specification. Wire 102 is made of a SMA material such as Nitinol. A shape-memory alloy, which shall be alternatively referred to as SMA, smart metal, memory metal, memory alloy, muscle wire, and/or smart alloy, is an alloy that "remembers" its original shape and that, when deformed, returns to its pre-deformed shape upon heating. NiTi alloys change from martensite to austenite upon heating. In an embodiment, the SMA wire 102 is made of a copper-aluminum-nickel alloy. In another embodiment the SMA wire 102 is made of a nickel-titanium alloy. In an embodiment, diameter of the wire 102 ranges between 0.1 to 6 mm, has a maximum strain of less than 10% in an uncoiled position and a maximum cross sectional dimension ranging from 5 mm to 60 mm in a coiled position. In an embodiment, for a 5% strain, and for wire diameters less than 0.75 mm, ranging between 0.75 mm and 1 mm, and greater than 1 mm, the diameters of the coiled up wires are less than 15 mm, between 15 mm and 20 mm, and greater than 20 mm respectively. In an embodiment, for a 10% strain, and for wire diameters of 1 mm, 1.25 mm, 1.5 mm, 1.7 mm, 2 mm and 2.5 mm the diameters of the coiled up wires are 10 mm, 12.5 mm, 15 mm, 17 mm, 20 mm and 25 mm respectively. In an embodiment, for a 6% strain, and for wire diameters of 0.6 mm, 0.7 5mm, 0.9 mm, 1.02 mm, 1.2 mm and 1.5 mm the diameters of the coiled up wires are 10 mm, 12.5 mm, 15 mm, 17 mm, 20 mm and 25 mm respectively. Further, in various embodiments, the wire 102 coils up into at least 2 loops upon delivery into a body.

$A_s$ and $A_f$ are the temperatures at which the transformation from martensite to austenite starts and finishes. Upon insertion into a human body and placement in an anastomosis site, wire 102 changes shape and coils up as 104 or 106 in response to the higher temperature of the human body relative to the room temperature. In various embodiments, the diameter of the wire 102 ranges between 0.1 mm to 10 mm and the length of the wire 102 ranges from 1 cm to 250 cm. In some embodiments, loops 108 are provided at one or more ends of the wire for attachment with a delivery catheter as explained with reference to FIGS. 23A and B. In various embodiments, the $A_f$ temperature of the wire is less than or equal to 40° C. and $A_s$ temperature of the wire is less than or equal to 37° C. In various embodiments the strain on the Nitinol wire in its martensite shape is less than or equal to 10%. In one embodiment, the coil has a circular cross-section with a radius r where the circumference of the coil is $2\pi r$ and the area of the coils is $\pi r^2$ wherein the coil creates an anastomotic opining of a radius approximately r and area $\pi r^2$. In some embodiments, the Af temperature (transition temperature) of the wire is greater than or equal to 37° C. and a mechanism for heating the wire is provided to assist in heating the wire to transform the wire from its martensite to austenite shape. In one embodiment, the mechanism for heating the wire comprises passing an electrical current through the wire. In some embodiments, the Af temperature (transition temperature) of the wire is greater than or equal to 20° C.

Figure 2:
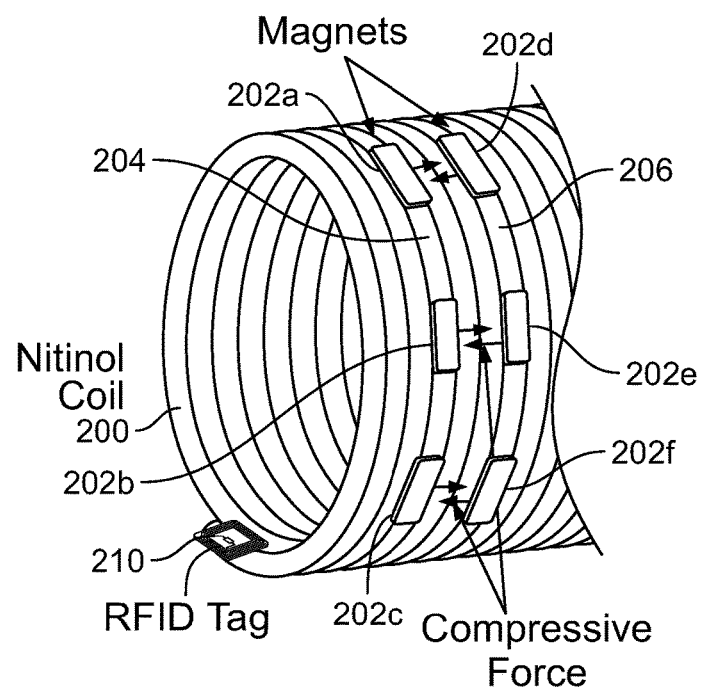
FIG. 2 illustrates a plurality of magnets threaded over loops of a SMA wire, in accordance with an embodiment of the present specification.

FIG. 2 illustrates a plurality of magnets 202a, 202b, 202c, 202d, 202e, 202f threaded through loops 204, 206 of a SMA wire, in accordance with an embodiment of the present specification. Magnets 202a, 202b, 202c, 202d, 202e, 202f are threaded through loops 204 and 206 of coil 200. In an embodiment, coil 200 is a Nitinol wire that coils up in response to temperature change. A repulsive force acts between adjacent magnets 202a, 202b and 202c which are threaded on the same loop 204, thereby maintaining a desired distance between said magnets. Similarly, a repulsive force acts between adjacent magnets 202d, 202e and 202f which are threaded on the same loop 206, thereby maintaining a desired distance between these magnets. An attractive force acts between the magnets threaded on loop 204 and the magnets on coil 206. Hence, there is attraction between the magnets 202a and 202d, between magnets 202b and 202e, and between magnets 202c and 202f. The attraction between the magnets on adjacent loops creates a compressive force 207 between loops of the coil, drawing the loops together to cut tissue between the loops and allow for anastomosis formation. In various embodiments, the compressive force ranges from 0.1 to 0.5 N and an associated pressure applied to layers of tissue caught between the loops ranges between 0.15 psi-145 psi (0.001 and 1 MPa). In an embodiment, at least two magnets are coupled with two adjacent loops of the coil 200 and the wire coils up into at least two loops. In an embodiment, the magnets are rare earth magnets covered with a biocompatible material such as gold, nickel, Teflon, parylene, copper, zinc, silicone, epoxy or titanium. In an embodiment, the coil 200 includes an RFID tag 210 to assist in the localization of the coil 200 after deployment and during anastomosis formation. Using an RFID scanner, the position of the coil can be identified, through communications with the embedded RFID tag, to determine the precise location of the coil in the patient without the need for radiation for visualization. In some embodiments, the grade of the magnet is N35 or greater.

In one embodiment, the Nitinol coil applies an amount of pressure less than or equal to 50 mm Hg (0.97 psi) on the tissue and the combined coil and magnets apply an amount of pressure greater than 50 mm Hg (0.97 psi) on the tissue. In another embodiment, the Nitinol coil applies an amount of pressure less than or equal to 80 mm Hg (1.57 psi) on the tissue and the combined coil and magnets apply an amount of pressure greater than 80 mm Hg (1.57 psi) on the tissue. In yet another embodiment, the Nitinol coil applies an amount of pressure less than or equal to 120 mm Hg (2.32 psi) on the tissue and the combined coil and magnets apply an amount of pressure greater than 120 mm Hg (2.32 psi) on the tissue. In yet another embodiment, the Nitinol coil applies an amount of pressure less than or equal to 150 mm Hg (2.90 psi) on the tissue and the combined coil and magnets apply an amount of pressure greater than 150 mm (2.90 psi) Hg on the tissue. In another embodiment, the Nitinol coil applies an amount of pressure less than or equal to 200 mm Hg (3.86) on the tissue and the combined coil and magnets apply an amount of pressure greater than 200 mm Hg (3.86) on the tissue. In an embodiment, the coil pressure at each coil tissue interface is sufficient to impede the capillary flow in the tissue by greater than 50%. In an embodiment, the coil creates a pressure of more than or equal to 20 mm Hg (0.39 psi) at more than one fourth of the circumference of coil and the pressure is relatively equally distributed among the two semicircles of each coil loop. In an embodiment, the pressure is more than or equal to 20 mm Hg (0.39 psi) at two or more points that are on the opposite sides on each coil loop.

In one of the embodiments, the majority of the compressive force, as described above, is initially provided by the SMA coil. However, as the magnets physically converge closer together, the magnetic compressive force overtakes the compressive force provided by the Nitinol coil and drives the anastomosis formation. In some embodiments, the process of anastomosis formation is accelerated by heating the coil via the passage of electrical current through the coil prior to deployment, thus damaging/coagulating or ablating the intervening tissue.

Figure 3A:
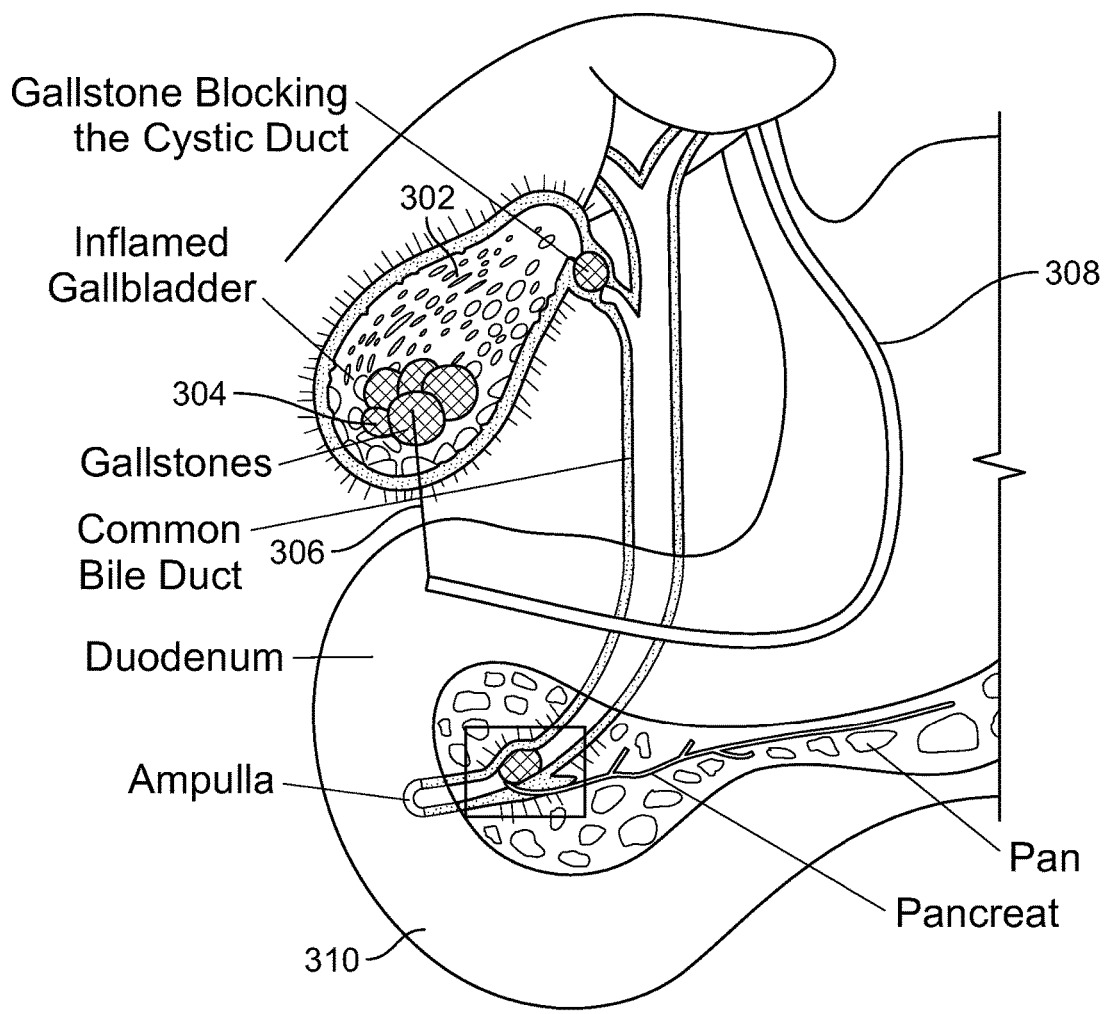
FIG. 3A illustrates a gall bladder with gallstones being punctured by using an endoscope for the placement of a SMA wire to create an anastomosis, in accordance with an embodiment of the present specification.

FIG. 3A illustrates a gall bladder 302 with cholecystitis and gallstones 304 being punctured by using a delivery catheter or needle and with an endoscope for the placement of a SMA anastomosis device to create an anastomosis, in accordance with an embodiment of the present specification. Gall bladder 302, having gall stones 304, is punctured by a delivery catheter or a needle 306 being delivered by means of an endoscope 308 inserted into a patient's duodenum 310. The catheter or needle 306 punctures a wall of the duodenum 310 and a gall bladder 302 in order to connect the gall bladder 302 with the duodenum 310 to form an anastomosis, using the devices of the present specification, for providing drainage to the gallbladder 302 and removal of the gall stones 304. The endoscope 308 in one embodiment is an echoendoscope and the puncture is made under ultrasonic visualization. The endoscope 308, in another embodiment, is a duodenoscope and the puncture is made under fluoroscopic visualization.

Figure 3B:
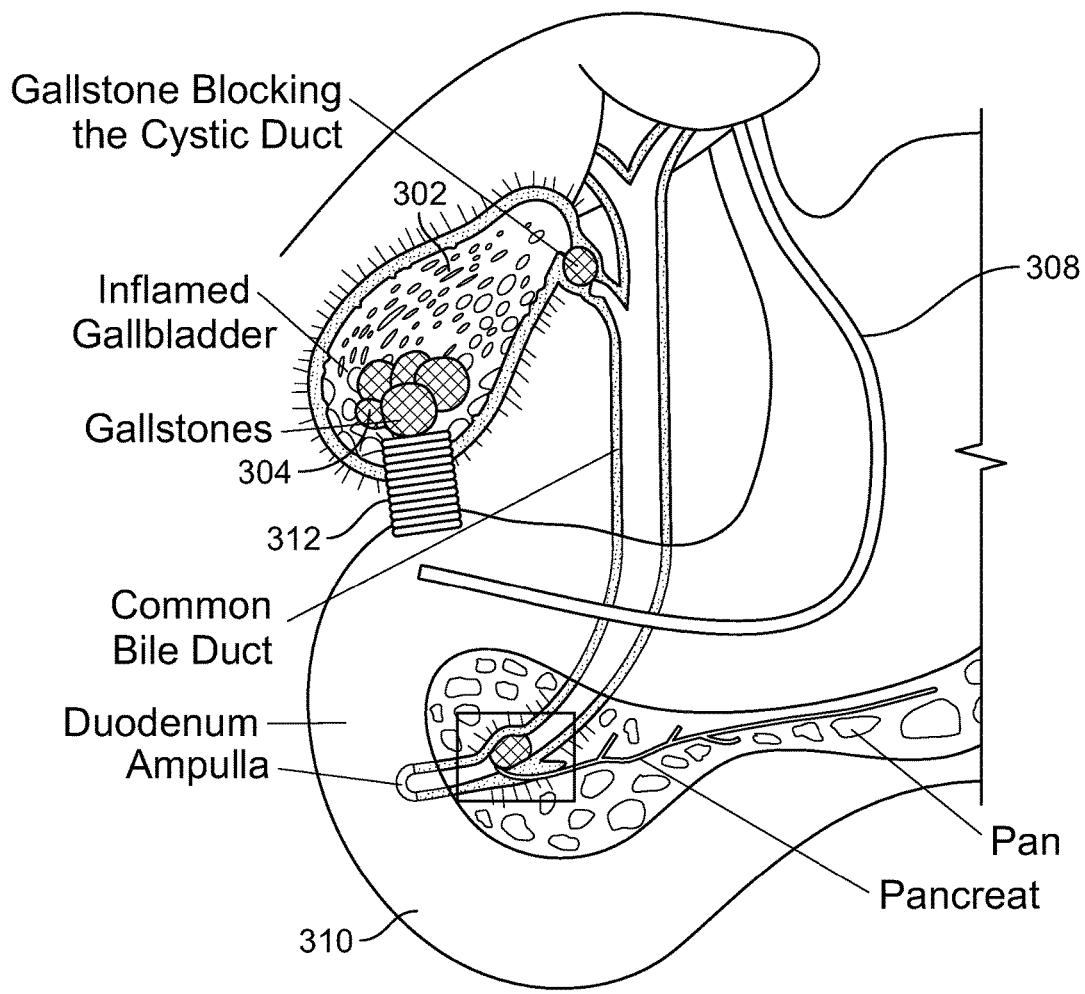
FIG. 3B illustrates a SMA coil forming an anastomosis between the gall bladder and duodenum shown in FIG. 3A, in accordance with an embodiment of the present specification.
Figure 3C:
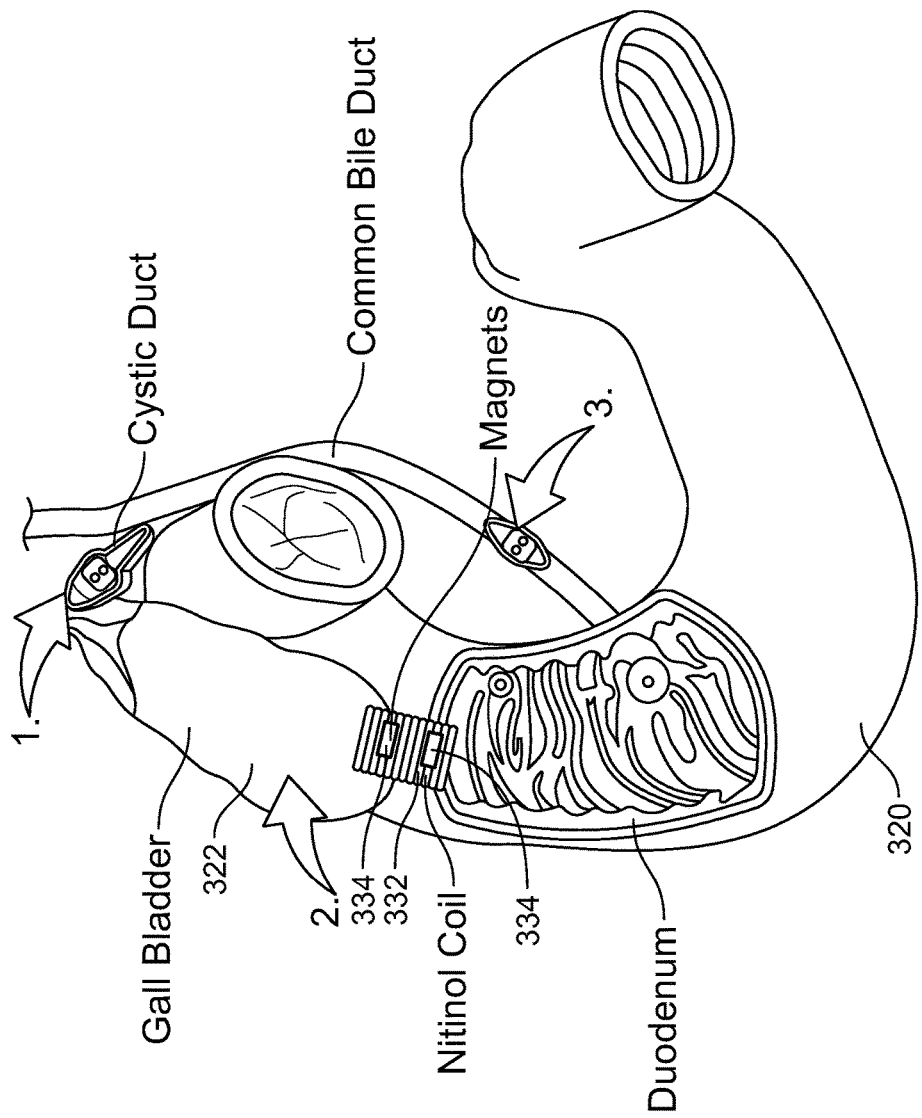
FIG. 3C illustrates a SMA coil threaded with magnets forming an anastomosis between a gall bladder and a duodenum, in accordance with another embodiment of the present specification.

FIG. 3B illustrates a SMA coil 312 deployed and forming an anastomosis between the gall bladder 302 and duodenum 310 shown in FIG. 3A, in accordance with an embodiment of the present specification. The SMA coil 312, which, in an embodiment, comprises a Nitinol wire, is delivered through the hole punctured by a catheter or needle in the gall bladder 302 wall via the endoscope 308. In response to exposure to body heat, the Nitinol wire changes shape and coils up, holding the tissue of the gall bladder 302 wall and the duodenum 310 wall in between the turns of coil 312 as shown in FIG. 3B, thereby forming an anastomosis between the gallbladder 302 and the duodenum 310. The coiling up of wire 312 causes a compressive force to act on the tissue caught between the coils, thereby cutting through the tissue to form the anastomosis. In an embodiment, magnets may be threaded in the coil 312 to further increase the compressive force, as shown in FIG. 2 and FIG. 3C. In various embodiments the anastomosis is formed over some time allowing time for neovascularization of the anastomosis resulting in a robust and stable anastomosis without significant leaks.

Figure 3D:
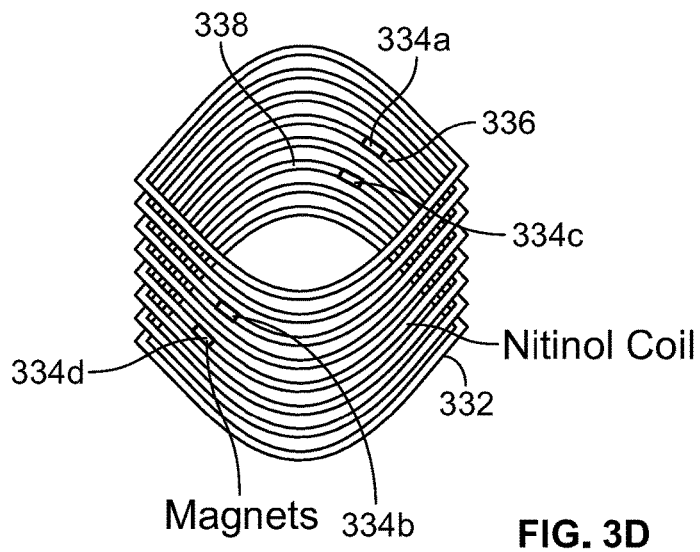
FIG. 3D is a close-up illustration of the SMA coil threaded with magnets shown in FIG. 3C, in accordance with an embodiment of the present specification.

FIG. 3C illustrates a SMA coil 332 threaded with magnets 334 forming an anastomosis between a gall bladder 322 and a duodenum 320, in accordance with another embodiment of the present specification. The SMA coil 332, which in an embodiment comprises Nitinol, is threaded with magnets 334 placed in different/adjacent coil loops. The magnets 334 placed in different coil loops attract each other, thereby further increasing the compressive force in the coil 332 and accelerating or improving the cutting of the walls of gall bladder and duodenum to form an anastomotic opening. FIG. 3D is a close-up illustration of the SMA coil 332 threaded with magnets shown in FIG. 3C, in accordance with an embodiment of the present specification. Coil 332 is threaded with magnet 334*a* and 334*b* in loop 336 and magnets 334*c* and 334*d* in loop 338. The poles of magnets 334*a* and 334*b* are arranged such that the magnets repel each other, thereby maintaining a constant pre-defined distance between each other on the loop 336. Similarly, the poles of the magnets 334*c* and 334*d* are arranged such that the magnets repel each other, thereby maintaining a constant pre-defined distance between each other on the loop 338. The poles of magnets 334*a* and 334*c* are arranged such that the magnets attract each other, thereby pulling the loops 336 and 338 of the coil 332 closer towards each other and increasing the compressive force exerted by the coil 332 on the tissue layers caught between the coil 332 loops. Similarly, a compressive force is caused by the attraction between magnets 334*b* and 334*d*. The compressive force gradually increases over time as the magnets cut through the tissue and get closer, slowly accelerating the cutting action and anastomosis formation once the two walls have had time to fuse together. This approach decreases the chances of a leak in situations where the anastomosis was performed too fast, not allowing for enough time for apposition and fusion of the two adjacent walls.

Figure 4A:
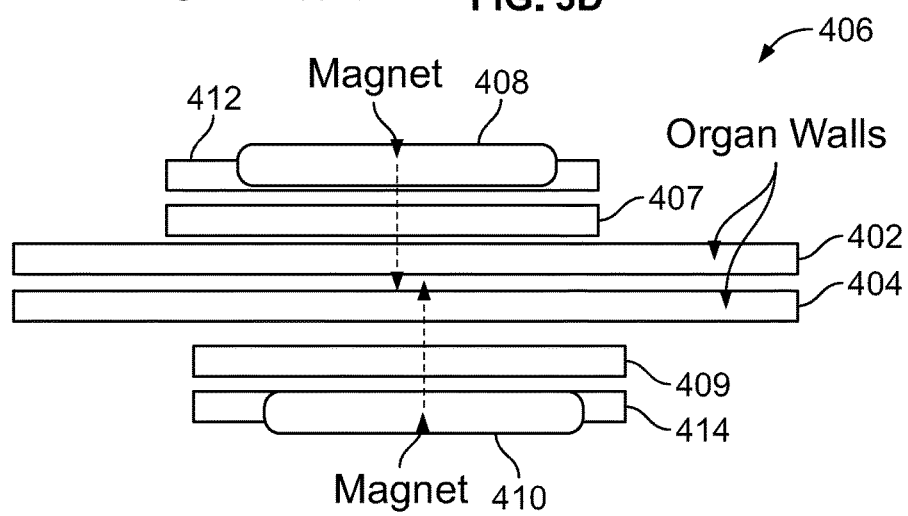
FIG. 4A illustrates a first stage of an anastomosis process, in accordance with an embodiment of the present specification.

FIG. 4A illustrates a first stage of an anastomosis process, in accordance with an embodiment of the present specification. As shown in the figure, organ walls 402 and 404 are caught between adjacent loops 407, 409 of coil 406. In an embodiment, the coil 406 is made of a SMA material, such as Nitinol, and is delivered into the organ as a straight piece of wire or an elongated relative straight coil, which, as a result of exposure to body heat, changes shape to form a coil of predetermined shape and dimension such that the adjacent organ walls are caught between the coil loops. With reference to FIG. 3A, in an embodiment, the organ wall 402 is the wall of the gall bladder 302 and the organ wall 404 is the adjoining wall of the duodenum 410. Referring to FIG. 4A, magnets 408 and 410 are coupled with loops 412 and 414 respectively of the coil 406. The poles of magnets 408 and 410 are arranged such that the magnets attract each other, thereby pulling the loops 407, 412 and 409, 414 closer towards each other and increasing the compressive force exerted by the coil 406 on the organ walls 402 and 404. The SMA wires exert relatively stable force over time while the magnets will exert a progressively increasing compressive force which accelerates as the anastomosis forms, thereby resulting in an initial fusion of the walls and later cutting through the walls once the two walls have fused. In some embodiments, the compressive surface is provided by two opposing magnets or a wire and a magnet.

Figure 4B:
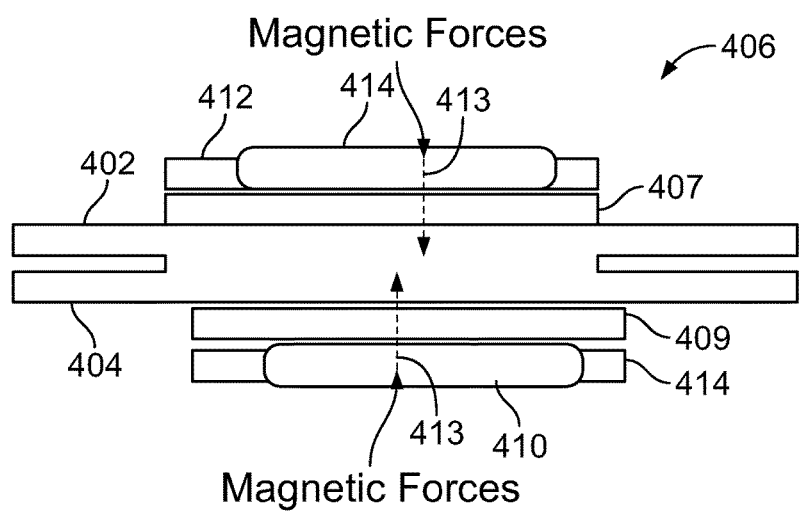
FIG. 4B illustrates a second stage of the anastomosis process shown in FIG. 4A, in accordance with an embodiment of the present specification.
Figure 4C:
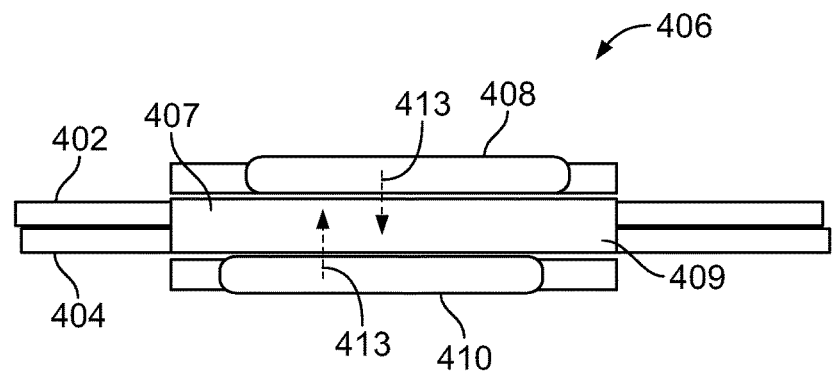
FIG. 4C illustrates a third stage of the anastomosis process shown in FIGS. 4A and 4B, in accordance with an embodiment of the present specification.
Figure 4D:
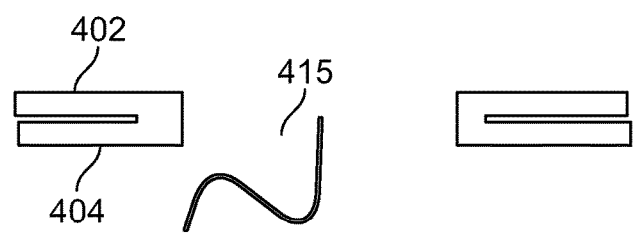
FIG. 4D illustrates formation of the anastomosis as a fourth and final stage of the anastomosis process shown in FIGS. 4A, 4B and 4C, in accordance with an embodiment of the present specification.

FIG. 4B illustrates the second stage of the anastomosis process shown in FIG. 4A, in accordance with an embodiment of the present specification. As shown in FIG. 4B, the loops 407, 412 and 409, 414 of coil 406 are pulled closer together by the magnetic forces 413 attracting magnets 408, 410 together, thereby compressing the organ walls 402 and 404 between loops 407 and 409 causing ischemia, followed by neovascularization fusing the two organ walls. FIG. 4C illustrates a third stage of the anastomosis process shown in FIGS. 4A and 4B, in accordance with an embodiment of the present specification. As shown, the compressive force of the coil 406, further enhanced due to the attractive magnetic force 413 between the magnets 408, 410, causing complete ischemia, apoptosis and ischemic necrosis of the tissue caught in the center of the coil and causes loops 407, 409 and/or the magnets 408 of the coil 406 to cut through the organ walls 402, 404. FIG. 4D illustrates formation of the anastomosis as a fourth and final stage of the anastomosis process shown in FIGS. 4A, 4B and 4C, in accordance with an embodiment of the present specification. As shown, an opening/anastomosis 415 is formed due to cutting through of organ walls 402, 404 by the coil, which then drops off and is naturally passed through without the need for an endoscopy. In one embodiment, the coil is designed to facilitate passage after cutting through the wall in either an antero-grade or retrograde direction. In another embodiment, the coil is configured to remain in the anastomosis for later removal with the use of an endoscope.

Figures 5, 6:
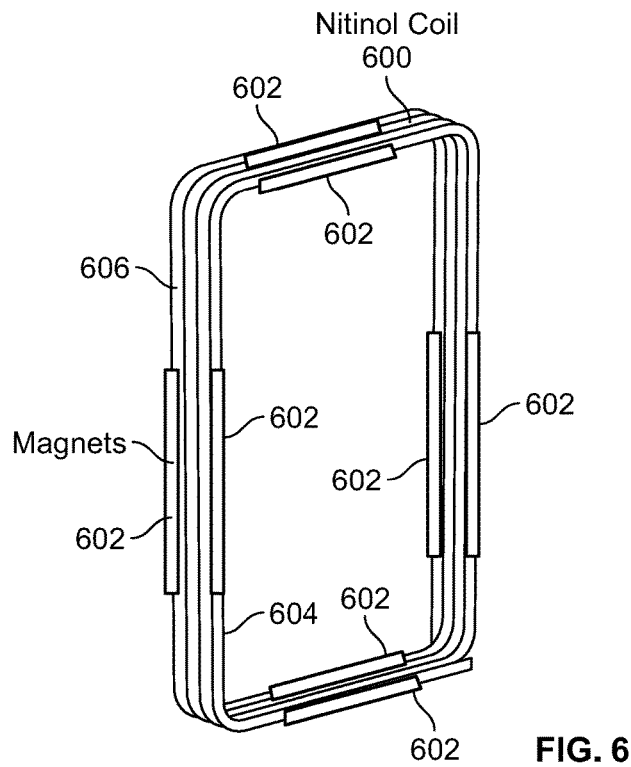
FIG. 5 illustrates a table showing exemplary dimensions of a SMA wire used for creating an anastomosis, in accordance with embodiments of the present specification.
FIG. 6 illustrates a square SMA coil coupled with magnets for creating an anastomosis, in accordance with an embodiment of the present specification.

FIG. 5 illustrates a table 500 showing exemplary dimensions of an anastomosis device used for creating an anastomosis, in accordance with embodiments of the present specification. Column 502 shows the exemplary diameters in mm of the coil, while columns 504, 506, 508, 510, and 512 show corresponding exemplary lengths in cm of a wire coiled up into 1, 2, 4, 8 and 16 loops respectively. The desired diameter of the anastomosis is between 0.5 cm and 5 cm and the desired length of the coil wire is from 3 cm to 250 cm. The preferred diameter of the anastomosis will depend on the specific organ and would be between 1-2 cm for a gall bladder, 0.5-1 cm for a bile duct, 1-2 cm for a cyst-gastrectomy or cystojejunostomy and 2-5 cm for a gastrojejunostomoy of entero-enterostomy. These are representative numbers, however, and, in practice, the diameter of the coil will be determined based on the diameter of the organ and the indication being treated. In various embodiments, the diameter of the coil is less than or equal to the diameter of the organ to be anastomosed. For example, in cases of biliary anastomosis, small bowel anastomosis, colonic anastomosis, gall bladder anastomosis, pseudocyst anastomosis, and vascular anastomosis, the diameters of the coil are less than or equal to 10 mm, less than or equal to 30 mm, less than or equal to 60 mm, less than or equal to 30 mm, less than or equal to 30 mm, and less than or equal to 25 mm respectively. The preferred number of loops will depend upon the total magnetic force needed to create the anastomosis, which in turn will depend upon the total thickness of the organ wall being anastomosed. In some embodiments, the SMA wire is delivered within a body by using an endoscope, hence, a length of the wire is required to be less than the length of the scope. In an embodiment, the length of the SMA wire is less than 250 cm, or more specifically less than 75 cm. In an embodiment where the length of the SMA wire is 75 cm, the number of coil loops that are obtained are 8. In an embodiment, where the length of the SMA wire is 100 cm, 16 coil loops having a diameter of 2 cm each or 8 coil loops having a diameter of 4 cm each are obtained. In an embodiment where the length of the SMA wire is 250 cm, 16 coil loops having a diameter of 5 cm each are obtained. Further, in various embodiments, a device having two coil loops, each comprising 8 magnets and another device having 8 coil loops, each comprising 2 magnets, each cause the same compression force on tissue caught between the respective coil loops. A size of the anastomosis required in a tissue governs the diameter of each coil loop, which in turn governs the number of magnets (and their lengths) being used in conjunction with the SMA wire causing the anastomosis. The compressive force required is a compressive pressure greater than the capillary blood flow in the tissue. In various embodiments, a pre-defined minimum pressure is required to be exerted by the SMA coil on the tissue being anastomosed, and said pressure is required to be distributed all along each coil loop. In an embodiment, said pressure is applied at least along four points on each coil loop. In other embodiments, pressure is applied along two or eight points along the circumference of each loop depending upon the dimensions of the loops.

In various embodiments, the diameter of a SMA wire being used for anastomosis ranges from 0.1 mm to 6 mm, while the pitch of the coil is less than 10 mm. In various embodiments, a maximum cross sectional diameter of a SMA coil ranges from 5 mm to 50 mm wherein the number of loops in the coil are at least two and maximum 100 and the total length of the coil wire is less than or equal to 250 cm.

The maximum strain in the wire in the straight position (martensite shape) is less than or equal to 10%. In various embodiments, the diameter of the coil will determine the diameter of the wire, with a coil less than or equal to 15 mm in diameter being best created with a wire diameter of less than or equal to 0.75 mm, a coil diameter of 15-25 mm being best created with a wire diameter of 0.75-1.0 mm and a coil diameter greater than or equal to 25 mm being best created with a wire diameter greater than or equal to 1 mm. In various embodiments, at the coil-tissue boundary interface, the magnets and SMA wire cause at least 0.15 psi, more preferably at least 1.0 psi pressure, and most preferably at least 2.50 psi pressure, to cut off blood supply in the tissue. In some embodiments, a pressure as high as 4.0 psi is applied. In various embodiments, at the coil-tissue boundary interface, the magnets and SMA wire cause pressure equal to or less than 145 psi.

In various embodiments, the magnets coupled with the SMA coil are rare-earth or permanent magnets, wherein each magnet has a maximum cross sectional length ranging from 0.2 mm to 7 mm, and a pull force ranging from 0.1 lb. to 4 lb (0.04-17.8 N). In some embodiments, a Neodymium magnet having a maximum energy product ranging from 35 to 55 is used. In some embodiments, the magnets are coated with materials such as Teflon, Parylene, silicone, epoxy, gold, titanium, nickel or copper. The ideal operating temperature of the magnet is less than 80° C. and the desired material grade for a Neodymium magnet is N30-N60. Ideally a neodymium magnet of N35-N110, N55, or a comparable rare earth magnet will be used.

In various embodiments, the shape of the anastomosis formed between two organs by using a SMA wire with or without magnets according to various embodiments of the present specification, such as those shown in FIGS. 4A-4D, is determined by the shape of the coiled SMA wire. For example, a square shaped coil would create a square shaped anastomosis. FIG. 6 illustrates a square SMA coil 600 coupled with magnets 602 for creating an anastomosis, in accordance with an embodiment of the present specification. The square shaped Nitinol coil 600 is coupled with eight magnets 602, four each on two separate loops 604 and 606 respectively. A repulsive force acts between the magnets coupled with the same loop, thereby keeping the magnets separated by a predefined distance. An attractive force acts between corresponding magnets placed on adjacent loops 604 and 606, thereby increasing the compressive force of the coil 600 and pulling loops 604 and 606 closer to each other for creating a square shaped cut in tissue.

FIG. 7A illustrates a hexagonal SMA coil 700 coupled with magnets 702 for creating an anastomosis, in accordance with an embodiment of the present specification. Hexagonally coiled SMA wire 700 coupled with magnets 702 creates a hexagonal shaped anastomosis between two organs by cutting through the organ walls hexagonally. FIG. 7B illustrates exemplary dimensions of the hexagonal SMA coil 700 shown in FIG. 7A, in accordance with an embodiment of the present specification. In an embodiment, a distance or separation 704 between two loops of the coil 700 or the pitch measures approximately 0.4 mm, a length 706 of one side of a hexagonal loop is approximately 6 mm, and a circumference 708 of the wire forming the coil is approximately 0.4 mm. In various embodiment's the pitch of the coil in its post-deployment (austenite shape) could vary from the diameter of the SMA wire to 5 times the diameter of the wire used in the coil and is always less than the diameter of the coil.

Figure 7C:
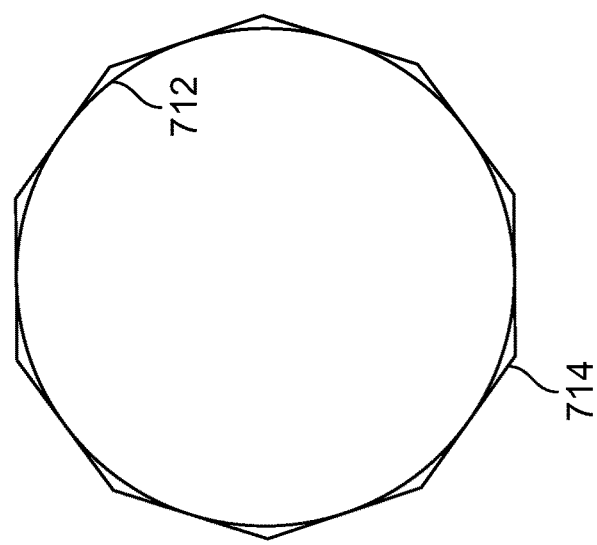
FIG. 7C illustrates a first decagonal SMA coil coupled with magnets for creating an anastomosis, in accordance with an embodiment of the present specification.
Figure 7D:
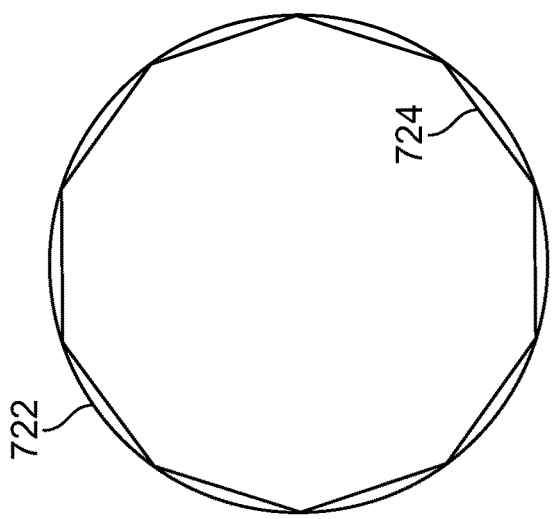
FIG. 7D illustrates a second decagonal SMA coil coupled with magnets for creating an anastomosis, in accordance with another embodiment of the present specification.

FIG. 7C illustrates a decagonal SMA coil 712 coupled with magnets 714 for creating an anastomosis, in accordance with an embodiment of the present specification. Referring to FIG. 7C, the magnets 714 are coupled to the coil 712 such that the magnets 714 are positioned predominantly on an outer surface of the coil 712. FIG. 7D illustrates a decagonal SMA coil 722 coupled with magnets 724 for creating an anastomosis, in accordance with another embodiment of the present specification. Referring to FIG. 7D, the magnets 724 are coupled to the coil 722 such that the magnets 724 are positioned predominantly on an inner surface of the coil 722. The coil in FIG. 7C is preferred in indications where it's desirable for the anastomotic device to spontaneously pass after the anastomosis is created while the coil in FIG. 7D is preferred in indications where it's desirable for the anastomotic device not to spontaneously pass after the anastomosis is created.

Figure 7E:
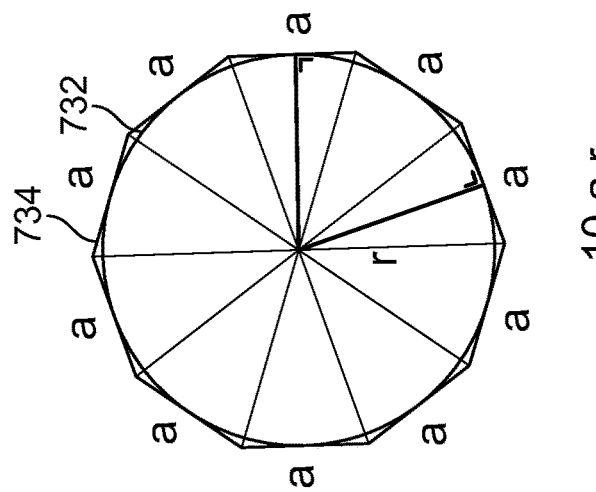
FIG. 7E illustrates exemplary dimensions of a decagonal SMA coil coupled with magnets for creating an anastomosis, in accordance with an embodiment of the present specification.

FIG. 7E illustrates exemplary dimensions of a decagonal SMA coil 732 coupled with magnets 734 for creating an anastomosis, in accordance with an embodiment of the present specification. The magnets 734 are coupled to the coil 732 such that the magnets 734 are positioned predominantly on an outer surface of the coil 732. In an embodiment, an area of the coil 732 with magnets 734, which would produce an anastomosis with a same area, is equal to $10*a*r/2$, where a is a length of each magnet 734 and r is a radius of a circle formed by the coil 732. In an embodiment, a perimeter of the coil 732 with magnets 734, which would produce an anastomosis with a same perimeter, is equal to $10*a$, where a is a length of each magnet 734.

Figure 7F:
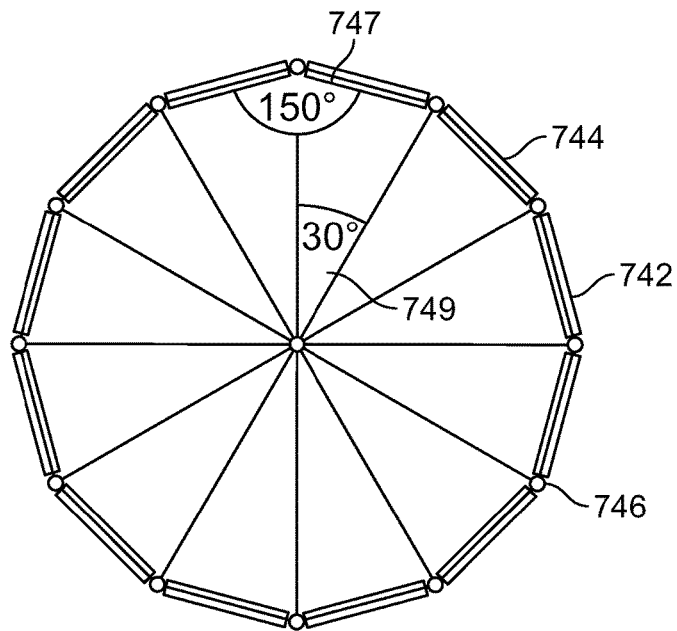
FIG. 7F illustrates a dodecagon SMA coil coupled with magnets for creating an anastomosis, in accordance with an embodiment of the present specification.

FIG. 7F illustrates a dodecagon SMA coil 742 coupled with magnets 744 for creating an anastomosis, in accordance with an embodiment of the present specification. Spacers 746 are included on the coil 742 between each pair of magnets 744. In an embodiment, spacers are included on the SMA coil for decreasing the number of magnets required for achieving a required compressive force. In an embodiment, the spacers 746 are composed of a non-ferromagnetic or biocompatible material. In various embodiments, the spacers 746 comprise silicone or Nitinol tubes or O-rings or circular balls. In an embodiment, an inner angle 747 formed between adjacent magnets 744 is equal to 150°. In an embodiment, an angle 749 formed at a center of a circle formed by the coil 742 and corresponding to each magnet 744 is equal to 30°. The non-ferromagnetic spacers prevents the magnets from sticking together while the coil is in its relatively straight, martensite pre-deployment shape and preventing it from assuming its coiled, austenite, post-deployment shape. The dimensions of the spacers are determined by the attractive forces between the two magnets and the bending force of the Nitinol coil such that the bending force of the coil is greater that than the attracting force between the ends of the magnet on the same coil allowing for the coil to achieve its pre-determined post-deployment shape. In an embodiment, an outer diameter of a spacer ring is between 25% and 300% of the outer diameter of the magnet and a length of a spacer ring is less than five times the length of the magnet.

Figure 7G:
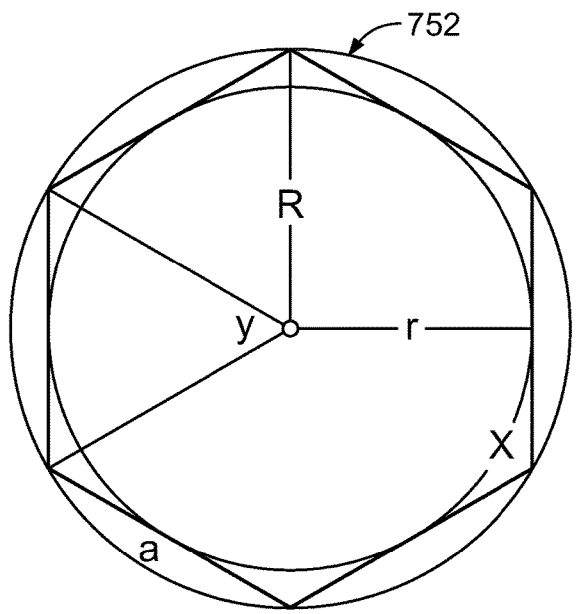
FIG. 7G illustrates exemplary dimensions of a hexagonal SMA coil in accordance with an embodiment of the present specification.
Figure 7H:
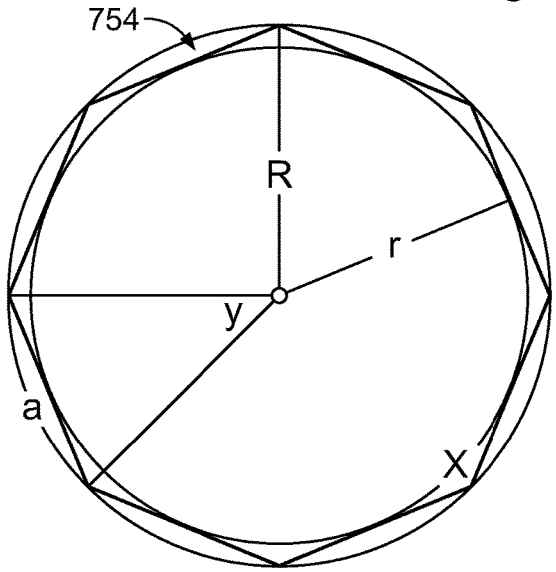
FIG. 7H illustrates exemplary dimensions of an octagonal SMA coil in accordance with an embodiment of the present specification.
Figure 7I:
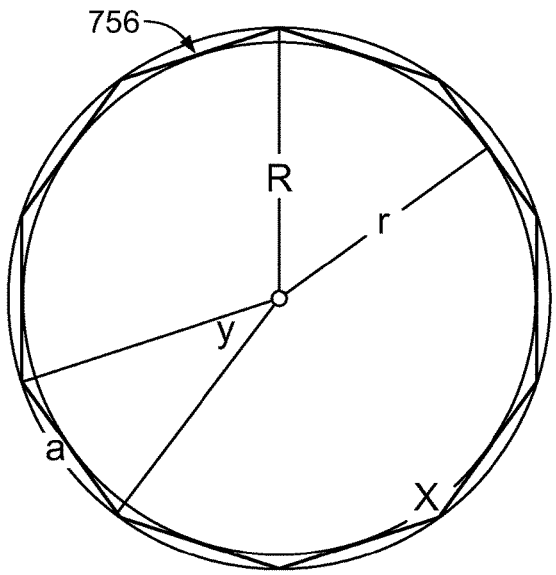
FIG. 7I illustrates exemplary dimensions of a decagonal SMA coil in accordance with an embodiment of the present specification.
Figure 7K:
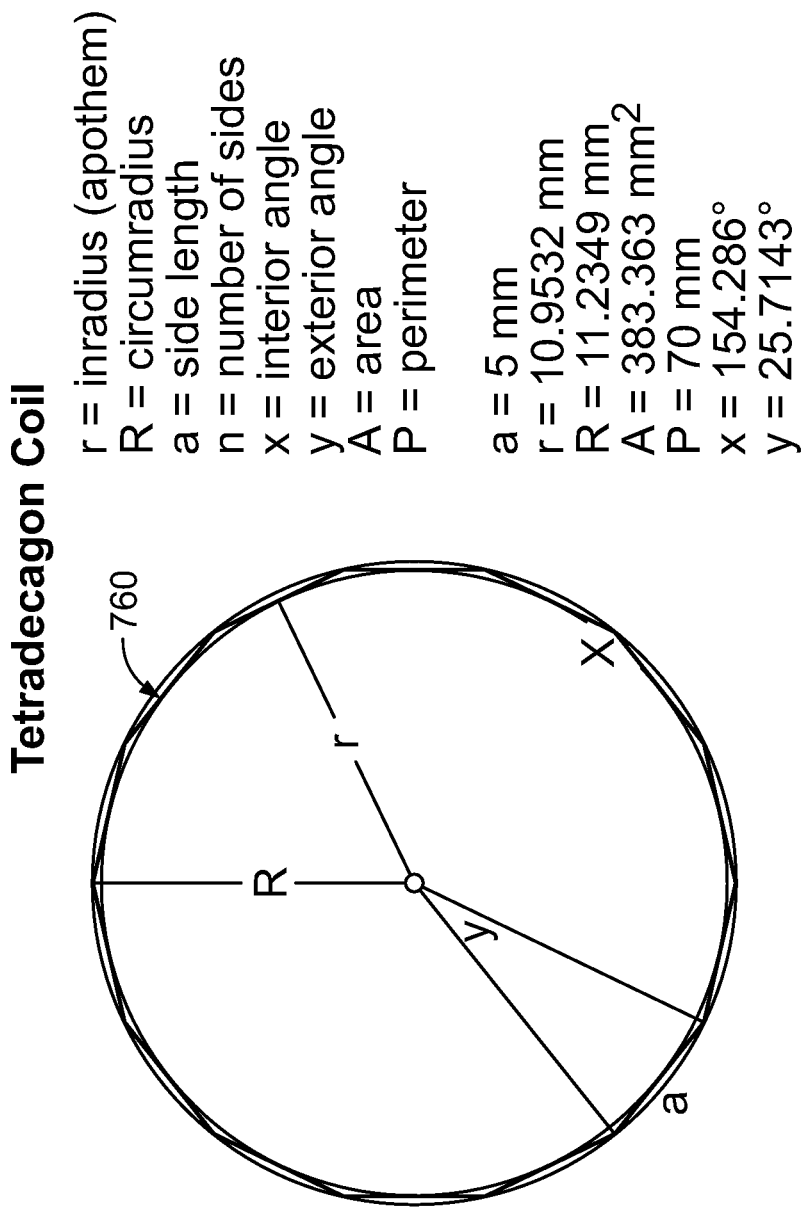
FIG. 7K illustrates exemplary dimensions of a tetradecagonal SMA coil in accordance with an embodiment of the present specification.

FIGS. 7G-7K illustrate various embodiments in which the coil has a regular polygonal cross-section that is both equiangular and equilateral where a=side length, r=in radius (apothem), R=circumradius, A=area, P=perimeter, x=interior angle, y=exterior angle and n=number of sides. The Side Length a is described by the formula $a=2r \tan(\pi/n)=2R \sin(\pi/n)$; the Inradius r is described by the formula $r=(1/2)a \cot(\pi/n)=R \cos(\pi/n)$; the circumradius R is described by the formula $R=(1/2) a \csc(\pi/n)=r \sec(n\pi/n)$; the Area A is described by the formula $A=(1/4)na^2 \cot(\pi/n)=nr^2 \tan(\pi/n)$; the Perimeter P is described by the formula $P=na$; the Interior Angle x is described by the formula $x=((n-2)\pi/n)$ radians$=(((n-2)/n) \times 180°)$ degrees and the Exterior Angle y is described by the formula $y=(2\pi/n)$ radians$=(360°/n)$ degrees. The shape and dimensions of the polygon determines the shape and dimensions of the anastomosis. In accordance with various embodiments of the present specification, FIG. 7G illustrates a hexagonal shaped SMA coil 752, FIG. 7H illustrates an octagonal shaped SMA coil 754, FIG. 7I illustrates a decagonal shaped SMA coil 756, FIG. 7J illustrates a dodecagonal shaped SMA coil 758, and FIG. 7K illustrates a tetradecagonal SMA coil 760.

Figure 8:
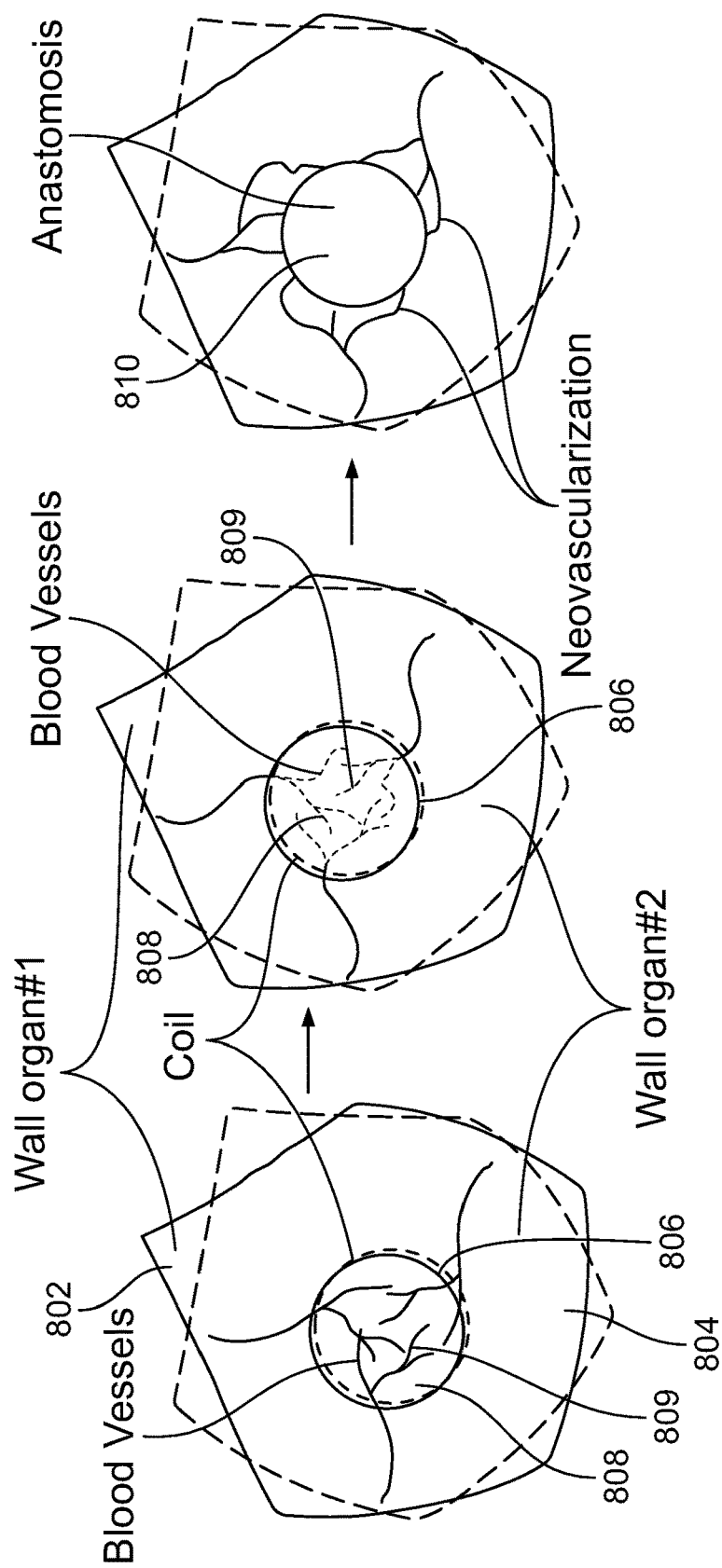
FIG. 8 illustrates a process of creating an anastomosis by using a SMA coil, in accordance with an embodiment of the present specification.

FIG. 8 illustrates a process of creating an anastomosis by using a SMA coil with or without magnets, in accordance with an embodiment of the present specification. As shown in the figure, first wall 802 of a first organ and second wall 804 of a second organ are compressed between the loops of a SMA wire 806 coiled up in a circular shape. A circular portion 808 of the tissue of both the first and the second organs is caught between the wire 806. Due to the pressure exerted by the wire 806, blood supply 809 to the portion 808 is slowly and incrementally reduced, resulting first in ischemia, inflammation, neovascularization and fusion of the adjacent walls and later as the pressure increase in ischemic damage and necrosis to the tissue 808, which eventually sloughs off, leaving a circular anastomosis 810 between the first and the second organ walls. In this embodiment, the slow and incremental increase in pressure allows for a neovascularization process occurs at the anastomosis site to ensure a healthy anastomosis.

Figure 9A:
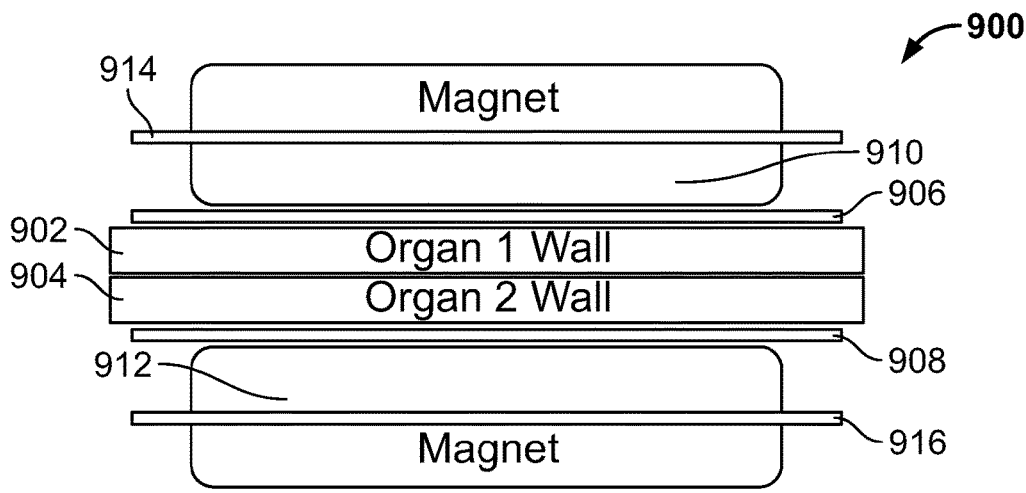
FIG. 9A illustrates walls of two organs compressed between loops of a SMA coil, in accordance with an embodiment of the present specification.
Figure 9B:
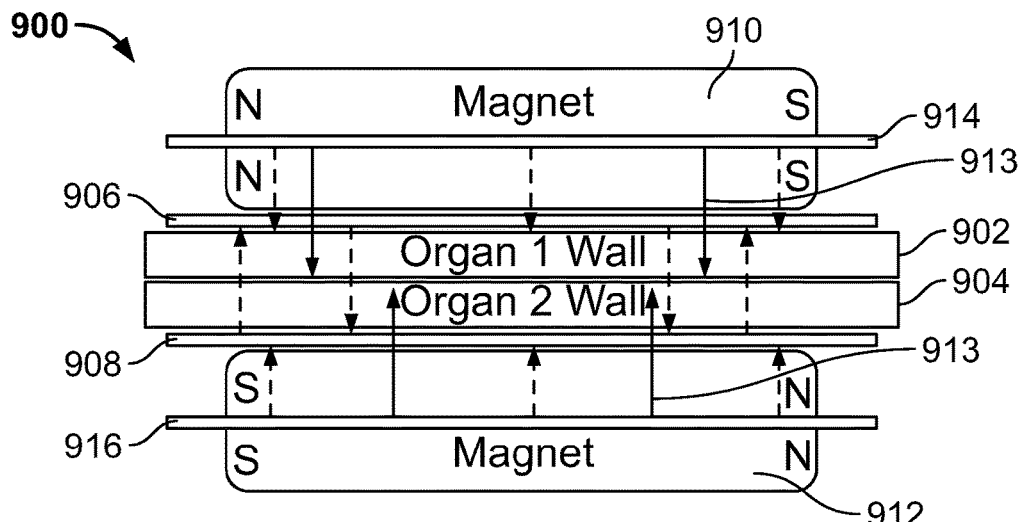
FIG. 9B illustrates walls of two organs compressed between loops of a SMA coil, the compressive force being enhanced with the use of magnets, in accordance with an embodiment of the present specification.

FIG. 9A illustrates walls 902, 904 of two organs compressed between loops 906, 908 of a SMA coil 900, in accordance with an embodiment of the present specification and the compressive force is provided by the combination of the Nitinol wires and the magnets and the cutting surface is created by the two SMA wires 906 and 908. FIG. 9B illustrates walls 902, 904 of two organs compressed between loops of a SMA coil 900, the compressive force being enhanced with the use of magnets, in accordance with an embodiment of the present specification. Referring to both FIGS. 9A and 9B, a wall 902 of a first organ and a wall 904 of a second organ are compressed between a first loop 906 and a second loop 908 of a SMA coil 900, which in an embodiment is a Nitinol wire coil. The pressure being exerted upon the organ walls 902, 904 is enhanced by the attractive force 913 between magnets 910 and 912 coupled with loops 914 and 916 respectively, of the SMA coil 900. In an embodiment, a first pressure greater than 0.19 psi (10 mmHg) is exerted by the combination of the coil and magnets upon the tissue caught in between the coil loops and the pressure incrementally increases to a pressure greater than or equal to 0.97 psi (50mm Hg) and further may increase to a pressure of 145 psi (7499 mm Hg), depending on the dimensions of the magnets and number of coils.

Figure 10:
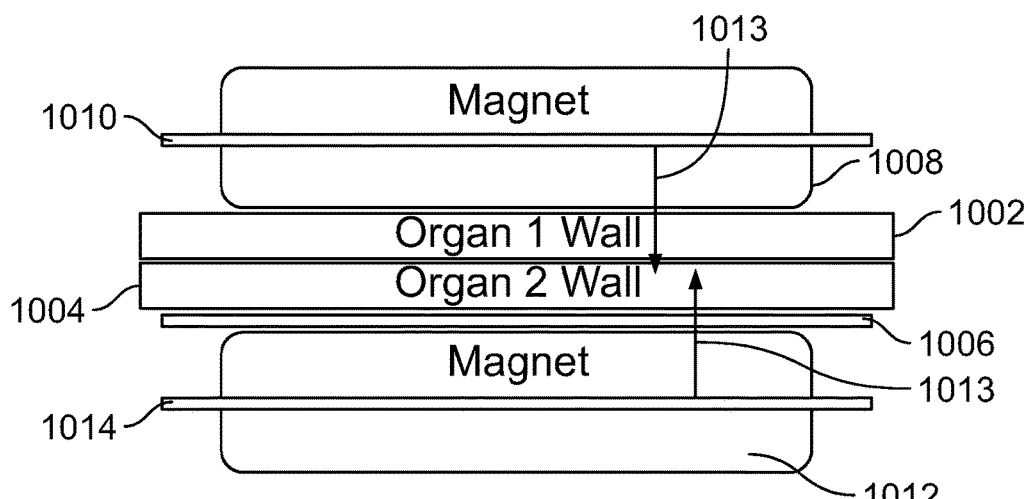
FIG. 10 illustrates walls of two organs compressed between a loop of a SMA coil and a magnet, in accordance with an embodiment of the present specification.

FIG. 10 illustrates walls 1002, 1004 of two organs compressed between a loop 1006 of a SMA coil 1000 and a magnet 1008, in accordance with an embodiment of the present specification. A wall 1002 of a first organ and a wall 1004 of a second organ are compressed between a first loop 1006 of a SMA coil 1000 and a magnet 1008 coupled with a second loop 1010 of a SMA coil. In an embodiment, the SMA coil 1000 is a Nitinol wire coil. The pressure being exerted upon the organ walls 1002, 1004 is enhanced by the attractive force 1013 between the magnet 1008 and another magnet 1012 coupled with another loop 1014 of the SMA coil 1000.

Figure 11:
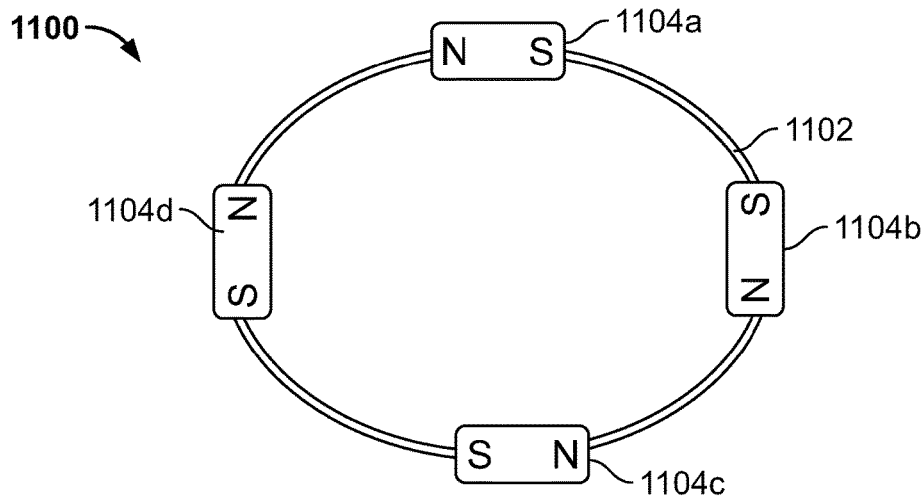
FIG. 11 illustrates a plurality of magnets coupled with a loop of a SMA coil for creating an anastomosis, in accordance with an embodiment of the present specification.
Figure 13:
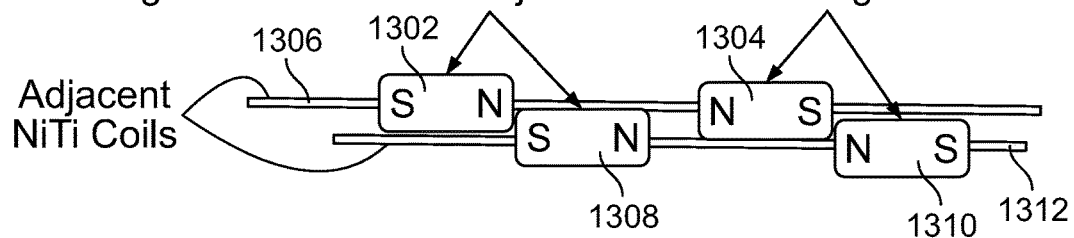
FIG. 13 illustrates placement of magnets coupled with adjacent loops of a SMA coil for creating an anastomosis, in accordance with an embodiment of the present specification.

It is important that the magnets do not attract and clump together in the pre-deployment shape interfering with the SMA coil to shape change to its pre-determined, post-deployment austenite shape. FIG. 11 illustrates a plurality of magnets 1104a, 1104b, 1104c, 1104d coupled with a loop 1102 of a SMA coil 1100 for creating an anastomosis, in accordance with an embodiment of the present specification. Magnets 1104a-1104d are arranged around a loop 1102 of a SMA coil 1100 being used for creating an anastomosis. In an embodiment, the SMA coil 1100 is made of Nitinol wire. In an embodiment, the combined length of all the magnets coupled with a SMA coil is less than half of the length of the SMA coil. In an embodiment, the magnets are coupled with the coil in a manner such that the magnets can slide over the coil (like beads in a necklace). In an embodiment, at least 50% of the adjacent magnets (such as magnets 1104a and 1104b) on each loop of the coil are arranged with like poles facing each other (as indicated by 'S' for south and 'N' for north on each magnet), creating a repulsive force between the two adjacent magnets in the same loop of the coil. This configuration is desired in situation where the anastomosis need to be created between a Nitinol wire and a magnet is as shown in FIGS. 10 and 13. In various embodiments, magnets on a single loop of coil are separated by a distance less than, equal to, or greater than a length of each of two adjacent magnets.

Figure 12:
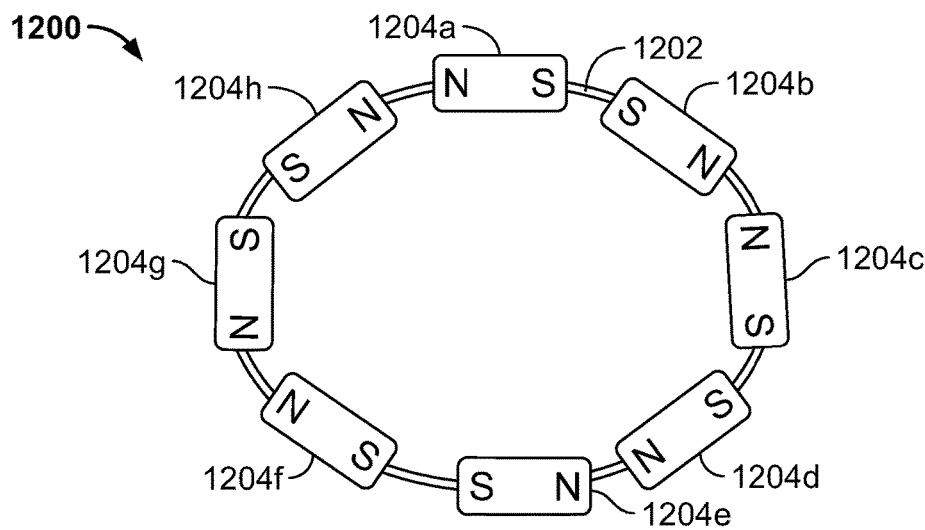
FIG. 12 illustrates a plurality of magnets coupled with a loop of a SMA coil for creating an anastomosis, in accordance with another embodiment of the present specification.

FIG. 12 illustrates a plurality of magnets 1204a, 1204b, 1204c, 1204d, 1204e, 1204f, 1204g, 1204h coupled with a loop 1202 of a SMA coil 1200 for creating an anastomosis, in accordance with another embodiment of the present specification. Magnets 1204a-1204h are arranged around a loop 1202 of a SMA coil 1200 being used for creating an anastomosis. In an embodiment, the SMA coil 1200 is made of Nitinol wire. In an embodiment, the combined length of all the magnets coupled with a SMA coil is greater than or equal to 50% but less than 99% of the length of the SMA coil. In an embodiment, the magnets 1204a-1204h are coupled with the coil loop 1202 in a manner such that the magnets can slide over the coil (like beads in a necklace). In an embodiment, at least 50% of the adjacent magnets (such as magnets 1204a and 1204b) on each loop of the coil are arranged with like poles facing each other (as indicated by 'S' for south and 'N' for north on each magnet), thereby creating a repulsive force between the two adjacent magnets in the same loop of the coil. It is important that the magnets do not clump together such that they would significantly interfere with the functionality of the Nitinol coil. It is also important that the repulsive forces between the magnets do not overpower the coil and significantly interfere with the functionality of the Nitinol coil. In some embodiments, an axis defining the direction of magnetic attraction between magnets on adjacent loops of the coil is perpendicular to a long axis of each magnet. In some embodiments, an axis defining the direction of magnetic attraction between magnets on adjacent loops of the coil is perpendicular to an axis extending through the center of the coil.

FIG. 13 illustrates placement of magnets 1302, 1304, 1308, 1310 coupled with adjacent loops 1306, 1312 of a SMA coil for creating an anastomosis, in accordance with an embodiment of the present specification. As shown, adjacent magnets 1302 and 1304 on wire loop 1306 are held at a distance greater than the length of each of the magnets. Similarly, adjacent magnets 1308 and 1310 on the adjacent wire loop 1312 are held at a distance greater than the length of each of the magnets, thereby allowing for a magnet 1308 to slide and occupy a position that is in between the magnets 1302 and 1304, such that opposite poles of the magnets 1308 and 1302 are aligned. This generates pressure between the magnets on the adjacent wire loops, which in turn assists the anastomosis process as explained earlier with respect to FIG. 10.

FIG. 14A illustrates an exemplary SMA wire 1400 coupled with magnets 1408, 1408a, 1408b, 1408c, 1408d prior to deployment in a body for creating an anastomosis, in accordance with an embodiment of the present specification. FIG. 14B illustrates the exemplary SMA wire 1400 coupled with magnets 1408 shown in FIG. 14A in a mid-deployment stage, in accordance with an embodiment of the present specification. FIG. 14C illustrates the exemplary SMA wire 1400 coupled with magnets 1408 shown in FIG. 14A after deployment in a body for creating an anastomosis, in accordance with an embodiment of the present specification. Referring to FIG. 14A, prior to deployment, SMA wire 1400 is straight and divided into at least three sections 1402, 1404 and 1406. Sections 1402 and 1406 are coupled with a plurality of magnets 1408, 1408a, 1408b, 1408c, 1408d such that positions of first magnets 1408a, 1408c and last magnets 1408b, 1408d of sections 1402 and 1404 respectively, are fixed and immovable. Remaining magnets 1408 of each section are movable/slidable in the space between the first and last magnets of each section. As shown, no magnets are provided on section 1404. Referring to FIG. 14B, SMA wire 1400 begins to coil up upon coming in contact with body heat. Referring to FIG. 14C, SMA wire 1400 forms a tight coil, cutting through tissue caught between the coil loops, with the cutting force being further strengthened due to attractive forces between magnets placed on adjacent loop sections 1402 and 1406. The mechanism of this anastomosis is shown in FIGS. 9A and 9B.

Figure 14D:
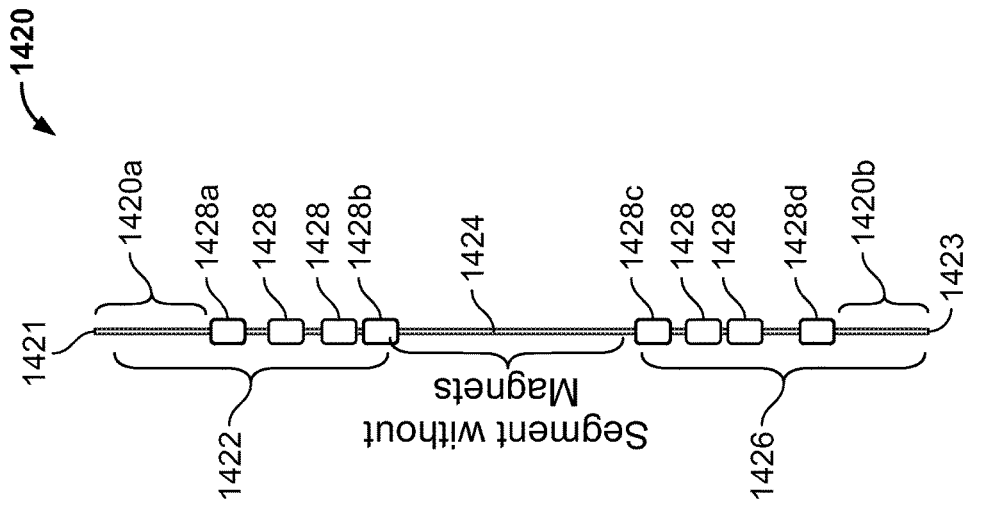
FIG. 14D illustrates an exemplary SMA wire coupled with magnets prior to deployment in a body for creating an anastomosis, in accordance with another embodiment of the present specification.
Figure 14C:
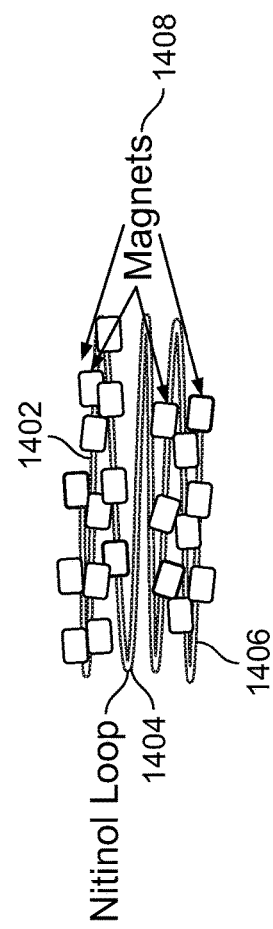
FIG. 14C illustrates the exemplary SMA wire coupled with magnets shown in FIG. 14A after deployment in a body for creating an anastomosis, in accordance with an embodiment of the present specification.

FIG. 14D illustrates an exemplary SMA wire 1420 coupled with magnets 1428, 1428a, 1428b, 1428c, 1428d prior to deployment in a body for creating an anastomosis, in accordance with another embodiment of the present specification. Prior to deployment, SMA wire 1420 is straight and divided into at least three sections 1422, 1424 and 1426. Sections 1422 and 1426 are coupled with a plurality of magnets 1428, 1428a, 1428b, 1428c, 1428d such that positions of first magnets 1428a, 1428c and last magnets 1428b, 1428d of sections 1422 and 1424 respectively, are fixed and immovable. Remaining magnets 1428 of each section are movable/slidable in the space between the first and last magnets of each section. As shown, no magnets are provided on section 1424. In addition, a first portion 1420a of the wire 1420, extending from a first end 1421 of the wire 1420 to magnet 1428a, and a second portion 1420b of the wire 1420, extending from a second end 1423 of the wire 1420 to magnet 1428d, include no magnets. In various embodiments, the portions 1420a, 1420b of bare wire are greater than or equal in length to one half of the circumference of one of the coil loops. The length of the bare segment in the middle of the device is also greater than or equal to one-half the circumference of the one of the coil loops of the coil depicted in FIG. 14F. The advantage of the bare portions at the end is that the SMA coil shapes better (more round) and consistently (under the influence of magnetic forces) if a loop has already formed which forces the following loops to shape. This is a result of the strain inherent in the wire.

Figure 14F:
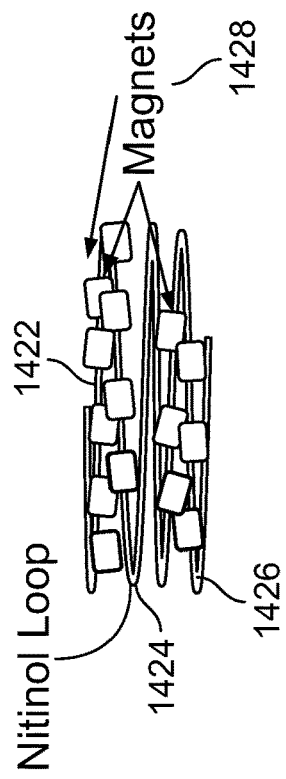
FIG. 14F illustrates the exemplary SMA wire coupled with magnets shown in FIG. 14D after deployment in a body for creating an anastomosis, in accordance with an embodiment of the present specification.
Figure 14E:
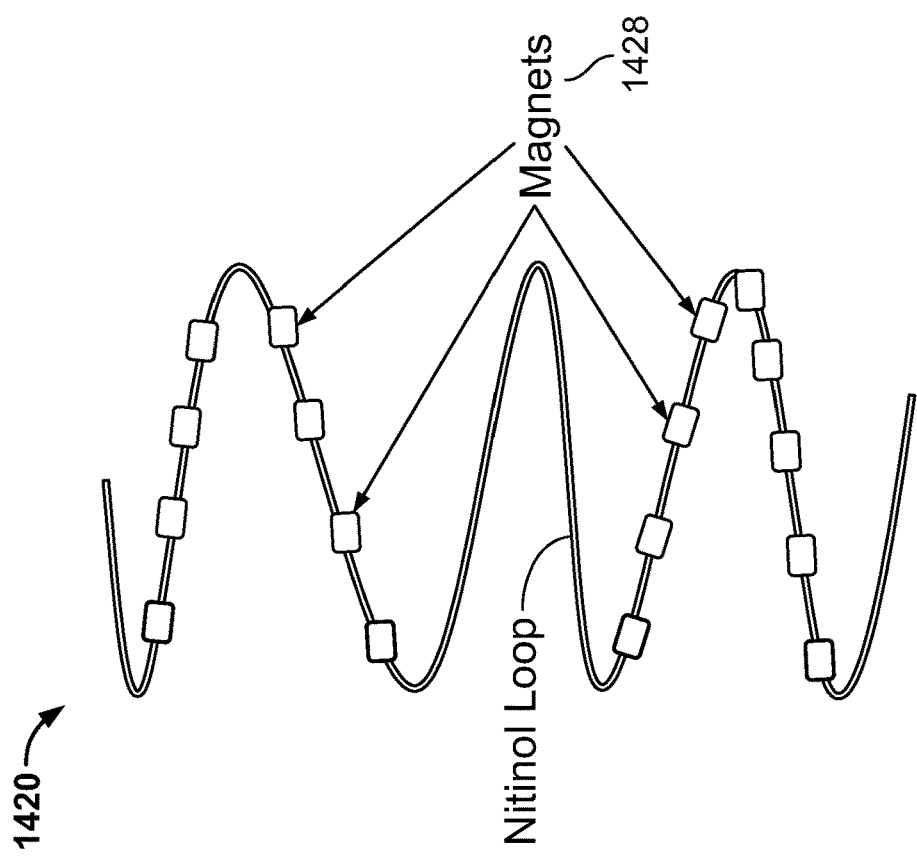
FIG. 14E illustrates the exemplary SMA wire coupled with magnets shown in FIG. 14D in a mid-deployment stage, in accordance with an embodiment of the present specification.

FIG. 14E illustrates the exemplary SMA wire 1420 coupled with magnets 1428 shown in FIG. 14D in a mid-deployment stage, in accordance with an embodiment of the present specification. FIG. 14F illustrates the exemplary SMA wire 1420 coupled with magnets 1428 shown in FIG. 14D after deployment in a body for creating an anastomosis, in accordance with an embodiment of the present specification. Referring to FIG. 14E, SMA wire 1420 begins to coil up upon coming in contact with body heat. Referring to FIG. 14F, SMA wire 1420 forms a tight coil, cutting through tissue caught between the coil loops, with the cutting force being further strengthened due to attractive forces between magnets placed on adjacent loop sections 1422 and 1426. The mechanism of this anastomosis is shown in FIGS. 9A and 9B.

FIG. 15A illustrates an exemplary SMA wire 1500 coupled with magnets 1502, 1502a, 1502b prior to deployment in a body for creating an anastomosis, in accordance with another embodiment of the present specification. FIG. 15B illustrates the exemplary SMA wire 1500 coupled with magnets 1502, 1502a, 1502b shown in FIG. 15A in a mid-deployment stage, in accordance with an embodiment of the present specification. FIG. 15C illustrates the exemplary SMA wire 1500 coupled with magnets 1502 shown in FIG. 15A after deployment in a body for creating an anastomosis, in accordance with an embodiment of the present specification. Referring to FIG. 15A, prior to deployment, SMA wire 1500 is straight and is coupled with a plurality of magnets 1502, 1502a, 1502b such that positions of a first magnet 1502a, and a last magnet 1502b in the series of magnets 1502 are fixed and immovable. Remaining magnets 1502 are movable/slidable in the space between the first and last magnets 1502a, 1502b. Referring to FIG. 15B, SMA wire 1500 begins to coil up upon coming in contact with body heat. Referring to FIG. 15C, SMA wire 1500 forms a tight coil, cutting through tissue caught between the coil loops, with the cutting force being further strengthened due to attractive forces between magnets 1502 placed on adjacent loops of coil 1500. The mechanism of the anastomosis is shown in FIG. 10. In certain embodiments the two cutting surfaces can be provided by two magnets as shown in FIG. 17. In some embodiments the movement of magnets 1502a and 1502b can be restricted by stoppers at the end, thereby preventing the end magnets from sliding off the SMA coil.

Figure 15D:
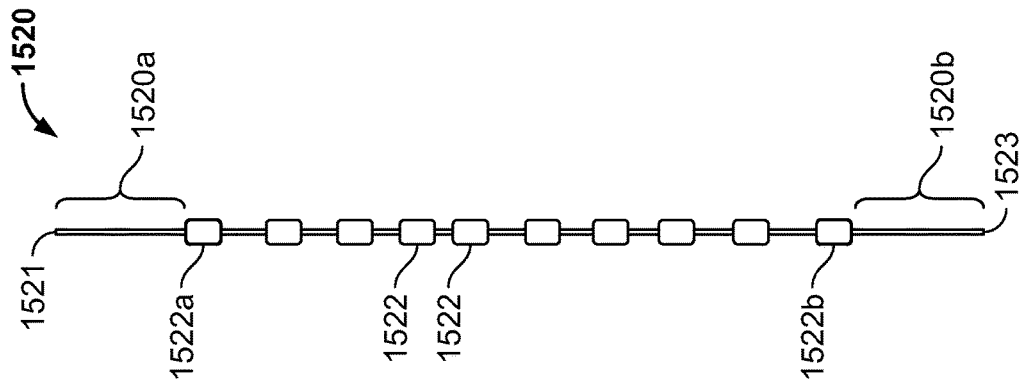
FIG. 15D illustrates an exemplary SMA wire coupled with magnets prior to deployment in a body for creating an anastomosis, in accordance with yet another embodiment of the present specification.
Figure 15C:
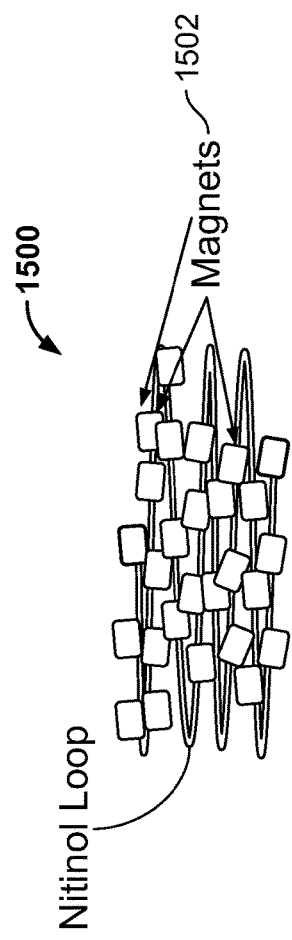
FIG. 15C illustrates the exemplary SMA wire coupled with magnets shown in FIG. 15A after deployment in a body for creating an anastomosis, in accordance with an embodiment of the present specification.

FIG. 15D illustrates an exemplary SMA wire 1520 coupled with magnets 1522, 1522a, 1522b prior to deployment in a body for creating an anastomosis, in accordance with yet another embodiment of the present specification. Prior to deployment, SMA wire 1520 is straight and is coupled with a plurality of magnets 1522, 1522a, 1522b such that positions of a first magnet 1522a, and a last magnet 1522b in the series of magnets 1502 are fixed and immovable. Remaining magnets 1522 are movable/slidable in the space between the first and last magnets 1522a, 1522b. A first portion 1520a of the wire 1520, extending from a first end 1521 of the wire 1520 to magnet 1522a, and a second portion 1520b of the wire 1520, extending from a second end 1523 of the wire 1520 to magnet 1522d, include no magnets. In various embodiments, the portions 1520a, 1520b of bare wire are greater than or equal in length to one half of the circumference of one of the coil loops. The length of the bare segment in the middle of the device is also greater than or equal to one-half the circumference of the one of the coil loops of the coil depicted in FIG. 15F. The advantage of the bare portions at the end is that the SMA coil shapes better (more round) and consistently (under the influence of magnetic forces) if a loop has already formed which forces the following loops to shape. This is a result of the strain inherent in the wire.

Figure 15F:
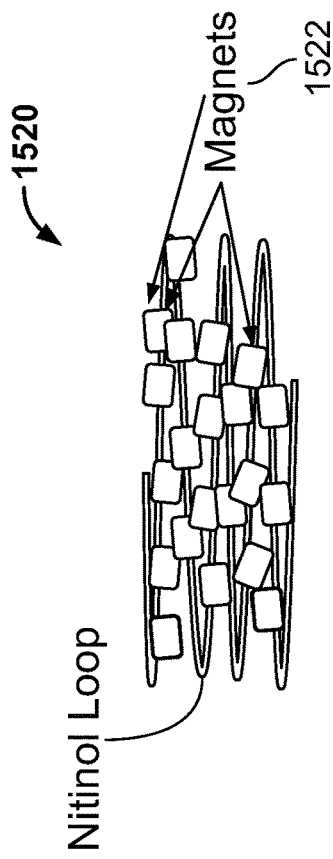
FIG. 15F illustrates the exemplary SMA wire coupled with magnets shown in FIG. 15D after deployment in a body for creating an anastomosis, in accordance with an embodiment of the present specification.
Figure 15E:
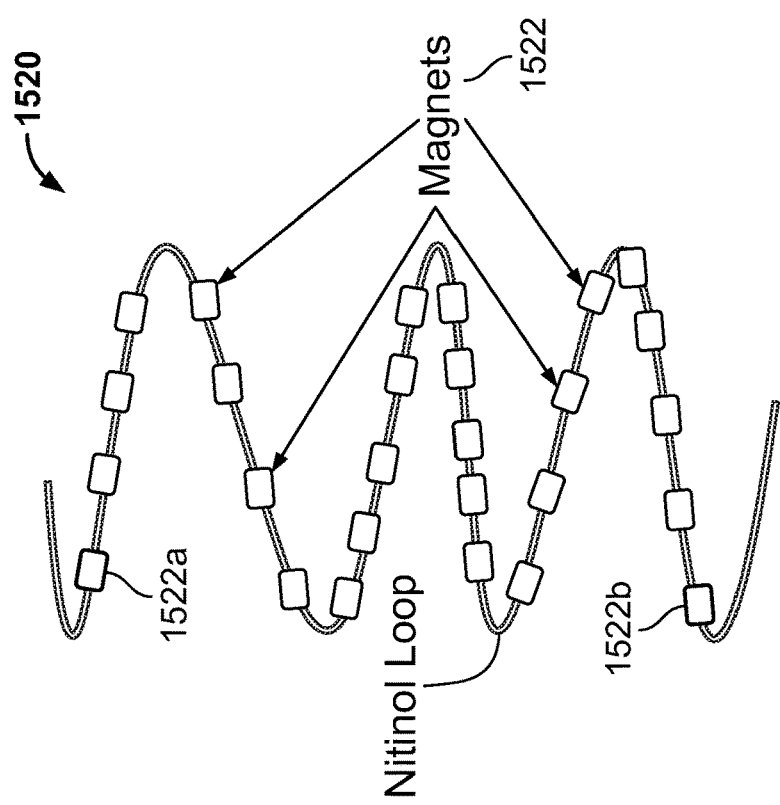
FIG. 15E illustrates the exemplary SMA wire coupled with magnets shown in FIG. 15D in a mid-deployment stage, in accordance with an embodiment of the present specification.

FIG. 15E illustrates the exemplary SMA wire 1520 coupled with magnets 1522, 1522a, 1522b shown in FIG. 15D in a mid-deployment stage, in accordance with an embodiment of the present specification. FIG. 15F illustrates the exemplary SMA wire 1520 coupled with magnets 1522 shown in FIG. 15D after deployment in a body for creating an anastomosis, in accordance with an embodiment of the present specification. Referring to FIG. 15E, SMA wire 1520 begins to coil up upon coming in contact with body heat. Referring to FIG. 15F, SMA wire 1520 forms a tight coil, cutting through tissue caught between the coil loops, with the cutting force being further strengthened due to attractive forces between magnets 1522 placed on adjacent loops of coil 1502. The mechanism of the anastomosis is shown in FIGS. 9A and 9B. In some embodiments, the two cutting surfaces can be provided by two magnets as shown in FIG. 17A. In some embodiments, the movement of magnets 1522a and 1522b is restricted by stoppers at the end, thereby preventing the end magnets from sliding off the SMA coil.

Figure 15G:
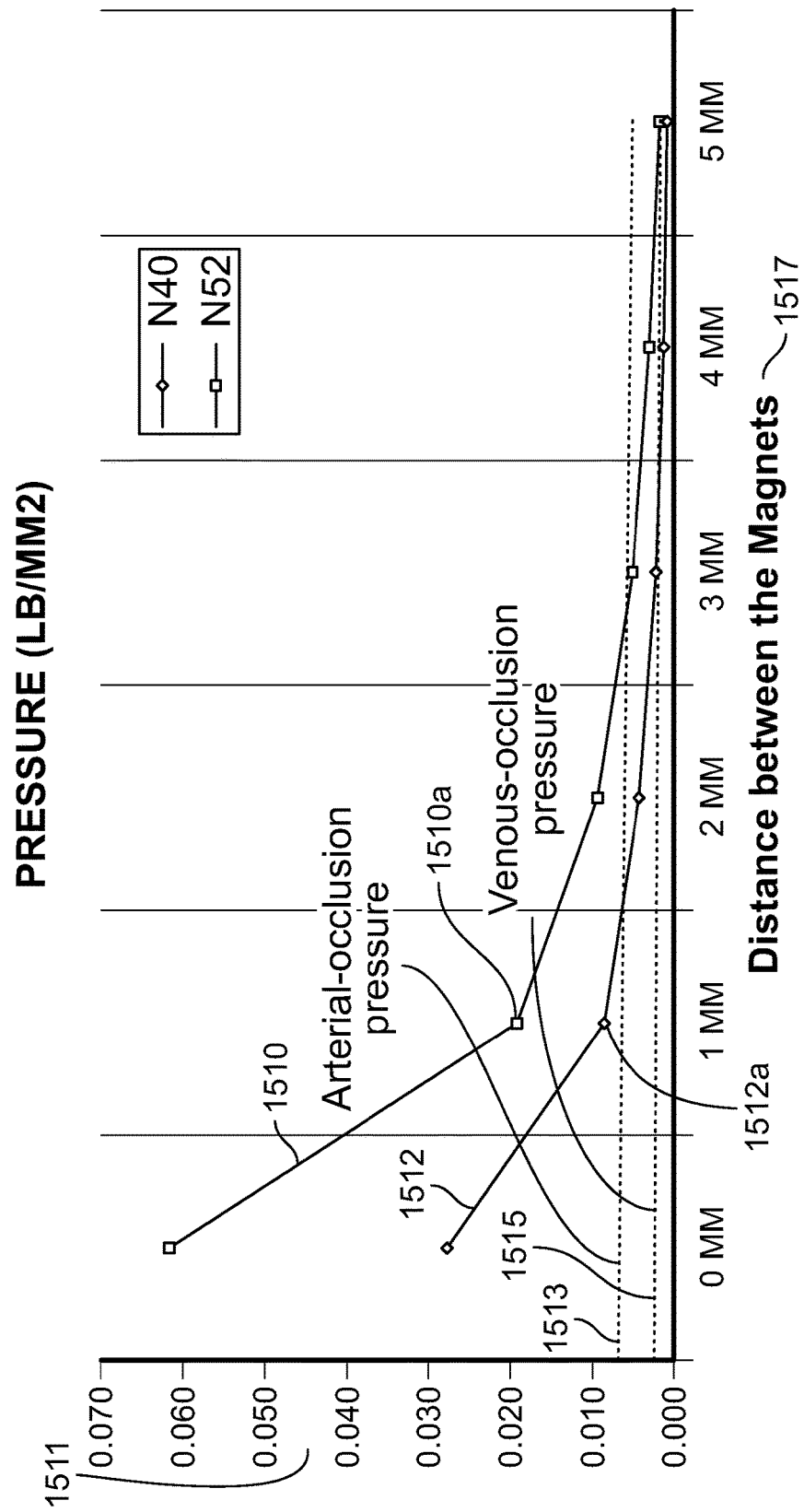
FIG. 15G is a graph illustrating the pressure exerted on body tissues by loops of a coil as the distance between magnets on the coil decreases, in accordance with an embodiment of the present specification.

FIG. 15G is a graph illustrating the pressure 1511 exerted on body tissues by loops of a coil as the distance 1517 between magnets on the coil decreases, in accordance with an embodiment of the present specification. A first curve 1510 represents the pressure exerted by a coil having N52 Neodymium magnets. A second curve 1512 represents the pressure exerted by a coil having N40 Neodymium magnets. The pressure 1511 exerted by the loops of coil represented by both curves 1510, 1512 increases as the distance 1517 between the magnets decreases, particularly at distances less than 2 mm. At a distance greater than or equal to 5 mm the anastomotic device causes occlusion of the capillary blood flow without occluding the arterial or venous blood flow, setting low level inflammation and fibrosis and causing fusion between the walls of two adjacent organs. Once the distance 1517 becomes 1 mm or less, the pressure exerted by both curves 1510, 1512 is greater than arterial-occlusion pressure 1513 and venous-occlusion pressure 1515, as depicted by points 1510a and 1512a on curves 1510 and 1512 respectively. Therefore, once the distance 1517 is 1 mm or less, the pressure 1511 exerted by the loops of the coil is great enough to cause occlusion of all blood vessels in the body tissue caught between said loops, thereby causing ischemic damage, necrosis of the tissue and leading to an anastomosis formation, the dimension of which approximates the dimensions of the Nitinol loop. This slow increase in pressure on the tissue allows for neovascularization, fusion of the adjacent tissue walls, and formation of a healthy anastomosis without the rate of anastomotic leaks typically seen with surgical anastomosis.

FIG. 16A illustrates an exemplary round shaped SMA coil 1602 used for creating an anastomosis, in accordance with an embodiment of the present specification. Coil 1602 comprises a plurality of round shaped loops 1604. FIG. 16B illustrates an exemplary round shaped SMA coil 1606 having a cutting edge 1610, used for creating an anastomosis, in accordance with an embodiment of the present specification. Coil 1606 comprises a plurality of round shaped loops 1608. One of the loops 1608 is provided with a pointed/sharp cutting edge 1610 for cutting through tissue compressed between the loops of the coil. FIG. 16C illustrates an exemplary square shaped SMA coil 1612 used for creating an anastomosis, in accordance with an embodiment of the present specification. Coil 1612 comprises a plurality of square shaped loops 1614. The sharp edges of the square loop provide for the cutting surface.

FIG. 17A illustrates an exemplary device 1700 comprising round shaped magnets 1702 coupled with a SMA coil used for creating an anastomosis, in accordance with an embodiment of the present specification. Round shaped magnets 1702 are each coupled with coil loops 1704 for creating an anastomosis when deployed in a body. FIG. 17B illustrates an exemplary device 1705 comprising round shaped magnets 1706 coupled with a SMA coil used for anastomosis, wherein at least one magnet comprises a cutting edge 1710, in accordance with an embodiment of the present specification. As shown, round shaped magnets 1706 are each coupled with coil lops 1708 for creating an anastomosis when deployed in a body. At least one of the magnets 1706 is provided with a pointed/sharp protrusion 1710 designed to interlock with other magnets/coil loops and enhance the cutting through the tissue compressed between the loops of the coil and magnets.

FIG. 17C illustrates an exemplary device 1711 comprising square shaped magnets 1712 coupled with a SMA coil with serrated edges, used for creating an anastomosis, in accordance with an embodiment of the present specification. Square shaped magnets 1712 are arranged around coil loops 1714 having serrated edges to prevent spinning action of the magnets 1712. In an embodiment, the magnets 1712 are arranged as shown in FIG. 17C such that edges 1716 of the magnets slide over each other, as the SMA wire changes shape and coils up, and is further enhanced by the attractive forces between the magnetic surfaces thereby creating a cutting action/force.

FIG. 17D illustrates an exemplary device 1721 comprising square shaped magnets 1718 coupled with a SMA coil used for creating an anastomosis, in accordance with an embodiment of the present specification. Square shaped magnets 1718 are each coupled with coil loops 1720 for creating an anastomosis when deployed in a body. FIG. 17E illustrates an exemplary device 1725 comprising square shaped magnets 1722 coupled with a SMA coil used for creating an anastomosis, wherein at least one magnet comprises a cutting edge 1726, in accordance with an embodiment of the present specification. As shown, square shaped magnets 1722 are each coupled with coil loops 1724 for creating an anastomosis when deployed in a body. At least one of the magnets 1722 is provided with a pointed/sharp protrusion 1726 designed to interlock with other magnets/coil loops and enhance the cutting through the tissue compressed between the loops of the coil and magnets.

Figure 17G:
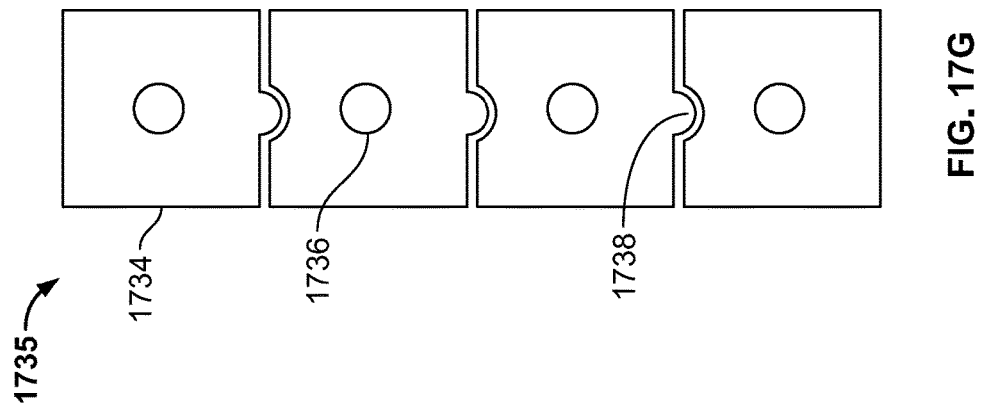
FIG. 17G illustrates a cross sectional view of an exemplary device comprising square shaped magnets coupled with a SMA coil used for creating an anastomosis, wherein the magnets comprise a protruding edge to assist with cutting, in accordance with an embodiment of the present specification.
Figure 17F:
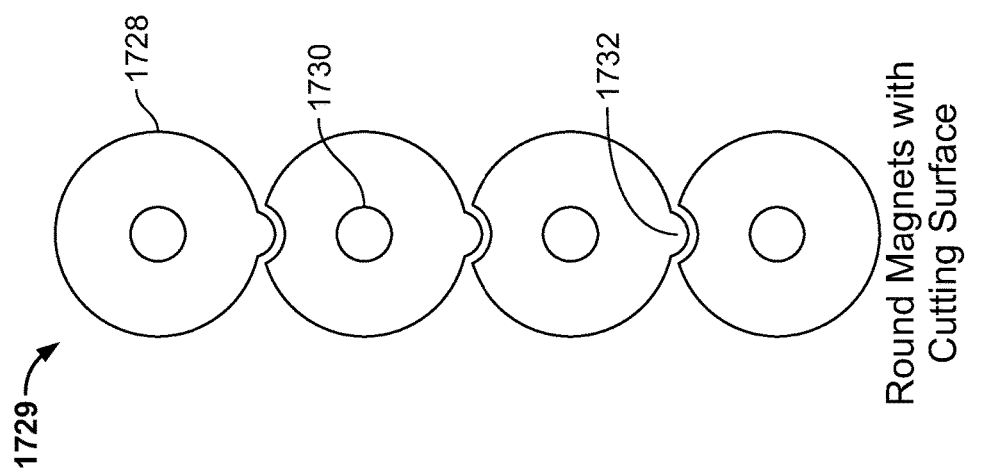
FIG. 17F illustrates a cross sectional view of an exemplary device comprising round shaped magnets coupled with a SMA coil used for creating an anastomosis, wherein the magnets comprise a protruding edge to assist with cutting, in accordance with an embodiment of the present specification.

FIG. 17F illustrates a cross sectional view of an exemplary device 1729 comprising round shaped magnets 1728 coupled with a SMA coil used for creating an anastomosis, wherein the magnets 1728 comprise a protruding edge 1732, in accordance with an embodiment of the present specification. Round shaped magnets 1728 are each coupled with coil loops 1730 for creating an anastomosis when deployed in a body. Magnets 1728 are provided with a protruding edge 1732 designed to interlock with other magnets/coil loops and enhance the cutting through the tissue compressed between the loops of the coil and magnets. FIG. 17G illustrates a cross sectional view of an exemplary device 1735 comprising square shaped magnets 1734 coupled with a SMA coil used for creating an anastomosis, wherein the magnets comprise a protruding edge 1738, in accordance with an embodiment of the present specification. Square shaped magnets 1734 are each coupled with coil loops 1736 for creating an anastomosis when deployed in a body. Magnets 1734 are provided with a protruding edge 1738 designed to interlock with other magnets/coil loops and enhance the cutting through the tissue compressed between the loops of the coil and magnets.

FIGS. 18A and 18B illustrate a plurality of magnets 1802, 1803 arranged around a loop 1804 of a SMA wire coil 1800, 1801 for creating an anastomosis, in accordance with embodiments of the present specification. Magnets 1802, 1803 are arranged equidistantly around a loop 1804 of a SMA wire coil in a manner such that opposite poles of adjacent magnets face each other, thereby creating a repulsive force which keeps the magnets 1802, 1803 fixed in a desired position on the loop 1804. Thus, the magnets 1802, 1803 do not clump together on the loop 1804. In an embodiment, as shown in FIG. 18A, magnets 1802 are provided with rings 1806 through which the loop 1804 is threaded for coupling the magnets 1802 with the loop 1804. In another embodiment, as shown in FIG. 18B, the magnets 1802 are coupled with the loop 1804 in wherein the magnets 1803 comprise a hollow conduit (not shown) through which the loop 1804 is threaded. In other embodiments, magnets are coupled to the loop in any suitable manner wherein the magnets may freely slide along the loop.

FIGS. 18C and 18D illustrate a plurality of magnets 1810, 1807 arranged around a loop 1812 of a SMA wire coil 1811, 1813 separated by non-ferromagnetic spacers 1814, for creating an anastomosis, in accordance with an embodiment of the present specification. As shown in FIG. 18C, rings 1808 of magnets 1810 are threaded through SMA coil loop 1812. The magnets 1810 are arranged such that opposite poles of adjacent magnets face each other, thereby creating an attractive force. Spacers 1814 made of a non-ferromagnetic material are placed between the magnets 1810 as shown, which keeps the magnets 1810 fixed in a desired position on the loop 1812, thereby ensuring that the magnets 1810 do not clump together on the loop 1812 and interfere with the shape-change from martensite shape to the austenite shape. In various embodiments, the spacers 1814 comprise silicone, Teflon, PTFE, or Nitinol tubes, O-rings or balls. In another embodiment, the spacers 1814 comprise only air, wherein each spacer 1814 is created by gluing or fixing each magnet 1810, 1807 onto the coil 1811, 1813 such that each magnet 1810, 1807 is positioned at a predefined distance from the next or previous magnet. In some embodiments, the predefined distance between adjacent magnets on a same loop of the coil is in a range of 1/128 inch to 1 inch. In other embodiments, the predefined distance between adjacent magnets on a same loop of the coil is in a range of 0.1 mm to 1 cm. In some embodiments, a minimum predefined distance is defined as a distance between adjacent magnets on a same loop of the coil sufficient to ensure that the magnets do not physically interfere with the formation of coil loops to any significant degree. In some embodiments, a minimum predefined distance is defined as a distance between adjacent magnets on a same loop of the coil sufficient to ensure that the magnets do not physically touch each other until the coil loop is completely formed. In some embodiments, a maximum predefined distance between adjacent magnets on a same loop of the coil is no more than 10 times a length of the magnet. In another embodiment, the maximum predefined distance between adjacent magnets on a same loop of the coil is <50% of the circumference of the coil. Referring to FIG. 18D, magnets 1807 of coil 1813 comprise a hollow conduit through which the coil loop 1812 is threaded. Spacers 1814 made of a non-ferromagnetic material are placed between the magnets 1807 as shown, thereby ensuring that the magnets 1807 do not clump together on the loop 1812.

Figures 18E, 18F:
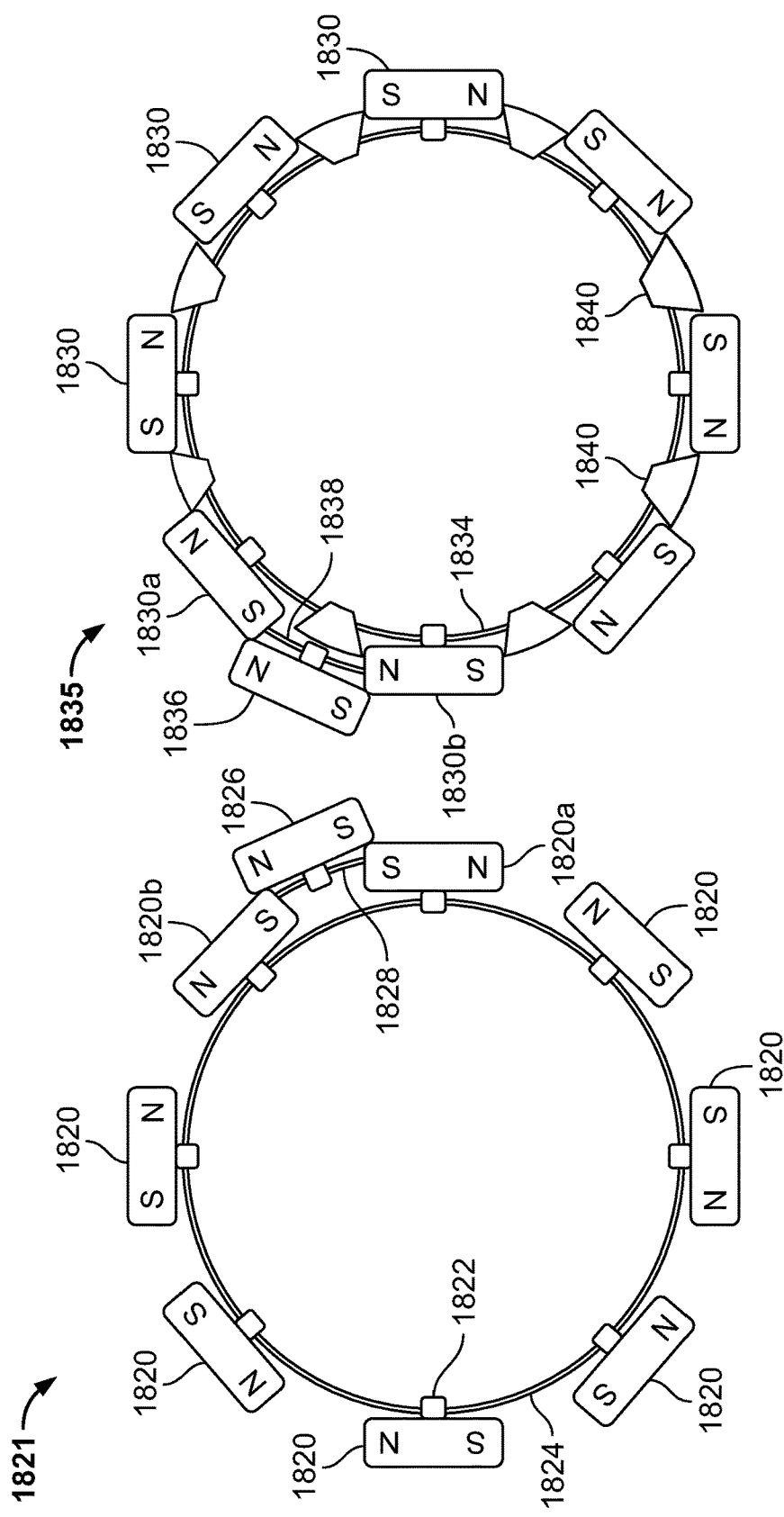
FIG. 18E illustrates a fifth configuration of magnets around a loop of a SMA coil for creating an anastomosis, in accordance with an embodiment of the present specification.
FIG. 18F illustrates a sixth configuration of magnets around a loop of a SMA coil for creating an anastomosis, in accordance with an embodiment of the present specification.

FIG. 18E illustrates an arrangement of magnets 1820, 1820*a*, 1820*b*, around a loop 1824 of a SMA coil 1821 for creating an anastomosis, in accordance with an embodiment of the present specification. Magnets 1820 are arranged by means of rings 1822 around a loop 1824 of a SMA coil 1821. A magnet 1826 of an adjacent loop 1828 is positioned, by means of magnetic attraction, proximate and between the magnetic poles of magnets 1820*a* and 1820*b* of the loop 1824. The magnet 1826 functions as a locking magnet, thereby locking each of the magnets 1820*a* and 1820*b* in their fixed respective positions on the coil loop 1824 forming a lasso. This allows for a fixed loop which can be used to pull the walls of the adjacent organ closer during deployment. This locking mechanism also prevents the loop from inadvertently slipping out of an organ during deployment.

FIG. 18F illustrates another arrangement of magnets 1830, 1830*a*, 1830*b* around a loop 1834 of a SMA coil 1835 for creating an anastomosis, in accordance with an embodiment of the present specification. Magnets 1830 are arranged around a loop 1834 of a SMA coil 1835. A magnet 1836 of an adjacent loop 1838 is positioned, by means of magnetic attraction, proximate and between the magnetic poles of magnets 1830*a* and 1830*b* of the loop 1834. The magnet 1836 functions as a locking magnet, thereby locking each of the magnets 1830*a* and 1830*b* in their fixed respective positions on the coil loop 1834. This allows for a fixed loop which can be used to pull the walls of the adjacent organ closer during deployment. This locking mechanism also prevents the loop from inadvertently slipping out of an organ during deployment as described above. Spacers 1840 made of a non-ferromagnetic material are also placed between the magnets 1830 as shown, thereby ensuring that the magnets 1830 do not clump together on the loop 1834. In various embodiments, the spacers 1840 comprise silicone, Teflon, PTFE, or Nitinol tubes.

Figures 19A, 19B, 19C:
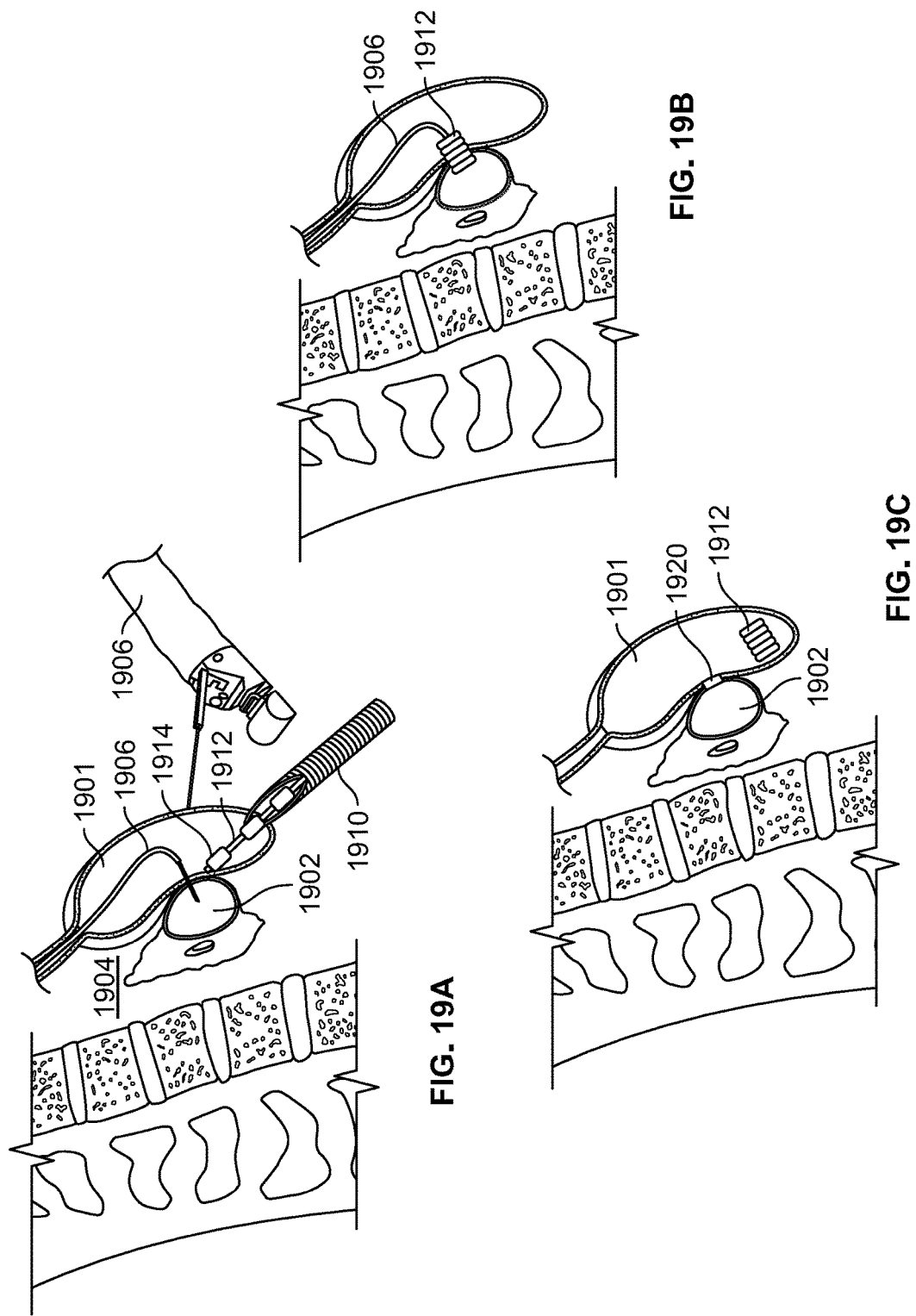
FIG. 19A illustrates a first step of forming an anastomosis between two organs in a human body, in accordance with an embodiment of the present specification.
FIG. 19B illustrates a second step of forming an anastomosis between two organs in a human body, in accordance with an embodiment of the present specification.
FIG. 19C illustrates a third step of forming an anastomosis between two organs in a human body, in accordance with an embodiment of the present specification.

FIG. 19A, 19B and 19C illustrate steps of formation of an anastomosis between two organs in a human body, in accordance with an embodiment of the present specification. In order to form an anastomosis between a pancreatic pseudocyst 1902 and a stomach 1901 wall, firstly, a stomach or duodenal wall adjacent to a pseudocyst wall is identified by means of an endoscope 1906. Using the endoscope 1906, a hollow needle or a catheter 1910 having a lumen for carrying a SMA wire 1912, which may be coupled with magnets 1914, is delivered at the identified location. The needle or catheter 1910 is used to pierce the organ walls and deliver the SMA wire 1912 therein. During deployment, the SMA wire 1912 is passed through the lumen of the needle or catheter 1910 until approximately ½ of the wire along, with the magnets 1914, is deployed in the pseudocyst 1902. The adjacent loops of the wire in the pseudocyst may attract together as described in FIGS. 18E and 18F and the loop can be used to pull the pseudocyst wall proximate to the gastric wall. Then the needle or catheter 1910 is retracted back into the stomach 1901 with the endoscope 1906 and the remaining ½ of the wire 1912 and magnets 1914 are deployed such that a portion of the wire resides in each of the pseudocyst and the stomach. Upon coming in contact with body heat, the straight SMA wire 1912 coils up and compresses the adjacent organs (pseudocyst 1902 and stomach 1901) together and the loops of the coil 1912 slowly cut through the walls of the adjacent organs, forming an anastomosis as described above. The compressive force can be provided by the coil alone or in conjunction with the magnets. Once the coil 1912 has completely cut through the two walls forming a stable anastomosis 1920, the coil 1912 spontaneously falls off and is naturally passed through the body, or may be retrieved using an endoscope or any other minimally invasive technique.

Figure 20A:
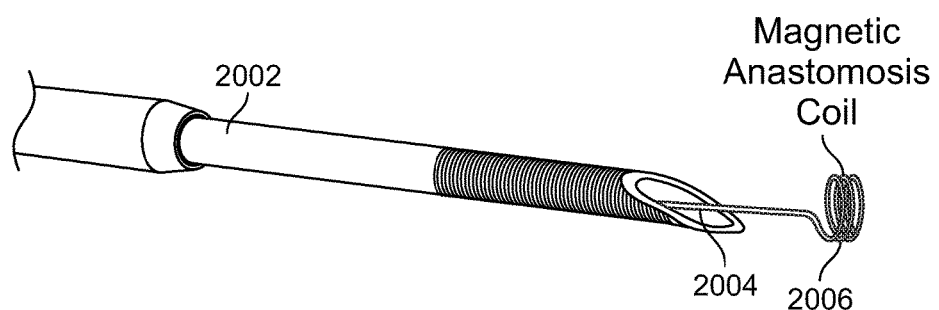
FIG. 20A illustrates a non-cautery needle that is used to deliver a SMA coil within a body, in accordance with an embodiment of the present specification.
Figure 20B:
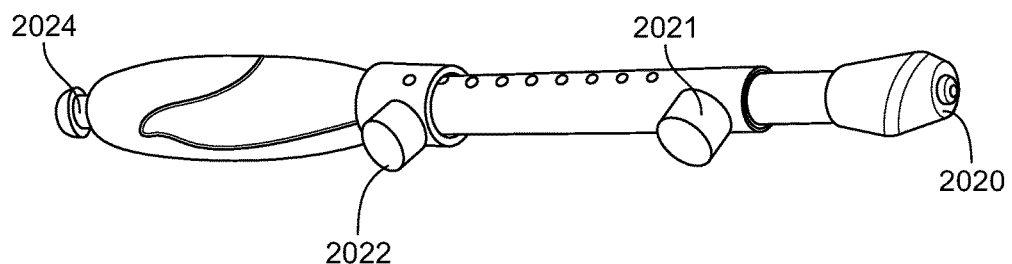
FIG. 20B illustrates the handle of the non-cautery needle shown in FIG. 20A, in accordance with an embodiment of the present specification.

FIG. 20A illustrates a non-cautery needle 2002 that is used to deliver a SMA coil 2006 within a body, in accordance with an embodiment of the present specification. Non-cautery hollow needle 2002 comprises a lumen 2004 in which a SMA anastomosis coil 2006 is placed for deployment via an endoscope into a human body. FIG. 20B illustrates the handle of the non-cautery needle shown in FIG. 20A. A tip portion 2020 engages with an endoscope. Knob 2021 controls the length of the catheter that can move in and out of the scope tip. Knob 2022 controls the length of the needle that can be withdrawn out of the catheter shaft at the needle tip. Port 24 allows for pushing cold saline into the needle lumen to help maintain the coil in the martensite shape and also accommodate the pusher catheter to push the coil out of the needle.

Figure 21:
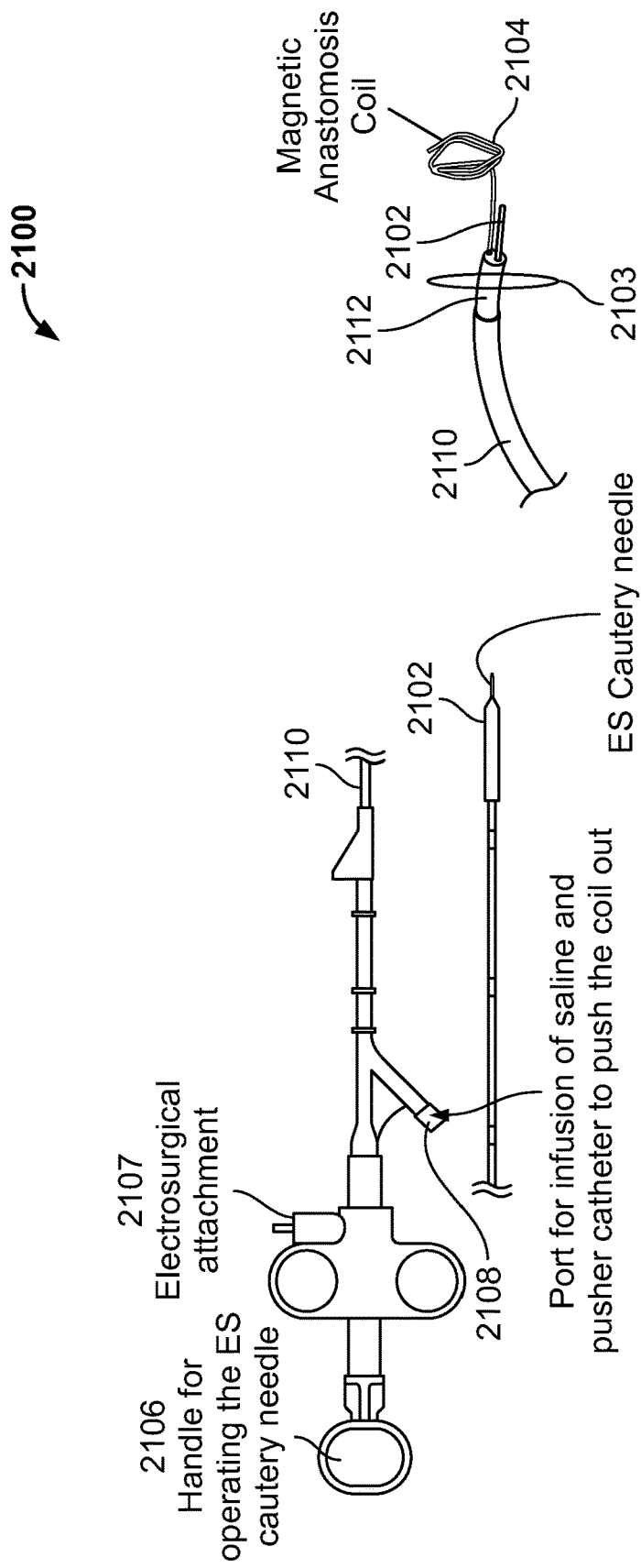
FIG. 21 illustrates a cautery needle device that is used to deliver a SMA coil within a body via an endoscope, in accordance with an embodiment of the present specification.

FIG. 21 illustrates a cautery needle device 2100 that is used to deliver a SMA coil 2104 within a body via an endoscope, in accordance with an embodiment of the present specification. The cautery needle device 2100 includes a port 2108, a body 2110, a handle 2106, a distal tip 2112, a needle 2102, and an electrosurgical attachment 2107 and is used to deliver a SMA anastomosis coil 2104 into a human body by means of an endoscope. The body 2110 of the needle device 2100 is inserted into a human body via an instrument channel of an endoscope such that the distal tip 2112 protrudes out of a distal end of the endoscope. The needle 2102 extends from the distal tip 2112 of the device 2100 via operation of handle 2106 for piercing a desired organ wall. The needle device 2100 includes a port 2108 for the infusion of cold saline into the needle lumen to help maintain the coil in the martensite shape and introduction of a pusher catheter. The SMA coil 2104 is delivered through the pierced site by means of the pusher catheter which is inserted into the port 2108 and pushes the coil 2104 out from the tip 2112 of the needle device 2100 and into the pierced organ wall. Optionally, in an embodiment, the device 2100 includes a balloon 2103 at its distal tip 2112 for positioning said tip 2112, approximating the two lumens proximate to each other and assisting with coil 2104 deployment. The pusher tube has marking or stopping mechanisms built into it assess the amount of coil that has been pushed out of the catheter.

Figure 22:
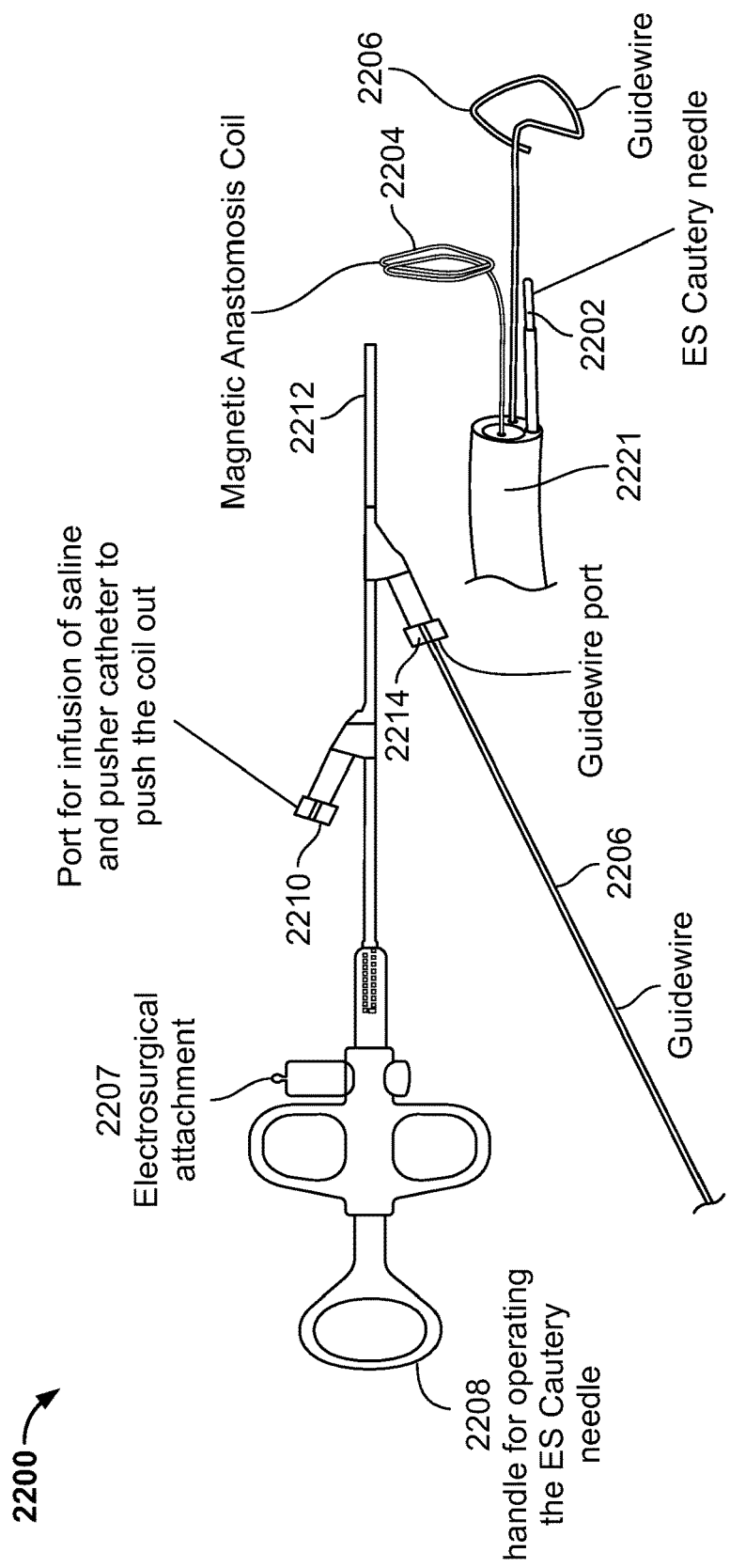
FIG. 22 illustrates a cautery needle device that is used to deliver a SMA coil within a body with the aid of a guidewire via an endoscope, in accordance with an embodiment of the present specification.

FIG. 22 illustrates a cautery needle device 2200 that is used to deliver a SMA coil 2204 within a body with the aid of a guidewire 2206 via an endoscope, in accordance with an embodiment of the present specification. A cautery needle device 2200, comprising a handle 2208, a body 2212, a first port 2210 for cold saline infusion, a second port 2214 for passage of a guidewire, a distal tip 2221, a needle 2202, and an electrosurgical attachment 2207, is used to deliver a SMA anastomosis coil 2204, with the help of a guide wire 2206, into a human body by means of an endoscope. The body 2212 of the needle device 2200 is inserted into a human body via a channel of an endoscope such that the distal tip 2221 protrudes out a distal end of the endoscope. The needle 2202 extends from distal tip 2221 via operation of handle 2208 to pierce a target tissue. Electrocautery is used to assist with the puncture. A guide wire 2206 is inserted via second port 2214 into the body 2212 of the needle device 2200 and extends from the distal tip 2221 into the punctured organ for maintaining position/access, for guiding placement of the catheter tip 2221 and the SMA coil 2204 in a desired location. The SMA coil 2204 is delivered into the lumen pierced by the needle 2202 by means of a pusher catheter which is introduced via the first port 2210 and pushes a portion of the coil 2204 out from the distal tip 2221 into the lumen of a second organ. The tip 2221 is retracted back into the lumen of a first organ and the remaining coil is deployed. The coil then changes shape and secures the two walls of the two organs together, fusing the two walls and then cutting out an anastomosis of a predetermined shape and dimension.

FIG. 23A illustrates a release mechanism of a SMA coil 2304 from a delivery catheter 2300, in accordance with an embodiment of the present specification. A coil coupling member 2302 at the end of a SMA coil 2304 to be deployed is attached to a delivery coupling member 2306 on a pusher element 2308 to move the coil 2304 in and out of the delivery catheter sheath 2310. In some embodiments, the coil coupling member 2302 comprises a coil loop and the delivery coupling member 2306 comprises a delivery loop. In various embodiments, the one or both of the coil coupling member 2302 and delivery coupling member 2306 are configurable between a first open configuration and a second closed configuration. A handle 2312 is provided for pushing in or out the pusher element 2308. FIG. 23B illustrates the SMA coil 2304 being released from the delivery catheter 2300 shown in FIG. 23A, in accordance with an embodiment of the present specification. The handle 2312 is pushed forward while holding the sheath 2310. As shown, as the coil 2304 is pushed out of the catheter sheath 2310, the delivery coupling member 2306 on the pusher 2308 or the coil 2304, or both, open up, disengaging the coil 2304 from the pusher 2308 and the catheter 2300.

FIG. 24A illustrates a release mechanism of a SMA coil 2404 from a delivery catheter 2400, in accordance with another embodiment of the present specification. A coil coupling member 2402 at the end of a SMA coil 2404 to be deployed is attached to a delivery coupling member 2406 on a pusher element 2408 to move the coil 2404 in and out of the delivery catheter sheath 2410. In some embodiments, the coil coupling member 2402 comprises a coil loop and the delivery coupling member 2406 comprises a delivery articulating grasper. In various embodiments, the one or both of the coil coupling member 2402 and delivery coupling member 2406 are configurable between a first open configuration and a second closed configuration. A handle 2412 is provided for pushing in or out the pusher element 2408. FIG. 24B illustrates the SMA coil 2404 being released from the delivery catheter 2400 shown in FIG. 24A, in accordance with an embodiment of the present specification. The handle 2412 is pushed forward while holding the sheath 2410. As shown, when the coil 2404 is pushed out of the catheter sheath 2410, the delivery coupling member 2406 on the pusher 2408 opens up disengaging the coil 2404 from the pusher 2408 and the catheter 2400. In an embodiment, the pusher 2408 comprises markings for alerting a user when a portion (less than the complete length) of the coil 2404 has been released from the catheter 2410. In another embodiment, the pusher 2408 comprises stopping mechanism for preventing a user from inadvertently deploying the complete length of the coil 2404 from the catheter 2410 at any one time.

Figure 25:
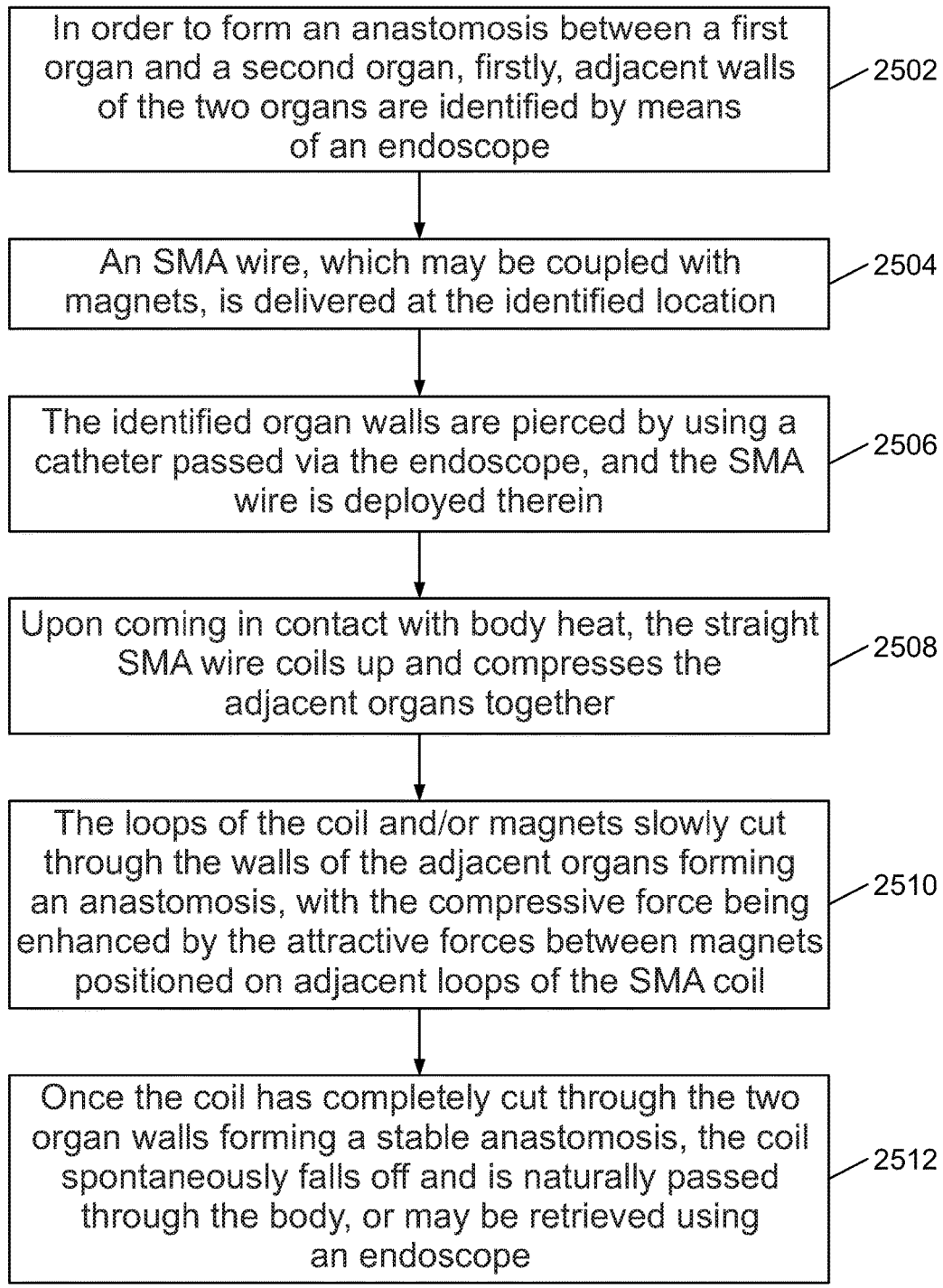
FIG. 25 is a flowchart illustrating the steps of creating an anastomosis by using an anastomosis instrument in accordance with an embodiment of the present specification.

FIG. 25 is a flowchart illustrating the steps of creating an anastomosis by using an anastomosis instrument in accordance with an embodiment of the present specification. At step 2502, in order to form an anastomosis between a first organ and a second organ, firstly, adjacent walls of the two organs are identified by means of an endoscope. Next, at step 2504, a SMA wire, which may be coupled with magnets, is delivered at the identified location. In an embodiment, the SMA coil is delivered using an endoscope via a hollow needle or catheter having a lumen for carrying the SMA wire which may be coupled with magnets. At step 2506 the identified organ walls are pierced and a portion of SMA wire is deployed in the lumen of the first organ and the remaining coil is deployed in the lumen of the second organ. At step 2508, upon coming in contact with body heat, the relatively straight SMA wire coils up to its predetermined austenite shape and compresses the adjacent organs together. At step 2510 the loops of the coil and/or magnets, if included, slowly cut through the walls of the walls of the two adjacent organs together forming an anastomosis over a period of time, with the compressive force being enhanced by the attractive forces between magnets positioned on adjacent loops of the SMA coil. The attractive forces increase over time as the loops of the coil and/or magnets cut through the walls of the two organs, thereby bringing the magnets closer to each other. At step 2512, once the coil has completely cut through the two organ walls forming a stable anastomosis, the coil spontaneously falls off and is naturally passed through the body, or may be retrieved using an endoscope or any other minimally invasive technique. In some embodiments, the coil is specifically shaped to promote its passage in a specific direction.

FIGS. 26A, 26B, and 26C illustrate first, second, and third views respectively, of an exemplary device 2600 for creating an anastomosis in a relatively straight pre-coiled configuration, in accordance with an embodiment of the present specification. The device comprises a shape memory alloy (SMA) wire 2602 with a plurality of magnets 2604 and spacers 2606 positioned coaxially about the wire 2602. In an embodiment, the wire 2602 is composed of Nitinol. In an embodiment, the spacers 2606 are composed of a non-ferromagnetic material. In various embodiments, the spacers 2606 comprise silicone, Teflon, PTFE, or Nitinol tubes or 0-rings or circular balls. In various embodiments, each magnet 2604 is separated from an adjacent magnet 2604 by a set of spacers 2606. In an embodiment, each set of spacers 2606 comprises three spacers 2606. FIGS. 26A-26C depict the device 2600 is a pre-coiled or pre-deployment configuration. The device 2600 has a curved shape when unrestrained by a delivery catheter and at room temperature. The device 2600 has a nearly straight shape when restrained in a delivery catheter (for example, as seen with device 1500 in FIG. 15A).

Figure 26D:
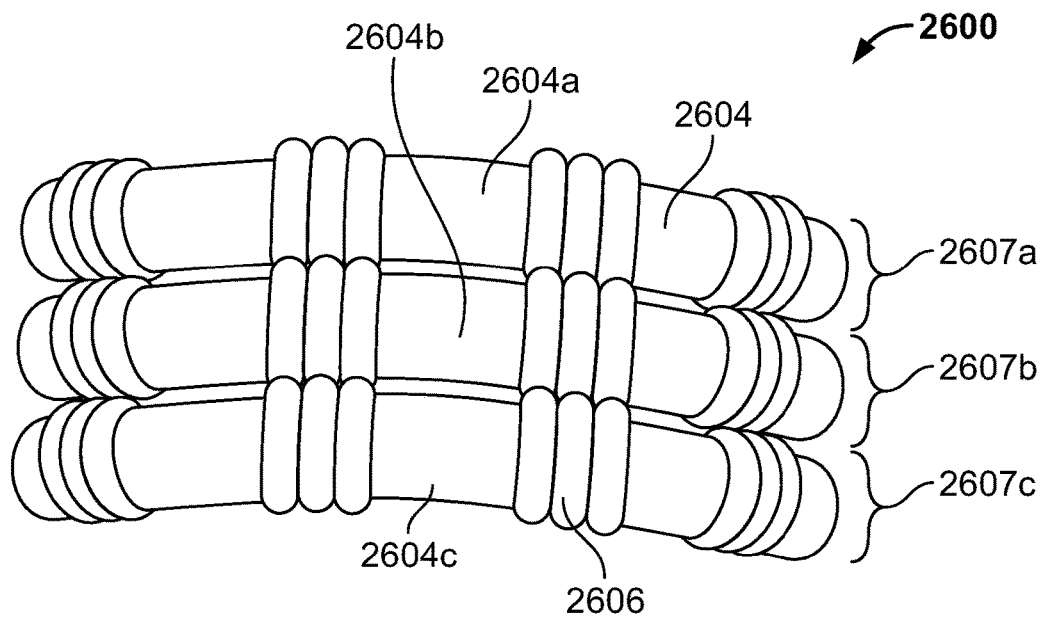
FIG. 26D illustrates a side view of the device for creating an anastomosis of FIG. 26A in a coiled configuration.
Figure 26E:
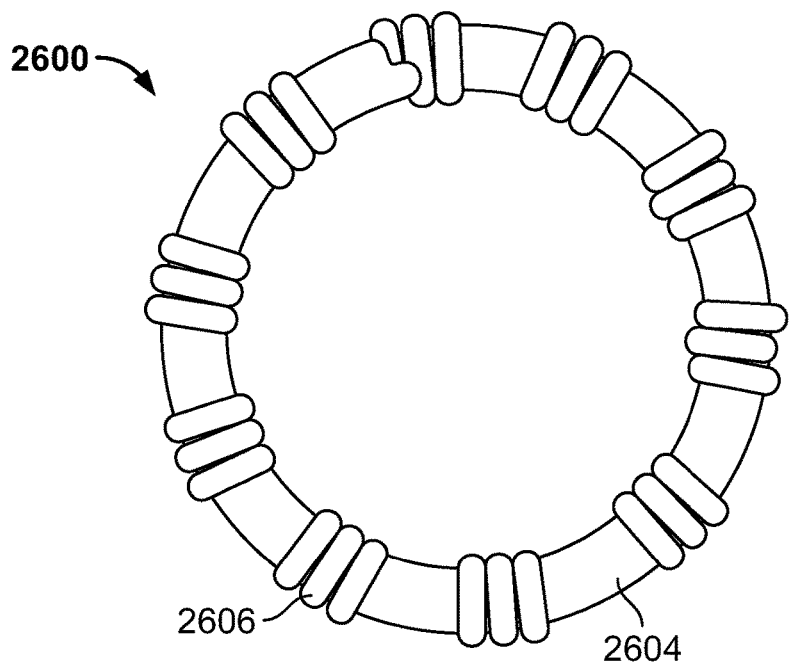
FIG. 26E illustrates an axial view of the device for creating an anastomosis of FIG. 26A in a coiled configuration.

FIGS. 26D and 26E illustrate side and axial views respectively, of the device 2600 for creating an anastomosis of FIG. 26A in a coiled configuration. After deployment, and when exposed to body temperature, the SMA wire coils to move the device 2600 from the curved configuration shown in FIGS. 26A-26C to the coiled configuration depicted in FIGS. 26D and 26E. The spacers 2606 ensure that the magnets 2604 do not clump together on the device 2600. Referring to FIG. 26D, magnetic force attraction between magnets 2604 on adjacent loops 2607a, 2607b, 2607c of the coiled device, for example, between magnets 2604a, 2604b, 2604c on adjacent loops 2607a, 2607b, 2607c, serves to pull the loops 2607a, 2607b, 2607c closer together and tighten the coil.

Figure 26F:
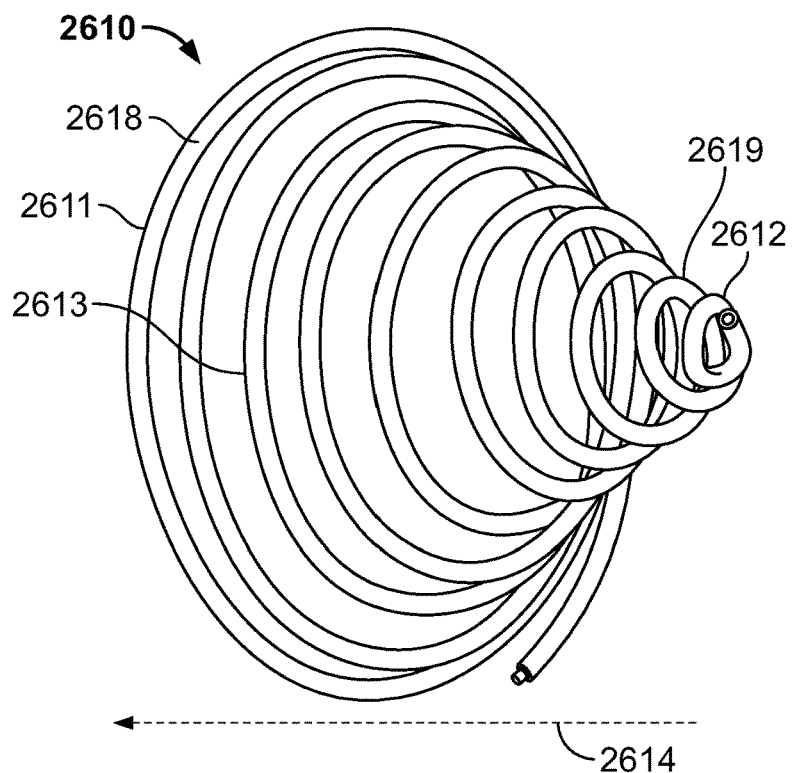
FIG. 26F illustrates a first exemplary device for creating an anastomosis in a post-deployment cone-shaped coil configuration, in accordance with one embodiment of the present specification.

FIG. 26F illustrates a first exemplary device 2610 for creating an anastomosis in a post-deployment cone-shaped coil configuration, in accordance with one embodiment of the present specification. The device 2610 is configured to pass from the tissue in only one direction following anastomosis formation. The device 2610 comprises a single shape memory wire which takes the shape of a coil 2613 once deployed. The device 2610 includes loops 2618 having a larger diameter at a first end 2611 of the coil 2613 compared with loops 2619 at a second, opposite end 2612 of the coil 2613. The diameter of the cutting loops 2618, 2619 of the coil 2613 determine the diameter of the anastomosis. Therefore, the resultant anastomosis will also have a cone or funnel shape, having a larger opening at a first end associated with the first end 2611 of the coil 2613 and a smaller opening at a second end associated with the second end 2612 of the coil 2613. Once the anastomosis has formed, the device 2610 will only be able to pass through the anastomosis in the direction indicated by arrow 2614, as the first end 2611 will be too large to pass through the anastomosis opening created by loops 2619 and device end 2612.

Figure 26G:
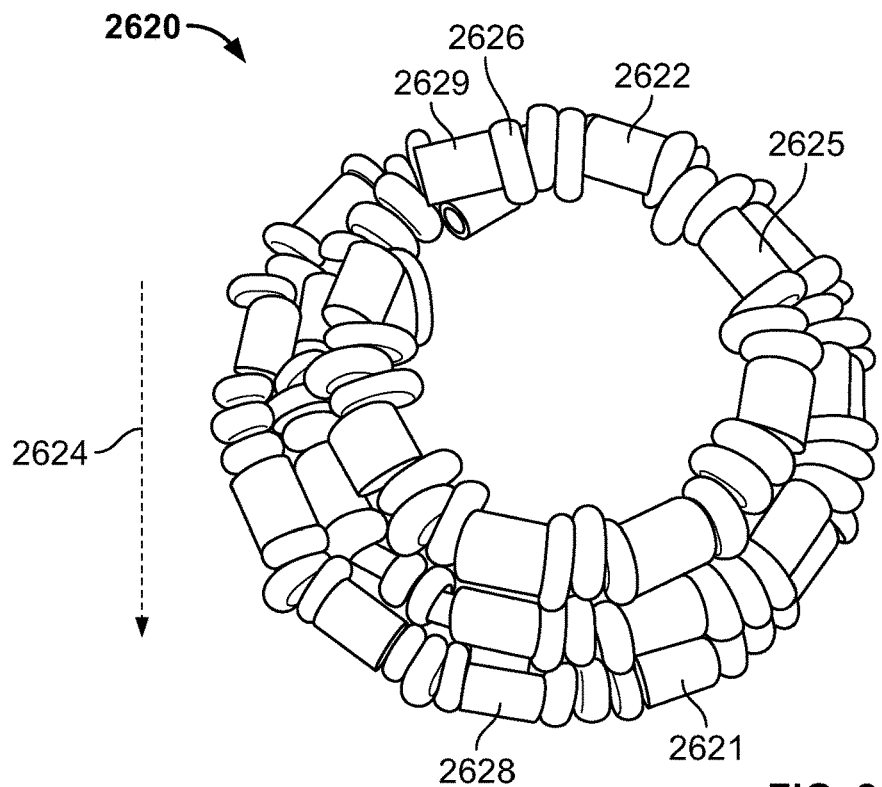
FIG. 26G illustrates a second exemplary device for creating an anastomosis in a post-deployment cone-shaped coil configuration, in accordance with one embodiment of the present specification.

FIG. 26G illustrates a second exemplary device 2620 for creating an anastomosis in a post-deployment cone-shaped coil configuration, in accordance with one embodiment of the present specification. The device 2620 is configured to pass from the tissue in only one direction following anastomosis formation. The device 2620 comprises a plurality of magnets 2625 separated by a plurality of spacers 2626 positioned on a shape memory wire. The device 2620 includes loops 2628 having a larger diameter at a first end 2621 of the device 2620 compared with loops 2629 at a second, opposite end 2622 of the device 2620. The diameter of the cutting loops 2628, 2629 of the device 2620 determine the diameter of the anastomosis. Therefore, the resultant anastomosis will also have a cone or funnel shape, having a larger opening at a first end associated with the first end 2621 of the device 2620 and a smaller opening at a second end associated with the second end 2622 of the device 2620. Once the anastomosis has formed, the device 2620 will only be able to pass through the anastomosis in the direction indicated by arrow 2624, as the first end 2621 will be too large to pass through the anastomosis opening created by loops 2629 and device end 2622.

Figure 26H:
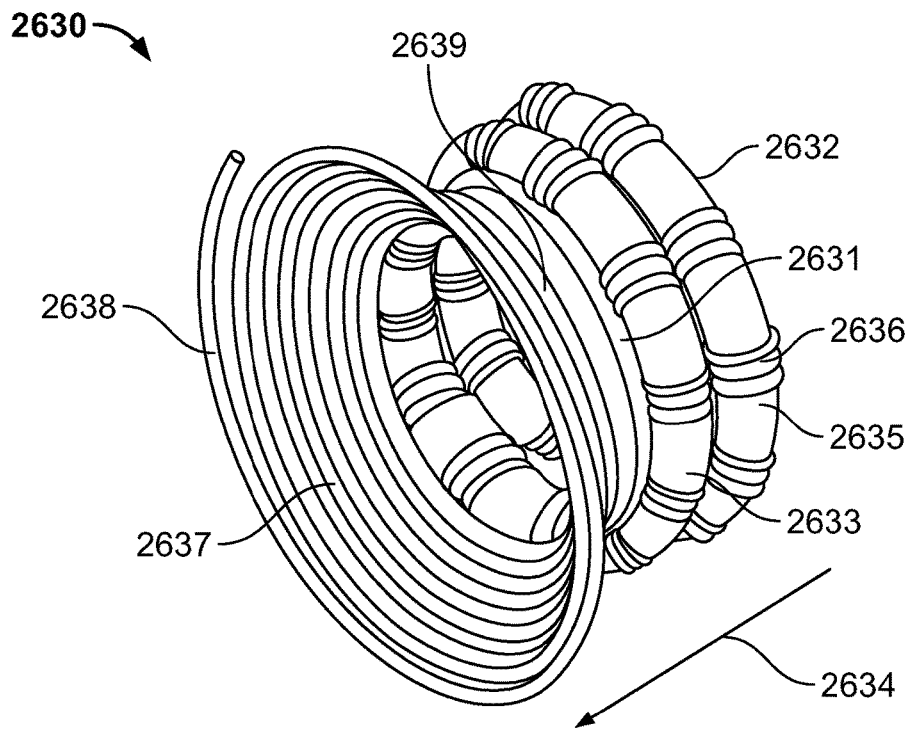
FIG. 26H illustrates an embodiment of a device for creating an anastomosis in a post-deployment coil configuration and comprising a single flange attached to one end of the coil.

FIG. 26H illustrates an embodiment of a device 2630 for creating an anastomosis in a post-deployment coil configuration and comprising a single flange 2637 attached to one end 2631 of the coil 2633. The device 2630 includes a coil 2633 having a first end 2631 and a second, opposite end 2632 and comprises a plurality of magnets 2635 separated by a plurality of spacers 2636 positioned on a shape memory wire. In an embodiment, a diameter of the first end 2631 of the coil 2633 is equal to a diameter of the second end 2632 of the coil 2633. The device 2630 further includes an extension or flange 2637 having a first end 2638 and a second end 2639. In an embodiment, the flange 2637 is cone shaped. The second end 2639 of the flange 2637 is attached to the first end 2631 of the coil 2633. The first end 2638 of the flange 2637 has a diameter that is greater than the diameter of the second end 2639 of the flange 2637 and greater than the diameters of both ends 2631, 2632 of the coil 2633. Once an anastomosis has formed, the device 2630 will pass only in the direction indicated by arrow 2634 (direction of the end including the flange), as the relatively larger diameter of the first end 2638 of the flange 2637 will prevent passage of the flange 2637 through the anastomosis formed by the relatively smaller diameter of the coil 2633.

Figure 26I:
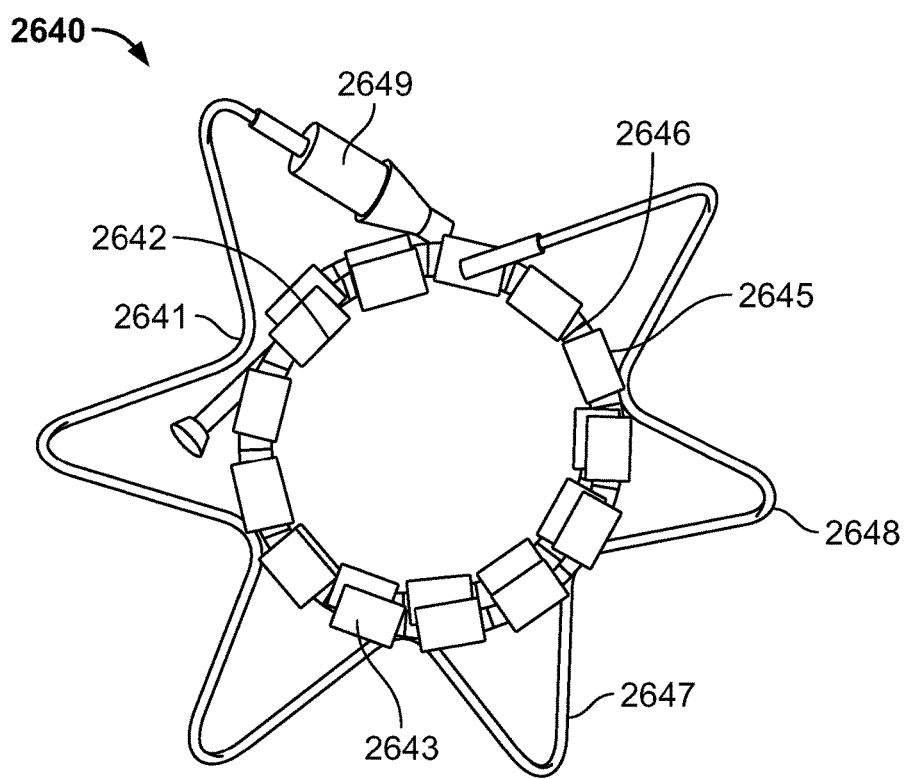
FIG. 26I illustrates another embodiment of a device for creating an anastomosis in a post-deployment coil configuration and comprising a single flange attached to one end of the coil.
Figure 26J:
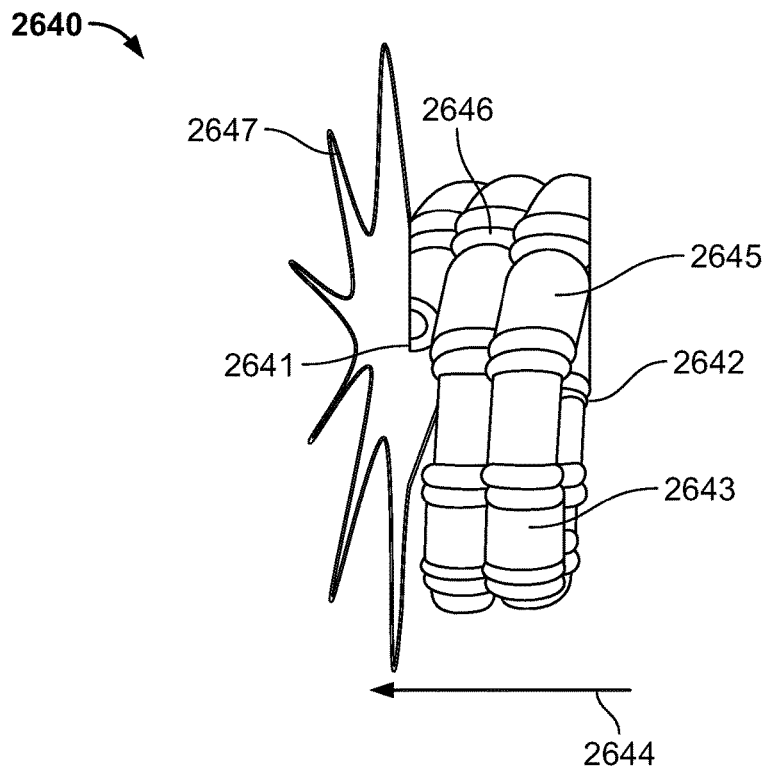
FIG. 26J illustrates a side view of the device for creating an anastomosis of FIG. 26I.

FIGS. 26I and 26J illustrate end and side views respectively, of another embodiment of a device 2640 for creating an anastomosis in a post-deployment coil configuration and comprising a single flange 2647 attached to one end 2641 of the coil 2643. The device 2640 includes a coil 2643 having a first end 2641 and a second, opposite end 2642 and comprises a plurality of magnets 2645 separated by a plurality of spacers 2646 positioned on a shape memory wire. In an embodiment, a diameter of the first end 2641 of the coil 2643 is equal to a diameter of the second end 2642 of the coil 2643. The device 2640 further includes a star or flower shaped extension or flange 2647 attached to the first end 2641 of the coil 2643. In an embodiment, the flange 2647 includes a cautery puncture component 2649 which is configured to receive an electrical current to generate heat and puncture a tissue to deliver the device 2640. The cautery puncture component 2649 is attached to an end of the flange 2647 via a screw connection. An opposite end of the flange 2647 includes another screw connection for attaching the flange 2647 to the coil 2643. The flange 2647 includes a plurality of angular protrusions 2648 which extend outwardly from a center of the device 2640 such that a diameter defined by the outer edges of the protrusions 2648 is greater than the diameters of both ends 2641, 2642 of the coil 2643. Once an anastomosis has formed, the device 2640 will pass only in the direction indicated by arrow 2644 (direction of the end including the flange), as the relatively larger diameter defined by the outer edges of the protrusions 2648 of the flange 2647 will prevent passage of the flange 2647 through the anastomosis formed by the relatively smaller diameter of the coil 2643.

Figure 26K:
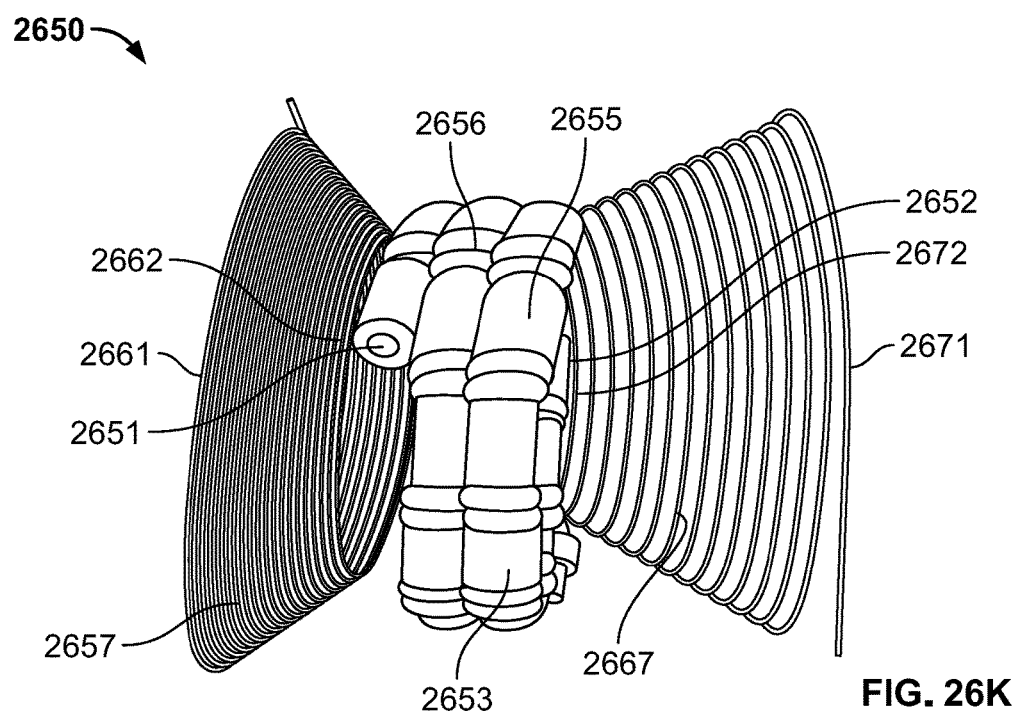
FIG. 26K illustrates an embodiment of a device for creating an anastomosis in a post-deployment coil configuration and comprising a flange attached to each end of the coil.

FIG. 26K illustrates an embodiment of a device 2650 for creating an anastomosis in a post-deployment coil configuration and comprising a flange 2657, 2667 attached to each end of the coil 2653. The device 2650 includes a coil 2653 having a first end 2651 and a second, opposite end 2652 and comprises a plurality of magnets 2655 separated by a plurality of spacers 2656 positioned on a shape memory wire. In an embodiment, a diameter of the first end 2651 of the coil 2653 is equal to a diameter of the second end 2652 of the coil 2653. The device 2650 further includes a first extension or flange 2657 and a second extension of flange 2667, each having a first end 2661, 2671 and a second end 2662, 2672. In an embodiment, each flange 2657, 2667 is cone shaped. The second end 2662 of the first flange 2657 is attached to the first end 2651 of the coil 2653 and the second end 2672 of the second flange 2667 is attached to the second end 2652 of the coil. The first ends 2661, 2671 of each flange 2657, 2667 each have a diameter that is greater than a diameter of each second end 2662, 2672 of the flanges 2657, 2667 and greater than the diameters of both ends 2651, 2652 of the coil 2653. Once an anastomosis has formed, the device 2650 will become fixed within the anastomosis and cannot be passed, as the relatively larger diameters of the first ends 2661, 2671 of the flanges 2657, 2667 will prevent passage of the device 2650 in either direction through the anastomosis formed by the relatively smaller diameter of the coil 2653. In this configuration, the diameter of the coil 2653 is smaller than the flanges 2657, 2667 on both ends and, after an anastomosis is formed, the coil 2653 would not spontaneously pass through the anastomosis as the flanges 2657, 2667 will become stuck.

Figure 26L:
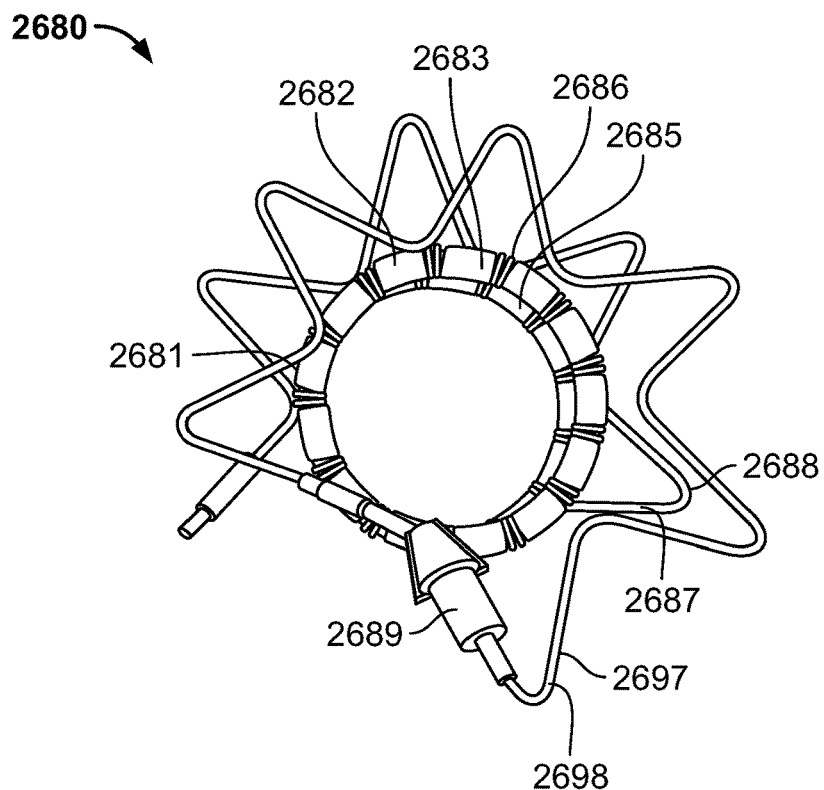
FIG. 26L illustrates another embodiment of a device for creating an anastomosis in a post-deployment coil configuration and comprising a flange attached to each end of the coil.
Figure 26M:
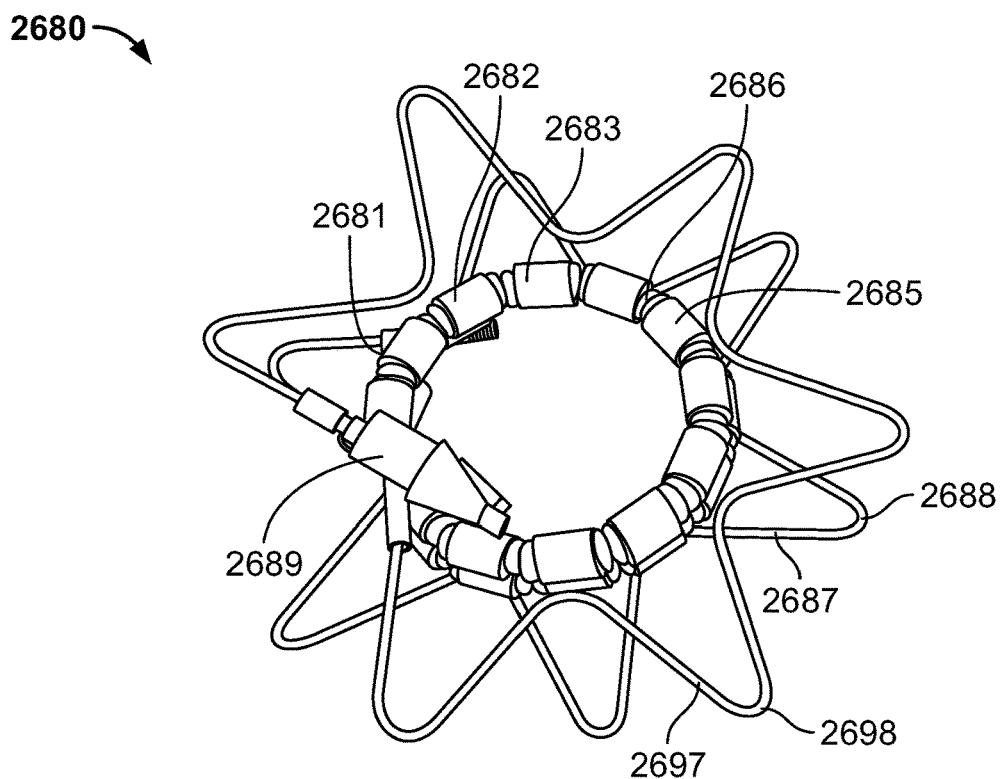
FIG. 26M illustrates an additional view of the device for creating an anastomosis of FIG. 26L.
Figure 26N:
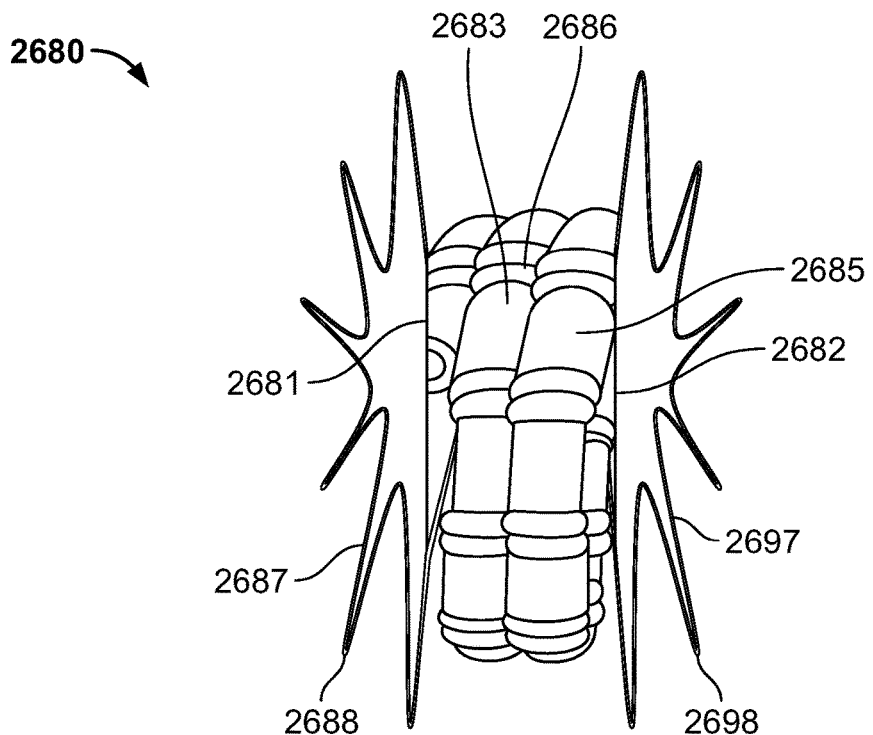
FIG. 26N illustrates a side view of the device for creating an anastomosis of FIG. 26L.

FIGS. 26L, 26M, and 26N illustrate end and side views of another embodiment of a device 2680 for creating an anastomosis in a post-deployment coil configuration and comprising a flange 2687, 2697 attached to each end of the coil 2683. The device 2680 includes a coil 2683 having a first end 2681 and a second, opposite end 2682 and comprises a plurality of magnets 2685 separated by a plurality of spacers 2686 positioned on a shape memory wire. In an embodiment, a diameter of the first end 2681 of the coil 2683 is equal to a diameter of the second end 2682 of the coil 2683. The device 2680 further includes a first star or flower shaped extension or flange 2687 attached to the first end 2681 of the coil 2683 and a second star or flower shaped extension or flange 2697 attached to the second end 2682 of the coil 2683. In an embodiment, one or each flange 2687, 2697 includes a cautery puncture component 2689 which is configured to receive an electrical current to generate heat and puncture a tissue to deliver the device 2680. A cautery puncture component 2689 is attached to an end of one or each flange 2687, 2697 via a screw connection. An opposite end of each flange 2687, 2697 includes another screw connection for attaching the flanges 2687, 2697 to the coil 2683. The flanges 2687, 2697 each include a plurality of angular protrusions 2688, 2698 which extend outwardly from a center of the device 2680 such that diameters defined by the outer edges of the protrusions 2688, 2698 are greater than the diameters of both ends 2681, 2682 of the coil 2683. Once an anastomosis has formed, the device 2680 will become fixed within the anastomosis and cannot be passed, as the relatively larger diameters defined by the protrusions 2688, 2698 of the flanges 2687, 2697 will prevent passage of the device 2680 in either direction through the anastomosis formed by the relatively smaller diameter of the coil 2683. The coil 2680 will not pass spontaneously after the anastomosis is formed.

Figure 26O:
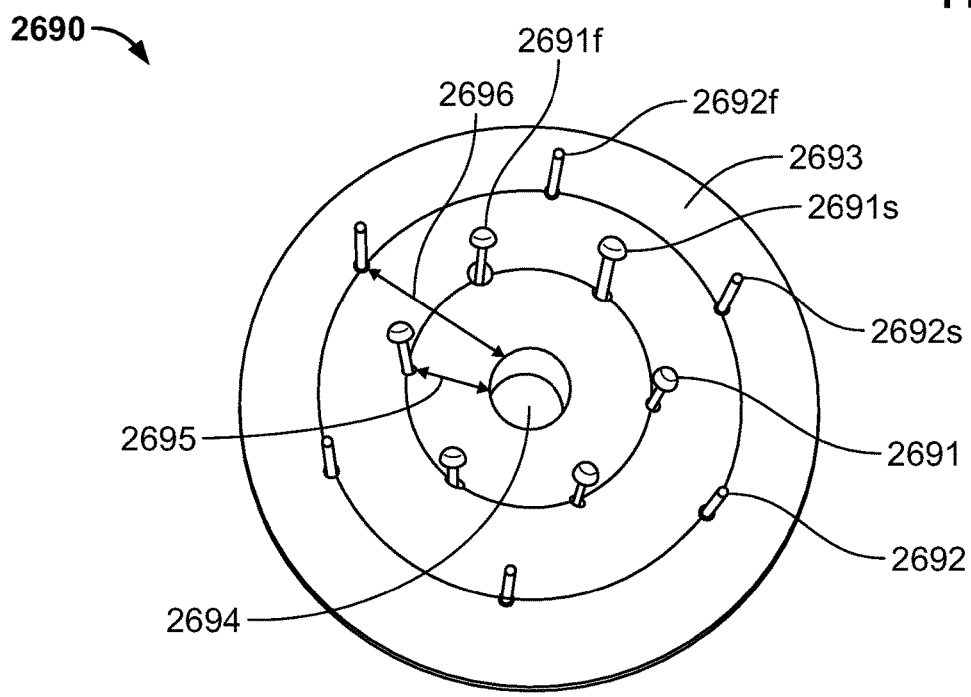
FIG. 26O illustrates a mold for creating the anastomosis device with flanges of FIG. 26L.

FIG. 26O illustrates a mold 2690 for creating the anastomosis device 2680 with flanges of FIG. 26L. The mold 2690 includes a first plurality of pins 2691 and a second plurality of pins 2692 extending perpendicularly from a base 2693 of the mold 2690. The first plurality of pins 2691 is positioned at a first distance 2695 from a center 2694 of the mold 2693 and the second plurality of pins 2692 is positioned at a second distance 2696 from the center 2694 of the mold 2693, wherein the second distance 2696 is greater than the first distance 2695. Referring to FIGS. 26L through 26O simultaneously, a diameter defined by the first plurality of pins 2691 corresponds to the diameter of the coil 2683 and a diameter defined by the second plurality of pins 2692 corresponds to the diameter defined by the outer edges of the protrusions 2688, 2698 of the flanges 2687, 2697. The coil 2683 of the anastomosis device 2680 is wrapped about the first plurality of pins 2691 to give the coil 2683 its coil shape. Each flange 2687, 2697 is wrapped about a first pin 2691f of the first plurality of pins 2691, then an adjacent first pin 2692f of the second plurality of pins 2692, then an adjacent second pin 2691s of said first plurality of pins 2691, then an adjacent second pin 2692s of said second plurality of pins 2692, and so on, in a clockwise direction (or, in another embodiment, in a counter-clockwise direction) to form a star or flower shaped flange.

FIG. 27 illustrates a SMA coil device 2702 for creating an anastomosis in a pre-deployment configuration with delivery catheter 2706, in accordance with an embodiment of the present specification. A cautery loop 2704 formed at a distal end of the SMA coil 2702 device is used to puncture a target tissue and cauterize the tissue as an opening is created for the anastomosis. A pusher delivery catheter 2706 pushes the coil 2702 out from a distal end of the catheter 2706. The SMA coil device 2702 comprises magnets 2710 which enable the coil to change shape and secure two walls of two organs together. The SMA coil device 2702 is attached to a loop/articulating grasper 2712 on a pusher element 2714 of the delivery catheter 2706 to move the coil device 2702 in and out of the delivery catheter sheath 2716. A handle 2718 is provided for pushing in or out the pusher element 2714. In an embodiment, an electrosurgical unit connector 2720 provides electrical contact for the pusher element 2714 and the SMA coil device 2702 with an electrosurgical generator.

FIG. 28 illustrates a SMA coil device 2800 for creating an anastomosis in a pre-deployment configuration with delivery catheter 2820, in accordance with another embodiment of the present specification. The SMA coil device 2800 includes a cautery loop 2804 formed at a distal end of a SMA wire 2802 and a plurality of magnets 2806 and spacers 2808 positioned coaxially about the SMA wire 2802. The cautery loop 2804 is used to puncture a target tissue and cauterize the tissue as an opening is created for the anastomosis. In an embodiment, the SMA wire 2802 is composed of Nitinol. In an embodiment, the spacers 2808 are composed of a non-ferromagnetic material. In various embodiments, the spacers 2808 comprise silicone or Nitinol tubes or O-rings or circular balls. A loop 2810 at a proximal end of the SMA wire 2802 is attached to a loop/articulating grasper 2812 on a pusher element 2814 to move the SMA wire 2802 in and out of a delivery catheter sheath 2816 of a delivery catheter 2820. In an embodiment, the SMA wire 2802 includes an insulation covering 2803. In various embodiments, the insulation covering 2803 is composed of silicone or Teflon. The insulation covering 2803 prevents the body of the SMA wire from transferring heat to the magnets 2806 and spacers 2808 as the cautery loop 2804 is heated via electrical current communicated to the SMA wire 2802 through the pusher element 2814 and loop/articulating grasper 2812. The SMA wire 2802 and the delivery catheter sheath 2816 are disposed within an outer catheter 2818 at a distal end of the delivery catheter 2820.

Figure 29A:
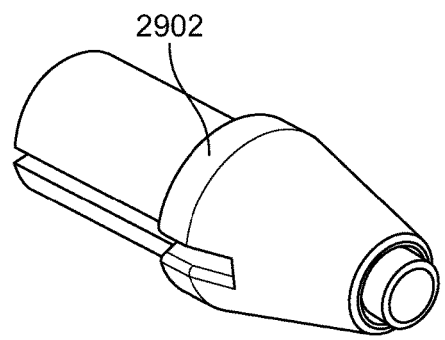
FIG. 29A illustrates a cautery tip for deployment with an anastomosis coil device, in accordance with various embodiments of the present specification.
Figure 29B:
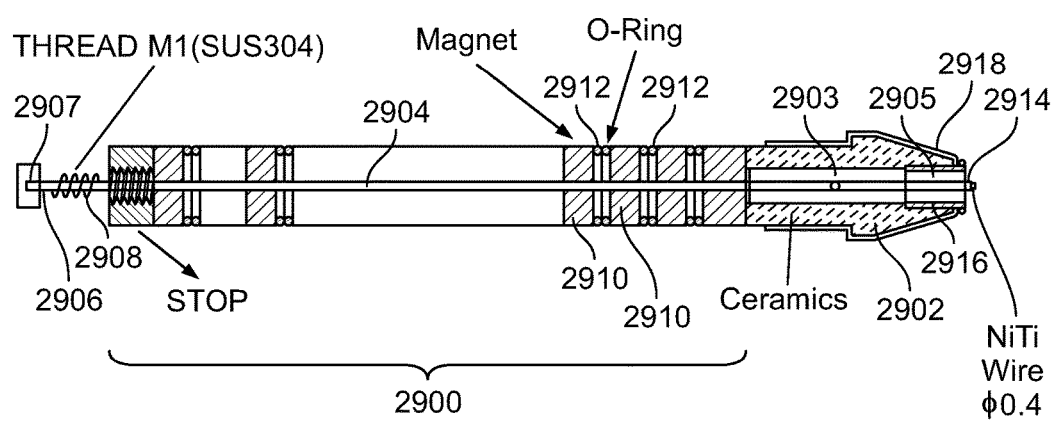
FIG. 29B illustrates an anastomosis coil device provided with a cautery tip in a pre-deployment configuration, in accordance with an embodiment of the present specification.

FIG. 29A illustrates a cautery tip 2902 for deployment with an anastomosis coil device, in accordance with various embodiments of the present specification. The cautery tip 2902 is configured to receive thermal energy from an electrical current source. As the cautery tip heats, it is advanced forward into a body tissue. The thermal energy cuts through the target tissue, creating an opening for creation of an anastomosis while simultaneously cauterizing and stopping blood loss from the tissue surrounding the newly formed opening. FIG. 29B illustrates an anastomosis coil device 2900 provided with a cautery tip 2902 in a pre-deployment configuration, in accordance with an embodiment of the present specification. Anastomosis coil device 2904 is detachably connected to a pusher 2907 comprising a cautery wire 2906 through thread connector 2908 at the proximal end of the anastomosis coil device 2904, which creates an electrical connection between the pusher 2907 with cautery wire 2906 and the anastomosis coil device 2904. The anastomosis coil device 2900 comprises an inner SMA wire 2904 with a plurality of magnets 2910 and spacers 2912 positioned coaxially thereabout. In an embodiment, the SMA wire 2904 is composed of Nitinol. The SMA wire 2904 extends distally through a lumen 2903 of the cautery tip 2902. A metal cylinder 2916 is positioned in the distal end of the lumen 2903 of the cautery tip 2902. The SMA wire 2904 further extends distally through a lumen 2905 of the metal cylinder 2916. A rivet 2914 connects the metal cylinder 2916 to the SMA wire 2904 at the distal end of the cautery tip 2902. An additional metal wire 2918 is connected to the rivet 2914 and, in various embodiments, extends along an outer surface of the cautery tip 2902. An electrical current is provided via the cautery wire 2906 and passes through the thread connector 2908, along the SMA wire 2904, and to the metal cylinder 2916 and metal wire 2918. The electrical current creates thermal energy in the metal cylinder 2916 and metal wire 2918 which is transferred to the cautery tip 2902 which, in various embodiments, is composed of ceramic or PEEK. The thermal energy heats the cautery tip 2902 which is used to puncture and cauterize tissue to create an opening for anastomosis creation. After deployment of the anastomosis coil device 2900, the pusher 2907 with cautery wire 2906 is disconnected from the SMA wire 2904.

Figure 30A:
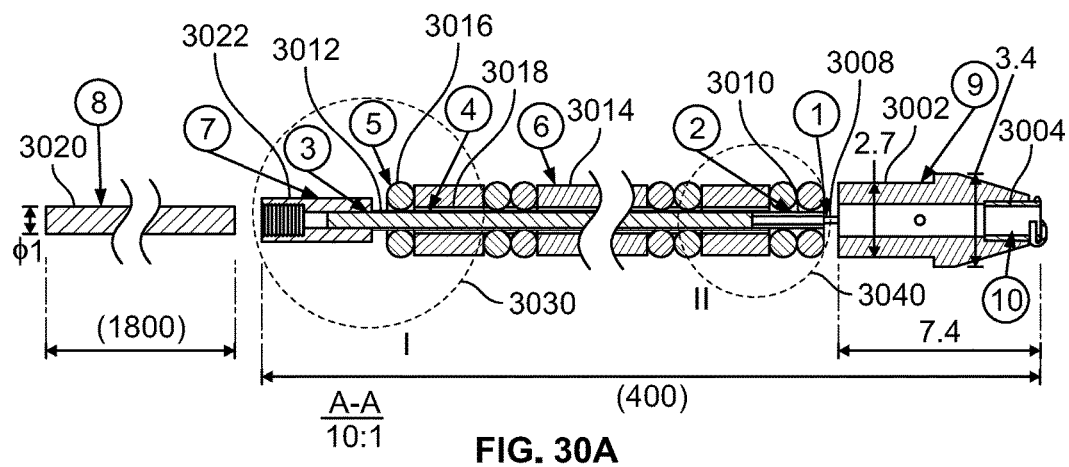
FIG. 30A illustrates a side cross sectional view of an anastomosis coil device with a distal cautery tip in a pre-deployment configuration, in accordance with an embodiment of the present specification.

FIG. 30A illustrates a side cross sectional view of an anastomosis coil device 3000 with a distal cautery tip 3002 in a pre-deployment configuration, in accordance with an embodiment of the present specification. In an embodiment, the cautery tip 3002 comprises a ceramic 'hot head' coupled with a cautery electrode 3004. The ceramic hot head design enables the catheter to puncture into the wall of an organ. In an embodiment, length of the ceramic head 3002 and the cautery electrode 3004 is approximately 7.4 mm. A stainless steel support wire 3008 and a clamping tube 3010 couple the cautery tip 3002 with a Nitinol wire 3012. A plurality of magnets 3014 and spacers 3016 are positioned coaxially about the Nitinol wire 3012. In an embodiment, the Nitinol wire 3012 is enveloped in an insulating PTFE, Teflon, or silicone sleeve 3018. The stainless steel wire 3008 couples the Nitinol wire 3012 to the cautery tip 3002 and a proximal stop 3022, attached to the proximal end of the Nitinol wire 3012, detachably couples with a steel pusher catheter 3020. Electrical current passes from the pusher catheter 3020 through the Nitinol wire 3012 and stainless steel wire 3008 and into the cautery tip 3002 and electrode 3004, heating up the cautery tip 3002 to enable electro-cautery puncture of a target tissue.

Figure 30B:
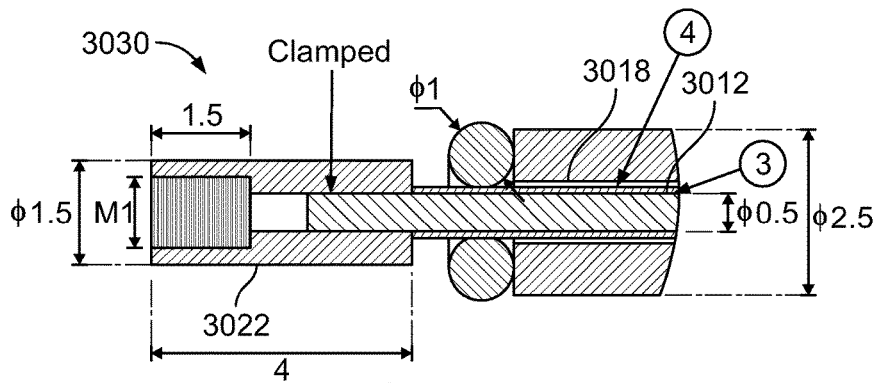
FIG. 30B illustrates a blown up view of the portion marked as 3030 in FIG. 30A.
Figure 30C:
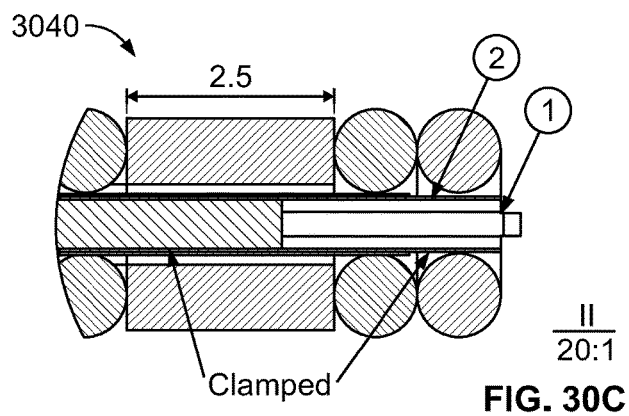
FIG. 30C illustrates a blown up view of the portion marked as 3040 in FIG. 30A.

FIG. 30B illustrates a blown up view of the portion marked as 3030 in FIG. 30A. In an embodiment, diameters of the Nitinol wire 3012 and each of the magnets 3014 are approximately 0.5 mm and 2.5 mm respectively, and a length and diameter of the proximal stop 3022 are approximately 4 mm and 1.5 mm respectively. FIG. 30C illustrates a blown up view of the portion marked as 3040 in FIG. 30A. In an embodiment, a length of each of the magnets 3014 is approximately 2.5 mm.

Figure 30D:
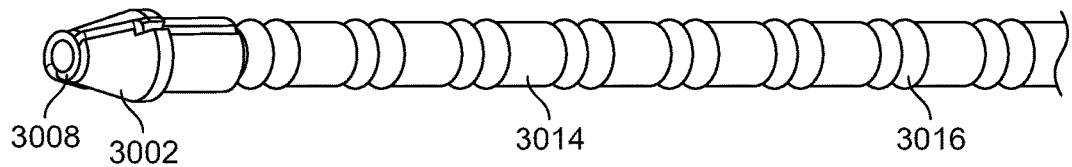
FIG. 30D illustrates another view of the cautery enabled anastomosis coil device with cautery tip shown in FIG. 30A.
Figure 30E:
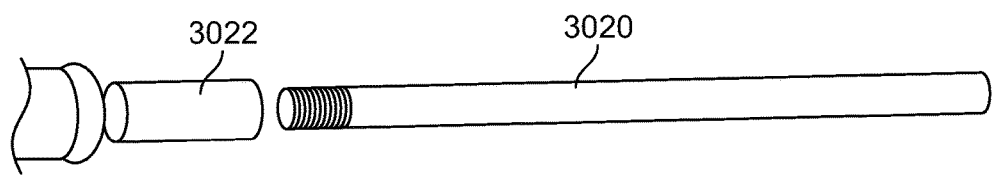
FIG. 30E illustrates a blown up view of the coupling mechanism of the proximal stop and pusher catheter of the anastomosis coil device shown in FIG. 30A.

FIG. 30D illustrates another view of the cautery enabled anastomosis coil device with cautery tip shown in FIG. 30A. The cautery tip 3002 is coupled to the Nitinol wire (not visible in the figure) covered with magnets 3014 and spacers 3016 via support wire 3008. FIG. 30E illustrates a blown up view of the coupling of the proximal stop 3022 and pusher catheter 3020 of the anastomosis coil device shown in FIG. 30A. The proximal stop 3022 is detachably coupled with the steel pusher catheter 3020 which allows electrical current to flow through the Nitinol wire all the way up to the cautery tip.

Figure 30F:
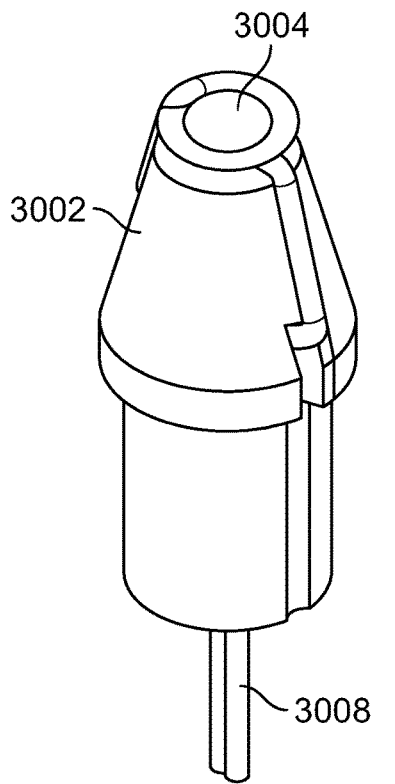
FIG. 30F illustrates a close up view of the cautery tip coupled with the cautery electrode of the anastomosis coil device shown in FIG. 30A.
Figure 30G:
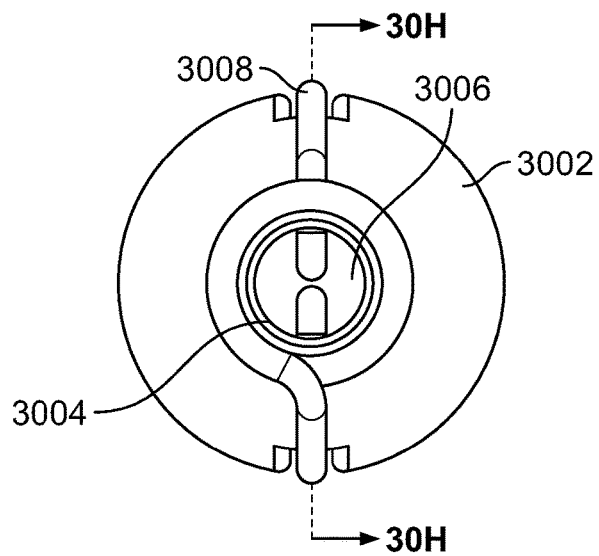
FIG. 30G illustrates a front on view of the cautery tip shown in FIG. 30F.
Figure 30H:
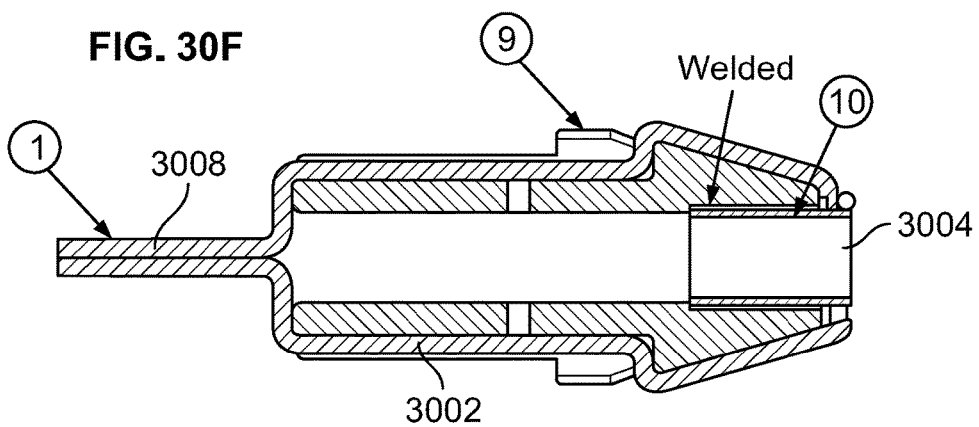
FIG. 30H illustrates a side cross sectional view of the cautery tip and cautery electrode shown in FIG. 30F.
Figure 30I:
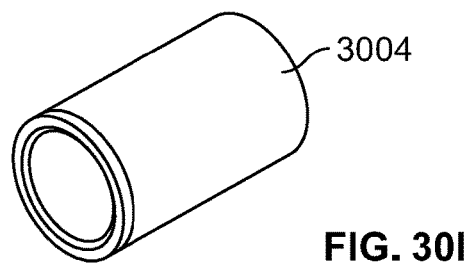
FIG. 30I illustrates the cautery electrode shown in FIG. 30F.

FIG. 30F illustrates a close up view of the cautery tip 3002 coupled with the cautery electrode 3004 of the anastomosis coil device shown in FIG. 30A. FIG. 30G illustrates a front on view of the cautery tip 3002 shown in FIG. 30F. As shown, the cautery tip 3002 has a substantially circular cross section with a circular opening 3006 in the center for accommodating the cautery electrode 3004. FIG. 30H illustrates a side cross sectional view of the cautery tip 3002 and cautery electrode 3004 shown in FIG. 30F. FIG. 30I illustrates the cautery electrode 3004 shown in FIG. 30F. As shown, the electrode 3004 is substantially cylindrical and fits into a circular opening 3006 provided at a distal end of the cautery tip 3002. In one embodiment, support wire 3008 forms a loop at a distal end of the cautery tip 3002 and assists with securing the electrode 3004 in place and with the electro-cautery puncture of an organ. An electrical current travels along wire 3008 to heat electrode 3004. Thermal energy is transferred to the cautery tip 3002 which is then used to puncture and cauterize a target tissue to create an opening for forming an anastomosis.

Figure 31A:
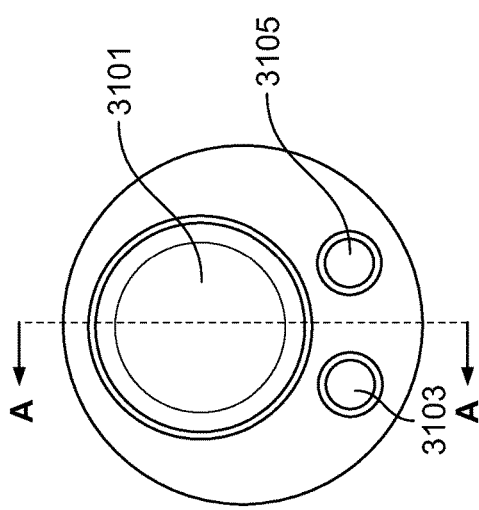
FIG. 31A illustrates a cross sectional view of a triple lumen catheter used for delivering an anastomosis coil device, in accordance with an embodiment of the present specification.
Figure 31B:
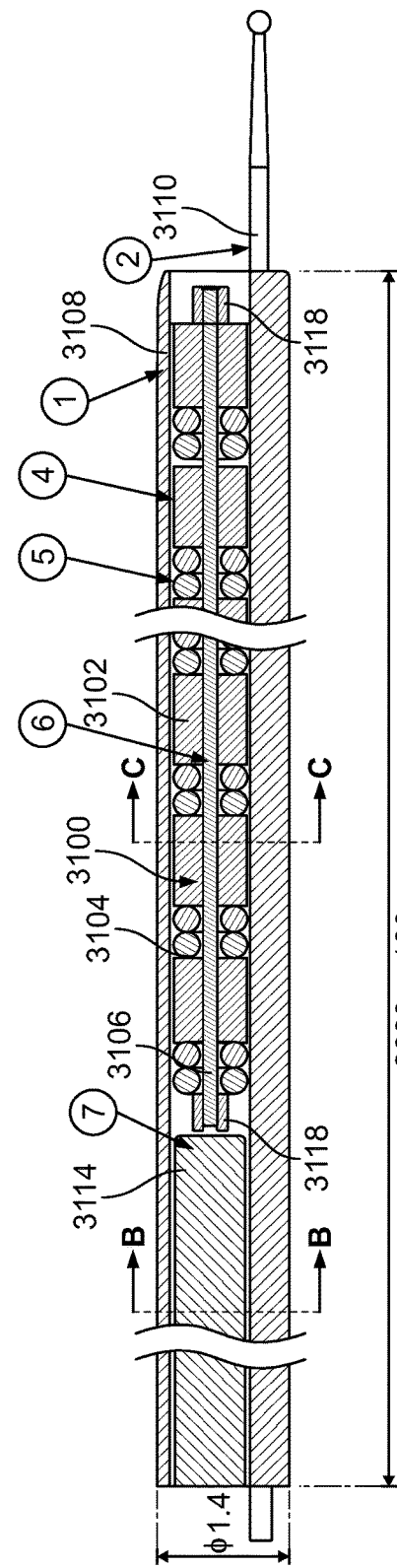
FIG. 31B illustrates a side cross sectional view of an anastomosis coil device in a pre-deployment configuration and a guide wire enveloped in a catheter for delivering the anastomosis coil device, in accordance with an embodiment of the present specification.
Figure 31C:
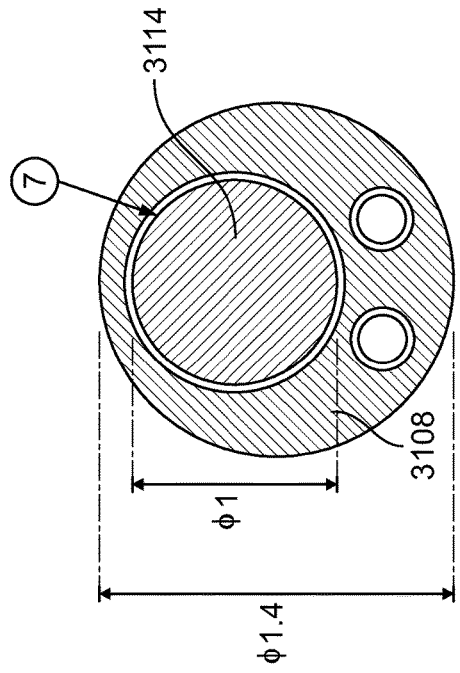
FIG. 31C illustrates a cross sectional view along the CC axis shown in FIG. 31B.
Figure 31D:
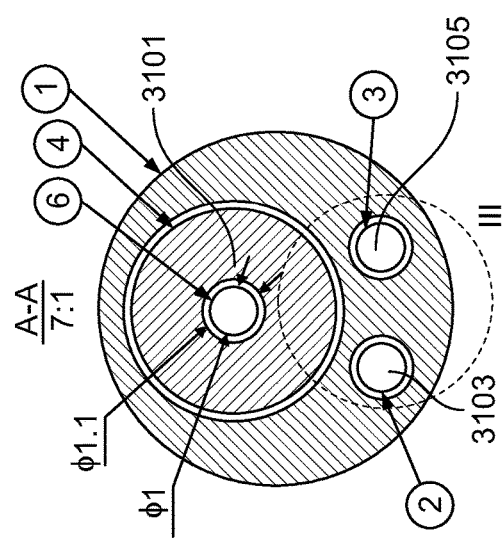
FIG. 31D illustrates a cross sectional view along the BB axis shown in FIG. 31B.
Figure 31E:
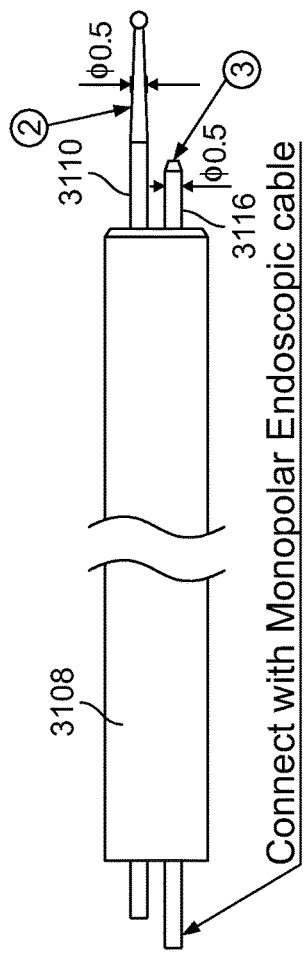
FIG. 31E illustrates another view of the catheter and a guide wire for delivering the anastomosis coil device shown in FIG. 31B.

FIG. 31A illustrates a triple lumen catheter used for delivering an anastomosis coil device, in accordance with an embodiment of the present specification. A first lumen 3101 is used for carrying the anastomosis coil device, a second lumen 3103 for carrying a guidewire and a third lumen 3105 is provided for optionally carrying a cautery wire for puncturing an organ. FIG. 31B illustrates a side cross sectional view of an anastomosis coil device 3100 in a pre-deployment configuration and a guide wire 3110 enveloped in a catheter 3108 for delivering the anastomosis coil device 3100, in accordance with an embodiment of the present specification. A plurality of magnets 3102 and spacers 3104 are positioned coaxially about a SMA wire 3106 as shown. In an embodiment, the wire 3106 is composed of Nitinol. In an embodiment, the spacers 3104 are composed of a non-ferromagnetic material. In various embodiments, the spacers 3104 comprise silicone or Nitinol tubes or O-rings or circular balls. Stop mechanisms 3118 are coupled to both ends of the wire 3106. In embodiments, the stop mechanisms 3118 are riveted or crimped to both ends of the wire 3106 after the magnets 3102 and spacers 3104 are assembled along the wire 3106. In an embodiment, a length of each of the stop mechanisms 3118 is 1 mm. A catheter 3108, similar to the triple lumen catheter depicted in FIG. 31A, delivers the anastomosis coil device 3100 through a first lumen in the catheter 3108 while a guidewire 3110 for guiding the placement of the anastomosis coil device 3100 at a desired location in a body is positioned within a second lumen of the catheter 3108. The anastomosis coil device 3100 is pushed out of catheter 3108 by a pusher tube 3114. A cautery wire (not shown in the figure) may optionally be passed through a third lumen, or keyhole (lumen 3105 in FIG. 31A) for heating a distal end of the anastomosis coil device 3100 to assist with puncturing and cauterizing a target tissue. FIG. 31C illustrates a cross sectional view along the CC axis shown in FIG. 31B. As shown, the first lumen 3101 for the anastomosis coil device, second lumen 3103 for the guidewire, and third lumen or keyhole 3105 for the cautery wire each have circular cross sections. In an embodiment, a diameter of the third lumen or keyhole 3105 is approximately 0.60 mm, a diameter of the second lumen 3103 is approximately 0.60 mm and a diameter of the first lumen 3101 is approximately 2.2 mm. FIG. 31D illustrates a cross sectional view along the BB axis shown in FIG. 31B. In an embodiment, a diameter of the pusher tube 3114 is approximately 2 mm and a diameter of catheter 3108 is approximately 3.5 mm. FIG. 31E illustrates another view of the catheter 3108 and a guide wire for delivering the anastomosis coil device shown in FIG. 31B. As shown, the catheter 3108 partially envelops the guidewire 3110 as well as a connector 3116 for connecting with a monopolar endoscopic cable, which is disposed within the third lumen or keyhole (lumen 3105 in FIG. 31C). In an embodiment, a diameter of the guidewire 3110 is approximately 0.5 mm and a diameter of the connector 3116 is approximately 0.5 mm.

FIG. 32A illustrates a cross sectional view of an anastomosis coil device 3200 in a pre-deployment configuration disposed in a delivery catheter 3208, in accordance with another embodiment of the present specification. The anastomosis coil device 3200 comprises a plurality of magnets 3202 and spacers 3204 positioned coaxially about a SMA wire 3206 as shown. In an embodiment, the wire 3206 is composed of Nitinol. In an embodiment, the spacers 3204 are composed of a non-ferromagnetic material. In various embodiments, the spacers 3204 comprise silicone or Nitinol tubes or O-rings or circular balls. A catheter 3208, in some embodiments made of PEEK or Teflon, envelops the anastomosis coil device 3200 and is coupled at a distal end with a conductor head 3210, in some embodiments made of ceramic or PEEK, for puncturing an organ by using electrocautery action. At a proximal end, the anastomosis coil device 3200 is coupled with a pusher tube 3212 as shown. Stop mechanisms 3216 are applied to both ends of the wire 3206 preventing the magnets 3202 and spacers 3204 from sliding off the wire 3206. In embodiments, the stop mechanisms 3216 are crimped or riveted to both ends of the wire 3206 after the magnets 3202 and spacers 3204 are assembled along the stent. The rivet or crimp stop mechanism 3216 at the proximal end is detachably coupled with the pusher tube 3212 allowing for release of the anastomosis coil device 3200 from the catheter 3208. In an embodiment, a length of each of the stop mechanisms 3216 is 1.5 mm. FIG. 32B illustrates a cross sectional view along the BB axis shown in FIG. 32A. As shown, the outer catheter 3208 and the conductor head 3210 have circular cross sections and diameters of approximately 3.3 mm and 2.2 mm respectively. Further, a conductor wire 3214 runs through the length of the catheter 3208 and is positioned proximate the conductor head 3210. Electrical current supplied to the conductor wire 3214 is converted to heat energy in the conductor head 3210 which assists with electrocautery and puncturing of a target tissue by the conductor head 3210 for anastomosis formation. FIG. 32C illustrates a cross sectional view along the CC axis shown in FIG. 32A. As shown, the wire 3206 and each of the magnets 3202 have circular cross sections. In an embodiment, diameters of each of the magnets 3202 are 2 mm and a diameter of a first lumen 3201 containing the anastomosis coil device is 2.2 mm. The conductor wire 3214 is depicted extending through a second lumen 3203 in a wall of the catheter 3208. FIG. 32D illustrates a cross sectional view along the DD axis shown in FIG. 32A. As shown, the pusher tube 3212 has a circular diameter which is approximately 1.9 mm and is disposed within the first lumen 3201, in an embodiment. Also, in an embodiment, the conductor wire 3214 has a circular cross section and a diameter of approximately 0.25 mm and is disposed within the second lumen 3203 which, in an embodiment, has a diameter of 0.30 mm.

FIG. 32E illustrates a blown up view of the conductor head 3210 shown in FIG. 32A. Outer catheter 3208 partially envelops the conductor wire 3214 and conductor head 3210 as shown in FIG. 32E. In an embodiment, the conductor wire 3214 is welded with conductor head 3210. In an embodiment, the conductor head has a cylindrical portion 3220 with flanges 3222 approximately 2.5 mm long, protruding around the circular portion as shown. In an embodiment, inner and outer diameters of the conductor head 3210 are approximately 2.2 mm and 2.4 mm respectively. FIG. 32F illustrates the anastomosis coil device 3200 shown in FIG. 32A in a post-deployment configuration after being delivered within a body. As shown, after delivery, the wire 3206 coils up catching body tissue within the turns of wire and magnets 3202 for causing anastomosis. FIG. 32G illustrates a cross sectional view of the anastomosis coil device 3200 shown in FIG. 32F. In an embodiment, a diameter of the wire 3206 is 0.4 mm. The magnets 3202 are shown aligning along a like plane in the post-deployment configuration of the device 3200. FIG. 32H illustrates an O-ring being used as a spacer 3204 as shown in FIG. 32B. In an embodiment, an outer diameter of the O-ring is approximately 2.2 mm and a diameter of an inner circular opening 3209 is approximately 0.6 mm.

FIG. 33A illustrates a dual handle delivery device 3300 for delivering an anastomosis coil device 3308 provided with a cauterizing tip 3318, in accordance with an embodiment of the present specification. As shown, the dual handle delivery device 3300 comprises a first handle 3302 coupled with an outer catheter 3306. The device 3300 also includes a second handle 3310 coupled with an inner catheter 3312. The second handle 3310 includes an electrosurgical unit connector 3316 in electrical communication with the inner catheter 3312 for delivering electrical current to the cauterizing tip 3318 of the anastomosis coil device 3308. The anastomosis coil device 3308, with cauterizing tip 3318, is positioned within the inner catheter 3312. The first handle 3302 and second handle 3310 are manipulated relative to one another to deploy the anastomosis coil device 3308. FIG. 33B illustrates a blown up view of the second handle 3310 and electrosurgical connector 3316 shown in FIG. 33A.

FIG. 34A illustrates a sectional view of a dual handle delivery device 3400 for delivering an anastomosis coil device provided with a cauterizing tip 3402, in accordance with an embodiment of the present specification. Anastomosis coil device comprising a cauterizing tip portion 3402 is delivered via a distal end of the delivery device 3400, which also comprises a handle portion 3406 at a proximal end for pushing out the anastomosis coil device from the distal end of the delivery device 3400. FIG. 34B illustrates a blown up sectional view of the tip portion 3402 shown in FIG. 34A. Tip portion 3402 comprises a ceramic head 3408 enveloping a cauterizing electrode 3410. A guidewire 3412 passes through the ceramic head 3408 from its proximal end all the way through and protrudes out from the distal end of the ceramic head 3408 adjacent cauterizing electrode 3410. In an embodiment, the guidewire 3412 has a diameter of approximately 0.025 inches. Ceramic head 3408 partially covers a guidewire support 3414 enveloped within an inner tube 3416 made of PEEK material. In an embodiment, the guidewire support 3414 has a diameter of approximately 0.89 mm. In an embodiment, the guidewire 3412 is coupled with the ceramic head 3408 by using ultraviolet glue. In an embodiment, the inner tube 3416 is coupled with the guidewire support 3414 by using ultraviolet glue. FIG. 34C illustrates a cross sectional view of the tip portion 3402 shown in FIG. 34B. As shown, the ceramic head 3408, guidewire 3412, guidewire support 3414 and inner tube 3416 have a circular cross section.

FIG. 34D illustrates a blown up sectional view of the guidewire portion 3404 shown in FIG. 34A. FIG. 34E illustrates a cross sectional view of the guidewire portion 3404 shown in FIG. 34D. Referring to FIGS. 34D and 34E, the guidewire support 3414 is enveloped within an inner tube 3416, which in turn is surrounded by a double lumen tube 3418 made of a PEEK material. The guidewire 3412 is threaded through one lumen of the double lumen tube 3418, while the guidewire support 3414 passes through another lumen of the double lumen tube 3418 as shown in FIG. 34E. The double lumen tube 3418 is partially enveloped by an outer tube 3420 which in an embodiment, is made of a braided mesh material.

FIG. 34F illustrates a blown up sectional view of the handle portion 3406 shown in FIG. 34A. The handle portion 3406 comprises a conductive plug/pins 3422 and a transparent knob tail 3424. The conductive plug/pins 3422 are in electrical communication with the guidewire 3412 for delivering electrical current to the electrode 3410 of FIG. 34B.

Figure 35:
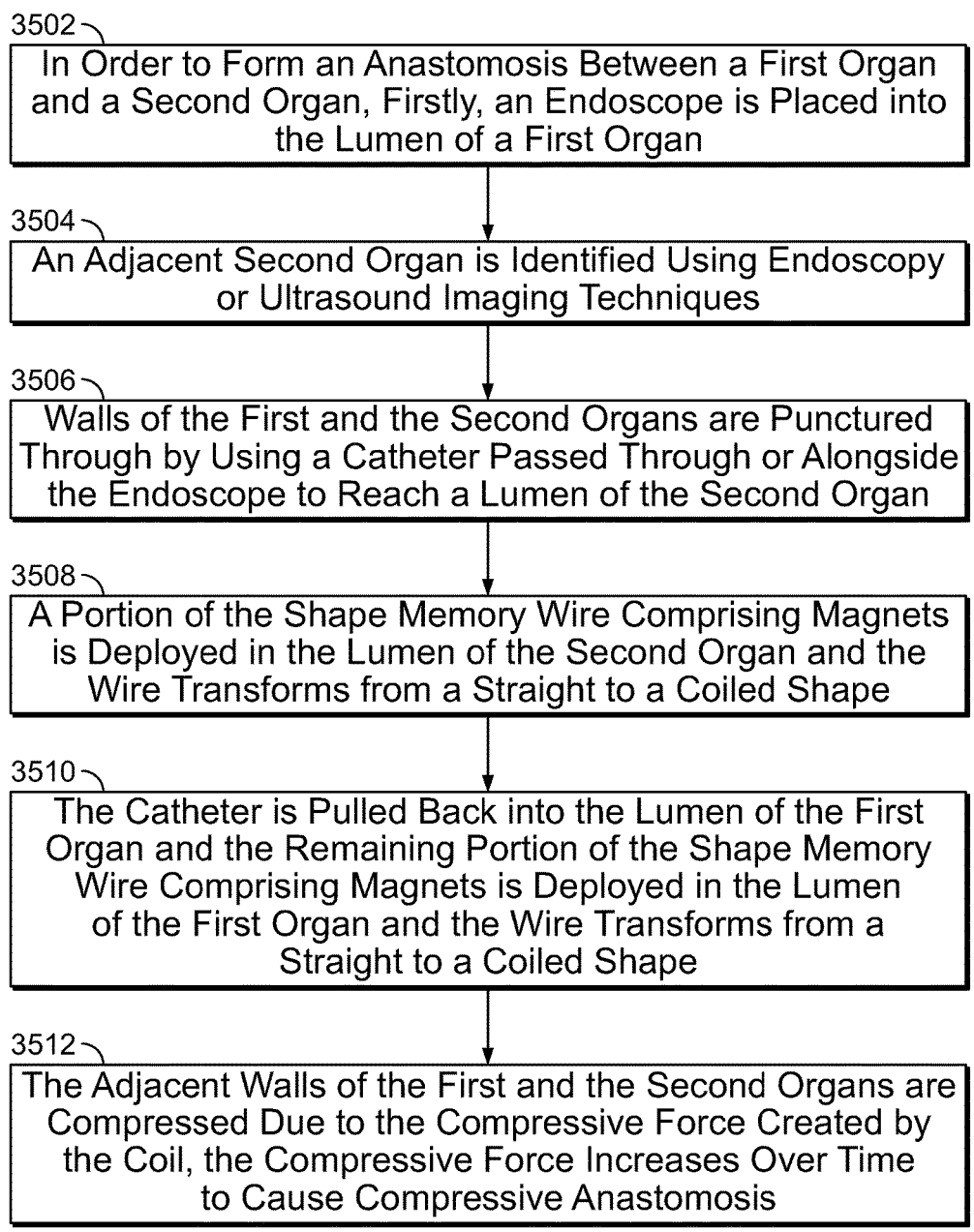

FIG. 35 is a flowchart illustrating the steps of creating an anastomosis by using a shape memory wire and magnetic compression forces between adjacent organs or structures, in accordance with an embodiment of the present specification. At step 3502, in order to form an anastomosis between a first organ and a second organ, firstly, an endoscope is placed into the lumen of a first organ. At step 3504, an adjacent second organ is identified using endoscopy, fluoroscopy, or ultrasound imaging techniques. At 3506, walls of the first and the second organs are punctured through by using a catheter passed through or alongside the endoscope to reach a lumen of the second organ. At step 3508, a portion of the shape memory wire comprising magnets is deployed in the lumen of the second organ and the wire transforms from a straight to a coiled shape. At step 3510, the catheter is pulled back into the lumen of the first organ and the remaining portion of the shape memory wire comprising magnets is deployed in the lumen of the first organ and the wire transforms from a straight to a coiled shape. At step 3512 the adjacent walls of the first and the second organs are compressed due to the compressive force created by the coil, the compressive force increases over time to cause compressive anastomosis.

FIG. 36 is a flowchart illustrating the steps of creating an anastomosis by using a shape memory coil with magnets between adjacent organs, in accordance with an embodiment of the present specification. At step 3602, in order to form an anastomosis between a first organ and a second organ, firstly, an endoscope is placed into the lumen of a first organ for inflating the lumen with a gas or fluid and allowing the gas or fluid to flow into the lumen of the adjacent second organ. At step 3604, an adjacent second organ is identified using endoscopy or ultrasound imaging techniques, wherein the gas or fluid assist in the identification. At 3606, walls of the first and the second organs are punctured through by using a catheter passed through or alongside the endoscope to reach a lumen of the second organ. At step 3608, a portion of the shape memory wire comprising magnets is deployed in the lumen of the second organ and the wire transforms from a straight to a coiled shape. At step 3610, the catheter is pulled back into the lumen of the first organ and the remaining portion of the shape memory wire comprising magnets is deployed in the lumen of the first organ and the wire transforms from a straight to a coiled shape. At step 3612 the adjacent walls of the first and the second organs are compressed due to the compressive force created by the coil, the compressive force increases over time to cause compressive anastomosis.

FIG. 37 is a flowchart illustrating the steps of creating an anastomosis by using a shape memory wire and magnetic compression forces between adjacent organs or structures, in accordance with an embodiment of the present specification. At step 3702, in order to form an anastomosis between a first organ and a second organ, firstly, an endoscope is placed into the lumen of a first organ. At step 3704, an adjacent second organ is identified using endoscopy or ultrasound imaging techniques. At 3706, walls of the first and the second organs are punctured through by using a catheter passed through or alongside the endoscope to reach a lumen of the second organ. At step 3708, a portion of the shape memory wire comprising magnets is deployed in the lumen of the second organ and the wire transforms from a straight to a coiled shape. At step 3710, the catheter is pulled back into the lumen of the first organ and the remaining portion of the shape memory wire comprising magnets is deployed in the lumen of the first organ and the wire transforms from a straight to a coiled shape. At step 3712 the adjacent walls of the first and the second organs are compressed due to the compressive force created by the coil, the compressive force increases over time to cause compressive anastomosis. At step 3714, once the anastomosis is formed, the shape memory coil falls off spontaneously and is eliminated naturally out of the body.

FIG. 38 is a flowchart illustrating the steps of creating an anastomosis by using a shape memory coil with magnets between adjacent organs, in accordance with an embodiment of the present specification. At step 3802, in order to form an anastomosis between a first organ and a second organ, firstly, an endoscope is placed into the lumen of a first organ for inflating the lumen with a gas or fluid and allowing the gas or fluid to flow into the lumen of the adjacent second organ. At step 3804, an adjacent second organ is identified using endoscopy or ultrasound imaging techniques, wherein the gas or fluid assist in the identification. At 3806, walls of the first and the second organs are punctured through by using a catheter passed through or alongside the endoscope to reach a lumen of the second organ. At step 3808, a portion of the shape memory wire comprising magnets is deployed in the lumen of the second organ and the wire transforms from a straight to a coiled shape. At step 3810, the catheter is pulled back into the lumen of the first organ and the remaining portion of the shape memory wire comprising magnets is deployed in the lumen of the first organ and the wire transforms from a straight to a coiled shape. At step 3812 the adjacent walls of the first and the second organs are compressed due to the compressive force created by the coil, the compressive force increases over time to cause compressive anastomosis. At step 3814, once the anastomosis is formed, the shape memory coil remains in the anastomosis, until removed out of the body by using an endoscope.

FIG. 39A illustrates an exemplary magnet 3902 used with a device for creating an anastomosis, in accordance with an embodiment of the present specification. As shown, force 3904 generated by the magnet 3902 and measured between two cylindrical outer surfaces 3902a, 3902b of the magnet 3902 is approximately 1.185 N. In various embodiments, the length, inner diameter and outer diameter of the magnet 3902 are 2.5 mm, 1.0 mm and 2.5 mm respectively. FIG. 39B illustrates an exemplary magnet 3906 used with a device for creating an anastomosis, in accordance with another embodiment of the present specification. As shown, force 3908 generated by the magnet 3906 and measured between two cylindrical outer surfaces 3906a, 3906b of the magnet 3906 is approximately 2.318 N. In various embodiments, the length, inner diameter and outer diameter of the magnet 3906 are 3 mm, 0.66 mm and 3 mm respectively. The force between the cylindrical surfaces 3906a, 3906b of the magnet 3906 is about 191% greater than the force between the cylindrical surfaces 3902a, 3902b of magnet 3902 of FIG. 39A.

As discussed above, the coil structure of the anastomosis devices of the present specification allows for the application of multiple magnetic layers (or coil loops), thereby increasing compressive force on a tissue surface, without increasing the complexity of a medical procedure. Magnetic anastomosis devices are subject to separation as a result of exposure to gastrointestinal forces. The likelihood of separation, defined by the distance between loops of a coiled device, is dependent upon the size of the magnets, number of coils or loops in the device, and the radius of the coil. Since embodiments of the anastomosis devices of the present specification include multiple coil loops on both sides of the anastomosis being formed, the coil loops are less likely to separate compared to the single loop, individual and physically separate devices of the prior art. In addition, since the embodiments of the present specification comprise a single integrated device, if, after the first magnetic element on a first coil loop attaches to a second magnetic element on a second coil loop, the two magnetic elements thereafter detach, the detachment will only be temporary and the two magnetic elements will automatically reattach over the target tissue region without requiring human intervention. In other words, the magnetic coil loops cannot travel away from one another since they are attached to a single device, and they will eventually reattach due to magnetic forces.

The following are case examples illustrating the effects of magnet size, number of coil loops, and coil radius on the distance between coil loops of deployed magnetic anastomosis devices of the present specification, and resultant likelihood of anastomosis separation (separation of two adjacent tissues). Operationally, the device, having a plurality of magnets in a fixed relation to each other, is endoscopically positioned proximate a tissue wall; the tissue wall is pierced with the device and a first set of the plurality of magnets is passed through the wall while concurrently a second set of the plurality of magnets is not passed through the tissue wall, thereby leaving some of the plurality of magnets on one side of the tissue wall and some of the plurality of magnets on the other side of the tissue wall; after the first set of the plurality of magnets form into at least one coil and the second set of the plurality of magnets form into at least one second coil, which occurs automatically and without further human intervention, one waits a period of time. When formed into coils, the first set and second set of the plurality of magnets, each of which has a diameter in a range of 1 mm to 4 mm, preferably 2 mm to 3 mm, are attracted to each other and automatically move toward each other, thereby compressing the tissue wall, which is approximately 10 to 15 mm thick, to a size of 2 mm to 8 mm thick, depending on the type of tissue being targeted.

In the case examples below, magnets having a maximum diameter up to 3 mm are used in order to accommodate endoscopic delivery. In other embodiments, anastomosis devices of the present specification have a maximum diameter of up to 7 mm. In some embodiments, the magnets are N52 magnets and each have a surface magnetic field in a range of 10,000 to 20,000 Gauss, preferably 14800 Gauss. In addition, several assumptions regarding the magnetic devices, human anatomy, and forces created by said devices and anatomy are made:

- The standard cumulative thickness of two walls to be anastomosed is assumed to be 8-10 mm.
- The ideal magnetic force for anastomosis formation is 0.1-0.3 N and the ideal pressure for anastomosis formation is 14.5-58 psi (0.1-0.4 MPa), although the disclosed range for applied pressure by the device is in a range of 1-145 psi (0.007-1 MPa).
- The average cumulative stress in a human stomach summed over a 30 minute period prior to gastric emptying is 160,000±70,000 dynes/cm$^2$ (0.016±0.007 MPa) fasted and 520,000±270,000 dynes/cm$^2$ (0.052±0.027 MPa) fed.
- The small intestine is capable of generating pressures greater than 1.93 psi (100 mm Hg; 0.013 MPa).
- The average normal stomach wall thickness is 5.1±1.1 mm, with a maximum thickness of 7 mm.
- The average normal small intestine wall thicknesses are as follows:
  - Duodenum: 1.53 ±0.58 mm.
  - Jejunum: 1.50±0.55 mm.
  - Ileum: 1.61±0.47 mm.
- The average normal gallbladder wall thickness is 2.6±1.6 mm, with a maximum thickness of 4 mm.
- The average gallstone thickness is 0.4±1.4 mm.
- The average gallbladder sludge thickness is 0.5±1.4 mm.
- The average wall thickness of a gallbladder with acute cholecystitis is 3.1±1.6 mm.
- The average common bile duct wall thickness is 0.8±0.4 mm.

CASE EXAMPLE 1

Devices Having One Coil Loop on Each Side of Anastomosis

FIG. 39C is a graph illustrating the relationship between compressive pressures and distances between coil loops provided by anastomosis devices having a single coil loop on each side of an anastomosis to be formed, in accordance with an embodiment of the present specification. In other words, each device represented in FIG. 39C includes a total of one pair of coil loops comprising a single coil loop on each side of an anastomosis to be formed. Curves 3910, 3911, and 3912 illustrate the relationship between pressure and distance between coil loops for devices having 1 pair of coil loops, an inner coil radius of 10 mm, and magnet widths or diameters of 2.0 mm, 2.5 mm, and 3.0 mm respectively. It is assumed that normal peristaltic motility of the gastrointestinal tract is capable of producing a maximum gastric pressure 3913 of approximately 7.25 psi (0.05 MPa) and a maximum small intestine pressure 3914 of approximately 1.88 psi (0.013 MPa). As can be seen in FIG. 39C, pressure (P) created by the anastomosis devices increases as the distance (d) between the coil loops decreases. In addition, the pressure created increases as the magnet width increases. For example, curve 3912 illustrates a pressure of approximately 7.25 psi (0.05 MPa) at a distance of approximately 0.36 cm for a device comprising magnets with a width of 3.0 mm compared to curve 3910 illustrating a pressure of approximately 3.63 psi (0.025 MPa) at the same distance for a device comprising magnets with a width of 2.0 mm.

To form a gastric anastomosis, devices comprising 2 mm or 3 mm diameter magnets will need to reach a distance of no more than 2 mm to 4 mm between loops, and hence magnets, respectively, such that gastric pressure cannot separate the loops. To form a small bowel anastomosis, devices comprising 2 mm or 3 mm magnets will need to reach a distance of no more than 6 mm to 8 mm between loops, and hence magnets, respectively, such that small intestinal pressure cannot separate the loops. Cumulative thickness of the organ walls is assumed to be greater than 10 mm.

As the distance between coil loops increases, the pressure created by the devices decreases and the risk of anastomosis separation increases. Box 3915 depicts the distances over which a gastric anastomosis formed by the devices represented in FIG. 39C is at risk for separation. Once each curve 3910, 3911, 3912 crosses below the assumed maximum gastric pressure 3913, each gastric anastomosis is at risk for separation. That is, each gastric anastomosis formed by the devices represented in FIG. 39C is at risk for separation at distances ranging from at least 0.36 cm to 1 cm as a result of exposure to gastric pressure. Box 3916 depicts the distances over which a small bowel anastomosis formed by the devices represented in FIG. 39C is at risk for separation. Once each curve 3910, 3911, 3912 crosses below the assumed maximum small intestinal pressure 3914, each small bowel anastomosis is at risk for separation. That is, each small bowel anastomosis formed by the devices represented in FIG. 39C is at risk for separation at distances ranging from at least 0.8 cm to 1 cm as a result of exposure to small intestinal pressure. Therefore, assuming the magnets are 3.0 mm in diameter and less than 3.6 mm apart, gastric peristalsis will not be sufficient to separate the magnets and/or dislodge them. Assuming the magnets are 3.0 mm in diameter and less than 8 mm apart, small bowel peristalsis will not be sufficient to separate the magnets and/or dislodge them. As noted earlier, the single device structure of the anastomosis devices of the present specification allows them to reattach automatically, and in the correct orientation, should separation occur. Since prior art devices require two separate devices for anastomosis formation, these devices are at risk for spontaneous separation, and resultant dislodgement without reattachment, at distances represented by boxes 3915 and 3916.

CASE EXAMPLE 2

Devices Having Two Coil Loops on Each Side of Anastomosis

FIG. 39D is a graph illustrating the relationship between compressive pressures and distances between coil loops provided by anastomosis devices having two coil loops on each side of an anastomosis to be formed, in accordance with an embodiment of the present specification. In other words, each device represented in FIG. 39D includes a total of two pairs of coil loops, with each pair comprising a single coil loop on each side of an anastomosis to be formed, for a total of 4 loops. Curves 3920, 3921, and 3922 illustrate the relationship between pressure and distance between coil loops for devices having 2 pairs of coil loops, an inner coil radius of 10 mm, and magnet widths or diameters of 2.0 mm, 2.5 mm, and 3.0 mm respectively. It is assumed that normal peristaltic motility of the gastrointestinal tract is capable of producing a maximum gastric pressure 3923 of approximately 7.25 psi (0.05 MPa) and a maximum small intestine pressure 3924 of approximately 1.88 psi (0.013 MPa). As can be seen in FIG. 39D, pressure (P) created by the anastomosis devices increases as the distance (d) between the coil loops decreases. In addition, the pressure created increases as the magnet width increases. For example, curve 3922 illustrates a pressure of approximately 7.25 psi (0.05 MPa) at a distance of approximately 0.55 cm for a device comprising magnets with a width of 3.0 mm compared to curve 3920 illustrating a pressure of approximately 3.63 psi (0.025 MPa) at the same distance for a device comprising magnets with a width of 2.0 mm. To form a gastric anastomosis, devices comprising 2 mm to 3 mm magnets will need to reach a distance of no more than 3.5 mm to 6 mm between loops, and hence magnets, respectively, such that gastric pressure cannot separate the loops. To form a small bowel anastomosis, devices comprising 2.5 mm to 3 mm magnets cannot be separated by small intestinal pressure, while devices comprising 2 mm magnets will need to reach a distance of no more 8 mm between loops, and hence magnets, such that small intestinal pressure cannot separate the loops. Cumulative thickness of the organ walls is assumed to be greater than 10 mm.

As the distance between coil loops increases, the pressure created by the devices decreases and the risk of anastomosis separation increases. Box 3925 depicts the distances over which a gastric anastomosis formed by the devices represented in FIG. 39D is at risk for separation. Once each curve 3920, 3921, 3922 crosses below the assumed maximum gastric pressure 3923, each gastric anastomosis is at risk for separation. That is, each gastric anastomosis formed by the devices represented in FIG. 39D is at risk for separation at distances ranging from at least 0.54 cm to 1 cm as a result of exposure to gastric pressure. Box 3926 depicts the distances over which a small bowel anastomosis formed by the devices represented in FIG. 39D is at risk for separation. Curves 3921 and 3922, representing devices having magnets with diameters of 2.5 mm and 3 mm respectively, do not cross under the assumed maximum small intestine pressure 3924 and, as such, these devices are not subject to separation. Once curve 3920 crosses below the assumed maximum small intestinal pressure 3914, the small bowel anastomosis formed by the device having magnets with a diameter of 2.0 mm is at risk for separation. That is, the small bowel anastomosis formed by the device having magnets with a diameter of 2.0 mm is at risk for separation at distances ranging from 0.8 cm to 1 cm as a result of exposure to small intestinal pressure. Therefore, assuming the magnets are 3.0 mm in diameter and less than 5.4 mm apart, gastric peristalsis will not be sufficient to separate the magnets and/or dislodge them. Assuming the magnets are 3.0 mm in diameter, no amount of normal small bowel peristalsis will be sufficient to separate the magnets and/or dislodge them. Therefore, increasing the coil pairs from 1 to 2 lowers the risk of anastomosis separation at greater distances for all the devices represented in FIG. 39D. As noted earlier, the single device structure of the anastomosis devices of the present specification allows them to reattach automatically, and in the correct orientation, should separation occur. Since prior art devices require two separate devices for anastomosis formation, these devices are at risk for spontaneous separation, and resultant dislodgement without reattachment, at distances represented by boxes 3925 and 3926.

CASE EXAMPLE 3

Devices Having Three Coil Loops on Each Side of Anastomosis

FIG. 39E is a graph illustrating the relationship between compressive pressures and distances between coil loops provided by anastomosis devices having three coil loops on each side of an anastomosis to be formed, in accordance with an embodiment of the present specification. In other words, each device represented in FIG. 39E includes a total of three pairs of coil loops, with each pair comprising a single coil loop on each side of an anastomosis to be formed, for a total of 6 loops. Curves 3930, 3931, and 3932 illustrate the relationship between pressure and distance between coil loops for devices having 3 pairs of coil loops, an inner coil radius of 10 mm, and magnet widths or diameters of 2.0 mm, 2.5 mm, and 3.0 mm respectively. It is assumed that normal peristaltic motility of the gastrointestinal tract is capable of producing a maximum gastric pressure 3933 of approximately 7.25 psi (0.05 MPa) and a maximum small intestine pressure 3934 of approximately 1.88 psi (0.013 MPa). As can be seen in FIG. 39E, pressure (P) created by the anastomosis devices increases as the distance (d) between the coil loops decreases. In addition, the pressure created increases as the magnet width increases. For example, curve 3932 illustrates a pressure of approximately 7.25 psi (0.05 MPa) at a distance of approximately 0.65 cm for a device comprising magnets with a width of 3.0 mm compared to curve 3930 illustrating a pressure of approximately 3.63 psi (0.025 MPa) at the same distance for a device comprising magnets with a width of 2.0 mm. To form a gastric anastomosis, devices comprising 2 mm to 3 mm magnets will need to reach a distance of no more than 4 mm to 7 mm between loops, and hence magnets, respectively, such that gastric pressure cannot separate the loops. Additional force from the coil and self-aligning feature may further prevent the coils from separating. All devices represented in FIG. 39E, comprising 2.0 mm, 2.5 mm, and 3 mm diameter magnets, cannot be separated by small intestinal pressure. Cumulative thickness of the organ walls is assumed to be greater than 10 mm.

As the distance between coil loops increases, the pressure created by the devices decreases and the risk of anastomosis separation increases. Box 3935 depicts the distances over which a gastric anastomosis formed by the devices represented in FIG. 39E is at risk for separation. Once each curve 3930, 3931, 3932 crosses below the assumed maximum gastric pressure 3933, each gastric anastomosis is at risk for separation. That is, each gastric anastomosis formed by the devices represented in FIG. 39E is at risk for separation at distances ranging from at least 0.65 cm to 1 cm as a result of exposure to gastric pressure. No devices are at risk for separation due to small intestinal pressure. Therefore, assuming the magnets are 3.0 mm in diameter and less than 6.5 mm apart, gastric peristalsis will not be sufficient to separate the magnets and/or dislodge them. Assuming the magnets are 3.0 mm in diameter, no amount of normal small bowel peristalsis will be sufficient to separate the magnets and/or dislodge them. Therefore, increasing the coil pairs from 1 to 3 further lowers the risk of anastomosis separation at greater distances for all the devices represented in FIG. 39E. As noted earlier, the single device structure of the anastomosis devices of the present specification allows them to reattach automatically, and in the correct orientation, should separation occur. Since prior art devices require two separate devices for anastomosis formation, these devices are at risk for spontaneous separation, and resultant dislodgement without reattachment, at distances represented by boxes 3935.

CASE EXAMPLE 4

Devices Having 2.0 mm Diameter Magnets and Varying Numbers of Coil Loops on Each Side of Anastomosis FIGS. 39F and 39G are graphs illustrating the relationship between compressive pressures and distances between coil loops and between force and distances between coil loops respectively, provided by anastomosis devices having 2.0 mm diameter magnets and varying numbers of coil loops on each side of an anastomosis to be formed, in accordance with embodiments of the present specification. As can be seen in FIGS. 39F and 39G, both pressure (P) and force (F) increase as the distance (d) between the coil loops decreases. Curves 3940 and 3950 represent devices having magnets with a width or diameter of 2.0, an inner coil radius of 10 mm, and one pair of coil loops (1 coil on each side of anastomosis to be formed). Curves 3941 and 3951 represent devices having magnets with a width or diameter of 2.0, an inner coil radius of 10 mm, and two pairs of coil loops (2 coils on each side of anastomosis to be formed). Curves 3942 and 3952 represent devices having magnets with a width or diameter of 2.0, an inner coil radius of 10 mm, and three pairs of coil loops (3 coils on each side of anastomosis to be formed). Curves 3943 and 3953 represent devices having magnets with a width or diameter of 2.0, an inner coil radius of 10 mm, and four pairs of coil loops (4 coils on each side of anastomosis to be formed). Increasing the number of coil loop pairs increases the pressure and force generated by the devices at the same distance. For example, a device having 4 coil loop pairs represented by curves 3943, 3953 generates a pressure of approximately 11.6 psi (0.08 MPa) and a force of approximately 16 N at a distance of approximately 0.6 cm between coil loops, while a device having only one pair of coil loop pairs represented by curves 3940, 3950 generates a pressure of approximately 2.9 psi (0.02 MPa) and a force of approximately 4 N at the same distance. Referring to FIG. 39F, spontaneous separation of a gastric anastomosis formed by all the devices represented in FIG. 39F can occur at distances ranging from 0.8 to 1.0 cm between coil loops, as depicted by box 3946, once the pressure generated by the devices drops below the assumed maximum gastric pressure 3944. Only the device having 1 pair of coil loops is susceptible to small bowel anastomosis separation, as depicted by curve 3940 dropping below the assumed maximum small intestinal pressure 3945. Therefore, assuming a 4 pair coil device includes magnets that are 2.0 mm in diameter and less than 8 mm apart, gastric peristalsis will not be sufficient to separate the magnets and/or dislodge them. Assuming a 4 pair coil device includes magnets that are 2.0 mm in diameter, no amount of normal small bowel peristalsis will be sufficient to separate the magnets and/or dislodge them.

CASE EXAMPLE 5

Devices Having 2.5 mm Diameter Magnets and Varying Numbers of Coil Loops on Each Side of Anastomosis FIGS. 39H and 39I are graphs illustrating the relationship between compressive pressures and distances between coil loops and between force and distances between coil loops respectively, provided by anastomosis devices having 2.5 mm diameter magnets and varying numbers of coil loops on each side of an anastomosis to be formed, in accordance with embodiments of the present specification. As can be seen in FIGS. 39H and 39I, both pressure (P) and force (F) increase as the distance (d) between the coil loops decreases. Curves 3960 and 3970 represent devices having magnets with a width or diameter of 2.5, an inner coil radius of 10 mm, and one pair of coil loops (1 coil on each side of anastomosis to be formed). Curves 3961 and 3971 represent devices having magnets with a width or diameter of 2.5, an inner coil radius of 10 mm, and two pairs of coil loops (2 coils on each side of anastomosis to be formed). Curves 3962 and 3972 represent devices having magnets with a width or diameter of 2.5, an inner coil radius of 10 mm, and three pairs of coil loops (3 coils on each side of anastomosis to be formed). Curves 3963 and 3973 represent devices having magnets with a width or diameter of 2.5, an inner coil radius of 10 mm, and four pairs of coil loops (4 coils on each side of anastomosis to be formed). Increasing the number of coil loop pairs increases the pressure and force generated by the devices at the same distance. For example, a device having 4 coil loop pairs represented by curves 3963, 3973 generates a pressure of approximately 11.6 psi (0.08 MPa) and a force of approximately 16 N at a distance of approximately 0.6 cm between coil loops, while a device having only one pair of coil loop pairs represented by curves 3960, 3970 generates a pressure of approximately 2.9 psi (0.02 MPa) and a force of approximately 4 N at the same distance. Referring to FIG. 39H, spontaneous separation of a gastric anastomosis formed by all the devices represented in FIG. 39H can occur at distances ranging from 0.8 to 1.0 cm between coil loops, as depicted by box 3966, once the pressure generated by the devices drops below the assumed maximum gastric pressure 3964. Only the device having 1 pair of coil loops is susceptible to small bowel anastomosis separation, as depicted by curve 3960 dropping below the assumed maximum small intestinal pressure 3965. Therefore, assuming a 4 pair coil device includes magnets that are 2.5 mm in diameter and less than 8 mm apart, gastric peristalsis will not be sufficient to separate the magnets and/or dislodge them.

Assuming a 4 pair coil device includes magnets that are 2.5 mm in diameter, no amount of normal small bowel peristalsis will be sufficient to separate the magnets and/or dislodge them.

CASE EXAMPLE 6

Devices Having 3.0 mm Diameter Magnets and Varying Numbers of Coil Loops on Each Side of Anastomosis FIGS. 39K and 39J are graphs illustrating the relationship between compressive pressures and distances between coil loops and between force and distances between coil loops respectively, provided by anastomosis devices having 3.0 mm diameter magnets and varying numbers of coil loops on each side of an anastomosis to be formed, in accordance with embodiments of the present specification. As can be seen in FIGS. 39K and 39J, both pressure (P) and force (F) increase as the distance (d) between the coil loops decreases. Curves 3980 and 3990 represent devices having magnets with a width or diameter of 3.0, an inner coil radius of 10 mm, and one pair of coil loops (1 coil on each side of anastomosis to be formed). Curves 3981 and 3991 represent devices having magnets with a width or diameter of 3.0, an inner coil radius of 10 mm, and two pairs of coil loops (2 coils on each side of anastomosis to be formed). Curves 3982 and 3992 represent devices having magnets with a width or diameter of 3.0, an inner coil radius of 10 mm, and three pairs of coil loops (3 coils on each side of anastomosis to be formed). Curves 3983 and 3993 represent devices having magnets with a width or diameter of 3.0, an inner coil radius of 10 mm, and four pairs of coil loops (4 coils on each side of anastomosis to be formed). Increasing the number of coil loop pairs increases the pressure and force generated by the devices at the same distance. For example, a device having 4 coil loop pairs represented by curves 3983, 3993 generates a pressure of approximately 11.6 psi (0.08 MPa) and a force of approximately 16 N at a distance of approximately 0.6 cm between coil loops, while a device having only one pair of coil loop pairs represented by curves 3980, 3990 generates a pressure of approximately 2.9 psi (0.02 MPa) and a force of approximately 4 N at the same distance. Referring to FIG. 39K, spontaneous separation of a gastric anastomosis formed by all the devices represented in FIG. 39K can occur at distances ranging from 0.84 to 1.0 cm between coil loops, as depicted by box 3986, once the pressure generated by the devices drops below the assumed maximum gastric pressure 3984. No devices are susceptible to small bowel anastomosis separation, as no curve drops below the assumed maximum small intestinal pressure 3985. Therefore, assuming a 4 pair coil device includes magnets that are 3.0 mm in diameter and less than 8.4 mm apart, gastric peristalsis will not be sufficient to separate the magnets and/or dislodge them. Assuming a 4 pair coil device includes magnets that are 3.0 mm in diameter, no amount of normal small bowel peristalsis will be sufficient to separate the magnets and/or dislodge them.

FIG. 40A illustrates an exemplary device 4000 for creating an anastomosis in a pre-coiled configuration, in accordance with an embodiment of the present specification. The device 4000 comprises a shape memory alloy (SMA) wire 4002 with a plurality of magnets 4004 and spacers 4006 positioned alternately and coaxially about the wire 4002. In an embodiment, the wire 4002 is composed of Nitinol. In an embodiment, the spacers 4006 are composed of a non-ferromagnetic material. In various embodiments, the spacers 4006 comprise silicone or Nitinol tubes or O-rings or circular balls. In an embodiment, as shown, a length of the device 4000 for creating an anastomosis, while in a pre-coiled configuration, is in a range of 440 to 460 mm. In an embodiment, a proximal end 4000p of the device 4000 includes a device connector 4008 for attaching the device 4000 for creating an anastomosis to a delivery device. In an embodiment, the device connector 4001 is a thread nut and the device 4000 connects to a delivery device via a screw mechanism.

FIGS. 40B and 40C illustrate the device 4000 for creating an anastomosis of FIG. 40A in a coiled configuration. Referring to FIGS. 40A, 40B and 40C, after deployment, and when exposed to body temperature, the SMA wire 4002 coils to move the device 4000 from the uncoiled configuration shown in FIG. 40A to the coiled configuration depicted in FIGS. 40B and 40C. The spacers 4006 ensure that the magnets 4004 do not clump together on the device 4000. In an embodiment, the device 4000 is provided with a connector 4008 at the proximal end of the wire 4002 for connecting with a delivery device. In an embodiment, a length of the anastomosis device 4000 in a coiled state is in a range of approximately 22 to 23 mm.

FIG. 40D illustrates a delivery device 4010 for delivering the anastomosis device 4000 shown in FIGS. 40A, 40B, and 40C in a desired location within a body, in accordance with an embodiment of the present specification. The delivery device 4010 includes a handle 4016 comprising a first proximal portion 4017 and a second distal portion 4019 having a port 4012, a body 4014 comprising an outer tubular sheath 4013 positioned coaxially about an inner shaft 4015, and a distal tip 4018, and is used to deliver the SMA anastomosis coil 4000 into a human body by means of an endoscope (not shown). The first proximal portion 4017 of the handle 4016 is movable relative to the second distal portion 4019 which moves the inner shaft 4015 in and out of the outer tubular sheath 4015 at the distal end of the delivery device body 4014. During delivery, a warm liquid may be introduced via port 4012 which, when contacting the shape memory alloy of the anastomosis device 4000, assists in changing the anastomosis device 4000 from its linear pre-deployment configuration to its coiled post-deployment configuration. FIGS. 40E, 40F and 40G illustrate the delivery device 4010 shown in FIG. 40D connected to the coiled anastomosis device 4000 shown in FIGS. 40B and 40C, in accordance with an embodiment of the present specification. In some embodiments, the distal tip 4018 of the inner shaft 4015 is provided with a delivery connector 4020 for connecting with the anastomosis device 4000 by means of the device connector 4008. In an embodiment, the delivery connector 4020 comprises a screw mandrel, the device connector 4008 comprises a thread nut, and together the delivery connector 4020 and device connector 4008 comprise a screw mechanism for connecting the delivery device 4010 to the device 4000 for creating an anastomosis. In an embodiment, prior to deployment, the anastomosis device 4000, in a linear configuration as depicted in FIG. 40A, is positioned within the outer tubular sheath 4013 of the delivery device body 4014, which helps restrain the anastomosis device 4000 and prevent it from coiling before being delivered to the desired location within a patient's body. The body 4014 is long and tubular and is inserted into a human body via a channel of an endoscope such that the distal tip 4018 connected to the anastomosis device 4000 (in a non-coiled shape) protrudes out of a distal end of the endoscope. Referring to FIGS. 40D, 40E, 40F and 40G, once the delivery device 4010 is positioned at the desired location within a human body, the handle 4016 is actuated to extrude the anastomosis device 4000 out of the outer sheath 4013 and disengage the delivery connector 4020 from the device connector 4008, allowing the anastomosis device 4000 to be deployed and change to its coiled configuration.

FIG. 40H is a flowchart listing the steps involved in a method of deploying an anastomosis device using a delivery device in accordance with one embodiment of the present specification. At step 4021, an endoscope is inserted into a patient's body with a distal end of the endoscope positioned proximate a desired anastomosis creation location. At step 4022, an anastomosis device with a device connector at its proximal end, and in a linear, pre-deployment configuration, is connected to a delivery device via a delivery connector at a distal end of the delivery device and retracted, using the delivery device handle, into a tubular sheath of the delivery device. The distal end of the delivery device, with anastomosis device attached, is inserted into an instrument channel of the endoscope at step 4023. Then, at step 4024, the user manipulates a handle of delivery device to advance the delivery device beyond said distal end of the endoscope and extend the anastomosis device out of said tubular sheath, positioning the anastomosis device proximate the desired anastomosis creation location. Optionally, at step 4025, the user injects warm fluid through a port on the delivery device handle or provides electrical current to the device to heat the device to assist with transformation of the anastomosis device from a linear, pre-deployment configuration to a coiled, post-deployment configuration. At step 4026, the user actuates the handle to disengage the delivery connector from the device connector, allowing the anastomosis device to separate from the delivery device, coil into its post-deployment configuration, and create an anastomosis. The delivery device and endoscope are removed from the patient at step 4027.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A method of creating an anastomosis between two adjacent body tissues comprising:
    positioning an anastomosis device, contained in a catheter, within a body cavity proximate at least one of said adjacent body tissues, wherein the anastomosis device comprises:
        a wire, wherein said wire has a first state and a second state, wherein, in said first state, the wire has a substantially linear form, wherein, in said second state, the wire forms a coil having at least a first loop and a second loop, and wherein said wire comprises a shape memory alloy that is adapted to transform from the first state to the second state when exposed to a temperature greater than a threshold value; and
        a plurality of magnets positioned over said wire, wherein each of said plurality of magnets has a lumen through which said wire extends, wherein, in each of said first loop and second loop, a portion of adjacent magnets of said plurality of magnets are configured to not attach to each other, and wherein a portion of said plurality of magnets in the first loop are configured to attract a portion of said plurality of magnets in the second loop;
    using a tip of the wire, piercing the adjacent body tissues and positioning the anastomosis device through a hole created by said piercing;
    before deploying the anastomosis device out of the catheter, heating the wire by passing electrical current through the wire, thereby causing the wire to transform from the first state to the second state; and
    deploying the anastomosis device out of the catheter such that, as it leaves the catheter and transforms from the first state to the second state, tissue between the two adjacent body tissues is caught between the first loop and the second loop, thereby being compressed and resulting in the anastomosis.

2. The method of claim 1 wherein the anastomosis device further comprises non-ferromagnetic spacers positioned between adjacent magnets of said plurality of magnets.

3. The method of claim 2 wherein each of said non-ferromagnetic spacers has a length sufficient to keep a force of attraction between opposite poles of the adjacent magnets below a bending force of the coil.

4. The method of claim 1 wherein, when in the second state, a maximum cross sectional diameter of the first loop and the second loop ranges from 5 mm to 50 mm.

5. The method of claim 1 wherein each of the plurality of magnets has a maximum cross sectional length or diameter ranging from 0.2 mm to 7 mm and a pull force ranging from 0.01 lb. to 4 lb.

6. The method of claim 1 wherein, in the first loop and in the second loop, at least 50% of the adjacent magnets of said plurality of magnets are arranged with like poles facing each other, thereby creating a repulsive force between said adjacent magnets in the first loop and a repulsive force between said adjacent magnets in the second loop of the coil.

7. The method of claim 1, wherein at least one end of the wire is connected to a delivery device.

8. The method of claim 1, wherein said threshold value is 20 degrees Celsius.

9. The method of claim 1, wherein said coil has at least one loop proximate to the first loop and at least one loop distal to the second loop.

10. The method of claim 1, wherein each of said plurality of magnets is cylindrically shaped and is a rare earth magnet covered with at least one of gold, nickel, Teflon, parylene, copper, zinc, silicone, epoxy and titanium.

11. The method of claim 1 wherein a diameter of the wire ranges between 0.1 mm to 10 mm and a length of the wire ranges from 1 cm to 250 cm.

12. The method of claim 1 wherein a diameter of the wire ranges between 0.1 mm and 6 mm and has a maximum strain of less than 10% in the first state and wherein a maximum cross sectional dimension of the first loop and second loop ranges from 5 mm to 60 mm in the second state.

13. The method of claim 1 wherein the adjacent body tissues comprise a gall bladder and a duodenum and a maximum diameter of the first loop and the second loop is less than or equal to 30 mm.

14. The method of claim 1 wherein the adjacent body tissues comprise pancreatic tissue and a maximum diameter of the first loop and the second loop is greater than or equal to 5 mm.

15. The method of claim 1 wherein the adjacent body tissues comprise biliary tissue and a maximum diameter of the first loop and the second loop is greater than or equal to 5 mm.

16. The method of claim 1 wherein a diameter of the wire is less than 0.5 mm and wherein a maximum cross sectional dimension of the first loop and second loop is less than or equal to 15 mm.

17. The method of claim 1 wherein a diameter of the wire ranges from 0.5 mm to 1.0 mm and wherein a maximum cross sectional dimension of the first loop and second loop ranges from 10 mm to 25 mm.

18. The method of claim 1 wherein a diameter of the wire is greater than 1 mm and wherein a maximum cross sectional dimension of the first loop and second loop is greater than 20 mm.

19. The method of claim 1 wherein the first loop and the second loop have at least one of a circular shape, polygonal shape, and a star shape with four or more points.

20. The method of claim 1 wherein a portion of the adjacent magnets of said plurality of magnets on the same loop are configured to repel each other.

21. A method of creating an anastomosis between two adjacent body tissues comprising:
   positioning an anastomosis device within a body cavity proximate at least one of said adjacent body tissues, wherein the anastomosis device is held inside a catheter and comprises:
      a wire comprising a shape memory alloy, wherein said wire has a martensite state and an austenite state, wherein, in said martensite state, the wire has a substantially linear form, wherein, in said austenite state, the wire forms a coil having at least a first loop and a second loop, and wherein said wire is adapted to transform from the martensite state to the austenite state when exposed to a temperature greater than 20 degrees Celsius; and
      a plurality of magnets positioned over said wire, wherein each of said plurality of magnets has a lumen through which said wire extends, wherein, in each of said first loop and second loop, a portion of adjacent magnets of said plurality of magnets are configured to not attach to each other, and wherein a portion of said plurality of magnets in the first loop are configured to attract a portion of said plurality of magnets in the second loop; and
   using a tip of the wire, piercing the adjacent body tissues and positioning the anastomosis device through a hole created by said piercing;
   before deploying the anastomosis device out of the catheter, heating the wire by passing electrical current through the wire, thereby causing the wire to transform from the martensite state to the austenite state; and
   deploying the anastomosis device out of the catheter such that, as it leaves the catheter and transforms from the martensite state to the austenite state, tissue between the two adjacent body tissues is caught between the first loop and the second loop, thereby being compressed with a pressure of at least 1 psi and resulting in an anastomosis.

22. The method of claim 21 wherein said pressure is greater than or equal to 0.3 psi at two or more points that are on opposite sides of at least one of the first loop and the second loop.

23. The method of claim 21 wherein the anastomosis device further comprises non-ferromagnetic spacers positioned between adjacent magnets of said plurality of magnets.

24. The method of claim 21 wherein the first loop and the second loop have at least one of a circular shape, polygonal shape, and a star shape with four or more points.

25. The method of claim 21 wherein each of the plurality of magnets has a maximum cross sectional length ranging from 0.2 mm to 7 mm and a pull force ranging from 0.01 lb. to 4 lb.

26. The method of claim 21 wherein, in the first loop and in the second loop, at least 50% of the adjacent magnets of said plurality of magnets are arranged with like poles facing each other, thereby creating a repulsive force between said adjacent magnets in the first loop and the second loop of the coil.

27. The method of claim 21 wherein said coil has at least one loop proximate to the first loop and at least one loop distal to the second loop.

28. The method of claim 21 wherein a diameter of the wire ranges between 0.1 mm to 10 mm and a length of the wire ranges from 1 cm to 250 cm and wherein a maximum cross sectional dimension of the first loop and second loop ranges from 5 mm to 60 mm in the second state.

* * * * *